United States Patent
Aron et al.

(10) Patent No.: US 11,505,533 B2
(45) Date of Patent: Nov. 22, 2022

(54) METABOLICALLY STABLE N-ACYLAMINOOXADIAZOLES USEFUL AS ANTIBACTERIAL AGENTS

(71) Applicants: MICROBIOTIX, INC., Worcester, MA (US); THE PENN STATE RESEARCH FOUNDATION, University Park, PA (US)

(72) Inventors: Zachary D. Aron, Acton, MA (US); Steven M. Kwasny, Blackstone, MA (US); Matthew C. Torhan, Worcester, MA (US); Jay P. Barbor, Worcester, MA (US); Steven C. Cardinale, Hopedale, MA (US); Michelle M. Butler, Auburn, MA (US); Timothy J. Opperman, Arlington, MA (US); Kenneth C. Keiler, Boalsburg, PA (US)

(73) Assignees: MICROBIOTIX, INC., Worcester, MA (US); THE PENN STATE RESEARCH FOUNDATION, University Park, PA (US)

( * ) Notice: Subject to any disclaimer, the term of this patent is extended or adjusted under 35 U.S.C. 154(b) by 0 days.

(21) Appl. No.: 16/640,642

(22) PCT Filed: Aug. 21, 2018

(86) PCT No.: PCT/US2018/047181
§ 371 (c)(1),
(2) Date: Feb. 20, 2020

(87) PCT Pub. No.: WO2019/040404
PCT Pub. Date: Feb. 28, 2019

(65) Prior Publication Data
US 2020/0361882 A1    Nov. 19, 2020

Related U.S. Application Data

(60) Provisional application No. 62/548,019, filed on Aug. 21, 2017.

(51) Int. Cl.
| | | |
|---|---|---|
| C07D 271/113 | (2006.01) | |
| A61P 31/04 | (2006.01) | |
| A01N 43/82 | (2006.01) | |
| C07D 413/12 | (2006.01) | |

(52) U.S. Cl.
CPC .......... C07D 271/113 (2013.01); A01N 43/82 (2013.01); A61P 31/04 (2018.01); C07D 413/12 (2013.01)

(58) Field of Classification Search
CPC .... C07D 271/113; C07D 413/12; A61P 31/04
See application file for complete search history.

(56) References Cited

U.S. PATENT DOCUMENTS

| | | | |
|---|---|---|---|
| 9,765,075 B2 * | 9/2017 | Blum | A61K 31/551 |
| 2007/0232620 A1 | 10/2007 | Dorsch et al. | |
| 2010/0063115 A1 | 3/2010 | Basu et al. | |
| 2015/0225388 A1 | 8/2015 | Willand et al. | |

FOREIGN PATENT DOCUMENTS

| | | |
|---|---|---|
| WO | 2010049841 | 5/2010 |
| WO | 2013/074965 | 5/2013 |
| WO | 2014/031681 | 2/2014 |
| WO | 2014/144710 | 9/2014 |
| WO | 2015/135946 | 9/2015 |
| WO | 2019/199496 | 10/2019 |

OTHER PUBLICATIONS

Alumasa et al., ACS Infect. Dis., Ribosome Rescue Inhibitors Kill Actively Growing and Nonreplicating Persister Mycobacterium tuberculosis Cells, 3:634-644 (2017).
Gordon et al., "Selective Mycobacterium tuberculosis Shikimate Kinase Inhibitors as Potential Antibacterials", Perspect. Medicin. Chem., 15(7):9-20 (2015) ).
Kim et al., Bioorg. Med. Chem., "Identification of *Bacillus anthracis* PurE inhibitors with antimicrobial activity", 23:1492-1499 (2015).
Maddry et al., Tuberculosis, "Antituberculosis activity of the molecular libraries screening center network library", 89(5): 354-363 (2009).
Opoku-Teneng et al., N-(1,3,4-osadiazol-2-yl)benzamide analogs, bacteriostatic agents against methicillin- and vancomycin-resistant bacteria, EU J Med. Chem., 155:797-805 (2018).
Ahmad et al., Characterization of pathogens involved in ventilator associated pneumonia in surgical medical intensive care units—A single center experience, Pak. J. of Pharm. Sci., 30(6):2091-2099 (2017).
Boucher, H. W. and G. Sakoulas, Perspectives on Daptomycin resistance, with emphasis on resistance in *Staphylococcus aureus*, Clin. Infect. Dis., 45(5):601-608 (2007).
Butler et al., Aminomethyl Spectinomycins as Therapeutics for Drug-Resistant Gonorrhea and Chlamydia Coinfections, Antimicrobial Agents Chemother., 62(5):e00321 (2018).
Camara et al., Molecular characterization of two high-level ceftriaxone-resistant *Neisseria gonorrhoeae* isolates detected in Catalonia, Spain, J. Antimicrob. Chemother., 67(8):1858-1860 (2012).

(Continued)

*Primary Examiner* — Kamal A Saeed
(74) *Attorney, Agent, or Firm* — David G. O'Brien, Esq.

(57) ABSTRACT

The present invention is related to the development of therapeutics and prophylactics for the treatment and/or prevention of bacterial infections in humans and other mammals. A new class of small molecules is disclosed that inhibits the bacterial trans-translation/ribosome rescue mechanism and thus blocks infection of host cells by bacteria. Also disclosed are methods of using the small molecule inhibitors in the treatment/prevention of bacterial infections.

32 Claims, 5 Drawing Sheets

(56) References Cited

OTHER PUBLICATIONS

CDC MMWR Weekly Rep., 56:332 (2007).
CDC MMWR Weekly Rep., 62:103 (2013).
Chaudhuri et al., Comprehensive identification of essential *Staphylococcus aureus* genes using Transposon-Mediated Differential Hybridisation (TMDH), BMC Genomics, 10:291 (2009).
Chen et al., First nationwide study regarding ceftriaxone resistance and molecular epidemiology of *Neisseria gonorrhoeae* in China, J. Antimicrob. Chemother., 71(1):92-99 (2016).
Choy et al., Lon protease degrades transfer-messenger RNA-tagged proteins, J. Bacteriol., 189(18):6564-6571 (2007).
Clark et al., Drug interactions between linezolid and selective serotonin reuptake inhibitors: case report involving sertraline and review of the literature, Pharmacotherapy, 26(2):269-276 (2006).
Clement et al., Evidence of an intracellular reservoir in the nasal mucosa of patients with recurrent *Staphylococcus aureus* rhinosinusitis, J. Infect. Dis., 192(6):1023-1028 (2005).
Clinical and Laboratory Standards Institute, 25(21):1-39 (2005).
Cornelissen, C.N. and A. Hollander, TonB-Dependent Transporters Expressed by *Neisseria gonorrhoeae*, Front. Microbiol., 2:117 (2011).
Ellington et al., Intracellular *Staphylococcus aureus*. A mechanism for the indolence of osteomyelitis, J. Bone Joint Surg. Br., 85(6):918-921 (2003).
Feaga et al., Human Cells Require Non-stop Ribosome Rescue Activity in Mitochondria, PLOS Genet., 12(3): e1005964 (2016).
Fey et al., A genetic resource for rapid and comprehensive phenotype screening of nonessential *Staphylococcus aureus* genes, MBio, 4(1):e00537-00512 (2013).
Flynn et al., Proc. Natl. Acad. Sci. USA, Overlapping recognition determinants within the ssrA degradation tag allow modulation of proteolysis, 98(19):10584-10589 (2001).
Goldstein et al., Factors related to increasing prevalence of resistance of ciprofloxacin and other antimicrobial drugs in *Neisseria gonorrhoeae*, United States, Emerg. Infect. Dis., 18(8):1290-1297 (2012).
Gottesman et al., The ClpXP and ClpAP proteases degrade proteins with carboxy-terminal peptide tails added by the SsrA-tagging system, Genes Dev., 12(9):1338-1347 (1998).
Gunther et al., MRSA decolonization failure—are biofilms the missing link?, Antimicrob. Resist. Infect. Control, 6:32 (2017).
Hess et al., Intracellular survival of *Staphylococcus aureus* within cultured enterocytes, J. Surg. Res., 114(1):42-49 (2003).
Hong et al., Cell cycle-regulated degradation of tmRNA is controlled by RNase R and SmpB, Mol. Microbiol., 57(2):565-575 (2005).
Huang et al., Charged tmRNA but not tmRNA-mediated proteolysis is essential for *Neisseria gonorrhoeae* viability, EMBO J., 19(5):1098-1107 (2000).
Hudson et al., Ends of the line for tmRNA-SmpB, Front. Microbiol., 5:421 (2014).
Ito et al., Nascentome analysis uncovers futile protein synthesis in *Escherichia coli*, PLoS One, 6:e28413 (2011).
Jain et al., Community-Acquired Pneumonia Requiring Hospitalization among U.S. Adults, N. Engl. J. Med., 373(5):415-427 (2015).
Julio et al., ssrA (tmRNA) plays a role in *Salmonella enterica* serovar Typhimurium pathogenesis, J. Bacteriol., 182(6):1558-1563 (2000).
Keiler, K. C., Mechanisms of ribosome rescue in bacteria, Nat. Rev. Microbiol., 13(5):285-297 (2015).
Keiler et al., Role of a peptide tagging system in degradation of protein synthesized from damaged messenger RNA, Science, 271(5251):990-993 (1996).
Kirkcaldy et al., Cephalosporin-resistant gonorrhea in North America, JAMA, 309(2):185-187 (2013).
Kollef et al., Global prospective epidemiologic and surveillance study of ventilator-associated pneumonia due to *Pseudomonas aeruginosa*, Crit. Care Med., 42(10):2178-2187 (2014); correct issue # in spec. 1 > 10.
Komine et al., A tRNA-like structure is present in 10Sa RNA, a small stable RNA from *Escherichia coli* Proc. Natl. Acad. Sci. USA, 91(20):9223-9227 (1994).
Li et al., *Staphylococcus aureus* Survives in Cystic Fibrosis Macrophages, Forming a Reservoir for Chronic Pneumonia, Infect. Immun., 85(5):e00883-16 (2017).
Liu et al., Clinical practice guidelines by the Infectious Diseases Society of America for the treatment of methicillin-resistant *Staphylococcus aureus* infections in adults and children, Clin. Infect. Dis., 52(3):e18-55 (2011).
Lodise et al., Relationship between initial vancomycin concentration-time profile and nephrotoxicity among hospitalized patients, Clin. Infect. Dis., 49(4):507-514 (2009); correct citation in specification re Lowy.
Magil et al., Multistate point-prevalence survey of health care-associated infections, N. Engl. J. Med., 370(13):1198-1208 (2014).
Mangili et al., Daptomycin-resistant, methicillin-resistant *Staphylococcus aureus* bacteremia, Clin. Infect. Dis., 40(7):1058-1060 (2005).
Mayor et al., Diagnosis and management of gonococcal infections, Am. Fam. Physician, 86:931-938 (2012).
Meka et al., Linezolid resistance in sequential *Staphylococcus aureus* isolates associated with a T2500A mutation in the 23S rRNA gene and loss of a single copy of rRNA, J. Infect. Dis., 190(2):311-317 (2004).
Morales et al., Resistance to linezolid is mediated by the cfr gene in the first report of an outbreak of linezolid-resistant *Staphylococcus aureus*, Clin. Infect. Dis., 50(6):821-825 (2010).
Neubauer et al., Decoding in the absence of a codon by tmRNA and SmpB in the ribosome, Science, 335(6074):1366-1369 (2012).
Newman et al., Global Estimates of the Prevalence and Incidence of Four Curable Sexually Transmitted Infections in 2012 Based on Systematic Review and Global Reporting, PLoS One, 10(12):e0143304 (2015).
Ohnishi et al., Is *Neisseria gonorrhoeae* initiating a future era of untreatable gonorrhea?: detailed characterization of the first strain with high-level resistance to ceftriaxone, Antimicrob. Agents Chemother., 55(7):3538-3545 (2011).
Okan et al., The smpB-ssrA mutant of *Yersinia pestis* functions as a live attenuated vaccine to protect mice against pulmonary plague infection, Infect. Immun., 78(3):1284-1293 (2010).
Pillai et al., Linezolid resistance in *Staphylococcus aureus*: characterization and stability of resistant phenotype, J. Infect. Dis., 186(11):1603-1607 (2002).
Purrello et al., J. Glob. Antimicrob. Resist., Methicillin-resistant *Staphylococcus aureus* infections: A review of the currently available treatment options, 7:178-186 (2016).
Ramadoss et al., tmRNA is essential in *Shigella flexneri*, PLoS ONE, 8(2):e57537 (2013).
Ramadoss et al., Small molecule inhibitors of trans-translation have broad-spectrum antibiotic activity, Proc. Natl. Acad. Sci. USA, 110(25):10282-10287 (2013).
Richter et al., A functional peptidyl-tRNA hydrolase, ICT1, has been recruited into the human mitochondrial ribosome, EMBO J., 29(6):1116-1125 (2010).
Sanchez-Garcia et al., Clinical outbreak of linezolid-resistant *Staphylococcus aureus* in an intensive care unit, JAMA, 303(22):2260-2264 (2010).
Reynolds et al., High throughput screening of a library based on kinase inhibitor scaffolds against *Mycobacterium tuberculosis* H37Rv, Tuberculosis, 92:72-83 (2012).
Simithy et al., Identification of shikimate kinase inhibitors among anti-*Mycobacterium tuberculosis* compounds by LC-MS, Tuberculosis, 94:152-158 (2014).
Soper, D. E., Pelvic inflammatory disease, Obstet. Gynecol., 116:419-428 (2010).
Stryjewski, M.E. and G.R. Corey, Methicillin-resistant *Staphylococcus aureus*: an evolving pathogen, Clin. Infect. Dis., 58 Suppl. 1:S10-19(2014).

(56) References Cited

OTHER PUBLICATIONS

Svetlanov et al., Francisella tularensis tmRNA system mutants are vulnerable to stress, avirulent in mice, and provide effective immune protection, Mol. Microbiol., 85(1):122-141 (2012).

Torres et al., Treatment guidelines and outcomes of hospital-acquired and ventilator-associated pneumonia, Clin. Infect. Dis., 51 Suppl 1:S43-53 (2010).
Unemo, M. and Shafer, W.M., Antibiotic resistance in *Neisseria gonorrhoeae*: origin, evolution, and lessons learned for the future, Ann. NY Acad. Sci., 1230:E19-28 (2011).
Unemo et al., High-level cefixime- and ceftriaxone-resistant *Neisseria gonorrhoeae* in France: novel penA mosaic allele in a successful international clone causes treatment failure, Antimicrob. Agents Chemother., 56(3):1273-1280 (2012).
Ushida et al., tRNA-like structures in 10Sa RNAs of *Mycoplasma capricolum* and *Bacillus subtilis* Nucleic Acids Res., 22(16):3392-3396 (1994).
Perera et al., Purification and characterization of the *Staphylococcus aureus* bacillithiol transferase BstA, Biochim Bioqhys Acta, 1840:2851-2861 (2014).
Whiley et al., The ticking time bomb: escalating antibiotic resistance in *Neisseria gonorrhoeae* is a public health disaster in waiting, J. Antimicrob. Chemother., 67:2059-2061 (2012).
Zhang et al., Global assessment of genomic regions required for growth in Mycobacterium tuberculosis, PloS Pathog., 8(9):e1002946 (2012).
Registry No. 1706253-38-4 (Aurora Fine Chemicals).

* cited by examiner

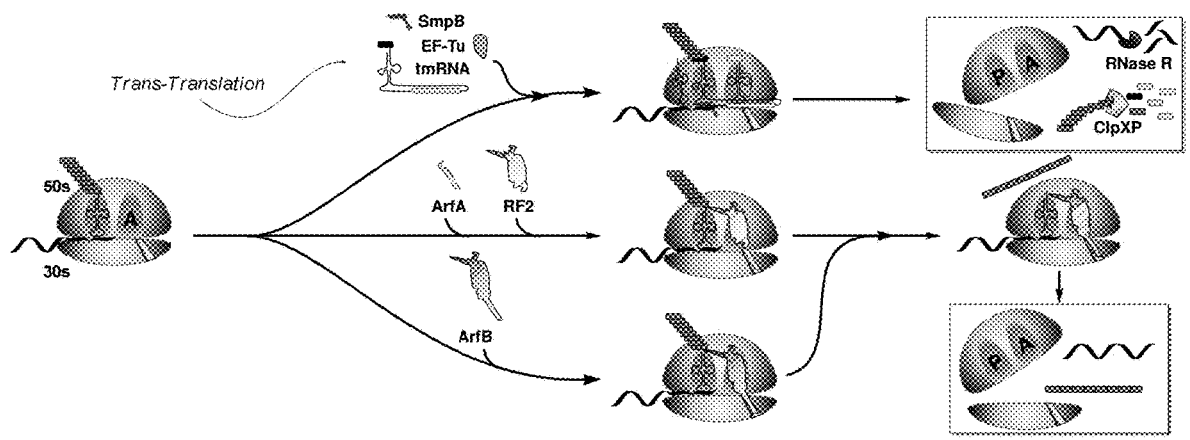

Ribosome rescue mechanisms. *Trans*-Translation, ArfA, and ArfB all rescue non-stop ribosomes. During trans-translation (top) tmRNA-SmpB inserts a reading frame within tmRNA in the mRNA channel, and the ribosome is released at a normal stop codon. The mRNA and nascent polypeptide are degraded. ArfA (middle) allows RF2 to hydrolyze the peptidyl-tRNA on a non-stop ribosome by an unknown mechanism. ArfB (bottom) binds in the empty A site and hydrolyzes the peptidyl-tRNA.

Fig. 1

METABOLICALLY STABLE N-ACYLAMINOOXADIAZOLES USEFUL AS ANTIBACTERIAL AGENTS

CROSS-REFERENCE TO RELATED APPLICATIONS

This application is a United States national stage filing under 35 U.S.C. § 371 of international (PCT) application no. PCT/US2018/047181, filed Aug. 21, 2018, and designating the US, which claims priority to U.S. Provisional Appln. No. 62/548,019 filed Aug. 21, 2017.

STATEMENT REGARDING FEDERALLY SPONSORED RESEARCH

This invention was made with government support under grants 5R43AI113993-02 and R01GM068720 awarded by the National Institutes of Health. The United States Government has certain rights in the invention.

FIELD OF THE INVENTION

This invention relates to metabolically stable antibacterial agents and to their use. More particularly, the invention relates to metabolically stable N-acylaminooxadiazole derivatives containing either ureido or aromatic amido moieties, their use in the preparation of a pharmaceutical composition and as a bactericide.

BACKGROUND OF THE INVENTION

The increase in multiple drug-resistant organisms (MDROs) poses a severe threat to human health (*Antibiotic Resistance Threats in the United States*, Centers for Disease Control, U.S. Dept. of Health and Human Services (2013)). There is an immediate need for new antibiotics to combat the threat of drug-resistant bacteria such as multidrug-resistant (MDR) *Neisseria gonorrhoeae* (Ng); extensively drug resistant (XDR) and MDR *Mycobacterium tuberculosis*; methicillin-resistant *Staphylococcus aureus* (MRSA); Community-Acquired Pneumonia (CAP) pathogens (MRSA, *Streptococcus pneumonia, Mycoplasma pneumonia, Moraxella catarrhalis, Legionella pneumophila,* and *Haemophilus influenzae*), and *Francisella tularensis*. The increased prevalence of multidrug resistance has reduced treatment options, leaving patients vulnerable to dangerous infections and complicating care.

Multidrug-resistant (MDR) gonorrhea is an urgent threat to public health. The CDC lists MDR *Neisseria gonorrhoeae* (Ng) as one of the three most urgent antibiotic resistance threats in the United States (*Antibiotic Resistance Threats in the United States*, Centers for Disease Control, U.S. Dept. of Health and Human Services (2013)). A Gram-negative fastidious organism, Ng causes gonorrhea, the second-most prevalent sexually transmitted bacterial infection (STI), with more than 800,000 cases in the United States and 78 million cases estimated worldwide [Cornelissen, C. N. and Hollander, A. *Frontiers in microbiology,* 2:117 (2011); Ohnishi et al., *Antimicrob Agents Chemother,* 55:3538 (2011); Newman et al., *PLoS One,* 10:e0143304 (2015)]. Left untreated, gonorrhea can cause pelvic inflammatory disease in women, leading to fallopian tube scarring and infertility (Soper, D. E., *Obstetrics and gynecology,* 116:419 (2010)), or may disseminate, causing joint and skin manifestations (Mayor et al., *American family physician,* 86:931 (2012)). Once easily treatable, Ng has evolved resistance to nearly every antibiotic used to treat it, leaving a combination of azithromycin (AZM) and ceftriaxone (CTX) as the only recommended treatment option (Whiley et al., *J Antimicrob Chemother,* 67:2059 (2012); *Obstetrics and gynecology,* 127(5):e95-99 (2016)). Strains resistant to sulfonamides (Unemo, M. and Shafer, W. M., *Annals of the New York Academy of Sciences,* 1230:E19 (2011)), penicillin, streptomycin, erythromycin, tetracycline, spectinomycin, fluoroquinolones (Goldstein et al., *Emerg. Infect. Dis.,* 18:1290 (2012) and CDC *MMWR Weekly Rep.,* 56: 332 (2007)), cefixime (Unemo et al., *Antimicrob. Agents Chemother.,* 56:1273 (2012)), AZM (Unemo, M. and Shafer, W. M., *Annals of the New York Academy of Sciences,* 1230:E19 (2011)), and CTX (Unemo et al., *Antimicrob. Agents Chemother.,* 56:1273 (2012); Chen et al., *J. Antimicrob. Chemother.,* 71:92 (2016); Camara et al., *J. Antimicrob. Chemother.,* 67:1858 (2012); CDC *MMWR Weekly Rep.,* 62:103 (2013)), have been reported. (See, also, Ohnishi et al., *Antimicrob. Agents Chemother.,* 55:3538 (2011).) Importantly, a cluster of cases was recently reported in Hawaii that are highly resistant to AZM and show reduced susceptibility to CTX (see, CDC webpage, https://www.cdc.gov/nchhstp/newsroom/2016/2016-std-prevention-conference-press-release.html, (2016)), highlighting the critical need for new therapeutics targeting antibiotic-resistant Ng infections. (See, also, Kirkcaldy et al., *JAMA,* 309:185 (2013)).

*Mycobacterium tuberculosis* (Mtb) alone is annually responsible for ~1.5 million deaths (Global Tuberculosis Report, World Health Organization, 2017). Over 1.8 billion people are infected with Mtb worldwide, 10% of whom are predicted to develop active disease. (Global Tuberculosis Teport, World Health Organization, 2017). These infections produce 1.5 million deaths annually. While antibiotic therapy represents the foundation for global health efforts to curb TB, the rise of multi-drug resistant (MDR-TB) and extensively drug resistant (XDR-TB) strains has produced an urgent need for new antibiotics. (Global Tuberculosis Teport, World Health Organization, 2017).

Methicillin-Resistant *Staphylococcus aureus* (MRSA) is another example of microbial drug resistance that poses a serious and immediate public health threat in the United States. MRSA is a Gram-positive bacterium responsible for several difficult-to-treat infections, including skin and soft tissue infections (SSTIs), bacteremia, infective endocarditis, pneumonia, bone and joint infections (osteomyelitis and septic arthritis) and meningitis, among others. (Liu et al., *Clin. Infect. Dis.,* 52(3): e18-55 (2011)). A pervasive organism found in both community and hospital settings, MRSA causes an estimated 80,000 invasive cases in the United States annually, resulting in ~11,000 fatalities. (CDC 2013) (2013). Non-invasive cases of MRSA are poorly tracked, but are thought to be far higher in number. (Stryjewski, M. E. and G. R. Corey, *Clin. Infect. Dis.,* 58 Suppl. 1: S10-19 (2014)). Although more stringent procedures in clinical settings have decreased the number of invasive MRSA cases, this pathogen remains problematic due to high mortality rates, growing antimicrobial resistance and high rates of hospitalization with a heavy burden of associated costs. MRSA is characterized by its resistance to methicillin, and various strains have exhibited resistance or decreased sensitivities towards all currently approved antibiotics. (Stryjewski, M. E. and G. R. Corey (2014) supra; Purrello et al., *J. Glob. Antimicrob. Resist.,* 7: 178-186 (2016)). Moreover, while several recently introduced antibacterial drugs are effective against MRSA (e.g., linezolid, daptomycin, tigecycline, and telavancin), the majority of these must be given intravenously, are limited to hospital use, and are not tolerated well by a significant number of patients. (Clark et al., *Pharmacotherapy*, 26(2): 269-276 (2006); Lodise et al., *Clin. Infect. Dis.*, 49(4): 507-514 (2009)). In addition, clinical resistance to linezolid and daptomycin have already been reported. (Pillai et al., *J. Infect. Dis.*, 186(11): 1603-1607 (2002); Meka et al., *J. Infect. Dis.*, 190(2): (2004); Mangili et al., *Clin. Infect. Dis.*, 40(7): 1058-1060 (2005); Boucher, H. W. and G. Sakoulas, *Clin. Infect. Dis.*, 45(5): 601-608 (2007); Morales et al., *Clin. Infect. Dis.*, 50(6): 821-825 (2010); Sanchez Garcia et al., *JAMA*, 303(22): 2260-2264 (2010)). This underscores the need for additional anti-MRSA agents. Finally, MRSA has a tendency to relapse and recurrence, likely through biofilm formation and its tendency to survive and multiply in eukaryotic cells, features that add additional challenges to treatment. (Lowy, T. P., *Clin. Infect. Dis.*, 49(4): 507-514 (2009); Ellington et al., *J. Bone Joint Surg. Br.*, 85(6): 918-921 (2003); Hess et al., *J. Surg. Res.*, 114(1): 42-49 (2003); Clement et al., *J. Infect. Dis.*, 192(6): 1023-1028 (2005); Gunther et al., *Antimicrob. Resist. Infect. Control*, 6: 32 (2017); Li et al., *Infect. Immun.*, 85(5): e00883-16 (2017)). The development of an intracellularly active antibiotic that targets MRSA through a novel mechanism to sidestep existing resistance mechanisms would provide a critically needed tool for the ongoing fight against this deadly and pervasive infectious agent.

Cases of Community-Acquired Pneumonia (CAP), caused by *Staphylococcus aureus, Streptococcus pneumonia, Mycoplasma pneumonia, Moraxella catarrhalis, Legionella pneumophila*, and *Haemophilus influenzae* result in an estimated 80,000 hospitalizations annually in the US. (Jain S et. al. *N. Engl. J. Med.* 373:415 (2015)) Similarly, Ventilator-Associated Pneumonia (VAP), caused predominantly by *S. aureus* as well as by various Enterobacteriaceae (including *Escherichia coli*), *Pseudomonas aeruginosa*, and *Acinetobacter baumannii* (Ahmad, S. et. al. *Pak. J. of Pharm. Sci.*, 30(6):2091 (2017)) affects 25% of patients mechanically ventilated for >48 h, (Torres, A. et. al. *Clin. Infect. Dis.* 51 Suppl 1:S48 (2010), Kollef, M. H. et. al. Crit. Care Med. 42(10):2178 (2014)) resulting in an estimated 61,000 cases in the US in 2011. (Magil, S. S. et. al. N. Engl. Med. 370(13):1198 (2014)). The specter of antibiotic resistance in nearly all of these pathogens signals an urgent need for development of new drugs (*Antibiotic Resistance Threats in the United States*, Centers for Disease Control, U.S. Dept. of Health and Human Services (2013)) that target novel bacterial processes and are capable of treating a wide array of infections.

One approach that has been explored for overcoming bacterial resistance mechanisms is targeting/inhibiting the bacterial trans-translation mechanism for ribosome rescue, which is required for viability or virulence in many species. The lack of nuclei in bacterial cells necessitates that the processes of transcription and translation are carried out in the same compartment. This can be advantageous in that it allows bacteria to rapidly adapt to environmental changes by making new proteins. However, this can have serious consequences as this limits the bacterial cell's ability for protein quality control due to limited mRNA proofreading. The bacterial trans-translation system functions to remove non-stop protein translation complexes where the ribosome has reached the 3' end of the mRNA without terminating at a stop codon. (Hong et al., *Mol. Microbiol.*, 57(2):565-575 (2005); Clinical and Laboratory Standards Institute, 25(21): 1-39 (2005); Ramadoss et al., *PLoS ONE*, 8(2):e57537 (2013)).

The trans-translation process resolves non-stop translation complexes using a ribonucleoprotein complex containing transfer-messenger RNA (tmRNA) and a small protein, SmpB. All species of bacteria tested to date require at least one ribosome rescue mechanism for viability. (Keiler, K. C., *Nat. Rev. Microbiol.*, 13:285 (2015)).

Genes encoding tmRNA and SmpB have been identified in >99.9% of sequenced bacterial genomes, demonstrating the ubiquity of trans-translation. (Hudson et al., *Front. Microbiol.*, 5:421 (2014)). Bacteria that can survive without trans-translation have either the ArfA or the ArfB alternative rescue pathway. (See, FIG. 1).

The trans-translation mechanism is a key component of multiple quality control pathways in bacteria that ensures proteins are synthesized with high fidelity in spite of challenges such as transcription errors, mRNA damage, and translational frameshifting. tmRNA, encoded by the ssrA gene, is a highly structured RNA with properties of both a tRNA and an mRNA. The 5' and 3' ends of tmRNA fold into a tRNA-like structure, which is charged with alanine by alanyl-tRNA synthetase (AlaRS). (Komine et al., *Proc. Natl. Acad. Sci. USA*, 91(20): 9223-9227 (1994); Ushida et al., *Nucleic Acids Res.*, 22(16): 3392-3396 (1994)). Another portion of tmRNA contains a specialized open reading frame that encodes a peptide with multiple proteolytic determinants. (Keiler et al., *Science*, 271(5251): 990-993 (1996); Gottesman et al., *Genes Dev.*, 12(9): 1338-1347 (1998); Flynn et al., *Proc. Natl. Acad. Sci. USA*, 98(19): 10584-10589; Choy et al., *J. Bacteriol.*, 189(18):6564-6571 (2007)). During trans-translation, tmRNA bound to SmpB is charged with alanine by AlaRS and binds EF-Tu (FIG. 1). The alanyl-tmRNA/SmpB/EF-Tu complex enters the A site of substrate ribosomes with the acceptor stem of tmRNA in the peptidyl transfer center and SmpB in the anticodon recognition site. (Neubauer et al., *Science*, 335(6074): 1366-1369 (2012)). The nascent polypeptide is transferred to alanyl-tmRNA by a normal transpeptidation reaction, and then the translational reading frame switches from the original mRNA to a reading frame within tmRNA. The original mRNA is released and degraded. Continued translation of the tmRNA reading frame results in the addition of a peptide tag to the nascent polypeptide and release of the ribosome. The tmRNA-encoded peptide tag targets the incomplete protein for rapid proteolysis.

In *E. coli*, 2-4% of protein synthesis reactions are targeted for trans-translation. At this rate, the average ribosome goes through trans-translation five times per cell cycle. (Ito et al., *PLoS One*, 6:e28413 (2011)). The ubiquity and abundance of this reaction suggests that it confers a significant competitive advantage. In fact, trans-translation is essential for viability in many species, including *S. aureus*, (Chaudhuri et al., *BMC Genomics*, 10:291 (2009); Fey et al., *MBio*, 4(1): e00537-00512 (2013)), *N. gonorrhoeae*, (Huang et al., *EMBO J.*, 19(5): 1098-1107 (2000)), *S. flexneri*, (Ramadoss et al., *PLoS One*, 8(2): e57537 (2013)), and *M. tuberculosis* (Zhang et al., *PLoS Pathog.*, 8(9): e1002946 (2012)). In other species, such as *Salmonella enterica, Yersinia pestis*, and *Francisella tularensis*, trans-translation is required for virulence. (Julio et al., *J. Bacteriol.*, 182(6): 1558-1563 (2000); Okan et al., *Infect. Immun.*, 78(3): 1284-1293 (2010); Svetlanov et al., *Mol. Microbiol.*, 85(1): 122-141 (2012)).

Therapeutics based on small molecule inhibitors of trans-translation represent a promising and safe opportunity for treating a broad range of bacterial infections, notably including *N. gonorrhoeae*, Methicillin-Resistant *Staphylococcus aureus* (MRSA), *B. anthracis, M.tuberculosis*, and *S. flexnieri*, among others. Target-related toxicity of inhibitors of non-stop ribosome rescue is unlikely as trans-translation genes are not found in metazoans. There are no homologs of any of the ribosome rescue pathways for translation in the eukaryotic cytosol, but mammalian mitochondria do have a homolog of ArfB (ICT1). (Feaga et al., *PLOS Genet.*, 12(3): e1005964 (2016)). As genetic knockdown of ICT1 results in apoptosis in cell culture, it is important to limit potential toxicity of non-stop ribosome rescue inhibitors by avoiding inhibitors of ICT1. (Richter et al., *EMBO J.* 29(6):1116-1125 (2010)). Therefore, compounds that target the trans-translation complex and inhibit trans-translation represent a promising approach to developing therapeutics for treatment and prevention of a number of bacterial infections.

Recently, to explore the potential for targeting bacterial trans-translation with small inhibitor molecules, a high-throughput luciferase-based reporter assay was developed and used to screen a library of 663,000 small molecules to isolate inhibitors of trans-translation. Briefly, to prepare the luciferase reporter assay, a copy of the trpAt transcriptional terminator was inserted before the stop codon of luc, the gene encoding firefly luciferase, on a multicopy plasmid. Induction of luc expression from this reporter (luc-trpAt) produces luc mRNA with no stop codon, and translation of the non-stop luc mRNA in cells with an active trans-translation system results in tagging and proteolysis of the luciferase protein. Alternatively, if trans-translation is inhibited, active luciferase will be released and accumulate in the cells. Therefore, trans-translation activity can be monitored by assaying luciferase activity in cells expressing luc-trpAt. Using the luciferase assay, 24 potential trans-translation inhibitor compounds were identified from the library. One compound, designated KKL-35, was shown to be a specific inhibitor of trans-translation with advantageously no effect on translation. Additionally, KKL-35 demonstrated a lack of cytotoxicity, even in the context of prolonged exposure, indicating that KKL-35 does not inhibit ICT1 and is unlikely to have target-related toxicity in mammalian systems.

KKL-35

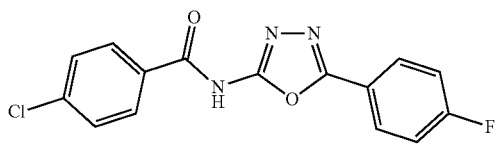

KKL-35, having an oxadiazole core structure, demonstrated an $IC_{50}$ value of 0.9 µM in a dose response assay. (Ramadoss et al., *PNAS*, 110(25):10282-87 (2013)). The combination of potent antimicrobial activity and lack of mammalian cytotoxicity suggested that KKL-35 was of potential interest for pharmaceutical development. Unfortunately, KKL-35 demonstrates poor stability in the presence of mouse or human liver microsomes in vitro and preliminary PK studies indicated extremely poor bioavailability in mice as evidenced by no detectable material after 5 min in the presence of microsomes or within 6 h of IV or IP dosing in mice at 10 mg/kg (data not shown), prohibiting further development of this and closely related analogs.

It has therefore been shown that trans-translation is a viable target for controlling bacterial infections, but there remains a need to develop trans-translation inhibitors with improved exposure in living systems that are suitable for safe and effective administration to mammals and in particular administration to humans. Therapeutic compositions based on effective trans-translation inhibitors have the potential for treating and/or preventing a wide range of both Gram-positive and Gram-negative bacterial infections.

SUMMARY OF THE INVENTION

The present invention is directed to the identification, isolation, and characterization of small molecule inhibitors of trans-translation for use in the treatment and/or prevention of bacterial infections in mammals, and in particular the treatment and/or prevention of bacterial infections in humans.

Accordingly, as described herein, the present invention is related to the discovery of novel broad-spectrum inhibitors of trans-translation as antibacterial agents suitable for treating and/or preventing a wide array of bacterial infections, methods of making such inhibitors, methods of using the inhibitors, pharmaceutical compositions comprising the inhibitors as active ingredients, and methods of treating and/or preventing bacterial infections by administration of one or more of the novel trans-translation inhibitors described herein. The inhibitors of trans-translation disclosed herein will also be useful as adjuncts to existing antibiotic therapies, and there are likely to be synergies between other antibiotics and the present inhibitors of trans-translation when used in combination. There is particular potential for combinations with drugs such as colistin that disrupt Gram-negative bacterial membranes that could provide improved spectrum and activity against multiple drug-resistant pathogens.

In a preferred embodiment, the present invention is related to the discovery of novel broad-spectrum antibacterial agents suitable for treating and/or preventing bacterial infections, the compounds comprising substituted N-acylaminooxadiazole derivatives. Specifically, compounds having trans-translation inhibitory properties comprising either a ureido oxadiazole moiety (as shown in Formula I and Formula Ia) or an aryl- or heteroaryl-amidooxadiazole moiety (as shown in Formula II and Formula IIa) are disclosed and claimed herein.

In one embodiment, the present invention is directed to a bacterial trans-translation inhibitor ureido oxadiazole compound having the structure of Formula I:

(I)

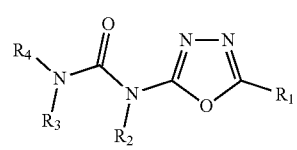

wherein:
$R_1$ is an aryl ring bearing 1-4 substituents (in addition to the oxadiazole group); a 6-membered heteroaryl ring bearing 1-4 substituents (in addition to the oxadiazole group); a 6-membered heteroaryl ring containing 2, 3, or 4 heteroatoms and bearing 0-3 substituents (in addition to the oxadiazole group); a 5-membered heteroaryl ring containing 2, 3, or 4 heteroatoms and bearing 0-3 substituents (in addition to the oxadiazole group); an unsubstituted cycloalkyl ring of 5, 6, or 7 carbon atoms; an unsubstituted linear or branched chain aliphatic group containing 5-8 carbon atoms; a substituted linear or branched chain aliphatic group containing 1-6 carbon atoms bearing 1-8 substituents (1-2 substituents per aliphatic chain carbon, or up to 3 substituents on a terminal aliphatic chain carbon) selected from alkyl, cycloalkyl, aryl, heteroaryl, haloalkyl, amino, nitro, halogen, alkoxy, alkylthio, haloalkoxy, sulfonyl, or sulfinyl; a substituted cycloalkyl ring of 3-8 carbon atoms bearing 1-8 substituents (1-2 substituents per ring carbon) selected from alkyl, cycloalkyl, aryl, heteroaryl, haloalkyl, amino, nitro, halogen, alkoxy, alkylthio, haloalkoxy, sulfonyl, or sulfinyl, which cycloalkyl ring may optionally be fused with one or more aryl, heteroaryl, cycloalkyl, or heterocycloalkyl rings; a 3-, 4-, 6-, 7-, or 8-member heterocyclic ring made up of carbon atoms and at least one ring heteroatom selected independently from oxygen, nitrogen and sulfur atoms, wherein the ring atom attached to the oxadiazole ring is carbon and said heterocyclic ring bears 0-8 substituents selected from alkyl, cycloalkyl, aryl, heteroaryl, haloalkyl, amino, nitro, halogen, alkoxy, alkylthio, haloalkoxy, sulfonyl, or sulfinyl, which heterocyclic ring may optionally be fused with one or more aryl, heteroaryl, cycloalkyl, or heterocycloalkyl rings; a 5-membered heterocyclic ring made up of carbon atoms and at least one ring heteroatom selected independently from oxygen, nitrogen and sulfur atoms, wherein the ring atom attached to the oxadiazole ring is carbon and with the proviso that the ring atoms at positions 2 and 5 (relative to the point of attachment at position 1 to the oxadiazole moiety) is not nitrogen, and wherein the ring atoms at positions 2 and 5 (relative to the point of attachment at position 1 to the oxadiazole moiety) may each optionally bear 1-2 substituents selected from alkyl, cycloalkyl, aryl, heteroaryl haloalkyl, amino, nitro, halogen, alkoxy, alkylthio, haloalkoxy, sulfonyl, or sulfinyl, and may optionally be fused with one or more aryl, heteroaryl, cycloalkyl, or heterocycloalkyl rings;

$R_2$ is hydrogen; a straight chain aliphatic group; a branched chain aliphatic group; cycloalkyl; haloalkyl; hydroxy; alkoxy; alkylamino; alkylthio; haloalkoxy; sulfonyl; sulfinyl; carboxy; alkoxycarbonyl; or an amido group;

$R_3$ is a straight chain aliphatic group; a branched chain aliphatic group; cycloalkyl; heterocycloalkyl; haloalkyl; thio; alkylthio; haloalkoxy; sulfonyl; sulfinyl; carboxy; aryl; or heteroaryl;

$R_4$ is a straight chain aliphatic group of 2-8 carbon atoms; a branched chain aliphatic group; a cycloalkyl; heterocycloalkyl; haloalkyl; thio; alkylthio; haloalkoxyalkyl; sulfonyl; sulfinyl; aryl; or heteroaryl; or, alternatively, $R_3$ and $R_4$ may be linked together to form a substituted 3-8-member cyclic or heterocyclic ring composed of carbon and oxygen and/or nitrogen atoms, the ring having 0-3 degrees of unsaturation and bearing up to four substituents on carbon and/or nitrogen ring members, with carbon substituents including alkyl, haloalkyl, nitro, halogen, alkoxy, alkylthio, haloalkoxy, sulfonyl, sulfinyl, carboxy, alkoxycarbonyl, aminocarbonyl, and/or a spirocycloalkyl/spirocycloheteroalkyl ring with 3-6 ring atoms bearing 1-2 substituents constituted of 1-6 heavy atoms such as carbon, nitrogen, oxygen, sulfur and/or halogen, and any number of hydrogen atoms, and with nitrogen substituents including alkyl, haloalkyl, nitro, halogen, alkoxy, alkylthio, haloalkoxy, sulfonyl, sulfinyl, carbonyl, alkoxycarbonyl, and/or aminocarbonyl groups, which substituents may optionally be fused with one or more aryl, heteroaryl, cycloalkyl, or heterocycloalkyl rings through either carbon or nitrogen attachments, and which substituents may also optionally link across the ring to form bridges of 1-4 carbon atoms and/or heteroatoms through carbon atom attachments;

or a pharmaceutically acceptable salt thereof.

In another embodiment, the present invention is directed to the use of compounds of Formula I in a method for treating or preventing a bacterial infection in a mammalian subject, comprising administering to a subject in need thereof an effective amount of at least one compound of Formula I:

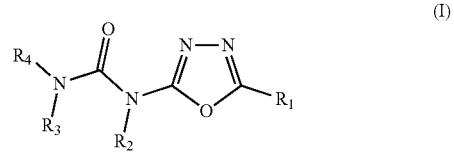

wherein:

$R_1$ is an aryl ring bearing 1-4 substituents (in addition to the oxadiazole group); a 6-membered heteroaryl ring bearing 1-4 substituents (in addition to the oxadiazole group); a 6-membered heteroaryl ring containing 2, 3, or 4 heteroatoms and bearing 0-3 substituents (in addition to the oxadiazole group); a 5-membered heteroaryl ring containing 2, 3, or 4 heteroatoms and bearing 0-3 substituents (in addition to the oxadiazole group); an unsubstituted cycloalkyl ring of 5, 6, or 7 carbon atoms; an unsubstituted linear or branched chain aliphatic group containing 5-8 carbon atoms; a substituted linear or branched chain aliphatic group containing 1-6 carbon atoms bearing 1-8 substituents (1-2 substituents per aliphatic chain carbon, or up to 3 substituents on a terminal aliphatic chain carbon) selected from alkyl, cycloalkyl, aryl, heteroaryl, haloalkyl, amino, nitro, halogen, alkoxy, alkylthio, haloalkoxy, sulfonyl, or sulfinyl; a substituted cycloalkyl ring of 3-8 carbon atoms bearing 1-8 substituents (1-2 substituents per ring carbon) selected from alkyl, cycloalkyl, aryl, heteroaryl, haloalkyl, amino, nitro, halogen, alkoxy, alkylthio, haloalkoxy, sulfonyl, or sulfinyl, which cycloalkyl ring may optionally be fused with one or more aryl, heteroaryl, cycloalkyl, or heterocycloalkyl rings; a 3-, 4-, 5-, 6-, 7-, or 8-member heterocyclic ring made up of carbon atoms and at least one ring heteroatom selected independently from oxygen, nitrogen and sulfur atoms, wherein the ring atom attached to the oxadiazole ring is carbon and said heterocyclic ring bears 0-8 substituents selected from alkyl, cycloalkyl, aryl, heteroaryl, haloalkyl, amino, nitro, halogen, alkoxy, alkylthio, haloalkoxy, sulfonyl, or sulfinyl, which heterocyclic ring may optionally be fused with one or more aryl, heteroaryl, cycloalkyl, or heterocycloalkyl rings;

$R_2$ is hydrogen; a straight chain aliphatic group; a branched chain aliphatic group; cycloalkyl; haloalkyl; hydroxy; alkoxy; alkylamino; alkylthio; haloalkoxy; sulfonyl; sulfinyl; carboxy; alkoxycarbonyl; or an amido group;

$R_3$ is a straight chain aliphatic group; a branched chain aliphatic group; cycloalkyl; heterocycloalkyl; haloalkyl; thio; alkylthio; haloalkoxy; sulfonyl; sulfinyl; carboxy; alkoxycarbonyl; aryl; or heteroaryl;

$R_4$ is a straight chain aliphatic group of 2-8 carbon atoms; a branched chain aliphatic group; a cycloalkyl; heterocycloalkyl; haloalkyl; thio; alkylthio; haloalkoxyalkyl; sulfonyl; sulfinyl; alkoxycarbonyl; aryl; or heteroaryl; or, alternatively, $R_3$ and $R_4$ may be linked together to form a substituted 3-8-member cyclic or heterocyclic ring composed of carbon and oxygen and/or nitrogen atoms, the ring having 0-3 degrees of unsaturation and bearing up to four substituents on carbon and/or nitrogen ring members, with carbon substituents including alkyl, haloalkyl, nitro, halogen, alkoxy, alkylthio, haloalkoxy, sulfonyl, sulfinyl, carboxy, or alkoxycarbonyl, aminocarbonyl, and/or a spirocycloalkyl/spirocycloheteroalkyl ring with 3-6 ring atoms bearing 1-2 substituents constituted of 1-6 heavy atoms (carbon, nitrogen, oxygen, sulfur and/or halogen) and any number of hydrogen atoms, and with nitrogen substituents including alkyl, haloalkyl, nitro, halogen, alkoxy, alkylthio, haloalkoxy, sulfonyl, sulfinyl, carbonyl, alkoxycarbonyl, and/or aminocarbonyl groups, which substituents may optionally be fused with one or more aryl, heteroaryl, cycloalkyl, or heterocycloalkyl rings through either carbon or nitrogen attachments, and which substituents may also optionally link across the ring to form bridges of 1-4 carbon atoms and/or heteroatoms through carbon atom attachments;
or a pharmaceutically acceptable salt thereof.

In another embodiment of the present invention, a trans-translation inhibitor aryl- or heteroaryl-amidooxadiazole compound has the structure of Formula II:

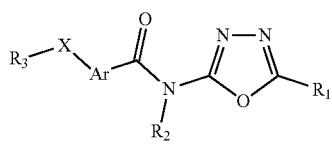

(II)

wherein:
$R_1$ is an aryl ring bearing 0-3 substituents (in addition to the oxadiazole group); a 6-membered heteroaryl ring bearing 0-3 substituents (in addition to the oxadiazole group); a 5-membered heteroaromatic ring containing 2, 3, or 4 heteroatoms bearing 0-3 substituents (in addition to the oxadiazole group); an unsubstituted cycloalkyl ring of 5, 6, or 7 carbon atoms; an unsubstituted linear or branched chain aliphatic group containing 5-8 carbon atoms; a substituted linear or branched chain aliphatic group containing 1-6 carbon atoms bearing 1-8 substituents (1-2 substituents per aliphatic chain carbon, or up to 3 substituents on a terminal aliphatic chain carbon) selected from alkyl, cycloalkyl, substituted aryl (bearing 1-4 substituents), heteroaryl, haloalkyl, amino, nitro, halogen, alkoxy, alkylthio, haloalkoxy, sulfonyl, or sulfinyl; a substituted cycloalkyl ring of 3-8 carbon atoms bearing 1-8 substituents (1-2 substituent per ring carbon) selected from alkyl, cycloalkyl, aryl, heteroaryl, haloalkyl, amino, nitro, halogen, alkoxy, alkylthio, haloalkoxy, sulfonyl, or sulfinyl, which cycloalkyl ring may optionally be fused with one or more aryl, heteroaryl, cycloalkyl, or heterocycloalkyl rings; a substituted heterocyclic ring of 3-8 ring atoms made up of carbon atoms and at least one ring member selected independently from oxygen, nitrogen, and sulfur atoms and bearing 1-8 substituents selected from alkyl, cycloalkyl, aryl, heteroaryl, haloalkyl, amino, nitro, halogen, alkoxy, alkylthio, haloalkoxy, sulfonyl, or sulfinyl, which heterocyclic ring may optionally be fused with one or more aryl, heteroaryl, cycloalkyl, or heterocycloalkyl rings;
$R_2$ is a hydrogen; a straight chain aliphatic group; a branched chain aliphatic group; cycloalkyl; haloalkyl; hydroxy; alkoxy; alkylamino; alkylthio; haloalkoxy; sulfonyl; sulfinyl; carboxy; alkoxycarbonyl; or an amido group;
Ar is a 5- or 6-membered aryl or heteroaryl ring bearing X—$R_3$ at C3 or C4 of a 6-membered ring relative to the carboxamide moiety or bearing X—$R_3$ at C3 of a 5-membered ring relative to the carboxamide moiety, wherein Ar may optionally bear up to 3 additional substituents selected from alkyl, cycloalkyl, aryl, heteroaryl, haloalkyl, nitro, halogen, hydroxy, alkoxy, amino, alkylamino, acylamino, thio, alkylthio, carboxy, alkoxycarbonyl, aminocarbonyl, haloalkoxy, sulfonyl, or sulfinyl;
X is oxygen, nitrogen, sulfur, or carbon, wherein if X is carbon, then X has the formula —CHR—, wherein R is hydrogen, C4-C8 alkyl, C4-C8 cycloalkyl, aryl, heteroaryl, haloalkyl, nitro, halogen, hydroxy, alkoxy, amino, alkylamino, acylamino, thio, alkylthio, carboxy, alkoxycarbonyl, aminocarbonyl, haloalkoxy, sulfonyl, or sulfinyl; wherein if X is a nitrogen, then X has the formula —NR—, wherein R is hydrogen, C4-C8 alkyl, C4-C8 cycloalkyl, aryl, heteroaryl, haloalkyl, nitro, halogen, hydroxy, alkoxy, amino, alkylamino, acylamino, thio, alkylthio, alkoxycarbonyl, aminocarbonyl, haloalkoxy, sulfonyl, or sulfinyl; and wherein if X is a sulfur, then X has the formula —S—, —SO—, —$SO_2$—, or —SNR—, wherein R is hydrogen or a linear, cyclic or branched chain aliphatic group; and
$R_3$ is a branched chain aliphatic group of 5-9 carbon atoms; a cycloalkyl group of 4-8 carbon atoms; a 4- to 8-member heterocyclic ring linked to X through a ring carbon atom, aryl, heteroaryl, arylalkyl, or heteroarylalkyl, bearing 1-4 substituents (in addition to the X moiety) selected from alkyl, cycloalkyl, aryl, heteroaryl, haloalkyl, nitro, halogen, hydroxy, alkoxy, amino, alkylamino, acylamino, thio, alkylthio, carboxy, alkoxycarbonyl, aminocarbonyl, haloalkoxy, sulfonyl, or sulfinyl; or, where Ar is a heteroaryl ring, then $R_3$ may be an unsubstituted 4- to 8-member heterocyclic ring or an aryl or heteroaryl ring; or, where X is nitrogen, then $R_3$ can also be unsubstituted aryl or heteroaryl; or, where X is carbon or nitrogen, $R_3$ can also be an unsubstituted 4- to 8-member heterocyclic ring, or X and $R_3$ can together form a non-aromatic, substituted 4- to 8-member heterocyclic ring bearing 1-4 carbon substituents and/or 1-2 nitrogen substituents (in addition to the Ar moiety), where the carbon substituents are selected from alkyl, haloalkyl, nitro, oxo (O=), halogen, alkoxy, alkylthio, haloalkoxy, sulfonyl, sulfinyl, carboxy, or alkoxycarbonyl and/or additional fused cycloalkyl, heterocycloalkyl, aryl or heteroaryl rings, and the nitrogen substituents are selected from alkyl, haloalkyl, nitro, halogen, alkoxy, alkylthio, haloalkoxy, sulfonyl, sulfinyl, alkoxycarbonyl, or aminocarbonyl groups and/or additional fused cycloalkyl, heterocycloalkyl, aryl or heteroaryl rings; or a pharmaceutically acceptable salt thereof.

In another embodiment, the present invention is directed to the use of compounds of Formula II in a method of treating or preventing a bacterial infection in a mammalian subject, comprising administering to a subject in need thereof an effective amount of at least one compound of Formula II:

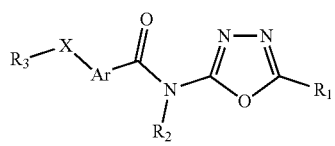

(II)

wherein:
$R_1$ is an aryl ring bearing 0-3 substituents (in addition to the oxadiazole group); a 6-membered heteroaryl ring bearing 0-3 substituents (in addition to the oxadiazole group); a 5-membered heteroaromatic ring containing 2, 3, or 4 heteroatoms bearing 0-3 substituents (in addition to the oxadiazole group); an unsubstituted cycloalkyl ring of 5, 6, or 7 carbon atoms; an unsubstituted linear or branched chain aliphatic group containing 5-8 carbon atoms; a substituted linear or branched chain aliphatic group containing 1-6 carbon atoms bearing 1-8 substituents (1-2 substituents per aliphatic chain carbon, or up to 3 substituents on a terminal aliphatic chain carbon) selected from alkyl, cycloalkyl, substituted aryl (bearing 1-4 substituents), heteroaryl, haloalkyl, amino, nitro, halogen, alkoxy, alkylthio, haloalkoxy, sulfonyl, or sulfinyl; a substituted cycloalkyl ring of 3-8 carbon atoms bearing 1-8 substituents (1-2 substituent per ring carbon) selected from alkyl, cycloalkyl, aryl, heteroaryl, haloalkyl, amino, nitro, halogen, alkoxy, alkylthio, haloalkoxy, sulfonyl, or sulfinyl, which cycloalkyl ring may optionally be fused with one or more aryl, heteroaryl, cycloalkyl, or heterocycloalkyl rings; a substituted heterocyclic ring of 3-8 ring atoms made up of carbon atoms and at least one ring member selected independently from oxygen, nitrogen, and sulfur atoms and bearing 1-8 substituents selected from alkyl, cycloalkyl, aryl, heteroaryl, haloalkyl, amino, nitro, halogen, alkoxy, alkylthio, haloalkoxy, sulfonyl, or sulfinyl, which heterocyclic ring may optionally be fused with one or more aryl, heteroaryl, cycloalkyl, or heterocycloalkyl rings;

R$_2$ is a hydrogen; a straight chain aliphatic group; a branched chain aliphatic group; cycloalkyl; haloalkyl; hydroxy; alkoxy; alkylamino; alkylthio; haloalkoxy; sulfonyl; sulfinyl; carboxy; alkoxycarbonyl; or an amido group;

Ar is a 5- or 6-membered aryl or heteroaryl ring bearing X—R$_3$ at C3 or C4 of a 6-membered ring relative to the carboxamide moiety or bearing X—R$_3$ at C3 of a 5-membered ring relative to the carboxamide moiety, wherein Ar may optionally bear up to 3 additional substituents selected from alkyl, cycloalkyl, aryl, heteroaryl, haloalkyl, nitro, halogen, hydroxy, alkoxy, amino, alkylamino, acylamino, thio, alkylthio, carboxy, alkoxycarbonyl, aminocarbonyl, haloalkoxy, sulfonyl, or sulfinyl;

X is oxygen, nitrogen, sulfur, or carbon, wherein if X is carbon, then X has the formula —CHR—, wherein R is hydrogen, C4-C8 alkyl, C4-C8 cycloalkyl, aryl, heteroaryl, haloalkyl, nitro, halogen, hydroxy, alkoxy, amino, alkylamino, acylamino, thio, alkylthio, carboxy, alkoxycarbonyl, aminocarbonyl, haloalkoxy, sulfonyl, or sulfinyl; wherein if X is a nitrogen, then X has the formula —NR—, wherein R is hydrogen, C4-C8 alkyl, C4-C8 cycloalkyl, aryl, heteroaryl, haloalkyl, nitro, halogen, hydroxy, alkoxy, amino, alkylamino, acylamino, thio, alkylthio, carboxy, alkoxycarbonyl, aminocarbonyl, haloalkoxy, sulfonyl, or sulfinyl; and wherein if X is a sulfur, then X has the formula —S—, —SO—, —SO$_2$—, or —SNR—, wherein R is hydrogen or a linear, cyclic or branched chain aliphatic group; and R$_3$ is a branched chain aliphatic group of 5-9 carbon atoms; a cycloalkyl group of 4-8 carbon atoms; a 4- to 8-member heterocyclic ring linked to X through a ring carbon atom, aryl, heteroaryl, arylalkyl, or heteroarylalkyl, bearing 1-4 substituents (in addition to the X moiety) selected from alkyl, cycloalkyl, aryl, heteroaryl, haloalkyl, nitro, halogen, hydroxy, alkoxy, amino, alkylamino, acylamino, thio, alkylthio, carboxy, alkoxycarbonyl, aminocarbonyl, haloalkoxy, sulfonyl, or sulfinyl; or, where Ar is a heteroaryl ring, then R$_3$ may be an unsubstituted 4- to 8-member heterocyclic ring or an aryl or heteroaryl ring; or, where X is nitrogen, then R$_3$ can also be unsubstituted aryl or heteroaryl; or, where X is carbon or nitrogen, R$_3$ can also be an unsubstituted 4- to 8-member heterocyclic ring, or X and R$_3$ can together form a non-aromatic, substituted 4- to 8-member heterocyclic ring bearing 1-4 carbon substituents and/or 1-2 nitrogen substituents (in addition to the Ar moiety), where the carbon substituents are selected from alkyl, haloalkyl, nitro, oxo, halogen, alkoxy, alkylthio, haloalkoxy, sulfonyl, sulfinyl, carboxy, or alkoxycarbonyl and/or additional fused cycloalkyl, heterocycloalkyl, aryl or heteroaryl rings, and the nitrogen substituents are selected from alkyl, haloalkyl, nitro, halogen, alkoxy, alkylthio, haloalkoxy, sulfonyl, sulfinyl, alkoxycarbonyl, or aminocarbonyl groups and/or additional fused cycloalkyl, heterocycloalkyl, aryl or heteroaryl rings; or a pharmaceutically acceptable salt thereof.

In another embodiment of the present invention, a trans-translation inhibitor ureido oxadiazole compound has the structure of Formula Ia:

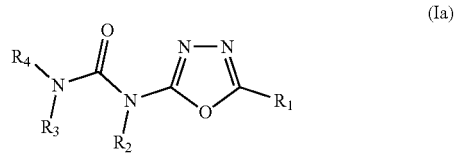

(Ia)

wherein:

R$_1$ is an aryl ring bearing 1-4 substituents (in addition to the oxadiazole group); a 6-membered heteroaryl ring bearing 1-4 substituents (in addition to the oxadiazole group); a 6-membered heteroaryl ring containing 2, 3, or 4 heteroatoms and bearing 0-3 substituents (in addition to the oxadiazole group); a 5-membered heteroaryl ring containing 2, 3, or 4 heteroatoms and bearing 0-3 substituents (in addition to the oxadiazole group); an unsubstituted cycloalkyl ring of 5, 6, or 7 carbon atoms; an unsubstituted linear or branched chain aliphatic group containing 5-8 carbon atoms; a substituted linear or branched chain aliphatic group containing 1-6 carbon atoms bearing 1-8 substituents (1-2 substituents per aliphatic chain carbon, or up to 3 substituents on a terminal aliphatic chain carbon) selected from alkyl, cycloalkyl, aryl, heteroaryl, haloalkyl, amino, nitro, halogen, alkoxy, alkylthio, haloalkoxy, sulfonyl, or sulfinyl; a substituted cycloalkyl ring of 3-8 carbon atoms bearing 1-8 substituents (1-2 substituents per ring carbon) selected from alkyl, cycloalkyl, aryl, heteroaryl, haloalkyl, amino, nitro, halogen, alkoxy, alkylthio, haloalkoxy, sulfonyl, or sulfinyl, which cycloalkyl ring may optionally be fused with one or more aryl, heteroaryl, cycloalkyl, or heterocycloalkyl rings; a 3-, 4-, 6-, 7-, or 8-member heterocyclic ring made up of carbon atoms and at least one ring heteroatom selected independently from oxygen, nitrogen and sulfur atoms, wherein the ring atom attached to the oxadiazole ring is carbon and said heterocyclic ring bears 0-8 substituents selected from alkyl, cycloalkyl, aryl, heteroaryl, haloalkyl, amino, nitro, halogen, alkoxy, alkylthio, haloalkoxy, sulfonyl, or sulfinyl, which heterocyclic ring may optionally be fused with one or more aryl, heteroaryl, cycloalkyl, or heterocycloalkyl rings; a 5-membered heterocyclic ring made up of carbon atoms and at least one ring heteroatom selected independently from oxygen, nitrogen and sulfur atoms, wherein the ring atom attached to the oxadiazole ring is carbon and with the proviso that the ring atoms at positions 2 and 5 (relative to the point of attachment at position 1 to the oxadiazole moiety) is not nitrogen, and wherein the ring atoms at positions 2 and 5 (relative to the point of attachment at position 1 to the oxadiazole moiety) may each optionally bear 1-2 substituents selected from alkyl, cycloalkyl, aryl, heteroaryl haloalkyl, amino, nitro, halogen, alkoxy, alkylthio, haloalkoxy, sulfonyl, or sulfinyl, and may optionally be fused with one or more aryl, heteroaryl, cycloalkyl, or heterocycloalkyl rings;

R₂ is hydrogen; a straight chain aliphatic group; a branched chain aliphatic group; cycloalkyl; haloalkyl; hydroxy; alkoxy; alkylamino; alkylthio; haloalkoxy; sulfonyl; sulfinyl; carboxy; alkoxycarbonyl; or an amido group;

R₃ is a straight chain aliphatic group; a branched chain aliphatic group; cycloalkyl; heterocycloalkyl; haloalkyl; thio; alkylthio; haloalkoxy; sulfonyl; sulfinyl; carboxy; aryl; or heteroaryl;

R₄ is a straight chain aliphatic group of 2-8 carbon atoms; a branched chain aliphatic group; a cycloalkyl; heterocycloalkyl; haloalkyl; thio; alkylthio; haloalkoxyalkyl; sulfonyl; sulfinyl; aryl; or heteroaryl; or, alternatively, R₃ and R₄ may be linked together to form a substituted 3-8-member cyclic or heterocyclic ring composed of carbon and oxygen and/or nitrogen atoms, the ring having 0-3 degrees of unsaturation and bearing at least 1 and up to four substituents on carbon and/or nitrogen ring members, with carbon substituents including alkyl, haloalkyl, nitro, halogen, alkoxy, alkylthio, haloalkoxy, sulfonyl, sulfinyl, carboxy, and/or alkoxycarbonyl, and with nitrogen substituents including alkyl, haloalkyl, nitro, halogen, alkoxy, alkylthio, haloalkoxy, sulfonyl, sulfinyl, carbonyl, alkoxycarbonyl, and/or aminocarbonyl groups, which substituents may optionally be fused with one or more aryl, heteroaryl, cycloalkyl, or heterocycloalkyl rings through either carbon or nitrogen attachments, or a pharmaceutically acceptable salt thereof.

In another embodiment, the present invention is directed to use of the compounds of Formula I(a) in a method for treating or preventing a bacterial infection in a mammal by administration of one or more of the compounds of Formula Ia:

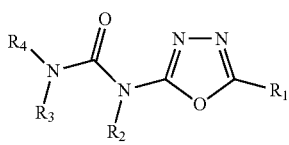

(Ia)

wherein:

R₁ is an aryl ring bearing 1-4 substituents (in addition to the oxadiazole group); a 6-membered heteroaryl ring bearing 1-4 substituents (in addition to the oxadiazole group); a 6-membered heteroaryl ring containing 2, 3, or 4 heteroatoms and bearing 0-3 substituents (in addition to the oxadiazole group); a 5-membered heteroaryl ring containing 2, 3, or 4 heteroatoms and bearing 0-3 substituents (in addition to the oxadiazole group); an unsubstituted cycloalkyl ring of 5, 6, or 7 carbon atoms; an unsubstituted linear or branched chain aliphatic group containing 5-8 carbon atoms; a substituted linear or branched chain aliphatic group containing 1-6 carbon atoms bearing 1-8 substituents (1-2 substituents per aliphatic chain carbon, or up to 3 substituents on a terminal aliphatic chain carbon) selected from alkyl, cycloalkyl, aryl, heteroaryl, haloalkyl, amino, nitro, halogen, alkoxy, alkylthio, haloalkoxy, sulfonyl, or sulfinyl; a substituted cycloalkyl ring of 3-8 carbon atoms bearing 1-8 substituents (1-2 substituents per ring carbon) selected from alkyl, cycloalkyl, aryl, heteroaryl, haloalkyl, amino, nitro, halogen, alkoxy, alkylthio, haloalkoxy, sulfonyl, or sulfinyl, which cycloalkyl ring may optionally be fused with one or more aryl, heteroaryl, cycloalkyl, or heterocycloalkyl rings; a 3-, 4-, 6-, 7-, or 8-member heterocyclic ring made up of carbon atoms and at least one ring heteroatom selected independently from oxygen, nitrogen and sulfur atoms, wherein the ring atom attached to the oxadiazole ring is carbon and said heterocyclic ring bears 0-8 substituents selected from alkyl, cycloalkyl, aryl, heteroaryl, haloalkyl, amino, nitro, halogen, alkoxy, alkylthio, haloalkoxy, sulfonyl, or sulfinyl, which heterocyclic ring may optionally be fused with one or more aryl, heteroaryl, cycloalkyl, or heterocycloalkyl rings; a 5-membered heterocyclic ring made up of carbon atoms and at least one ring heteroatom selected independently from oxygen, nitrogen and sulfur atoms, wherein the ring atom attached to the oxadiazole ring is carbon and with the proviso that the ring atoms at positions 2 and 5 (relative to the point of attachment at position 1 to the oxadiazole moiety) is not nitrogen, and wherein the ring atoms at positions 2 and 5 (relative to the point of attachment at position 1 to the oxadiazole moiety) may each optionally bear 1-2 substituents selected from alkyl, cycloalkyl, aryl, heteroaryl haloalkyl, amino, nitro, halogen, alkoxy, alkylthio, haloalkoxy, sulfonyl, or sulfinyl, and may optionally be fused with one or more aryl, heteroaryl, cycloalkyl, or heterocycloalkyl rings;

R₂ is hydrogen; a straight chain aliphatic group; a branched chain aliphatic group; cycloalkyl; haloalkyl; hydroxy; alkoxy; alkylamino; alkylthio; haloalkoxy; sulfonyl; sulfinyl; carboxy; alkoxycarbonyl; or an amido group;

R₃ is a straight chain aliphatic group; a branched chain aliphatic group; cycloalkyl; heterocycloalkyl; haloalkyl; thio; alkylthio; haloalkoxy; sulfonyl; sulfinyl; carboxy; alkoxycarbonyl, aryl; or heteroaryl;

R₄ is a straight chain aliphatic group of 2-8 carbon atoms; a branched chain aliphatic group; a cycloalkyl; heterocycloalkyl; haloalkyl; thio; alkylthio; haloalkoxyalkyl; sulfonyl; sulfinyl; alkoxycarbonyl, aryl; or heteroaryl; or, alternatively, R₃ and R₄ may be linked together to form a substituted 3-8-member cyclic or heterocyclic ring composed of carbon and oxygen and/or nitrogen atoms, the ring having 0-3 degrees of unsaturation and bearing at least 1 and up to four substituents on carbon and/or nitrogen ring members, with carbon substituents including alkyl, haloalkyl, nitro, halogen, alkoxy, alkylthio, haloalkoxy, sulfonyl, sulfinyl, carboxy, and/or alkoxycarbonyl, and with nitrogen substituents including alkyl, haloalkyl, nitro, halogen, alkoxy, alkylthio, haloalkoxy, sulfonyl, sulfinyl, carbonyl, alkoxycarbonyl, and/or aminocarbonyl groups, which substituents may optionally be fused with one or more aryl, heteroaryl, cycloalkyl, or heterocycloalkyl rings through either carbon or nitrogen attachments, or a pharmaceutically acceptable salt thereof.

In another embodiment of the present invention, a trans-translation inhibitor aryl- or heteroaryl-amidooxadiazole compound has the structure of Formula IIa:

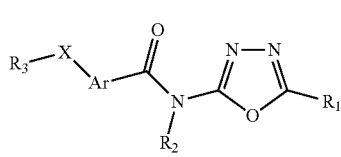

(IIa)

wherein:

R₁ is an aryl ring bearing 0-3 substituents (in addition to the oxadiazole group); a 6-membered heteroaryl ring bearing 0-3 substituents (in addition to the oxadiazole group); a 5-membered heteroaromatic ring containing 2, 3, or 4 heteroatoms bearing 0-3 substituents (in addition to the oxadiazole group); an unsubstituted cycloalkyl ring of 5, 6, or 7 carbon atoms; an unsubstituted linear or branched chain aliphatic group containing 5-8 carbon atoms; a substituted linear or branched chain aliphatic group containing 1-6 carbon atoms bearing 1-8 substituents (1-2 substituents per aliphatic chain carbon, or up to 3 substituents on a terminal aliphatic chain carbon) selected from alkyl, cycloalkyl, substituted aryl (bearing 1-4 substituents), heteroaryl, haloalkyl, amino, nitro, halogen, alkoxy, alkylthio, haloalkoxy, sulfonyl, or sulfinyl; a substituted cycloalkyl ring of 3-8 carbon atoms bearing 1-8 substituents (1-2 substituent per ring carbon) selected from alkyl, cycloalkyl, aryl, heteroaryl, haloalkyl, amino, nitro, halogen, alkoxy, alkylthio, haloalkoxy, sulfonyl, or sulfinyl, which cycloalkyl ring may optionally be fused with one or more aryl, heteroaryl, cycloalkyl, or heterocycloalkyl rings; a substituted heterocyclic ring of 3-8 ring atoms made up of carbon atoms and at least one ring member selected independently from oxygen, nitrogen, and sulfur atoms and bearing 1-8 substituents selected from alkyl, cycloalkyl, aryl, heteroaryl, haloalkyl, amino, nitro, halogen, alkoxy, alkylthio, haloalkoxy, sulfonyl, or sulfinyl, which heterocyclic ring may optionally be fused with one or more aryl, heteroaryl, cycloalkyl, or heterocycloalkyl rings;

$R_2$ is a hydrogen; a straight chain aliphatic group; a branched chain aliphatic group; cycloalkyl; haloalkyl; hydroxy; alkoxy; alkylamino; alkylthio; haloalkoxy; sulfonyl; sulfinyl; carboxy; alkoxycarbonyl; or an amido group;

Ar is a 5- or 6-membered aryl or heteroaryl ring bearing X—$R_3$ at C3 or C4 of a 6-membered ring relative to the carboxamide moiety or bearing X—$R_3$ at C3 of a 5-membered ring relative to the carboxamide moiety, wherein Ar may optionally bear up to 3 additional substituents selected from alkyl, cycloalkyl, aryl, heteroaryl, haloalkyl, nitro, halogen, hydroxy, alkoxy, amino, alkylamino, acylamino, thio, alkylthio, carboxy, alkoxycarbonyl, aminocarbonyl, haloalkoxy, sulfonyl, or sulfinyl;

X is oxygen, nitrogen, sulfur, or carbon, wherein if X is carbon, then X has the formula —CHR—, wherein R is hydrogen, C4-C8 alkyl, C4-C8 cycloalkyl, aryl, heteroaryl, haloalkyl, nitro, halogen, hydroxy, alkoxy, amino, alkylamino, acylamino, thio, alkylthio, carboxy, alkoxycarbonyl, aminocarbonyl, haloalkoxy, sulfonyl, or sulfinyl; wherein if X is a nitrogen, then X has the formula —NR—, wherein R is hydrogen, C4-C8 alkyl, C4-C8 cycloalkyl, aryl, heteroaryl, haloalkyl, nitro, halogen, hydroxy, alkoxy, amino, alkylamino, acylamino, thio, alkylthio, alkoxycarbonyl, aminocarbonyl, haloalkoxy, sulfonyl, or sulfinyl; and wherein if X is a sulfur, then X has the formula —S—, —SO—, —SO$_2$—, or —SNR—, wherein R is hydrogen or a linear, cyclic or branched chain aliphatic group; and $R_3$ is a branched chain aliphatic group of 5-9 carbon atoms; a cycloalkyl group of 4-8 carbon atoms; a 4- to 8-member heterocyclic ring linked to X through a ring carbon atom, aryl, heteroaryl, arylalkyl, or heteroarylalkyl, bearing 1-4 substituents (in addition to the X moiety) selected from alkyl, cycloalkyl, aryl, heteroaryl, haloalkyl, nitro, halogen, hydroxy, alkoxy, amino, alkylamino, acylamino, thio, alkylthio, carboxy, alkoxycarbonyl, aminocarbonyl, haloalkoxy, sulfonyl, or sulfinyl; or, where Ar is a heteroaryl ring, then $R_3$ may be an unsubstituted 4- to 8-member heterocyclic ring or an aryl or heteroaryl ring; or, where X is nitrogen, then $R_3$ can also be unsubstituted aryl or heteroaryl; or, where X is carbon or nitrogen, $R_3$ can also be an unsubstituted 4- to 8-member heterocyclic ring, or X and $R_3$ can together form a non-aromatic, substituted 4- to 8-member heterocyclic ring bearing 1-4 carbon substituents and/or 1-2 nitrogen substituents (in addition to the Ar moiety), where the carbon substituents are selected from alkyl, haloalkyl, nitro, oxo (O=), halogen, alkoxy, alkylthio, haloalkoxy, sulfonyl, sulfinyl, carboxy, or alkoxycarbonyl and/or additional fused cycloalkyl, heterocycloalkyl, aryl or heteroaryl rings, and the nitrogen substituents are selected from alkyl, haloalkyl, nitro, halogen, alkoxy, alkylthio, haloalkoxy, sulfonyl, sulfinyl, alkoxycarbonyl, or aminocarbonyl groups and/or additional fused cycloalkyl, heterocycloalkyl, aryl or heteroaryl rings; or a pharmaceutically acceptable salt thereof.

In another embodiment the present invention is directed to the use of one or more compounds of Formula IIa in a method for treating or preventing a bacterial infection in a mammalian subject by administration of at least one trans-translator inhibitor compound according to Formula IIa:

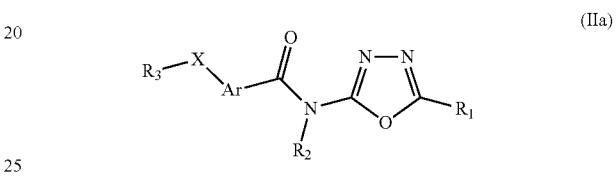

(IIa)

wherein:

$R_1$ is an aryl ring bearing 0-3 substituents (in addition to the oxadiazole group); a 6-membered heteroaryl ring bearing 0-3 substituents (in addition to the oxadiazole group); a 5-membered heteroaromatic ring containing 2, 3, or 4 heteroatoms bearing 0-3 substituents (in addition to the oxadiazole group); an unsubstituted cycloalkyl ring of 5, 6, or 7 carbon atoms; an unsubstituted linear or branched chain aliphatic group containing 5-8 carbon atoms; a substituted linear or branched chain aliphatic group containing 1-6 carbon atoms bearing 1-8 substituents (1-2 substituents per aliphatic chain carbon, or up to 3 substituents on a terminal aliphatic chain carbon) selected from alkyl, cycloalkyl, substituted aryl (bearing 1-4 substituents), heteroaryl, haloalkyl, amino, nitro, halogen, alkoxy, alkylthio, haloalkoxy, sulfonyl, or sulfinyl; a substituted cycloalkyl ring of 3-8 carbon atoms bearing 1-8 substituents (1-2 substituent per ring carbon) selected from alkyl, cycloalkyl, aryl, heteroaryl, haloalkyl, amino, nitro, halogen, alkoxy, alkylthio, haloalkoxy, sulfonyl, or sulfinyl, which cycloalkyl ring may optionally be fused with one or more aryl, heteroaryl, cycloalkyl, or heterocycloalkyl rings; a substituted heterocyclic ring of 3-8 ring atoms made up of carbon atoms and at least one ring member selected independently from oxygen, nitrogen, and sulfur atoms and bearing 1-8 substituents selected from alkyl, cycloalkyl, aryl, heteroaryl, haloalkyl, amino, nitro, halogen, alkoxy, alkylthio, haloalkoxy, sulfonyl, or sulfinyl, which heterocyclic ring may optionally be fused with one or more aryl, heteroaryl, cycloalkyl, or heterocycloalkyl rings;

$R_2$ is a hydrogen; a straight chain aliphatic group; a branched chain aliphatic group; cycloalkyl; haloalkyl; hydroxy; alkoxy; alkylamino; alkylthio; haloalkoxy; sulfonyl; sulfinyl; carboxy; alkoxycarbonyl; or an amido group;

Ar is a 5- or 6-membered aryl or heteroaryl ring bearing X—$R_3$ at C3 or C4 of a 6-membered ring relative to the carboxamide moiety or bearing X—$R_3$ at C3 of a 5-membered ring relative to the carboxamide moiety, wherein Ar may optionally bear up to 3 additional substituents selected from alkyl, cycloalkyl, aryl, heteroaryl, haloalkyl, nitro, halogen, hydroxy, alkoxy, amino, alkylamino, acylamino, thio, alkylthio, carboxy, alkoxycarbonyl, aminocarbonyl, haloalkoxy, sulfonyl, or sulfinyl;

X is oxygen, nitrogen, sulfur, or carbon, wherein if X is carbon, then X has the formula —CHR—, wherein R is hydrogen, C4-C8 alkyl, C4-C8 cycloalkyl, aryl, heteroaryl, haloalkyl, nitro, halogen, hydroxy, alkoxy, amino, alkylamino, acylamino, thio, alkylthio, carboxy, alkoxycarbonyl, aminocarbonyl, haloalkoxy, sulfonyl, or sulfinyl; wherein if X is a nitrogen, then X has the formula —NR—, wherein R is hydrogen, C4-C8 alkyl, C4-C8 cycloalkyl, aryl, heteroaryl, haloalkyl, nitro, halogen, hydroxy, alkoxy, amino, alkylamino, acylamino, thio, alkylthio, alkoxycarbonyl, aminocarbonyl, haloalkoxy, sulfonyl, or sulfinyl; and wherein if X is a sulfur, then X has the formula —S—, —SO—, —SO$_2$—, or —SNR—, wherein R is hydrogen or a linear, cyclic or branched chain aliphatic group; and $R_3$ is a branched chain aliphatic group of 5-9 carbon atoms; a cycloalkyl group of 4-8 carbon atoms; a 4- to 8-member heterocyclic ring linked to X through a ring carbon atom, aryl, heteroaryl, arylalkyl, or heteroarylalkyl, bearing 1-4 substituents (in addition to the X moiety) selected from alkyl, cycloalkyl, aryl, heteroaryl, haloalkyl, nitro, halogen, hydroxy, alkoxy, amino, alkylamino, acylamino, thio, alkylthio, carboxy, alkoxycarbonyl, aminocarbonyl, haloalkoxy, sulfonyl, or sulfinyl; or, where Ar is a heteroaryl ring, then $R_3$ may be an unsubstituted 4- to 8-member heterocyclic ring or an aryl or heteroaryl ring; or, where X is nitrogen, then $R_3$ can also be unsubstituted aryl or heteroaryl; or, where X is carbon or nitrogen, $R_3$ can also be an unsubstituted 4- to 8-member heterocyclic ring, or X and $R_3$ can together form a non-aromatic, substituted 4- to 8-member heterocyclic ring bearing 1-4 carbon substituents and/or 1-2 nitrogen substituents (in addition to the Ar moiety), where the carbon substituents are selected from alkyl, haloalkyl, nitro, oxo (O═), halogen, alkoxy, alkylthio, haloalkoxy, sulfonyl, sulfinyl, carboxy, or alkoxycarbonyl and/or additional fused cycloalkyl, heterocycloalkyl, aryl or heteroaryl rings, and the nitrogen substituents are selected from alkyl, haloalkyl, nitro, halogen, alkoxy, alkylthio, haloalkoxy, sulfonyl, sulfinyl, alkoxycarbonyl, or aminocarbonyl groups and/or additional fused cycloalkyl, heterocycloalkyl, aryl or heteroaryl rings; or a pharmaceutically acceptable salt thereof.

Also disclosed are pharmaceutical compositions comprising a therapeutically effective amount of at least one aminooxadiazole compound of Formula I, Formula Ia, Formula II and/or Formula IIa, or a pharmaceutically acceptable salt, solvate, or polymorph thereof, and a pharmaceutically acceptable carrier.

The pharmaceutical compositions are suitable for use in the disclosed methods for treating or preventing a bacterial infection in a mammalian subject. In a preferred embodiment the mammalian subject is a human. The pharmaceutical compositions may be formulated for both parenteral and/or nonparenteral administration to a subject or patient in need thereof.

Also disclosed are methods for treating or preventing a bacterial infection in a human subject comprising the step of administering to the human subject a therapeutically effective amount of at least one of the aminooxadiazole compounds according to Formula I, Formula Ia, Formula II and/or Formula IIa, or a pharmaceutically acceptable salt, solvate, or polymorph thereof.

In a preferred embodiment, the novel aminooxadiazole derivatives of the present invention act as inhibitors of the trans-translation mechanism found in most bacterial species. As inhibitors of trans-translation, the compounds of the present invention are suitable for treating or preventing bacterial infections by preventing the synthesis of proteins necessary for bacterial cell viability and infectivity.

In another embodiment, the novel compounds of the present invention may be administered to a subject in need thereof optionally in combination with one or more known antibacterial agents.

In another embodiment, the compounds of the present invention are formulated into a pharmaceutically acceptable carrier and are administered to a mammalian subject in need thereof by an injection, including, without limitation, intradermal, transdermal, intramuscular, intraperitoneal and intravenous injection. According to another embodiment of the invention, the administration is oral and the compound may be presented, for example, in the form of a tablet or encased in a gelatin capsule or a microcapsule, which simplifies oral administration. The production of these forms of administration is within the general technical experience of practitioners in this art. Multiple routes of administration are envisioned for these drug-like molecules, and highly cost-effective production strategies can be easily achieved.

In preferred embodiments, the antibacterial aminooxadiazole compounds of the present invention exhibit an inhibitory concentration of ≤10 µM against trans-translation and a cytotoxicity ($CC_{50}$) of ≥25 µM.

In another embodiment, trans-translation inhibitors according to Formula I, Formula Ia, Formula II, and/or Formula IIa, are suitable to disinfect devices and surfaces such as bandages, bodily appliances, catheters, surgical instruments, patient examination tables, counters, etc. The trans-translation inhibitors described herein are particularly useful in preventing or inhibiting bacterial growth on surfaces exposed to or contaminated with Gram-positive and/or Gram-negative bacteria. Such surfaces include, but are not limited to, surfaces of implantable medical devices (including, but not limited to, central venous catheters (CVCs), implantable pumps, artificial heart valve, and cardiac pacemakers); cardiopulmonary bypass (CPB) pumps (heart-lung machine); dialysis equipment; artificial respirators; breathing apparatuses (oxygen and air supplies); water pipes; plumbing fixtures; and air ducts.

Thus, the present invention also provides a method for inhibiting bacterial contamination or colonization on a solid surface comprising treating said surface with at least one compound of Formula I, Formula Ia, Formula II, and/or Formula IIa. The trans-translation inhibitor compound may be applied to the surface prior to its exposure or infection with a bacterium, after bacteria have contacted the surface, or after a bacterial colony has already formed on the surface. The trans-translation inhibitor compounds disclosed herein may thus be advantageously employed to prevent bacterial contamination of a surface or to arrest bacterial colonization on a surface. Preferably, a trans-translation inhibitor compound described herein is applied to a surface prior to the formation of a bacterial colony on the surface. More preferably, a trans-translation inhibitor compound described herein is applied to or present on a surface before bacteria contact the surface.

A trans-translation inhibitor described herein may be applied to a desired solid surface by any of a variety methods including, but not limited to, coating, impregnation, and covalent conjugation. A trans-translation inhibitor described herein may also be employed in a solution or suspension to fill the lumen of a catheter or other medical device prior to use.

BRIEF DESCRIPTION OF THE DRAWINGS

FIG. 1 is a schematic diagram illustrating three known mechanisms in bacterial cells for correcting non-stop ribosomes: Trans-translation, ArfA, and ArfB. In the trans-translation mechanism (illustrated at top), a tmRNA-SmpB complex inserts a reading frame in the mRNA channel, and the ribosome is released at a normal stop codon, after which the mRNA and nascent polypeptide are degraded. In the ArfA (middle) and ArfB (bottom) pathways, the peptidyl-tRNA is degraded.

DEFINITIONS

Figure 2:
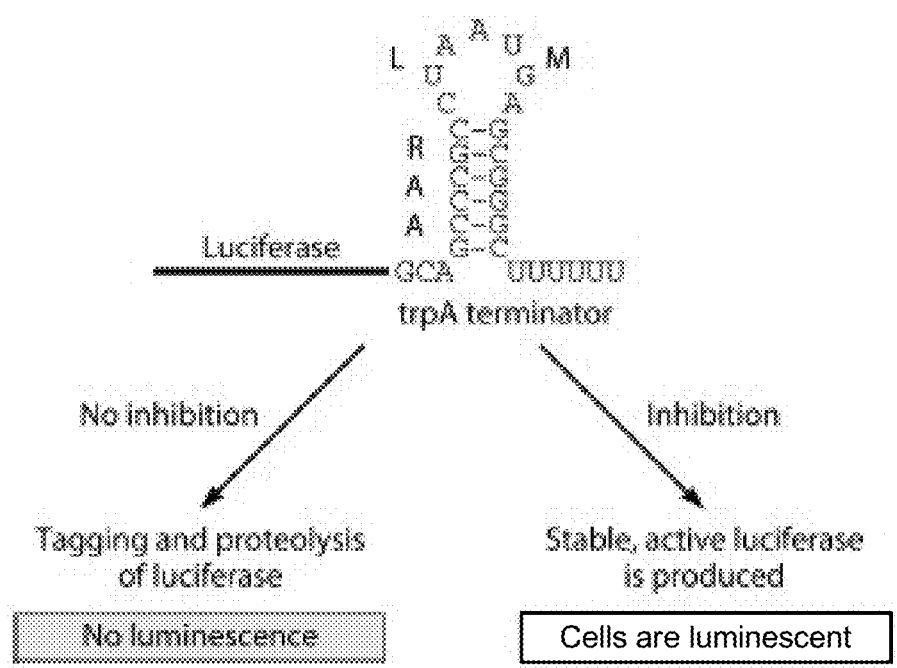
FIG. 2 is a schematic diagram illustrating the luciferase-trpA terminator reporter assay. A multicopy plasmid was constructed with a trpAt transcriptional terminator inserted just before the stop codon of a luc gene encoding firefly luciferase. Induction of luc gene expression leads to production of luc mRNA with no stop codon, and translation of the non-stop mRNA in cells having an active trans-translation rescue mechanism results in tagging and proteolysis of the luciferase transcript, resulting in an absence of luminescence. However, in cells where the trans-translation mechanism is inhibited, active luciferase accumulates, and the cells are luminescent. Trans-translation inhibition activity can thus be monitored by observing luciferase activity in cells expressing the luciferase-trpAt construct.

A composition or method described herein as "comprising" (or which "comprises") one or more named elements or steps is open-ended, meaning that the named elements or steps are essential, but other elements or steps may be added within the scope of the composition or method. To avoid prolixity, it is also understood that any composition or method described as "comprising" one or more named elements or steps also describes the corresponding, more limited, composition or method "consisting essentially of" (or which "consists essentially of") the same named elements or steps, meaning that the composition or method includes the named essential elements and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or which "consists of") the named elements or steps to the exclusion of any other element or step. In any composition or method disclosed herein, known or disclosed equivalents of any named essential element or step may be substituted for that element or step, respectively.

A weight percent (wt. %) of a component, unless specifically stated to the contrary, is based on the total weight of the formulation or composition in which the component is included.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level of a therapeutic for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidentally with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

The term "pharmaceutically acceptable" describes a material that is not biologically or otherwise undesirable, i.e., without causing an unacceptable level of undesirable biological effects or interacting in a deleterious manner.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain additives such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "polymorph" refers to different crystal structures of a crystalline compound. The different polymorphs may result from differences in crystal packing (packing polymorphism) or differences in packing between different conformers of the same molecule (conformational polymorphism).

As used herein, the term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of the present invention may be prepared, e.g., in crystalline form, and may be solvated. Suitable solvates include pharmaceutically acceptable solvates and further include both stoichiometric solvates and non-stoichiometric solvates. The term "solvate" encompasses both solution-phase and isolable solvates. Representative solvates include hydrates, ethanolates, and methanolates.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

As used herein, the term "subject" can be a human, non-human primate, horse, pig, rabbit, dog, sheep, goat, cow, cat, guinea pig or rodent. A "patient" or "subject in need thereof" refers to a mammal afflicted with a disease or disorder. The term "patient" includes human and veterinary subjects.

Terms such as "parenteral", "parenterally", and the like, refer to routes or modes of administration of a compound or composition to an individual other than along the alimentary canal. Examples of parenteral routes of administration include, without limitation, subcutaneous (s.c.), intravenous (i.v.), intramuscular (i.m.), intra-arterial (i.a.), intraperitoneal (i.p.), transdermal (absorption through the skin or dermal layers), nasal ("intranasal"; absorption across nasal mucosa), pulmonary (e.g., by inhalation for absorption across the lung tissue), vaginal, direct injections or infusions into body cavities or organs other than those of the alimentary canal, as well as by implantation of any of a variety of devices into the body (e.g., of a composition, depot, or device that permits active or passive release of a compound or composition into the body).

The terms "non-parenteral", "non-parenterally", "enteral", "enterally", "oral", "orally", and the like, refer to administration of a compound or composition to an individual by a route or mode along the alimentary canal. Examples of enteral routes of administration include, without limitation, oral, as in swallowing solid (e.g., tablet) or liquid (e.g., syrup) dosage forms, sublingual (absorption through the mucosal membranes lining the floor of the mouth, e.g., under the tongue), buccal (absorption through the mucosal membranes lining the cheeks), nasojejunal or gastrostomy tubes (delivery into the stomach), intraduodenal administration, as well as rectal administration (e.g., suppositories for release of a drug composition into and absorption by the lower intestinal tract of the alimentary canal).

In the present description, in a structural formula allowing for one or more substituent at a given position and listing suitable substituents, it will be understood that substituents may be "stacked" or combined to form compound substituents. For example, in a listing of suitable substituents including alkyl and aryl substituents, the compound aralkyl and alkaryl substituents are also contemplated.

The term "aliphatic group" is intended to mean a saturated hydrocarbon radical having 1-10 carbon atoms, which may be straight-chain or branched, e.g., methyl, ethyl, n-propyl, isopropyl, n-butyl, tert-butyl, n-pentyl, n-hexyl, n-heptyl and n-octyl, etc.

The term "halo" or "halogen" means fluorine, chlorine, bromine, or iodine.

The term "alkyl" as used herein is intended to mean a branched, straight-chain, or cyclic saturated hydrocarbon group of 1 to 24 carbon atoms, preferably 1-10 carbon atoms, such as methyl, ethyl, n-propyl, isopropyl, n-butyl, isobutyl, s-butyl, t-butyl, n-pentyl, isopentyl, s-pentyl, neopentyl, cyclopentyl, hexyl, cyclohexyl, heptyl, cycloheptyl, octyl, cyclooctyl, nonyl, decyl, and the like. An alkyl group can be cyclic or acyclic. An alkyl group can be branched or unbranched. An alkyl group can also be substituted or unsubstituted. For example, the term "substituted alkyl" denotes an alkyl group substituted with one or more groups including, but not limited to, alkyl, haloalkyl, nitro, halogen, alkoxy, alkylthio, haloalkoxy, sulfonyl, sulfinyl, carboxy, alkoxycarbonyl, amino, or amido groups.

The term "sulfonyl" is intended to mean a sulfur radical that is doubly bound to two oxygens ($-SO_2-$). A sulfonyl group may be linked via the sulfur atom with an amino, alkylamino, alkyl, cycloalkyl, aryl, heterocycloalkyl, or heteroaryl moiety to produce a monovalent radical.

The term "sulfinyl" is intended to mean a sulfur radical that is doubly bound to one oxygen ($-S(O)-$), and the sulfur atom may be substituted with an amino, alkylamino, alkyl, cycloalkyl, aryl, heterocycloalkyl, or heteroaryl moiety to produce a monovalent radical.

The term "hydroxyl" or "hydroxy" is intended to mean the radical —OH.

The term "alkoxy" is intended to mean the radical —OR, where R is an alkyl or cycloalkyl group.

The term "haloalkyl" is intended to mean an alkyl moiety wherein one or more hydrogen atoms is replaced with the same or different halogen atoms, e.g., $-CH_2Cl$, $-CF_3$, $-CH_2CF_3$, $-CH_2CCl_3$, and the like.

The term "haloalkoxy" is intended to mean an alkoxy radical wherein one or more hydrogen atoms are replaced with the same or different halogen atoms, e.g. $-OCHF_2$, $-OCF_3$, $-OCH_2CF_3$, $-OCH_2CCl_3$, and the like.

The term "alkenyl" is intended to mean a straight-chain, branched, or cyclic hydrocarbon radical having from 2-8 carbon atoms and at least one double bond, e.g., ethenyl, 3-buten-1-yl, 3-hexen-1-yl, cyclopent-1-en-3-yl, and the like. The alkenyl group can be unsubstituted or substituted with one or more groups including, but not limited to, alkyl, haloalkyl, nitro, halogen, alkoxy, alkylthio, haloalkoxy, sulfonyl, sulfinyl, carboxy, alkoxycarbonyl, amido, cycloalkyl, alkenyl, cycloalkenyl, alkynyl, cycloalkynyl, aryl, heteroaryl, aldehyde, amino, carboxylic acid, ester, ether, hydroxy, ketone, or thiol.

The term "alkynyl" is intended to mean a straight-chain or branched hydrocarbon radical having from 2-8 carbon atoms an at least one triple bond, e.g., ethynyl, 3-butyn-1-yl, 2-butyn-1-yl, 3-pentyn-1-yl, and the like. The alkynyl group can be unsubstituted or substituted with one or more groups including, but not limited to, alkyl, haloalkyl, nitro, halogen, alkoxy, alkylthio, haloalkoxy, sulfonyl, sulfinyl, carboxy, alkoxycarbonyl, amido, cycloalkyl, alkenyl, cycloalkenyl, alkynyl, cycloalkynyl, aryl, heteroaryl, aldehyde, amino, carboxylic acid, ester, ether, hydroxy, ketone, azide, nitro, or thiol, as described herein.

The term "carbon substituent" is intended to refer to substituent groups wherein the first atom of the substituent bound at the site of attachment is carbon, e.g., as in $-CH_3$ (methyl), —COOH (carboxyl), $-C_6H_5$ (phenyl), —C≡N (cyano), etc., which may be contrasted with "nitrogen substituents" such as $-NH_2$ (amino), $-NO_2$ (nitro), etc., wherein the first atom bound at the site of attachment is nitrogen.

The term "cycloalkyl" or "aliphatic ring" is intended to mean a non-aromatic monovalent cyclic or polycyclic hydrocarbon radical having from 3-12 carbon atoms. "Substituted cycloalkyl" groups, e.g., substituted cyclopentyl, cyclohexyl, decalinyl, may be substituted with one or more groups including, but not limited to, alkyl, haloalkyl, nitro, halogen, alkoxy, alkylthio, haloalkoxy, sulfonyl, sulfinyl, carboxy, alkoxycarbonyl, amido, cycloalkyl, alkoxy, amino, ether, hydroxy, or thiol as described herein.

The term "heterocycloalkyl" is intended to mean a non-aromatic monovalent monocyclic or polycyclic radical having from 2-12 carbon atoms, and 1-5 heteroatoms selected from nitrogen (N), oxygen (O), or sulfur (S). "Substituted heterocycloalkyl" groups, e.g., substituted pyrrolodinyl, tetrahydropyranyl, morpholinyl, piperazinyl, oxiranyl groups, and the like, may be substituted with one or more groups including, but not limited to, alkyl, haloalkyl, nitro, halogen, alkoxy, alkylthio, haloalkoxy, sulfonyl, sulfinyl, carboxy, alkoxycarbonyl, amido, cycloalkyl, alkoxy, amino, ether, hydroxy, or thiol as described herein.

The term "aryl" is intended to mean an aromatic, monovalent monocyclic or polycyclic radical comprising from 5 and 18 carbon ring members, e.g., phenyl, biphenyl, naphthyl, phenanthryl, and the like. A "substituted aryl" group is an aryl group substituted with one or more groups including, but not limited to, alkyl, haloalkyl, nitro, halogen, alkoxy, alkylthio, haloalkoxy, sulfonyl, sulfinyl, carboxy, alkoxycarbonyl, amino, amido, cycloalkyl, alkoxy, alkenyl, cycloalkenyl, alkynyl, cycloalkynyl, aryl, heteroaryl, aldehyde, carboxylic acid, ester, ether, hydroxy, ketone, or thiol as described herein. In addition, the aryl group can be a single ring structure or comprise multiple ring structures that are either fused ring structures or attached via one or more bridging groups such as a carbon-carbon bond, a hydrocarbon bridge (such as alkylene), or an ether or alkylether bridge.

The term "heteroaryl" is intended to mean an aromatic, monovalent monocyclic or polycyclic radical comprising from 3 and 18 carbon ring members and at least 1 heteroatom selected from nitrogen (N), oxygen (O), or sulfur (S), e.g., pyridyl, pyrazinyl, pyridizinyl, pyrimidinyl, furanyl, thienyl, triazolyl, quinolinyl, imidazolinyl, benzimidazolinyl, indolyl, and the like. "Substituted heteroaryl" is a heteroaryl group substituted with one or more groups including, but not limited to, alkyl, haloalkyl, nitro, halogen, alkoxy, alkylthio, haloalkoxy, sulfonyl, sulfinyl, carboxy, alkoxycarbonyl, amido, cycloalkyl, amino, ether, hydroxy, or thiol as described herein. Heteroaryl groups can be monocyclic, or alternatively fused ring systems.

The term "aryloxy" is intended to mean the radical —OAr where Ar is an aryl group.

The term "heteroaryloxy" is intended to mean the radical —O(heteroAr) where heteroAr is a heteroaryl group.

The term "acyl" is intended to mean a —C(O)R radical, where R is alkyl, alkenyl, alkynyl, cycloalkyl, aryl, heteroaryl, or heterocycloalkyl, e.g., acetyl, benzoyl, and the like.

The term "carboxy" is intended to mean the radical —C(O)OH.

The term "alkoxycarbonyl" is intended to mean a RO—C(O)— radical where R is alkyl or cycloalkyl.

The term "alkylcarbonyl" refers to a RC(O)— radical where R is alkyl or cycloalkyl.

The term "aryloxycarbonyl" is intended to mean a RO—C(O)— radical where R is aryl; "heteroaryloxycarbonyl" refers to a radical of the same structure RO—C(O)— where R is heteroaryl.

The term "amino" is intended to mean the radical $-NH_2$.

The term "alkylamino" is intended to mean the radical —NHR where R is an alkyl group, or —NRR', where R and R' are each independently, hydrogen or alkyl. Representative examples include, but are not limited to, methylamino, ethylamino, propylamino, isopropylamino, butylamino, isobutylamino, (sec-butyl)amino, (tert-butyl)amino, pentylamino, isopentylamino, (tert-pentyl)amino, hexylamino, dimethylamino, methylethylamino, diethylamino, methylpentylamino, and the like.

The term "acylamino" is intended to mean the radical —NHC(O)R, where R is a monovalent organic radical such as, e.g., alkyl, alkenyl, alkynyl, cycloalkyl, aryl, heteroaryl, or heterocycloalkyl.

The term "amido" in intended to mean the radical —C(O)NRR' where R and R' are, independently, hydrogen, or monovalent organic radicals, such as, e.g., alkyl, alkenyl, alkynyl, cycloalkyl, aryl, heteroaryl, or heterocycloalkyl.

The term "amidino" is intended to mean the radical —C(:NR)NR'R", where R, R', and R" are, independently, hydrogen, alkyl, alkenyl, alkynyl, cycloalkyl, aryl, or heteroaryl, and wherein R, R', and R" may form heterocycloalkyl rings, e.g. carboxamido, imidazolinyl, tetrahydropyrimidinyl.

The term "guanidine" is intended to mean the radical —NHC(:NR)NR'R", where R, R', and R" are, independently, hydrogen, alkyl, alkenyl, alkynyl, cycloalkyl, aryl, or heteroaryl, and wherein R, R', and R" may form heterocycloalkyl rings.

The term "sulfonylamino" is intended to mean the radical —NHSO$_2$R where R is a monvalent organic radical such as, e.g., alkyl, alkenyl, alkynyl, cycloalkyl, aryl, heteroaryl, or heterocycloalkyl.

The term "aminosulfonyl" is intended to mean the radical —SO$_2$NRR' where R and R' are, independently, hydrogen, or a monovalent organic radical such as, e.g., alkyl, alkenyl, alkynyl, cycloalkyl, aryl, or heteroaryl, or heterocycloalkyl.

The term "sulfhydryl" or "mercapto" is intended to mean the radical —SH.

The term "alkylthio" is intended to mean the radical —SR where R is an alkyl or cycloalkyl group.

The term "arylthio" is intended to mean the radical —SAr where Ar is an aryl group.

DETAILED DESCRIPTION OF THE INVENTION

The present invention is directed to the identification, isolation, and characterization of small molecule inhibitors of the bacterial trans-translation mechanism for use in the treatment and/or prevention of bacterial infections in mammals, and in particular the treatment and/or prevention of bacterial infections in humans. The compounds of the present invention may also be used for the sterilization or pretreatment of surfaces, e.g., catheters, colonized by bacteria to kill or prevent bacterial growth.

The lack of nuclei in bacterial cells necessitates that the processes of transcription and translation are carried out in the same compartment. This can be advantageous in that it allows bacteria to rapidly adapt to environmental changes by making new proteins. However, this can have serious consequences as this limits the bacterial cell's ability for protein quality control due to limited mRNA proofreading.

The trans-translation mechanism is a key component of multiple quality control pathways in bacteria that ensure proteins are synthesized with high fidelity in spite of challenges such as transcription errors, mRNA damage, and translational frameshifting. The trans-translation process is carried out by a ribonucleoprotein complex composed of tmRNA, a specialized RNA with properties of both a tRNA and mRNA, and the small protein SmpB. The tmRNA-SmpB complex interacts with translational complexes stalled at the 3' end of an mRNA to release the stalled ribosomes and target the nascent polypeptides and mRNAs for degradation. The released ribosomes can then be recycled and reused for a new translation process. (See, FIG. 1.)

Therefore, compounds that target the trans-translation complex and inhibit trans-translation represent a promising approach to developing pharmaceuticals for treating or preventing a wide range of bacterial infections. Advantageously, target-related toxicity of inhibitors of non-stop ribosome rescue is unlikely as trans-translation genes are not found in metazoans. There are no homologs of the trans-translation ribosome rescue pathway in the eukaryotic cytosol.

Initial trans-translation inhibitor compounds were discovered via a high-throughput luciferase-based reporter assay that was developed and used to screen a library of 663,000 small molecules. In the luciferase reporter assay, a copy of the trpAt transcriptional terminator was inserted before the stop codon of luc, the gene encoding firefly luciferase, on a multicopy plasmid. Induction of luc expression from this reporter (luc-trpAt) produces luc mRNA with no stop codon, and translation of the nonstop luc mRNA in cells with an active trans-translation system results in tagging and proteolysis of the luciferase protein. Alternatively, if trans-translation is inhibited, active luciferase will be produced and will accumulate in the cells. The assay is shown schematically in FIG. 2. Using this assay, trans-translation activity was monitored by assaying luciferase activity in cells expressing luc-trpAt. Screening the small molecule library identified twenty-four potential trans-translation inhibitor compounds.

An initial trans-translation inhibitor, KKL-35, having a core acylaminooxadiazole structure was isolated but showed poor bioavailability and poor microsomal stability. (See, Ramadoss et al., *PNAS,* 110(25):10282-87 (2013)). The discovery research described herein was initiated to synthesize and test more complex variations on the aminooxadiazole scaffold in order to discover whether improved inhibitors of the bacterial trans-translation mechanism could be obtained. This work has led to the identification of two families of candidate trans-translation inhibitor compounds useful in treating a wide array of bacterial infections in mammals, and in particular, treating and/or preventing a wide array of bacterial infections in humans.

Therefore, it is an object of the present invention to develop new antibacterial compounds that defeat the trans-translation correction mechanism in bacteria critical for resolving non-stop ribosome complexes. Without in any way being limited to a particular scientific theory on the mechanism of action, it is believed that one way the novel compounds of the invention exert their inhibitory effect is by targeting a binding site on the stalled ribosome and thereby, preventing dissociation of the ribosomes, i.e., by preventing "ribosome rescue" and recycling of the ribosomes from the stalled translation complex. Ribosome rescue is essential for continued translation and survival of the bacterial cell, and therefore targeting this rescue mechanism represents an effective method for treating or preventing a host of bacterial infections.

Potent drug-like small molecules having a ureido-aminooxadiazole structure appear to target the stalled ribosome complex and show low to sub-μM activity. This novel ureido-aminooxadiazole series provides potent and broad protection against bacterial infections. Further, the antibacterial utility of compounds described herein is novel since no similar compounds have been described previously as inhibitors of trans-translation. In addition, an aryl- or heteroaryl-amidooxadiazole series of compounds has been identified that contains effective inhibitors of bacterial trans-translation. Both series of trans-translation inhibitor compounds advantageously target the stalled ribosome complex at low to sub-µM potency and the core scaffolds are generally stable to microsomal degradation, unlike the original hit series, making them excellent candidates for the development of novel therapeutics to treat or prevent a wide variety of bacterial infections.

Therefore, in one embodiment, the present invention is directed to a bacterial trans-translation inhibitor ureido oxadiazole compound having the structure of Formula I:

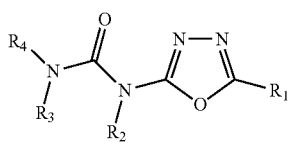

(I)

wherein:

$R_1$ is an aryl ring bearing 1-4 substituents (in addition to the oxadiazole group); a 6-membered heteroaryl ring bearing 1-4 substituents (in addition to the oxadiazole group); a 6-membered heteroaryl ring containing 2, 3, or 4 heteroatoms and bearing 0-3 substituents (in addition to the oxadiazole group); a 5-membered heteroaryl ring containing 2, 3, or 4 heteroatoms and bearing 0-3 substituents (in addition to the oxadiazole group); an unsubstituted cycloalkyl ring of 5, 6, or 7 carbon atoms; an unsubstituted linear or branched chain aliphatic group containing 5-8 carbon atoms; a substituted linear or branched chain aliphatic group containing 1-6 carbon atoms bearing 1-8 substituents (1-2 substituents per aliphatic chain carbon, or up to 3 substituents on a terminal aliphatic chain carbon) selected from alkyl, cycloalkyl, aryl, heteroaryl, haloalkyl, amino, nitro, halogen, alkoxy, alkylthio, haloalkoxy, sulfonyl, or sulfinyl; a substituted cycloalkyl ring of 3-8 carbon atoms bearing 1-8 substituents (1-2 substituents per ring carbon) selected from alkyl, cycloalkyl, aryl, heteroaryl, haloalkyl, amino, nitro, halogen, alkoxy, alkylthio, haloalkoxy, sulfonyl, or sulfinyl, which cycloalkyl ring may optionally be fused with one or more aryl, heteroaryl, cycloalkyl, or heterocycloalkyl rings; a 3-, 4-, 6-, 7-, or 8-member heterocyclic ring made up of carbon atoms and at least one ring heteroatom selected independently from oxygen, nitrogen and sulfur atoms, wherein the ring atom attached to the oxadiazole ring is carbon and said heterocyclic ring bears 0-8 substituents selected from alkyl, cycloalkyl, aryl, heteroaryl, haloalkyl, amino, nitro, halogen, alkoxy, alkylthio, haloalkoxy, sulfonyl, or sulfinyl, which heterocyclic ring may optionally be fused with one or more aryl, heteroaryl, cycloalkyl, or heterocycloalkyl rings; a 5-membered heterocyclic ring made up of carbon atoms and at least one ring heteroatom selected independently from oxygen, nitrogen and sulfur atoms, wherein the ring atom attached to the oxadiazole ring is carbon and with the proviso that the ring atoms at positions 2 and 5 (relative to the point of attachment at position 1 to the oxadiazole moiety) is not nitrogen, and wherein the ring atoms at positions 2 and 5 (relative to the point of attachment at position 1 to the oxadiazole moiety) may each optionally bear 1-2 substituents selected from alkyl, cycloalkyl, aryl, heteroaryl haloalkyl, amino, nitro, halogen, alkoxy, alkylthio, haloalkoxy, sulfonyl, or sulfinyl, and may optionally be fused with one or more aryl, heteroaryl, cycloalkyl, or heterocycloalkyl rings;

$R_2$ is hydrogen; a straight chain aliphatic group; a branched chain aliphatic group; cycloalkyl; haloalkyl; hydroxy; alkoxy; alkylamino; alkylthio; haloalkoxy; sulfonyl; sulfinyl; carboxy; alkoxycarbonyl; or an amido group;

$R_3$ is a straight chain aliphatic group; a branched chain aliphatic group; cycloalkyl; heterocycloalkyl; haloalkyl; thio; alkylthio; haloalkoxy; sulfonyl; sulfinyl; carboxy; aryl; or heteroaryl;

$R_4$ is a straight chain aliphatic group of 2-8 carbon atoms; a branched chain aliphatic group; a cycloalkyl; heterocycloalkyl; haloalkyl; thio; alkylthio; haloalkoxyalkyl; sulfonyl; sulfinyl; aryl; or heteroaryl; or, alternatively, $R_3$ and $R_4$ may be linked together to form a substituted 3-8-member cyclic or heterocyclic ring composed of carbon and oxygen and/or nitrogen atoms, the ring having 0-3 degrees of unsaturation and bearing up to four substituents on carbon and/or nitrogen ring members, with carbon substituents including alkyl, haloalkyl, nitro, halogen, alkoxy, alkylthio, haloalkoxy, sulfonyl, sulfinyl, carboxy, alkoxycarbonyl, aminocarbonyl, and/or a spirocycloalkyl/spirocycloheteroalkyl ring with 3-6 ring atoms bearing 1-2 substituents constituted of 1-6 heavy atoms (carbon, nitrogen, oxygen, sulfur and/or halogen) and any number of hydrogen atoms, and with nitrogen substituents including alkyl, haloalkyl, nitro, halogen, alkoxy, alkylthio, haloalkoxy, sulfonyl, sulfinyl, carbonyl, alkoxycarbonyl, and/or aminocarbonyl groups, which substituents may optionally be fused with one or more aryl, heteroaryl, cycloalkyl, or heterocycloalkyl rings through either carbon or nitrogen attachments, and which substituents may also optionally link across the ring to form bridges of 1-4 carbon atoms and/or heteroatoms through carbon atom attachments;

or a pharmaceutically acceptable salt thereof.

Compounds of Formula I according to the present invention include but are not limited to, the following:

| Compound No. MBX- | Structure |
|---|---|
| 4132 | 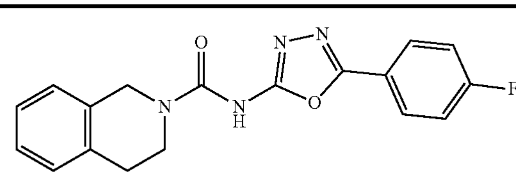 |

| Compound No. MBX- | Structure |
|---|---|
| 4198 | 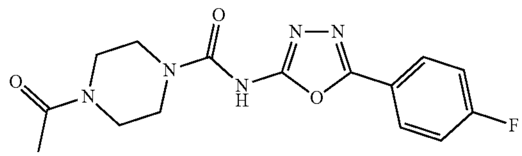 [SMILES: CC(=O)N1CCN(C(=O)Nc2nnc(-c3ccc(F)cc3)o2)CC1] |
| 4199 | 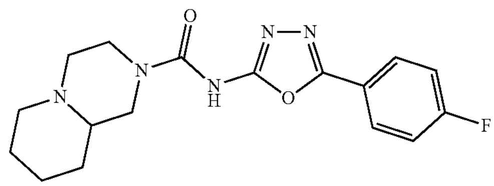 [SMILES: O=C(Nc1nnc(-c2ccc(F)cc2)o1)N1CCN2CCCCC2C1] |
| 4200 | 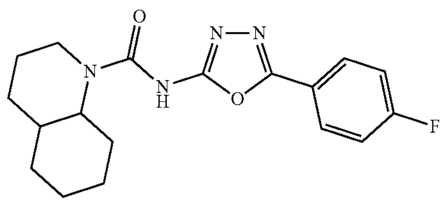 [SMILES: O=C(Nc1nnc(-c2ccc(F)cc2)o1)N1CCCC2CCCCC21] |
| 4201 | 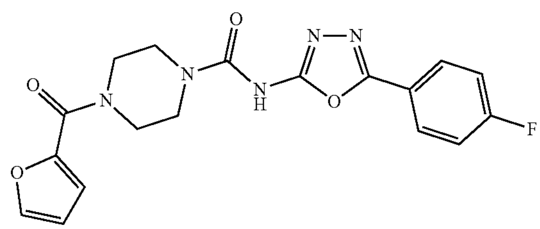 [SMILES: O=C(Nc1nnc(-c2ccc(F)cc2)o1)N1CCN(C(=O)c2ccco2)CC1] |
| 4330 | 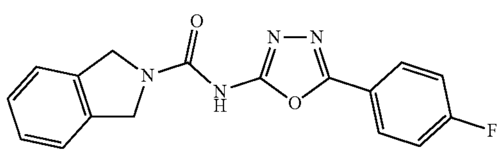 [SMILES: O=C(Nc1nnc(-c2ccc(F)cc2)o1)N1Cc2ccccc2C1] |
| 4331 | 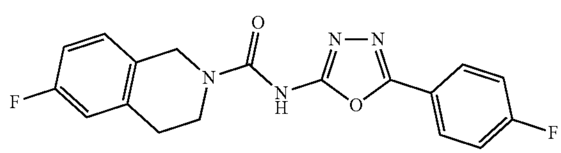 [SMILES: O=C(Nc1nnc(-c2ccc(F)cc2)o1)N1CCc2cc(F)ccc2C1] |
| 4332 | 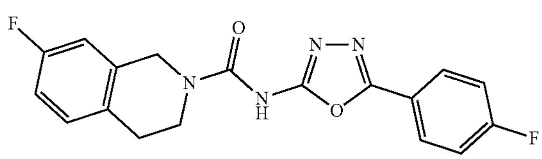 [SMILES: O=C(Nc1nnc(-c2ccc(F)cc2)o1)N1CCc2ccc(F)cc2C1] |
| 4333 | 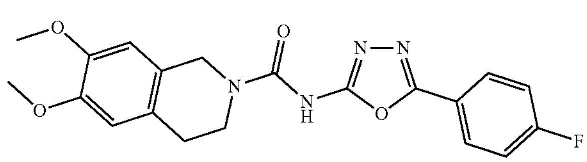 [SMILES: COc1cc2c(cc1OC)CN(C(=O)Nc1nnc(-c3ccc(F)cc3)o1)CC2] |
| 4345 | 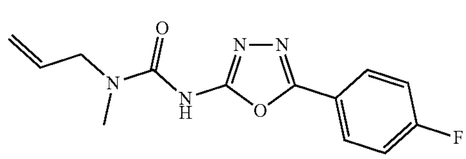 [SMILES: C=CCN(C)C(=O)Nc1nnc(-c2ccc(F)cc2)o1] |

| Compound No. MBX- | Structure |
|---|---|
| 4346 | 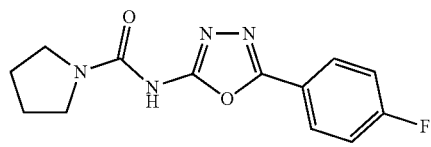 [SMILES: O=C(Nc1nnc(-c2ccc(F)cc2)o1)N1CCCC1] |
| 4347 | 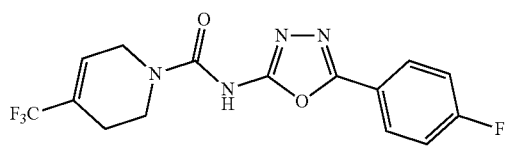 [SMILES: O=C(Nc1nnc(-c2ccc(F)cc2)o1)N1CC=C(C(F)(F)F)CC1] |
| 4348 | 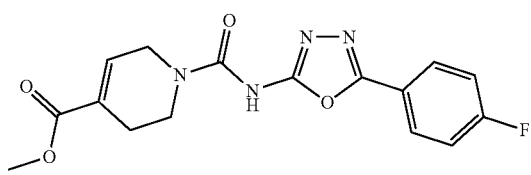 |
| 4349 | 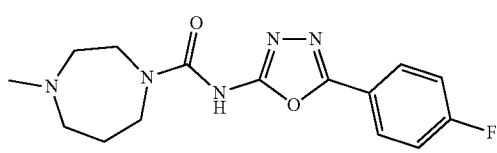 [SMILES: CN1CCCN(C(=O)Nc2nnc(-c3ccc(F)cc3)o2)CC1] |
| 4350 | 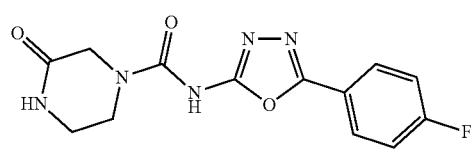 [SMILES: O=C1CN(C(=O)Nc2nnc(-c3ccc(F)cc3)o2)CCN1] |
| 4351 | 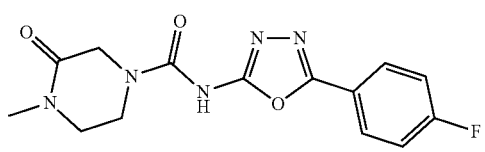 [SMILES: CN1CCN(C(=O)Nc2nnc(-c3ccc(F)cc3)o2)CC1=O] |
| 4366 | 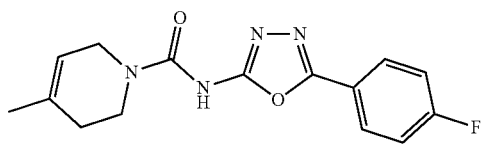 [SMILES: CC1=CCN(C(=O)Nc2nnc(-c3ccc(F)cc3)o2)CC1] |
| 4380 | 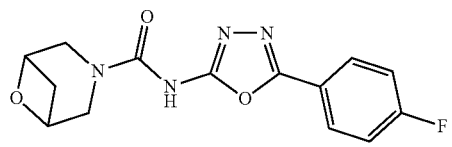 [SMILES: O=C(Nc1nnc(-c2ccc(F)cc2)o1)N1CC2CC(C1)O2] |
| 4381 | 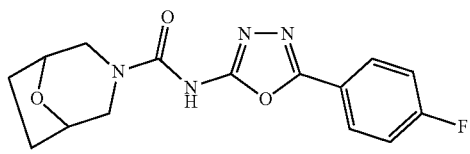 [SMILES: O=C(Nc1nnc(-c2ccc(F)cc2)o1)N1CC2CCC(C1)O2] |

| Compound No. MBX- | Structure |
|---|---|
| 4406 | 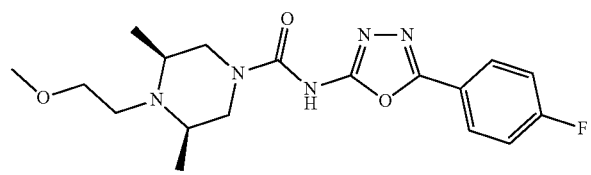 [SMILES: COCCN1[C@H](C)CN(C(=O)Nc2nnc(-c3ccc(F)cc3)o2)C[C@@H]1C] |
| 4464 | 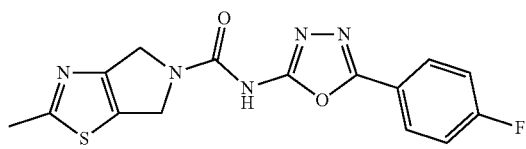 [SMILES: Cc1nc2c(s1)CN(C(=O)Nc1nnc(-c3ccc(F)cc3)o1)C2] |
| 4465 | 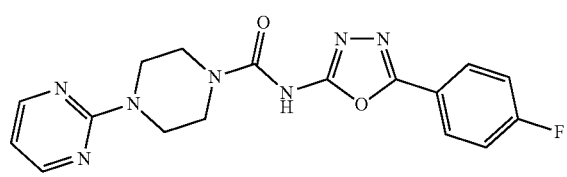 [SMILES: O=C(Nc1nnc(-c2ccc(F)cc2)o1)N1CCN(c2ncccn2)CC1] |
| 4497 | 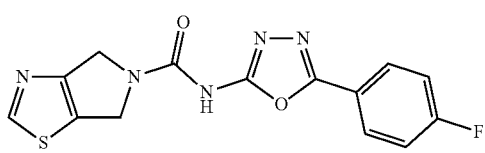 |
| 4684 | 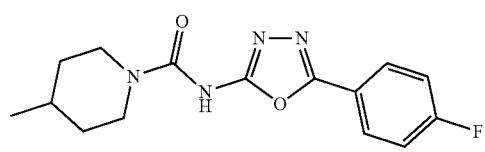 [SMILES: CC1CCN(C(=O)Nc2nnc(-c3ccc(F)cc3)o2)CC1] |
| 4685 | 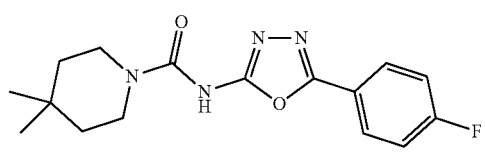 [SMILES: CC1(C)CCN(C(=O)Nc2nnc(-c3ccc(F)cc3)o2)CC1] |
| 4686 | 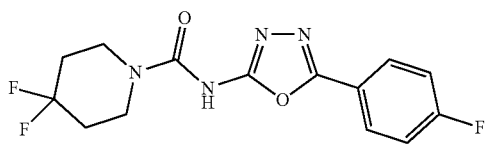 [SMILES: O=C(Nc1nnc(-c2ccc(F)cc2)o1)N1CCC(F)(F)CC1] |
| 4697 | 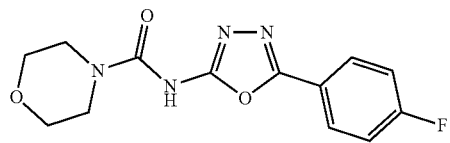 [SMILES: O=C(Nc1nnc(-c2ccc(F)cc2)o1)N1CCOCC1] |
| 4698 | 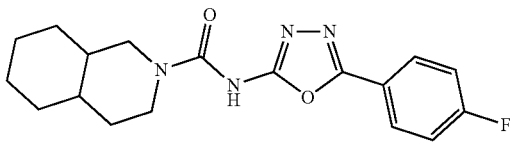 [SMILES: O=C(Nc1nnc(-c2ccc(F)cc2)o1)N1CCC2CCCCC2C1] |

-continued
| Compound No. MBX- | Structure |
|---|---|
| 4699 | 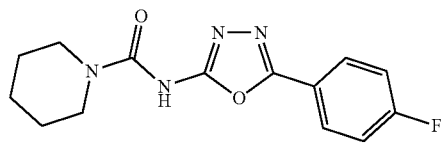 [SMILES: O=C(Nc1nnc(-c2ccc(F)cc2)o1)N1CCCCC1] |
| 4700 | 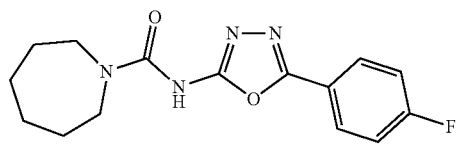 [SMILES: O=C(Nc1nnc(-c2ccc(F)cc2)o1)N1CCCCCC1] |
| 4701 | 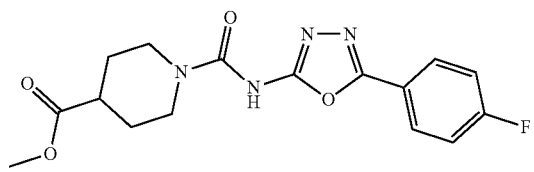 [SMILES: COC(=O)C1CCN(C(=O)Nc2nnc(-c3ccc(F)cc3)o2)CC1] |
| 4702 | 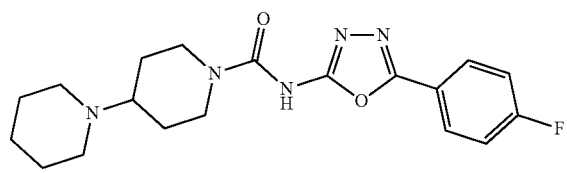 [SMILES: O=C(Nc1nnc(-c2ccc(F)cc2)o1)N1CCC(N2CCCCC2)CC1] |
| 4734 | 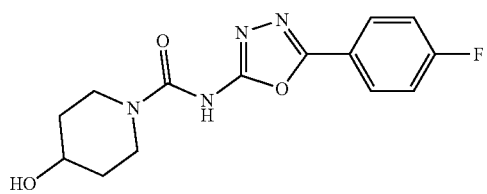 [SMILES: O=C(Nc1nnc(-c2ccc(F)cc2)o1)N1CCC(O)CC1] |
| 4735 | 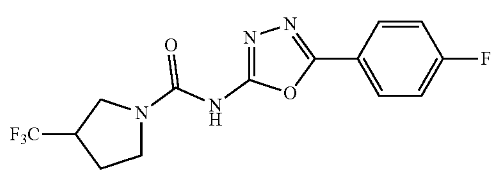 [SMILES: O=C(Nc1nnc(-c2ccc(F)cc2)o1)N1CCC(C(F)(F)F)C1] |
| 4736 | 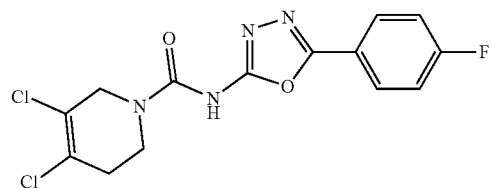 [SMILES: O=C(Nc1nnc(-c2ccc(F)cc2)o1)N1CCC(Cl)=C(Cl)C1] |
| 4737 | 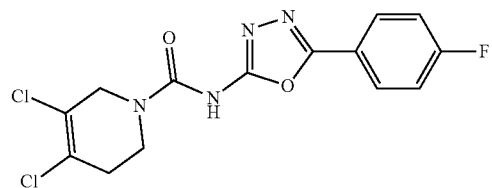 [SMILES: O=C(Nc1nnc(-c2ccc(F)cc2)o1)N1CCC(Cl)=C(Cl)C1] |

-continued

| Compound No. MBX- | Structure |
|---|---|
| 4738 | 3,4-dimethyl-3,6-dihydro-2H-pyridine-1-carboxylic acid [5-(4-fluorophenyl)-1,3,4-oxadiazol-2-yl]amide |
| 4739 | 2-oxa-7-azaspiro[3.5]nonane-7-carboxylic acid [5-(4-fluorophenyl)-1,3,4-oxadiazol-2-yl]amide |
| 4740 | 4-(oxetan-3-yl)piperidine-1-carboxylic acid [5-(4-fluorophenyl)-1,3,4-oxadiazol-2-yl]amide |
| 4741 | 4-(phenylamino)piperidine-1-carboxylic acid [5-(4-fluorophenyl)-1,3,4-oxadiazol-2-yl]amide |
| 4767 | 3-methylpiperidine-1-carboxylic acid [5-(4-fluorophenyl)-1,3,4-oxadiazol-2-yl]amide |
| 4768 | 3,5-dimethylpiperidine-1-carboxylic acid [5-(4-fluorophenyl)-1,3,4-oxadiazol-2-yl]amide |
| 4769 | 3-(trifluoromethyl)piperidine-1-carboxylic acid [5-(4-fluorophenyl)-1,3,4-oxadiazol-2-yl]amide |
| 4776 | 5,5-difluoroazepane-1-carboxylic acid [5-(4-fluorophenyl)-1,3,4-oxadiazol-2-yl]amide |

-continued

| Compound No. MBX- | Structure |
|---|---|
| 4777 | 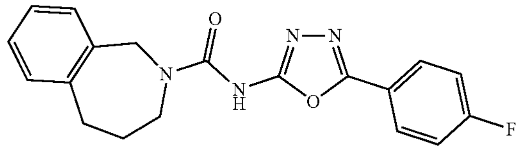 [SMILES: O=C(Nc1nnc(-c2ccc(F)cc2)o1)N1CCCc2ccccc2C1] |
| 4778 | 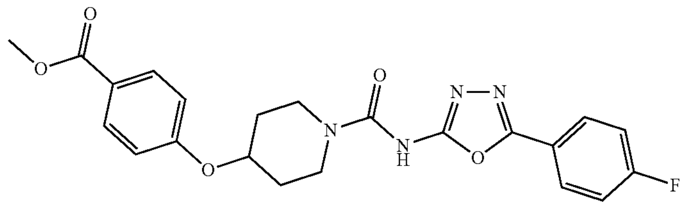 [SMILES: COC(=O)c1ccc(OC2CCN(C(=O)Nc3nnc(-c4ccc(F)cc4)o3)CC2)cc1] |
| 4779 | 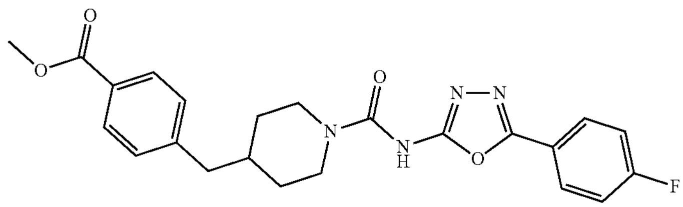 [SMILES: COC(=O)c1ccc(CC2CCN(C(=O)Nc3nnc(-c4ccc(F)cc4)o3)CC2)cc1] |
| 4805 | 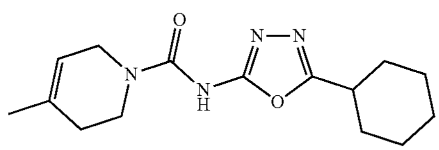 [SMILES: CC1=CCN(C(=O)Nc2nnc(C3CCCCC3)o2)CC1] |
| 4806 | 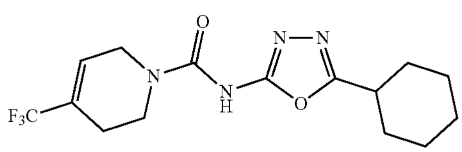 [SMILES: O=C(Nc1nnc(C2CCCCC2)o1)N1CC=C(C(F)(F)F)CC1] |
| 4807 | 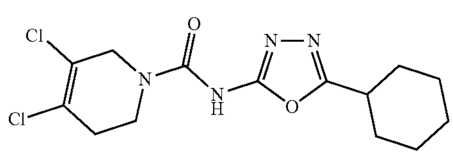 [SMILES: O=C(Nc1nnc(C2CCCCC2)o1)N1CCC(Cl)=C(Cl)C1] |
| 4808 | 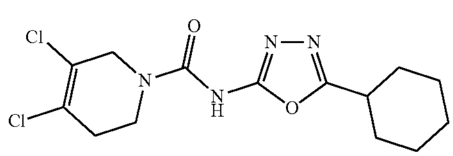 [SMILES: O=C(Nc1nnc(C2CCCCC2)o1)N1CCC(Cl)=C(Cl)C1] |
| 4839 | 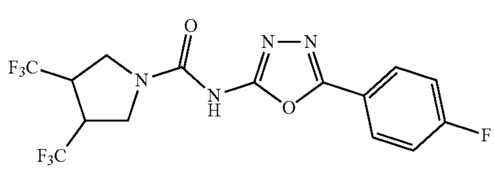 [SMILES: O=C(Nc1nnc(-c2ccc(F)cc2)o1)N1CC(C(F)(F)F)C(C(F)(F)F)C1] |
| 4840 | 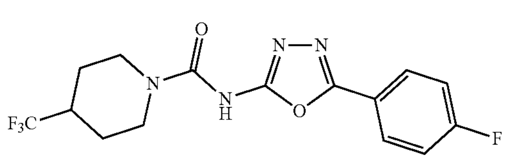 [SMILES: O=C(Nc1nnc(-c2ccc(F)cc2)o1)N1CCC(C(F)(F)F)CC1] |

| Compound No. MBX- | Structure |
|---|---|
| 4841 | 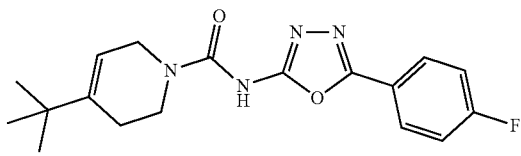 [SMILES: CC(C)(C)C1=CCN(C(=O)Nc2nnc(-c3ccc(F)cc3)o2)CC1] |
| 4842 | 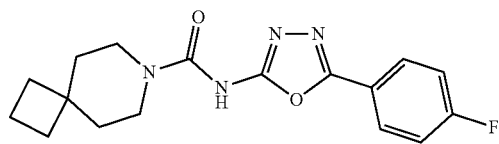 [SMILES: O=C(Nc1nnc(-c2ccc(F)cc2)o1)N1CCC2(CCC2)CC1] |
| 4843 | 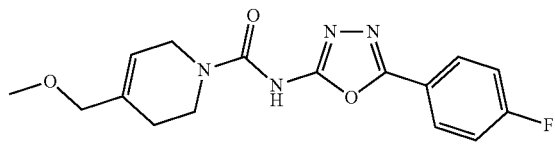 [SMILES: COCC1=CCN(C(=O)Nc2nnc(-c3ccc(F)cc3)o2)CC1] |
| 4922 | 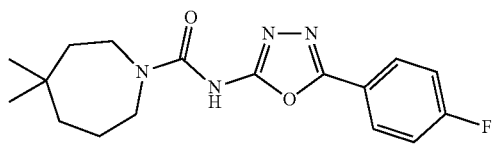 [SMILES: CC1(C)CCCN(C(=O)Nc2nnc(-c3ccc(F)cc3)o2)CC1] |
| 4923 | 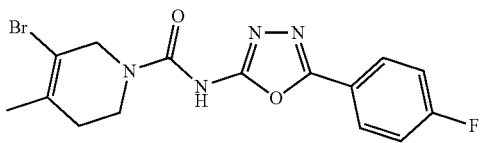 [SMILES: CC1=C(Br)CN(C(=O)Nc2nnc(-c3ccc(F)cc3)o2)CC1] |
| 4930 | 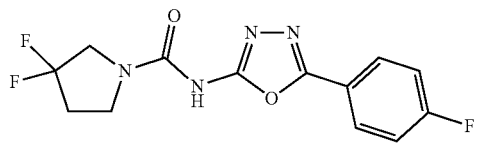 [SMILES: O=C(Nc1nnc(-c2ccc(F)cc2)o1)N1CCC(F)(F)C1] |
| 4931 | 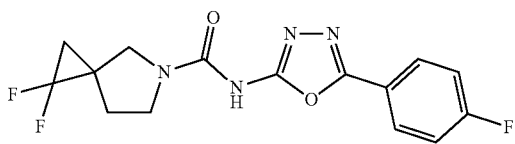 [SMILES: O=C(Nc1nnc(-c2ccc(F)cc2)o1)N1CCC2(C1)CC2(F)F] |
| 4932 | 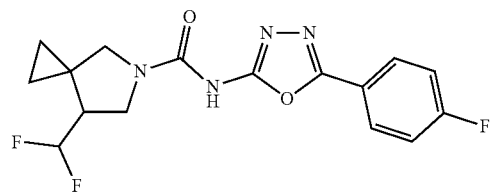 [SMILES: O=C(Nc1nnc(-c2ccc(F)cc2)o1)N1CC(C(F)F)C2(CC2)C1] |
| 4933 | 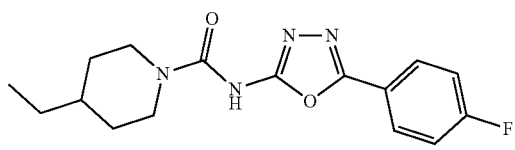 [SMILES: CCC1CCN(C(=O)Nc2nnc(-c3ccc(F)cc3)o2)CC1] |

-continued

| Compound No. MBX- | Structure |
|---|---|
| 4934 | 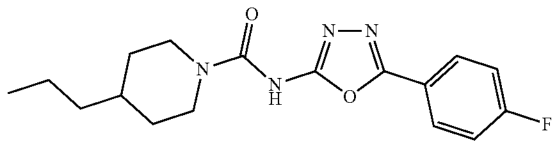 [SMILES: CCCC1CCN(C(=O)Nc2nnc(-c3ccc(F)cc3)o2)CC1] |
| 4935 | 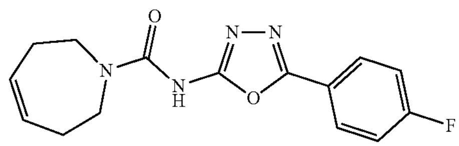 [SMILES: O=C(Nc1nnc(-c2ccc(F)cc2)o1)N1CCC=CCC1] |
| 4936 | 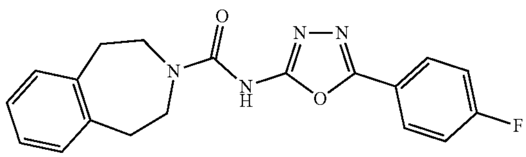 [SMILES: O=C(Nc1nnc(-c2ccc(F)cc2)o1)N1CCc2ccccc2CC1] |
| 4937 | 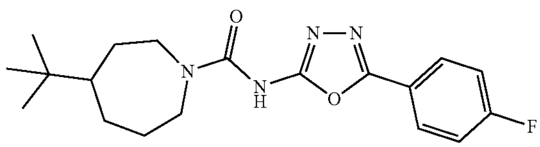 [SMILES: CC(C)(C)C1CCCN(C(=O)Nc2nnc(-c3ccc(F)cc3)o2)CC1] |
| 4938 | 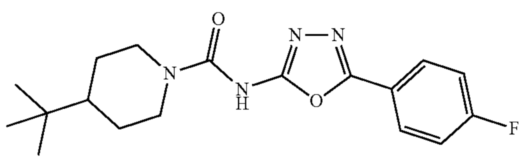 [SMILES: CC(C)(C)C1CCN(C(=O)Nc2nnc(-c3ccc(F)cc3)o2)CC1] |
| 4939 | 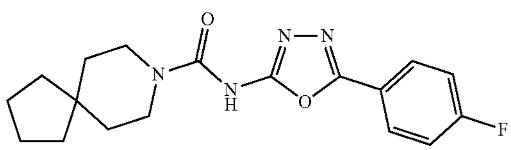 [SMILES: O=C(Nc1nnc(-c2ccc(F)cc2)o1)N1CCC2(CCCC2)CC1] |
| 4940 | 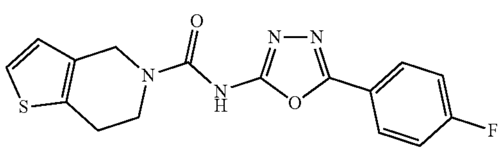 [SMILES: O=C(Nc1nnc(-c2ccc(F)cc2)o1)N1CCc2sccc2C1] |
| 4993 | 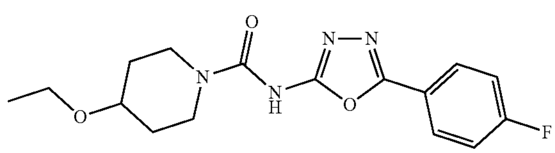 [SMILES: CCOC1CCN(C(=O)Nc2nnc(-c3ccc(F)cc3)o2)CC1] |
| 4994 | 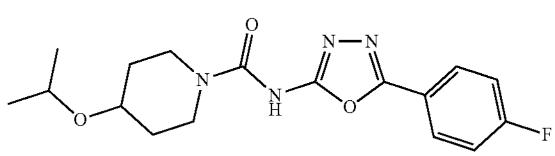 [SMILES: CC(C)OC1CCN(C(=O)Nc2nnc(-c3ccc(F)cc3)o2)CC1] |
| 4995 | 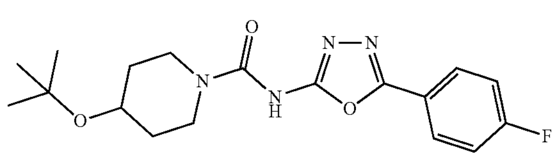 [SMILES: CC(C)(C)OC1CCN(C(=O)Nc2nnc(-c3ccc(F)cc3)o2)CC1] |

| Compound No. MBX- | Structure |
|---|---|
| 5154 | 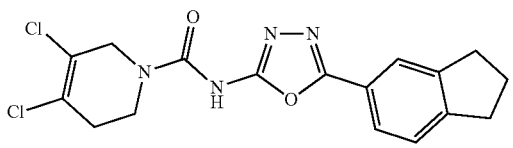 [SMILES: O=C(Nc1nnc(-c2ccc3c(c2)CCC3)o1)N1CCC(Cl)=C(Cl)C1] |
| 5155 | 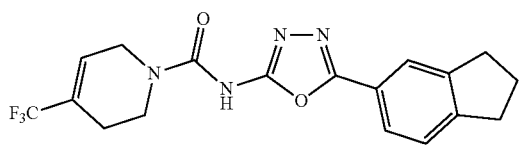 [SMILES: O=C(Nc1nnc(-c2ccc3c(c2)CCC3)o1)N1CC=C(C(F)(F)F)CC1] |
| 5199 | 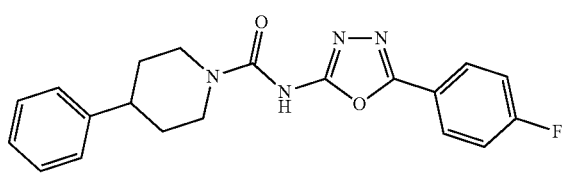 [SMILES: O=C(Nc1nnc(-c2ccc(F)cc2)o1)N1CCC(c2ccccc2)CC1] |
| 5200 | 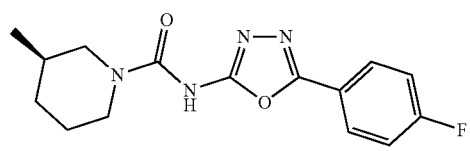 [SMILES: C[C@@H]1CCCN(C(=O)Nc2nnc(-c3ccc(F)cc3)o2)C1] |
| 5201 | 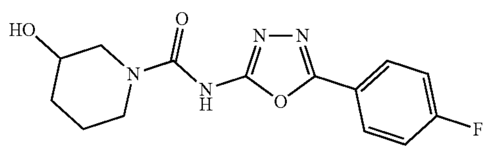 [SMILES: O=C(Nc1nnc(-c2ccc(F)cc2)o1)N1CCCC(O)C1] |
| 5202 | 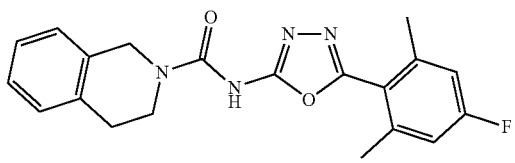 [SMILES: Cc1cc(F)cc(C)c1-c1nnc(NC(=O)N2CCc3ccccc3C2)o1] |
| 5203 | 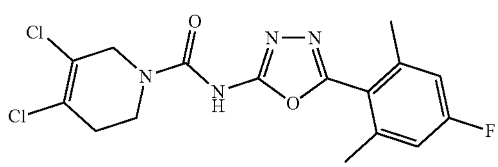 [SMILES: Cc1cc(F)cc(C)c1-c1nnc(NC(=O)N2CCC(Cl)=C(Cl)C2)o1] |
| 5204 | 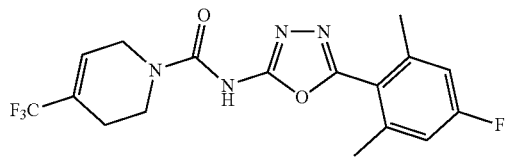 [SMILES: Cc1cc(F)cc(C)c1-c1nnc(NC(=O)N2CC=C(C(F)(F)F)CC2)o1] |
| 5212 | 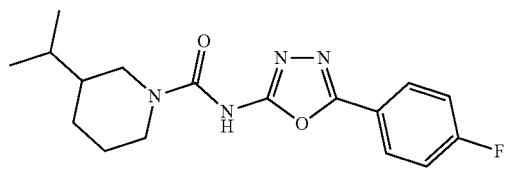 [SMILES: CC(C)C1CCCN(C(=O)Nc2nnc(-c3ccc(F)cc3)o2)C1] |

| Compound No. MBX- | Structure |
|---|---|
| 5214 | 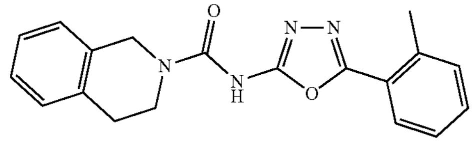 [SMILES: Cc1ccccc1-c1nnc(NC(=O)N2CCc3ccccc3C2)o1] |
| 5215 | 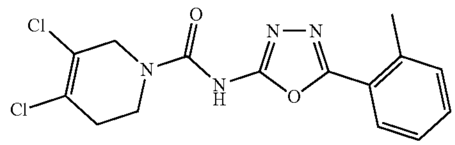 [SMILES: Cc1ccccc1-c1nnc(NC(=O)N2CCC(Cl)=C(Cl)C2)o1] |
| 5216 | 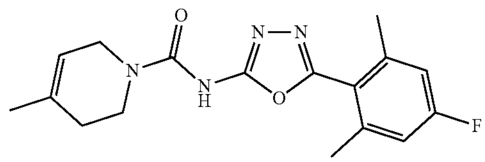 [SMILES: CC1=CCN(C(=O)Nc2nnc(-c3c(C)cc(F)cc3C)o2)CC1] |
| 5222 | 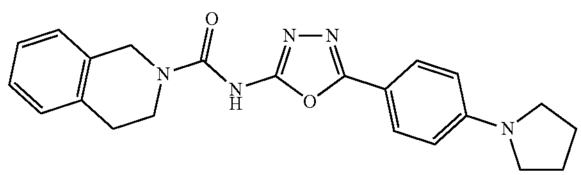 [SMILES: O=C(Nc1nnc(-c2ccc(N3CCCC3)cc2)o1)N1CCc2ccccc2C1] |
| 5223 | 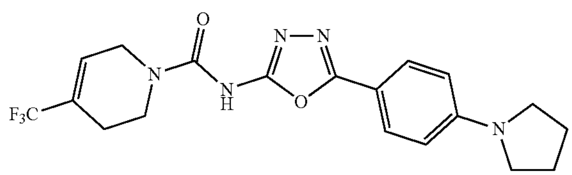 [SMILES: O=C(Nc1nnc(-c2ccc(N3CCCC3)cc2)o1)N1CC=C(C(F)(F)F)CC1] |

In another embodiment, the present invention is directed to the use of ureido oxadiazole compounds of Formula I in a method of treating or preventing a bacterial infection in a mammalian subject, comprising administering to a subject in need thereof an effective amount of at least one compound of Formula I:

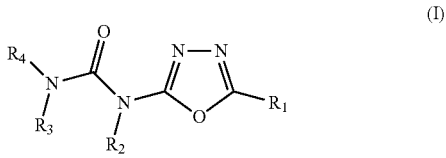

wherein:

$R_1$ is an aryl ring bearing 1-4 substituents (in addition to the oxadiazole group); a 6-membered heteroaryl ring bearing 1-4 substituents (in addition to the oxadiazole group); a 6-membered heteroaryl ring containing 2, 3, or 4 heteroatoms and bearing 0-3 substituents (in addition to the oxadiazole group); a 5-membered heteroaryl ring containing 2, 3, or 4 heteroatoms and bearing 0-3 substituents (in addition to the oxadiazole group); an unsubstituted cycloalkyl ring of 5, 6, or 7 carbon atoms; an unsubstituted linear or branched chain aliphatic group containing 5-8 carbon atoms; a substituted linear or branched chain aliphatic group containing 1-6 carbon atoms bearing 1-8 substituents (1-2 substituents per aliphatic chain carbon, or up to 3 substituents on a terminal aliphatic chain carbon) selected from alkyl, cycloalkyl, aryl, heteroaryl, haloalkyl, amino, nitro, halogen, alkoxy, alkylthio, haloalkoxy, sulfonyl, or sulfinyl; a substituted cycloalkyl ring of 3-8 carbon atoms bearing 1-8 substituents (1-2 substituents per ring carbon) selected from alkyl, cycloalkyl, aryl, heteroaryl, haloalkyl, amino, nitro, halogen, alkoxy, alkylthio, haloalkoxy, sulfonyl, or sulfinyl, which cycloalkyl ring may optionally be fused with one or more aryl, heteroaryl, cycloalkyl, or heterocycloalkyl rings; a 3-, 4-, 5-, 6-, 7-, or 8-member heterocyclic ring made up of carbon atoms and at least one ring heteroatom selected independently from oxygen, nitrogen and sulfur atoms, wherein the ring atom attached to the oxadiazole ring is carbon and said heterocyclic ring bears 0-8 substituents selected from alkyl, cycloalkyl, aryl, heteroaryl, haloalkyl, amino, nitro, halogen, alkoxy, alkylthio, haloalkoxy, sulfonyl, or sulfinyl, which heterocyclic ring may optionally be fused with one or more aryl, heteroaryl, cycloalkyl, or heterocycloalkyl rings;

$R_2$ is hydrogen; a straight chain aliphatic group; a branched chain aliphatic group; cycloalkyl; haloalkyl; hydroxy; alkoxy; alkylamino; alkylthio; haloalkoxy; sulfonyl; sulfinyl; carboxy; alkoxycarbonyl; or an amido group;

$R_3$ is a straight chain aliphatic group; a branched chain aliphatic group; cycloalkyl; heterocycloalkyl; haloalkyl;

thio; alkylthio; haloalkoxy; sulfonyl; sulfinyl; carboxy; alkoxycarbonyl; aryl; or heteroaryl;

$R_4$ is a straight chain aliphatic group of 2-8 carbon atoms; a branched chain aliphatic group; a cycloalkyl; heterocycloalkyl; haloalkyl; thio; alkylthio; haloalkoxyalkyl; sulfonyl; sulfinyl; alkoxycarbonyl; aryl; or heteroaryl; or, alternatively, $R_3$ and $R_4$ may be linked together to form a substituted 3-8-member cyclic or heterocyclic ring composed of carbon and oxygen and/or nitrogen atoms, the ring having 0-3 degrees of unsaturation and bearing up to four substituents on carbon and/or nitrogen ring members, with carbon substituents including alkyl, haloalkyl, nitro, halogen, alkoxy, alkylthio, haloalkoxy, sulfonyl, sulfinyl, carboxy, alkoxycarbonyl, aminocarbonyl, and/or a spirocycloalkyl/spirocycloheteroalkyl ring with 3-6 ring atoms bearing 1-2 substituents constituted of 1-6 heavy atoms (carbon, nitrogen, oxygen, sulfur and/or halogen) and any number of hydrogen atoms, and with nitrogen substituents including alkyl, haloalkyl, nitro, halogen, alkoxy, alkylthio, haloalkoxy, sulfonyl, sulfinyl, carbonyl, alkoxycarbonyl, and/or aminocarbonyl groups, which substituents may optionally be fused with one or more aryl, heteroaryl, cycloalkyl, or heterocycloalkyl rings through either carbon or nitrogen attachments, and which substituents may also optionally link across the ring to form bridges of 1-4 carbon atoms and/or heteroatoms through carbon atom attachments;

or a pharmaceutically acceptable salt thereof.

Compounds of Formula I for use in a method for treating or preventing bacterial infection according to the present invention include but are not limited to, the following:

| Compound No. MBX- | Structure |
| --- | --- |
| 4132 | 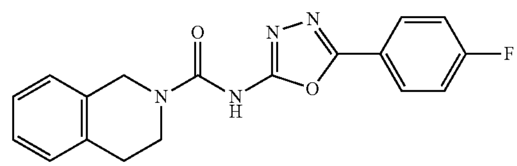 [SMILES: O=C(Nc1nnc(-c2ccc(F)cc2)o1)N1CCc2ccccc2C1] |
| 4198 | 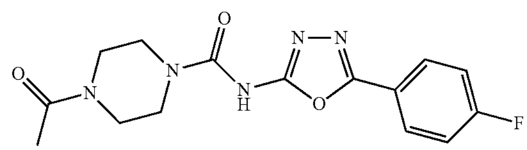 [SMILES: CC(=O)N1CCN(C(=O)Nc2nnc(-c3ccc(F)cc3)o2)CC1] |
| 4199 | 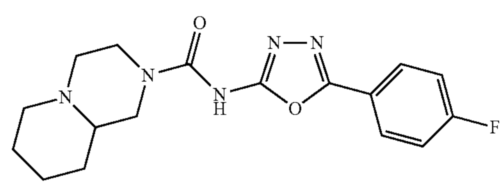 [SMILES: O=C(Nc1nnc(-c2ccc(F)cc2)o1)N1CCN2CCCCC2C1] |
| 4200 | 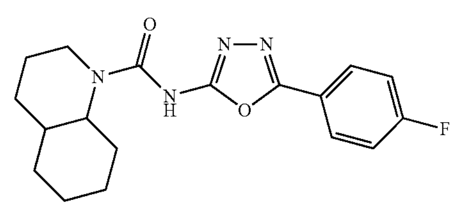 [SMILES: O=C(Nc1nnc(-c2ccc(F)cc2)o1)N1CCCC2CCCCC21] |
| 4201 | 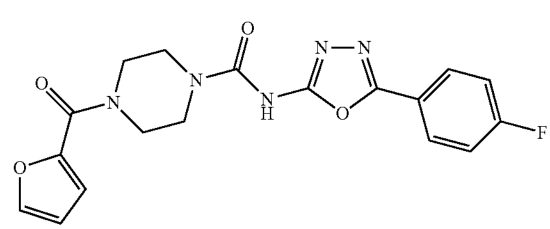 [SMILES: O=C(Nc1nnc(-c2ccc(F)cc2)o1)N1CCN(C(=O)c2ccco2)CC1] |
| 4330 | 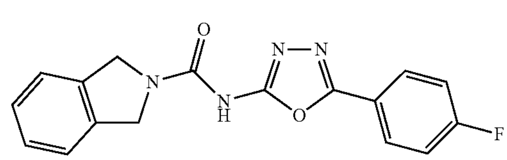 [SMILES: O=C(Nc1nnc(-c2ccc(F)cc2)o1)N1Cc2ccccc2C1] |

-continued

| Compound No. MBX- | Structure |
|---|---|
| 4331 | (6-fluoro-3,4-dihydroisoquinolin-2(1H)-yl)-C(=O)-NH-[1,3,4-oxadiazol-2-yl]-(4-fluorophenyl) |
| 4332 | (7-fluoro-3,4-dihydroisoquinolin-2(1H)-yl)-C(=O)-NH-[1,3,4-oxadiazol-2-yl]-(4-fluorophenyl) |
| 4333 | (6,7-dimethoxy-3,4-dihydroisoquinolin-2(1H)-yl)-C(=O)-NH-[1,3,4-oxadiazol-2-yl]-(4-fluorophenyl) |
| 4345 | N-allyl-N-methyl-C(=O)-NH-[1,3,4-oxadiazol-2-yl]-(4-fluorophenyl) |
| 4346 | (pyrrolidin-1-yl)-C(=O)-NH-[1,3,4-oxadiazol-2-yl]-(4-fluorophenyl) |
| 4347 | (4-trifluoromethyl-1,2,3,6-tetrahydropyridin-1-yl)-C(=O)-NH-[1,3,4-oxadiazol-2-yl]-(4-fluorophenyl) |
| 4348 | (4-methoxycarbonyl-1,2,3,6-tetrahydropyridin-1-yl)-C(=O)-NH-[1,3,4-oxadiazol-2-yl]-(4-fluorophenyl) |
| 4349 | (4-methyl-1,4-diazepan-1-yl)-C(=O)-NH-[1,3,4-oxadiazol-2-yl]-(4-fluorophenyl) |
| 4350 | (3-oxopiperazin-1-yl)-C(=O)-NH-[1,3,4-oxadiazol-2-yl]-(4-fluorophenyl) |
| 4351 | (4-methyl-3-oxopiperazin-1-yl)-C(=O)-NH-[1,3,4-oxadiazol-2-yl]-(4-fluorophenyl) |

-continued
| Compound No. MBX- | Structure |
|---|---|
| 4366 | 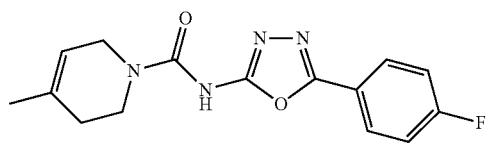 [SMILES: CC1=CCN(C(=O)Nc2nnc(-c3ccc(F)cc3)o2)CC1] |
| 4380 | 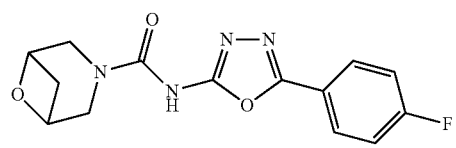 |
| 4381 | 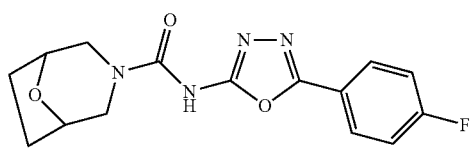 |
| 4406 | 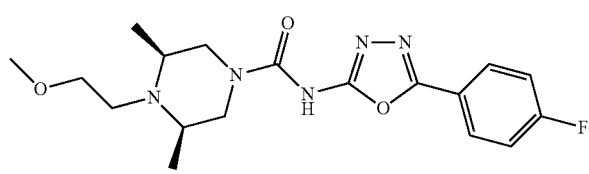 [SMILES: COCCN1[C@H](C)CN(C(=O)Nc2nnc(-c3ccc(F)cc3)o2)C[C@@H]1C] |
| 4464 | 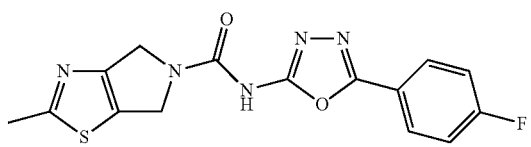 [SMILES: Cc1nc2c(s1)CN(C(=O)Nc1nnc(-c3ccc(F)cc3)o1)C2] |
| 4465 | 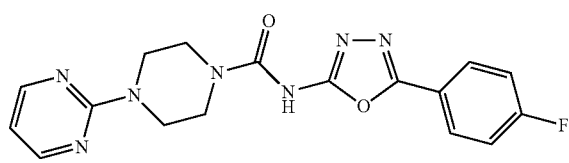 [SMILES: O=C(Nc1nnc(-c2ccc(F)cc2)o1)N1CCN(c2ncccn2)CC1] |
| 4497 | 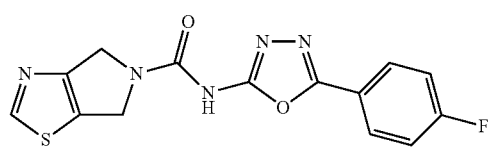 [SMILES: O=C(Nc1nnc(-c2ccc(F)cc2)o1)N1Cc2ncsc2C1] |
| 4684 | 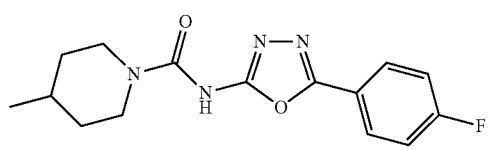 [SMILES: CC1CCN(C(=O)Nc2nnc(-c3ccc(F)cc3)o2)CC1] |
| 4685 | 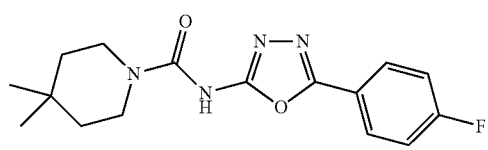 [SMILES: CC1(C)CCN(C(=O)Nc2nnc(-c3ccc(F)cc3)o2)CC1] |

| Compound No. MBX- | Structure |
|---|---|
| 4686 | 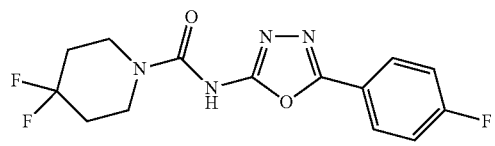 [SMILES: O=C(Nc1nnc(-c2ccc(F)cc2)o1)N1CCC(F)(F)CC1] |
| 4697 | 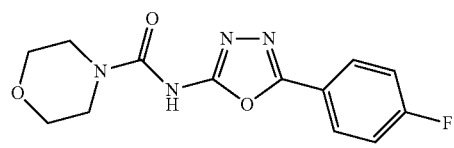 [SMILES: O=C(Nc1nnc(-c2ccc(F)cc2)o1)N1CCOCC1] |
| 4698 | 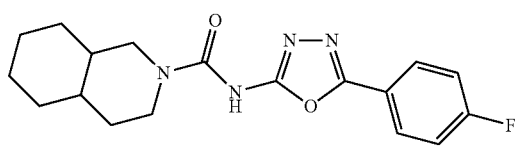 [SMILES: O=C(Nc1nnc(-c2ccc(F)cc2)o1)N1CCC2CCCCC2C1] |
| 4699 | 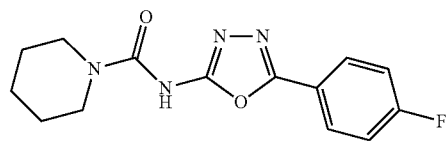 [SMILES: O=C(Nc1nnc(-c2ccc(F)cc2)o1)N1CCCCC1] |
| 4700 | 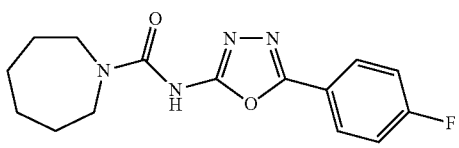 [SMILES: O=C(Nc1nnc(-c2ccc(F)cc2)o1)N1CCCCCC1] |
| 4701 | 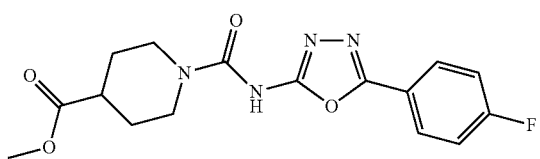 [SMILES: COC(=O)C1CCN(C(=O)Nc2nnc(-c3ccc(F)cc3)o2)CC1] |
| 4702 | 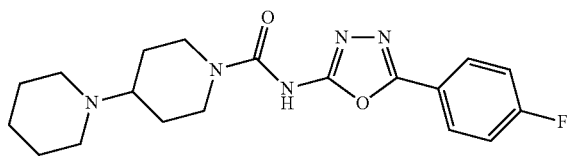 [SMILES: O=C(Nc1nnc(-c2ccc(F)cc2)o1)N1CCC(N2CCCCC2)CC1] |
| 4734 | 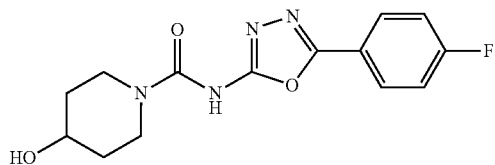 [SMILES: O=C(Nc1nnc(-c2ccc(F)cc2)o1)N1CCC(O)CC1] |
| 4735 | 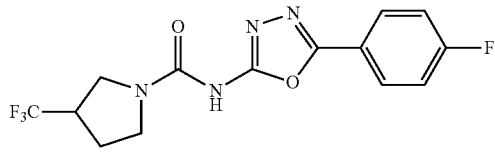 |

-continued

| Compound No. MBX- | Structure |
|---|---|
| 4736 | *3,4-dichloro-3,6-dihydro-2H-pyridine-1-carboxamide linked to 5-(4-fluorophenyl)-1,3,4-oxadiazol-2-yl* |
| 4737 | *3,4-dichloro-3,6-dihydro-2H-pyridine-1-carboxamide linked to 5-(4-fluorophenyl)-1,3,4-oxadiazol-2-yl* |
| 4738 | *3,4-dimethyl-3,6-dihydro-2H-pyridine-1-carboxamide linked to 5-(4-fluorophenyl)-1,3,4-oxadiazol-2-yl* |
| 4739 | *2-oxa-7-azaspiro[3.5]nonane-7-carboxamide linked to 5-(4-fluorophenyl)-1,3,4-oxadiazol-2-yl* |
| 4740 | *4-(oxetan-3-yl)piperidine-1-carboxamide linked to 5-(4-fluorophenyl)-1,3,4-oxadiazol-2-yl* |
| 4741 | *4-(phenylamino)piperidine-1-carboxamide linked to 5-(4-fluorophenyl)-1,3,4-oxadiazol-2-yl* |
| 4767 | *3-methylpiperidine-1-carboxamide linked to 5-(4-fluorophenyl)-1,3,4-oxadiazol-2-yl* |
| 4768 | *3,5-dimethylpiperidine-1-carboxamide linked to 5-(4-fluorophenyl)-1,3,4-oxadiazol-2-yl* |
| 4769 | *3-(trifluoromethyl)piperidine-1-carboxamide linked to 5-(4-fluorophenyl)-1,3,4-oxadiazol-2-yl* |

| Compound No. MBX- | Structure |
|---|---|
| 4776 | 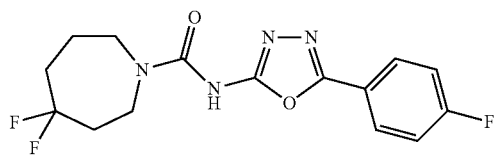 [SMILES: O=C(Nc1nnc(-c2ccc(F)cc2)o1)N1CCCC(F)(F)CC1] |
| 4777 | 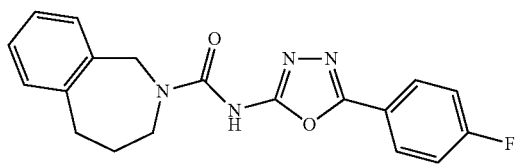 [SMILES: O=C(Nc1nnc(-c2ccc(F)cc2)o1)N1CCCc2ccccc2C1] |
| 4778 | 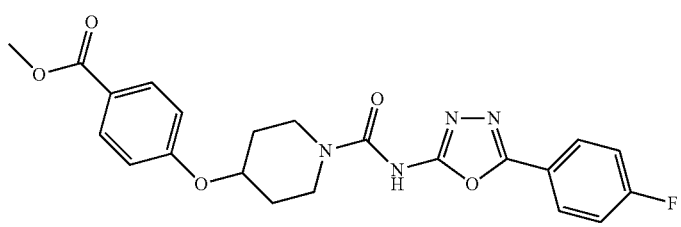 [SMILES: COC(=O)c1ccc(OC2CCN(C(=O)Nc3nnc(-c4ccc(F)cc4)o3)CC2)cc1] |
| 4779 | 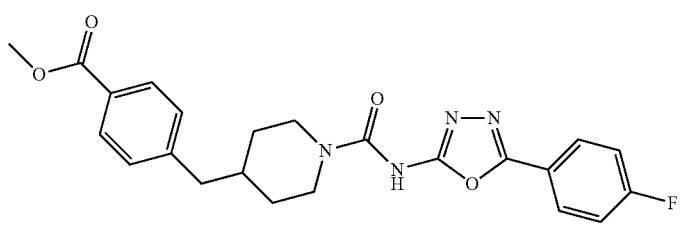 [SMILES: COC(=O)c1ccc(CC2CCN(C(=O)Nc3nnc(-c4ccc(F)cc4)o3)CC2)cc1] |
| 4805 | 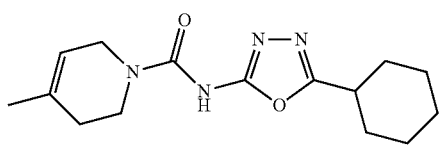 [SMILES: CC1=CCN(C(=O)Nc2nnc(C3CCCCC3)o2)CC1] |
| 4806 | 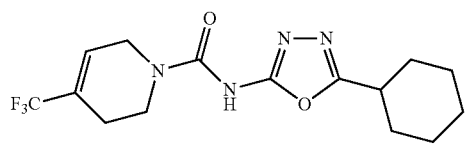 [SMILES: O=C(Nc1nnc(C2CCCCC2)o1)N1CC=C(C(F)(F)F)CC1] |
| 4807 | 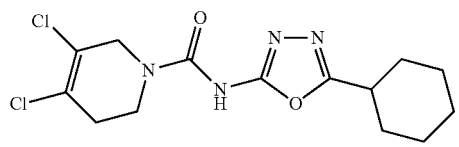 |
| 4808 | 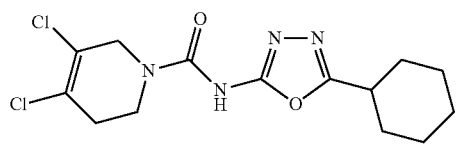 [SMILES: O=C(Nc1nnc(C2CCCCC2)o1)N1CCC(Cl)=C(Cl)C1] |

-continued
| Compound No. MBX- | Structure |
|---|---|
| 4839 | 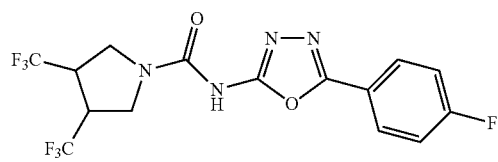 [SMILES: O=C(Nc1nnc(-c2ccc(F)cc2)o1)N1CC(C(F)(F)F)C(C(F)(F)F)C1] |
| 4840 | 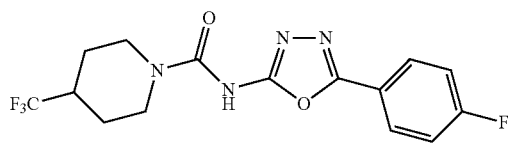 [SMILES: O=C(Nc1nnc(-c2ccc(F)cc2)o1)N1CCC(C(F)(F)F)CC1] |
| 4841 | 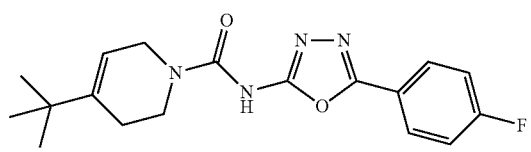 [SMILES: CC(C)(C)C1=CCN(C(=O)Nc2nnc(-c3ccc(F)cc3)o2)CC1] |
| 4842 | 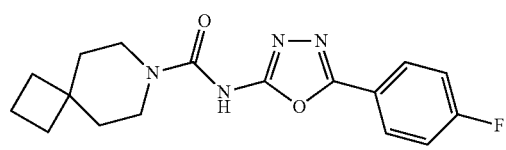 [SMILES: O=C(Nc1nnc(-c2ccc(F)cc2)o1)N1CCC2(CCC2)CC1] |
| 4843 | 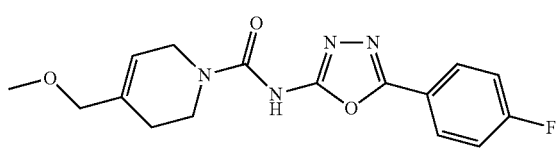 [SMILES: COCC1=CCN(C(=O)Nc2nnc(-c3ccc(F)cc3)o2)CC1] |
| 4922 | 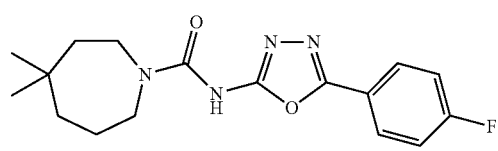 [SMILES: CC1(C)CCCN(C(=O)Nc2nnc(-c3ccc(F)cc3)o2)CC1] |
| 4923 | 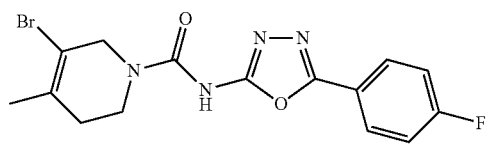 [SMILES: CC1=C(Br)CN(C(=O)Nc2nnc(-c3ccc(F)cc3)o2)CC1] |
| 4930 | 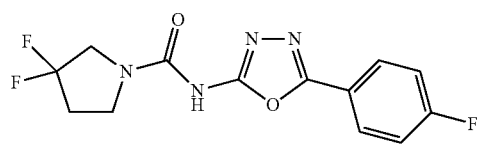 [SMILES: O=C(Nc1nnc(-c2ccc(F)cc2)o1)N1CCC(F)(F)C1] |
| 4931 | 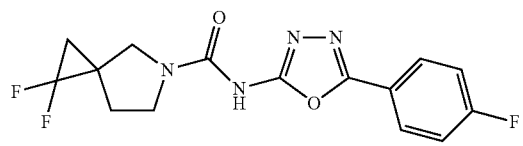 [SMILES: O=C(Nc1nnc(-c2ccc(F)cc2)o1)N1CCC2(C1)CC2(F)F] |

-continued
| Compound No. MBX- | Structure |
|---|---|
| 4932 | 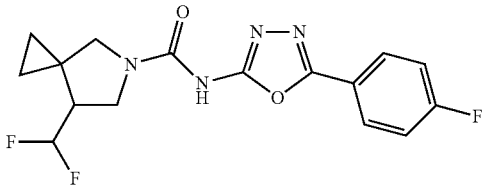 [SMILES: O=C(Nc1nnc(-c2ccc(F)cc2)o1)N1CC(C(F)F)C2(CC2)C1] |
| 4933 | 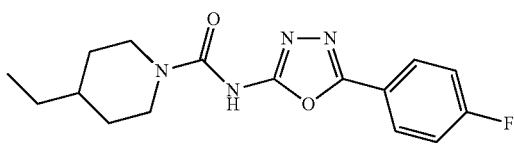 [SMILES: CCC1CCN(C(=O)Nc2nnc(-c3ccc(F)cc3)o2)CC1] |
| 4934 | 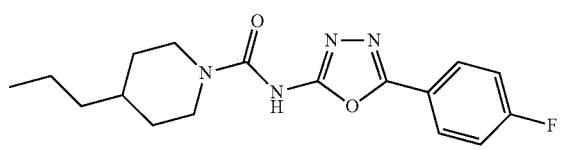 |
| 4935 | 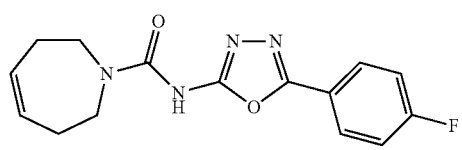 [SMILES: O=C(Nc1nnc(-c2ccc(F)cc2)o1)N1CCC=CCC1] |
| 4936 | 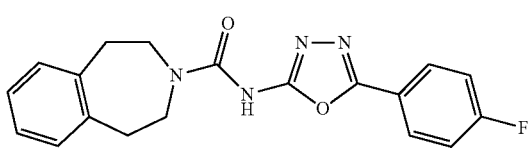 [SMILES: O=C(Nc1nnc(-c2ccc(F)cc2)o1)N1CCc2ccccc2CC1] |
| 4937 | 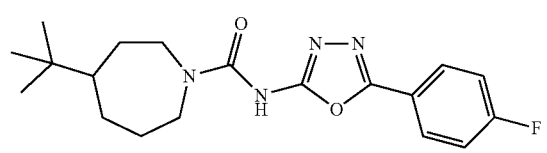 [SMILES: CC(C)(C)C1CCCN(C(=O)Nc2nnc(-c3ccc(F)cc3)o2)CC1] |
| 4938 | 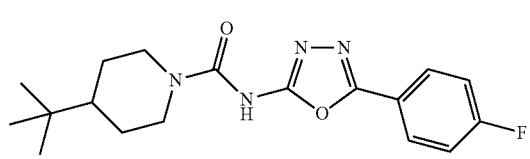 |
| 4939 | 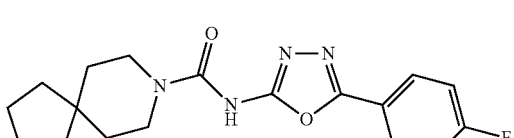 |
| 4940 | 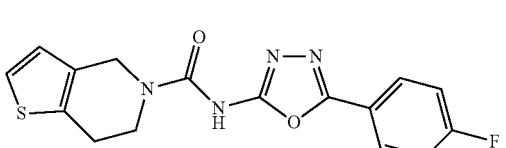 |
| 4993 | 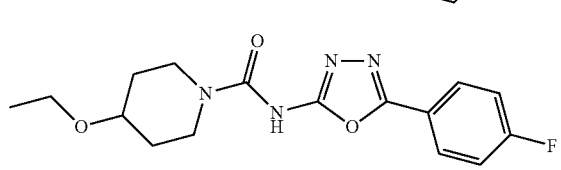 |

| Compound No. MBX- | Structure |
|---|---|
| 4994 | 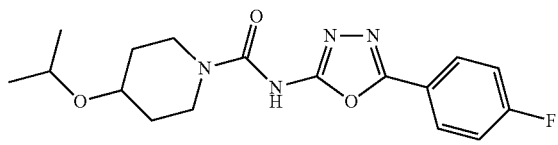 [SMILES: CC(C)OC1CCN(C(=O)Nc2nnc(-c3ccc(F)cc3)o2)CC1] |
| 4995 | 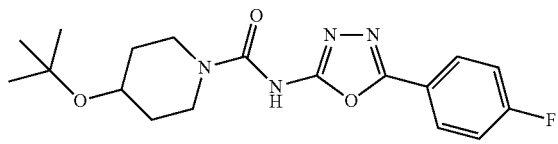 [SMILES: CC(C)(C)OC1CCN(C(=O)Nc2nnc(-c3ccc(F)cc3)o2)CC1] |
| 5154 | 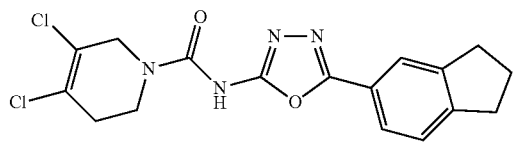 [SMILES: O=C(Nc1nnc(-c2ccc3c(c2)CCC3)o1)N1CCC(Cl)=C(Cl)C1] |
| 5155 | 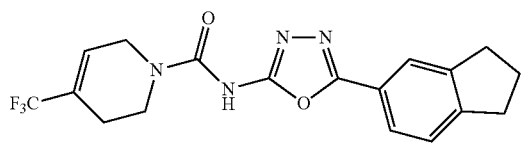 [SMILES: O=C(Nc1nnc(-c2ccc3c(c2)CCC3)o1)N1CC=C(C(F)(F)F)CC1] |
| 5199 | 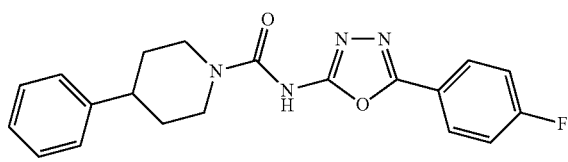 [SMILES: O=C(Nc1nnc(-c2ccc(F)cc2)o1)N1CCC(c2ccccc2)CC1] |
| 5200 | 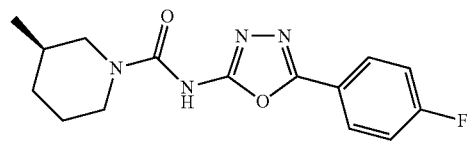 [SMILES: C[C@@H]1CCCN(C(=O)Nc2nnc(-c3ccc(F)cc3)o2)C1] |
| 5201 | 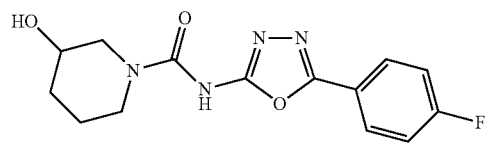 [SMILES: O=C(Nc1nnc(-c2ccc(F)cc2)o1)N1CCCC(O)C1] |
| 5202 | 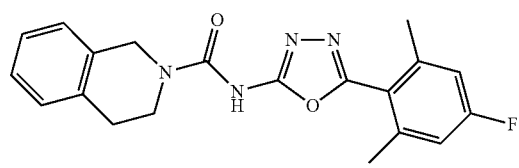 [SMILES: Cc1cc(F)cc(C)c1-c1nnc(NC(=O)N2CCc3ccccc3C2)o1] |
| 5203 | 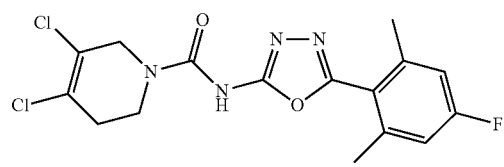 [SMILES: Cc1cc(F)cc(C)c1-c1nnc(NC(=O)N2CCC(Cl)=C(Cl)C2)o1] |

-continued

| Compound No. MBX- | Structure |
|---|---|
| 5204 | 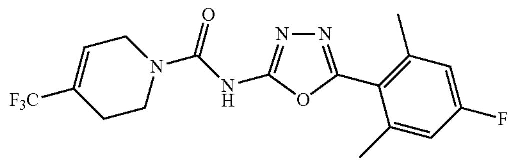 [SMILES: Cc1cc(F)cc(C)c1-c1nnc(NC(=O)N2CC=C(C(F)(F)F)CC2)o1] |
| 5212 | 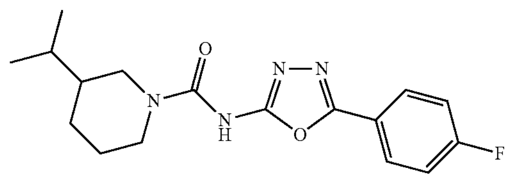 [SMILES: CC(C)C1CCCN(C(=O)Nc2nnc(-c3ccc(F)cc3)o2)C1] |
| 5214 | 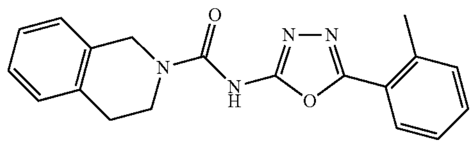 [SMILES: Cc1ccccc1-c1nnc(NC(=O)N2CCc3ccccc3C2)o1] |
| 5215 | 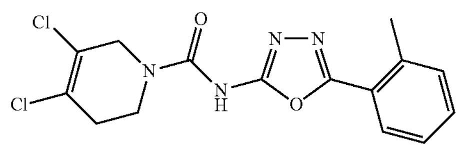 [SMILES: Cc1ccccc1-c1nnc(NC(=O)N2CCC(Cl)=C(Cl)C2)o1] |
| 5216 | 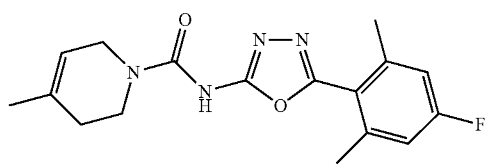 [SMILES: CC1=CCN(C(=O)Nc2nnc(-c3c(C)cc(F)cc3C)o2)CC1] |
| 5222 | 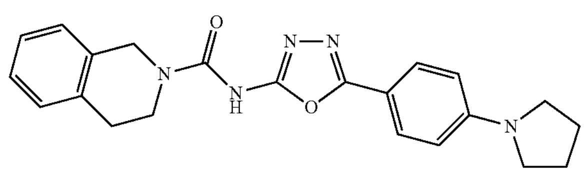 [SMILES: O=C(Nc1nnc(-c2ccc(N3CCCC3)cc2)o1)N1CCc2ccccc2C1] |
| 5223 | 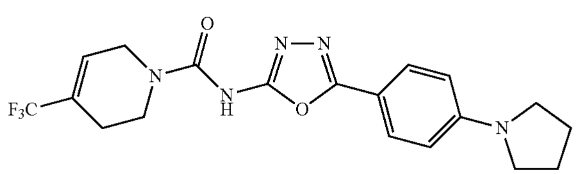 [SMILES: O=C(Nc1nnc(-c2ccc(N3CCCC3)cc2)o1)N1CC=C(C(F)(F)F)CC1] |

In another embodiment, the present invention is directed to a trans-translation inhibitor aryl- or heteroaryl-amidooxadiazole compound having the structure of Formula II:

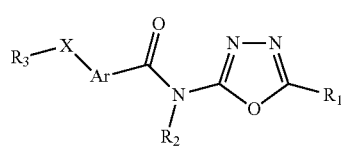

wherein:

$R_1$ is an aryl ring bearing 0-3 substituents (in addition to the oxadiazole group); a 6-membered heteroaryl ring bearing 0-3 substituents (in addition to the oxadiazole group); a 5-membered heteroaromatic ring containing 2, 3, or 4 heteroatoms bearing 0-3 substituents (in addition to the oxadiazole group); an unsubstituted cycloalkyl ring of 5, 6, or 7 carbon atoms; an unsubstituted linear or branched chain aliphatic group containing 5-8 carbon atoms; a substituted linear or branched chain aliphatic group containing 1-6 carbon atoms bearing 1-8 substituents (1-2 substituents per aliphatic chain carbon, or up to 3 substituents on a terminal aliphatic chain carbon) selected from alkyl, cycloalkyl, substituted aryl (bearing 1-4 substituents), heteroaryl, haloalkyl, amino, nitro, halogen, alkoxy, alkylthio, haloalkoxy, sulfonyl, or sulfinyl; a substituted cycloalkyl ring of 3-8 carbon atoms bearing 1-8 substituents (1-2 substituent per ring carbon) selected from alkyl, cycloalkyl, aryl, heteroaryl, haloalkyl, amino, nitro, halogen, alkoxy, alkylthio, haloalkoxy, sulfonyl, or sulfinyl, which cycloalkyl ring may optionally be fused with one or more aryl, heteroaryl, cycloalkyl, or heterocycloalkyl rings; a substituted heterocyclic ring of 3-8 ring atoms made up of carbon atoms and at least one ring member selected independently from oxygen, nitrogen, and sulfur atoms and bearing 1-8 substituents selected from alkyl, cycloalkyl, aryl, heteroaryl, haloalkyl, amino, nitro, halogen, alkoxy, alkylthio, haloalkoxy, sulfonyl, or sulfinyl, which heterocyclic ring may optionally be fused with one or more aryl, heteroaryl, cycloalkyl, or heterocycloalkyl rings;

$R_2$ is a hydrogen; a straight chain aliphatic group; a branched chain aliphatic group; cycloalkyl; haloalkyl; hydroxy; alkoxy; alkylamino; alkylthio; haloalkoxy; sulfonyl; sulfinyl; carboxy; alkoxycarbonyl; or an amido group;

Ar is a 5- or 6-membered aryl or heteroaryl ring bearing X—$R_3$ at C3 or C4 of a 6-membered ring relative to the carboxamide moiety or bearing X—$R_3$ at C3 of a 5-membered ring relative to the carboxamide moiety, wherein Ar may optionally bear up to 3 additional substituents selected from alkyl, cycloalkyl, aryl, heteroaryl, haloalkyl, nitro, halogen, hydroxy, alkoxy, amino, alkylamino, acylamino, thio, alkylthio, carboxy, alkoxycarbonyl, aminocarbonyl, haloalkoxy, sulfonyl, or sulfinyl;

X is oxygen, nitrogen, sulfur, or carbon, wherein if X is carbon, then X has the formula or —CHR—, wherein R is hydrogen, C4-C8 alkyl, C4-C8 cycloalkyl, aryl, heteroaryl, haloalkyl, nitro, halogen, hydroxy, alkoxy, amino, alkylamino, acylamino, thio, alkylthio, carboxy, alkoxycarbonyl, aminocarbonyl, haloalkoxy, sulfonyl, or sulfinyl; wherein if X is a nitrogen, then X has the formula —NR—, wherein R is hydrogen, C4-C8 alkyl, C4-C8 cycloalkyl, aryl, heteroaryl, haloalkyl, nitro, halogen, hydroxy, alkoxy, amino, alkylamino, acylamino, thio, alkylthio, alkoxycarbonyl, aminocarbonyl, haloalkoxy, sulfonyl, or sulfinyl; and wherein if X is a sulfur, then X has the formula —S—, —SO—, —SO$_2$—, or —SNR—, wherein R is hydrogen or a linear, cyclic or branched chain aliphatic group; and $R_3$ is a branched chain aliphatic group of 5-9 carbon atoms; a cycloalkyl group of 4-8 carbon atoms; a 4- to 8-member heterocyclic ring linked to X through a ring carbon atom, aryl, heteroaryl, arylalkyl, or heteroarylalkyl, bearing 1-4 substituents (in addition to the X moiety) selected from alkyl, cycloalkyl, aryl, heteroaryl, haloalkyl, nitro, halogen, hydroxy, alkoxy, amino, alkylamino, acylamino, thio, alkylthio, carboxy, alkoxycarbonyl, aminocarbonyl, haloalkoxy, sulfonyl, or sulfinyl; or, where Ar is a heteroaryl ring, then $R_3$ may be an unsubstituted 4- to 8-member heterocyclic ring or an aryl or heteroaryl ring; or, where X is nitrogen, then $R_3$ can also be unsubstituted aryl or heteroaryl; or, where X is carbon or nitrogen, $R_3$ can also be an unsubstituted 4- to 8-member heterocyclic ring, or X and $R_3$ can together form a non-aromatic, substituted 4- to 8-member heterocyclic ring bearing 1-4 carbon substituents and/or 1-2 nitrogen substituents (in addition to the Ar moiety), where the carbon substituents are selected from alkyl, haloalkyl, nitro, oxo, halogen, alkoxy, alkylthio, haloalkoxy, sulfonyl, sulfinyl, carboxy, or alkoxycarbonyl and/or additional fused cycloalkyl, heterocycloalkyl, aryl or heteroaryl rings, and the nitrogen substituents are selected from alkyl, haloalkyl, nitro, halogen, alkoxy, alkylthio, haloalkoxy, sulfonyl, sulfinyl, alkoxycarbonyl, or aminocarbonyl groups and/or additional fused cycloalkyl, heterocycloalkyl, aryl or heteroaryl rings; or a pharmaceutically acceptable salt thereof.

Compounds according to Formula II of the present invention include, but are not limited to, the following:

| Compound No. mBX- | Structure |
|---|---|
| 4237 | 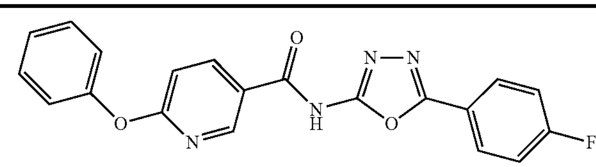 |
| 4258 | 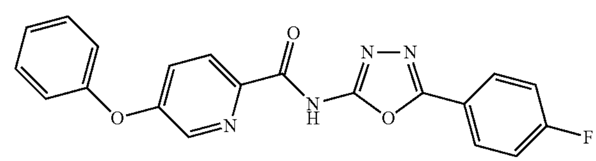 [SMILES: O=C(Nc1nnc(-c2ccc(F)cc2)o1)c1ccc(Oc2ccccc2)cn1] |
| 4284 | 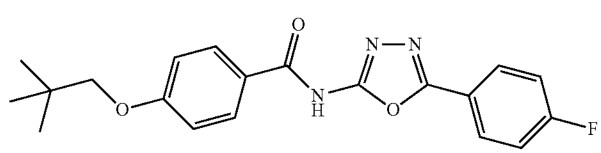 [SMILES: CC(C)(C)COc1ccc(C(=O)Nc2nnc(-c3ccc(F)cc3)o2)cc1] |
| 4285 | 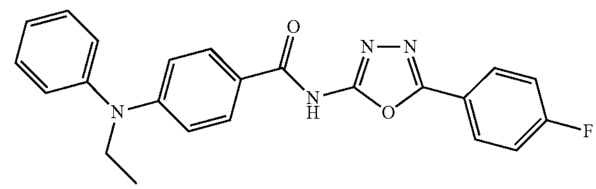 [SMILES: CCN(c1ccccc1)c1ccc(C(=O)Nc2nnc(-c3ccc(F)cc3)o2)cc1] |

-continued

| Compound No. mBX- | Structure |
|---|---|
| 4288 | Boc-azetidin-3-yloxy-phenyl-C(O)NH-[1,3,4-oxadiazol-2-yl]-(4-fluorophenyl) |
| 4289 | Boc-piperidin-4-yloxy-phenyl-C(O)NH-[1,3,4-oxadiazol-2-yl]-(4-fluorophenyl) |
| 4290 | (5-methylpyrazin-2-yl)oxy-phenyl-C(O)NH-[1,3,4-oxadiazol-2-yl]-(4-fluorophenyl) |
| 4292 | cyclohexyloxy-phenyl-C(O)NH-[1,3,4-oxadiazol-2-yl]-(4-fluorophenyl) |
| 4293 | cyclopentyloxy-phenyl-C(O)NH-[1,3,4-oxadiazol-2-yl]-(4-fluorophenyl) |
| 4304 | (3-hydroxyphenoxy)-phenyl-C(O)NH-[1,3,4-oxadiazol-2-yl]-(4-fluorophenyl) |
| 4305 | (4-methylphenoxy)-phenyl-C(O)NH-[1,3,4-oxadiazol-2-yl]-(4-fluorophenyl) |
| 4306 | (3-methylphenoxy)-phenyl-C(O)NH-[1,3,4-oxadiazol-2-yl]-(4-fluorophenyl) |
| 4307 | (2-methylphenoxy)-phenyl-C(O)NH-[1,3,4-oxadiazol-2-yl]-(4-fluorophenyl) |

-continued

| Compound No. mBX- | Structure |
|---|---|
| 4308 | 3,5-dimethylphenoxy-phenyl-C(O)NH-[1,3,4-oxadiazole]-4-fluorophenyl |
| 4309 | 3-methoxyphenoxy-phenyl-C(O)NH-[1,3,4-oxadiazole]-4-fluorophenyl |
| 4310 | 4-methoxyphenoxy-phenyl-C(O)NH-[1,3,4-oxadiazole]-4-fluorophenyl |
| 4314 | 2-phenoxy-pyrimidine-5-C(O)NH-[1,3,4-oxadiazole]-4-fluorophenyl |
| 4357 | 4-(1-phenylethoxy)phenyl-C(O)NH-[1,3,4-oxadiazole]-4-fluorophenyl |
| 4468 | 6-phenoxy-pyridine-3-C(O)NH-[1,3,4-oxadiazole]-methyl |
| 4469 | 6-phenoxy-pyridine-3-C(O)NH-[1,3,4-oxadiazole]-cyclobutyl |
| 4470 | 6-phenoxy-pyridine-3-C(O)NH-[1,3,4-oxadiazole]-cyclopentyl |
| 4498 | 6-phenoxy-pyridine-3-C(O)NH-[1,3,4-oxadiazole]-2-methylphenyl |

-continued
| Compound No. mBX- | Structure |
|---|---|
| 4499 | 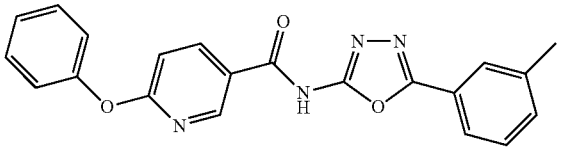 [SMILES: Cc1cccc(-c2nnc(NC(=O)c3ccc(Oc4ccccc4)nc3)o2)c1] |
| 4770 | 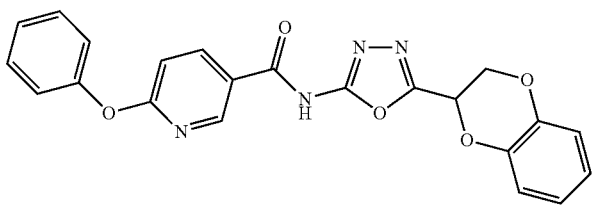 [SMILES: O=C(Nc1nnc(C2COc3ccccc3O2)o1)c1ccc(Oc2ccccc2)nc1] |
| 4780 | 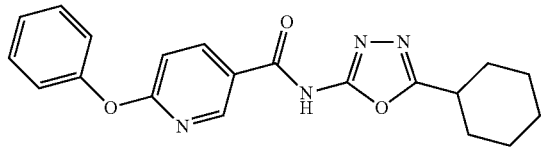 [SMILES: O=C(Nc1nnc(C2CCCCC2)o1)c1ccc(Oc2ccccc2)nc1] |
| 4801 | 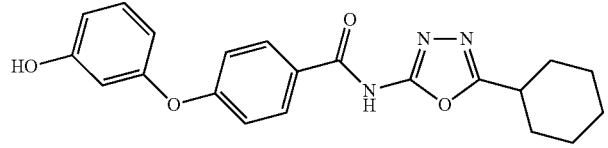 [SMILES: O=C(Nc1nnc(C2CCCCC2)o1)c1ccc(Oc2cccc(O)c2)cc1] |
| 4802 | 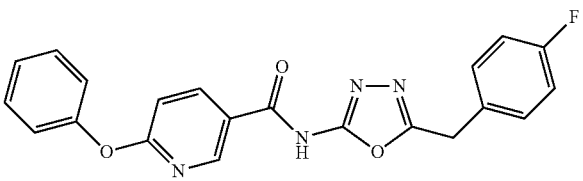 [SMILES: O=C(Nc1nnc(Cc2ccc(F)cc2)o1)c1ccc(Oc2ccccc2)nc1] |
| 4925 | 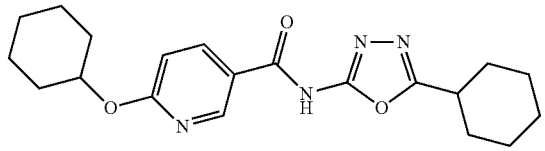 [SMILES: O=C(Nc1nnc(C2CCCCC2)o1)c1ccc(OC2CCCCC2)nc1] |
| 4926 | 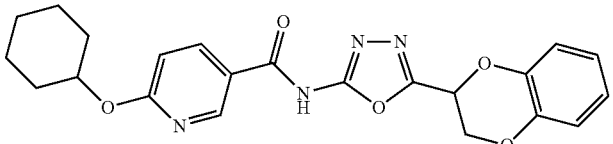 |
In another embodiment, the present invention is directed to use of the aryl- or heteroaryl-amidooxadiazole compound of Formula II in a method of treating or preventing a bacterial infection in a mammalian subject, comprising administering to a subject in need thereof an effective amount of at least compound of Formula II:

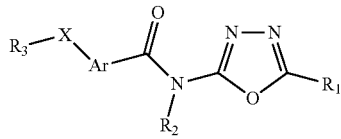

(II)

wherein:

R₁ is an aryl ring bearing 0-3 substituents (in addition to the oxadiazole group); a 6-membered heteroaryl ring bearing 0-3 substituents (in addition to the oxadiazole group); a 5-membered heteroaromatic ring containing 2, 3, or 4 heteroatoms bearing 0-3 substituents (in addition to the oxadiazole group); an unsubstituted cycloalkyl ring of 5, 6, or 7 carbon atoms; an unsubstituted linear or branched chain aliphatic group containing 5-8 carbon atoms; a substituted linear or branched chain aliphatic group containing 1-6 carbon atoms bearing 1-8 substituents (1-2 substituents per aliphatic chain carbon, or up to 3 substituents on a terminal aliphatic chain carbon) selected from alkyl, cycloalkyl, substituted aryl (bearing 1-4 substituents), heteroaryl, haloalkyl, amino, nitro, halogen, alkoxy, alkylthio, haloalkoxy, sulfonyl, or sulfinyl; a substituted cycloalkyl ring of 3-8 carbon atoms bearing 1-8 substituents (1-2 substituent per ring carbon) selected from alkyl, cycloalkyl, aryl, heteroaryl, haloalkyl, amino, nitro, halogen, alkoxy, alkylthio, haloalkoxy, sulfonyl, or sulfinyl, which cycloalkyl ring may optionally be fused with one or more aryl, heteroaryl, cycloalkyl, or heterocycloalkyl rings; a substituted heterocyclic ring of 3-8 ring atoms made up of carbon atoms and at least one ring member selected independently from oxygen, nitrogen, and sulfur atoms and bearing 1-8 substituents selected from alkyl, cycloalkyl, aryl, heteroaryl, haloalkyl, amino, nitro, halogen, alkoxy, alkylthio, haloalkoxy, sulfonyl, or sulfinyl, which heterocyclic ring may optionally be fused with one or more aryl, heteroaryl, cycloalkyl, or heterocycloalkyl rings;

R₂ is a hydrogen; a straight chain aliphatic group; a branched chain aliphatic group; cycloalkyl; haloalkyl; hydroxy; alkoxy; alkylamino; alkylthio; haloalkoxy; sulfonyl; sulfinyl; carboxy; alkoxycarbonyl; or an amido group;

Ar is a 5- or 6-membered aryl or heteroaryl ring bearing X—R₃ at C3 or C4 of a 6-membered ring relative to the carboxamide moiety or bearing X—R₃ at C3 of a 5-membered ring relative to the carboxamide moiety, wherein Ar may optionally bear up to 3 additional substituents selected from alkyl, cycloalkyl, aryl, heteroaryl, haloalkyl, nitro, halogen, hydroxy, alkoxy, amino, alkylamino, acylamino, thio, alkylthio, carboxy, alkoxycarbonyl, aminocarbonyl, haloalkoxy, sulfonyl, or sulfinyl;

X is oxygen, nitrogen, sulfur, or carbon, wherein if X is carbon, then X has the formula or —CHR—, wherein R is hydrogen, C4-C8 alkyl, C4-C8 cycloalkyl, aryl, heteroaryl, haloalkyl, nitro, halogen, hydroxy, alkoxy, amino, alkylamino, acylamino, thio, alkylthio, carboxy, alkoxycarbonyl, aminocarbonyl, haloalkoxy, sulfonyl, or sulfinyl; wherein if X is a nitrogen, then X has the formula —NR—, wherein R is hydrogen, C4-C8 alkyl, C4-C8 cycloalkyl, aryl, heteroaryl, haloalkyl, nitro, halogen, hydroxy, alkoxy, amino, alkylamino, acylamino, thio, alkylthio, alkoxycarbonyl, aminocarbonyl, haloalkoxy, sulfonyl, or sulfinyl; and wherein if X is a sulfur, then X has the formula —S—, —SO—, —SO₂—, or —SNR—, wherein R is hydrogen or a linear, cyclic or branched chain aliphatic group; and R₃ is a branched chain aliphatic group of 5-9 carbon atoms; a cycloalkyl group of 4-8 carbon atoms; a 4- to 8-member heterocyclic ring linked to X through a ring carbon atom, aryl, heteroaryl, arylalkyl, or heteroarylalkyl, bearing 1-4 substituents (in addition to the X moiety) selected from alkyl, cycloalkyl, aryl, heteroaryl, haloalkyl, nitro, halogen, hydroxy, alkoxy, amino, alkylamino, acylamino, thio, alkylthio, carboxy, alkoxycarbonyl, aminocarbonyl, haloalkoxy, sulfonyl, or sulfinyl; or, where Ar is a heteroaryl ring, then R₃ may be an unsubstituted 4- to 8-member heterocyclic ring or an aryl or heteroaryl ring; or, where X is nitrogen, then R₃ can also be unsubstituted aryl or heteroaryl; or, where X is carbon or nitrogen, R₃ can also be an unsubstituted 4- to 8-member heterocyclic ring, or X and R₃ can together form a non-aromatic, substituted 4- to 8-member heterocyclic ring bearing 1-4 carbon substituents and/or 1-2 nitrogen substituents (in addition to the Ar moiety), where the carbon substituents are selected from alkyl, haloalkyl, nitro, oxo, halogen, alkoxy, alkylthio, haloalkoxy, sulfonyl, sulfinyl, carboxy, or alkoxycarbonyl and/or additional fused cycloalkyl, heterocycloalkyl, aryl or heteroaryl rings, and the nitrogen substituents are selected from alkyl, haloalkyl, nitro, halogen, alkoxy, alkylthio, haloalkoxy, sulfonyl, sulfinyl, alkoxycarbonyl, or aminocarbonyl groups and/or additional fused cycloalkyl, heterocycloalkyl, aryl or heteroaryl rings; or a pharmaceutically acceptable salt thereof.

Compounds according to Formula II of the present invention suitable for use in a method for treating or preventing a bacterial infection include, but are not limited to, the following:

| Compound No. MBX- | Structure |
|---|---|
| 4237 | 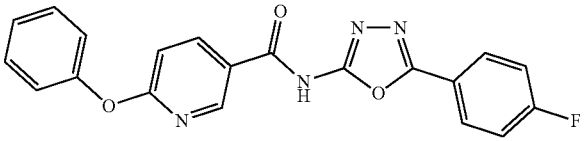 [SMILES: O=C(Nc1nnc(-c2ccc(F)cc2)o1)c1ccc(Oc2ccccc2)nc1] |
| 4258 | 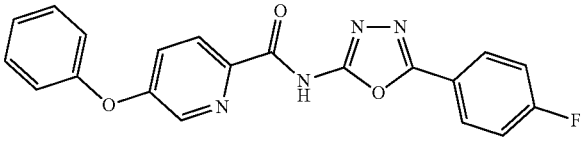 [SMILES: O=C(Nc1nnc(-c2ccc(F)cc2)o1)c1ccc(Oc2ccccc2)cn1] |

-continued

| Compound No. MBX- | Structure |
|---|---|
| 4284 | neopentyl-O-C6H4-C(O)NH-[1,3,4-oxadiazole]-C6H4-F |
| 4285 | Ph(Et)N-C6H4-C(O)NH-[1,3,4-oxadiazole]-C6H4-F |
| 4288 | Boc-azetidin-3-yl-O-C6H4-C(O)NH-[1,3,4-oxadiazole]-C6H4-F |
| 4289 | Boc-piperidin-4-yl-O-C6H4-C(O)NH-[1,3,4-oxadiazole]-C6H4-F |
| 4290 | (6-methylpyrazin-2-yl)-O-C6H4-C(O)NH-[1,3,4-oxadiazole]-C6H4-F |
| 4292 | cyclohexyl-O-C6H4-C(O)NH-[1,3,4-oxadiazole]-C6H4-F |
| 4293 | cyclopentyl-O-C6H4-C(O)NH-[1,3,4-oxadiazole]-C6H4-F |
| 4304 | (3-hydroxyphenyl)-O-C6H4-C(O)NH-[1,3,4-oxadiazole]-C6H4-F |
| 4305 | (4-methylphenyl)-O-C6H4-C(O)NH-[1,3,4-oxadiazole]-C6H4-F |

| Compound No. MBX- | Structure |
|---|---|
| 4306 | 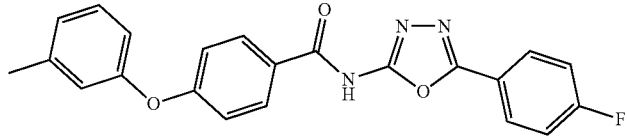 [SMILES: Cc1cccc(Oc2ccc(C(=O)Nc3nnc(-c4ccc(F)cc4)o3)cc2)c1] |
| 4307 | 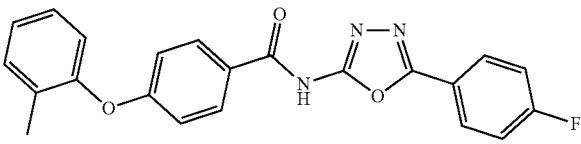 [SMILES: Cc1ccccc1Oc1ccc(C(=O)Nc2nnc(-c3ccc(F)cc3)o2)cc1] |
| 4308 | 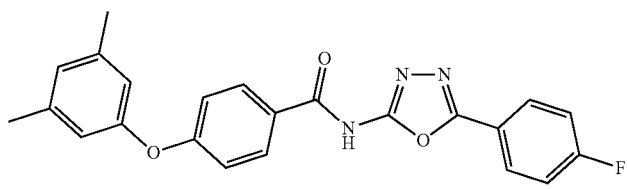 [SMILES: Cc1cc(C)cc(Oc2ccc(C(=O)Nc3nnc(-c4ccc(F)cc4)o3)cc2)c1] |
| 4309 | 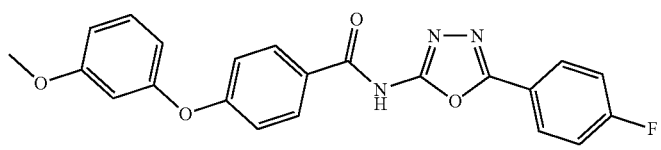 [SMILES: COc1cccc(Oc2ccc(C(=O)Nc3nnc(-c4ccc(F)cc4)o3)cc2)c1] |
| 4310 | 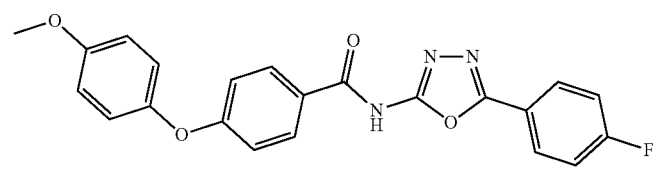 [SMILES: COc1ccc(Oc2ccc(C(=O)Nc3nnc(-c4ccc(F)cc4)o3)cc2)cc1] |
| 4314 | 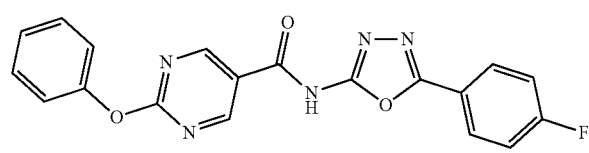 [SMILES: O=C(Nc1nnc(-c2ccc(F)cc2)o1)c1cnc(Oc2ccccc2)nc1] |
| 4357 | 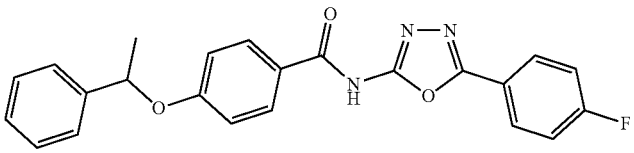 [SMILES: CC(Oc1ccc(C(=O)Nc2nnc(-c3ccc(F)cc3)o2)cc1)c1ccccc1] |
| 4468 | 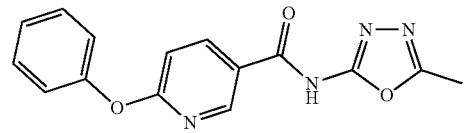 [SMILES: Cc1nnc(NC(=O)c2ccc(Oc3ccccc3)nc2)o1] |
| 4469 | 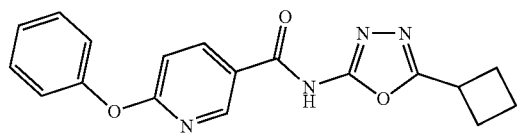 [SMILES: O=C(Nc1nnc(C2CCC2)o1)c1ccc(Oc2ccccc2)nc1] |
| 4470 | 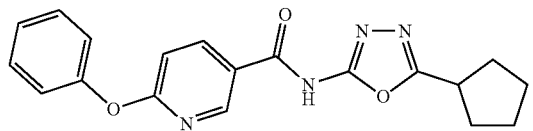 [SMILES: O=C(Nc1nnc(C2CCCC2)o1)c1ccc(Oc2ccccc2)nc1] |

-continued
| Compound No. MBX- | Structure |
|---|---|
| 4498 | 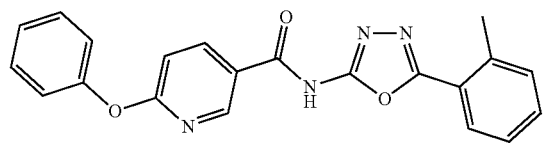 [SMILES: Cc1ccccc1-c1nnc(NC(=O)c2ccc(Oc3ccccc3)nc2)o1] |
| 4499 | 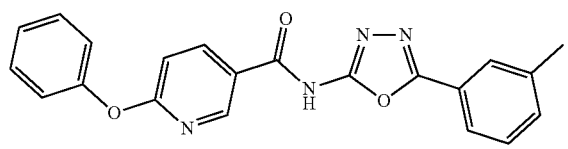 [SMILES: Cc1cccc(-c2nnc(NC(=O)c3ccc(Oc4ccccc4)nc3)o2)c1] |
| 4770 | 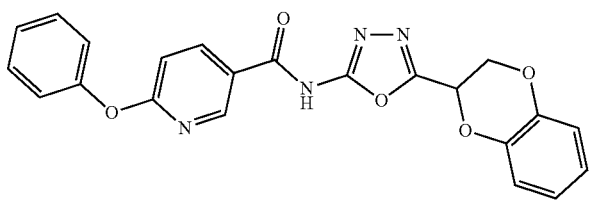 [SMILES: O=C(Nc1nnc(C2COc3ccccc3O2)o1)c1ccc(Oc2ccccc2)nc1] |
| 4780 | 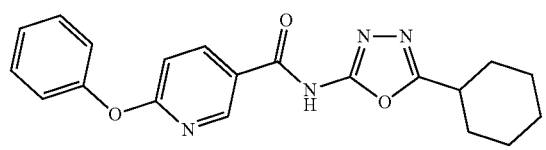 [SMILES: O=C(Nc1nnc(C2CCCCC2)o1)c1ccc(Oc2ccccc2)nc1] |
| 4801 | 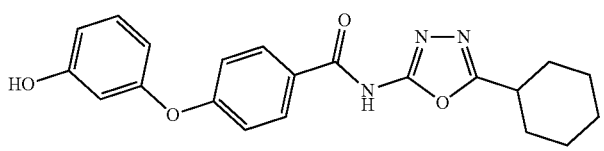 [SMILES: O=C(Nc1nnc(C2CCCCC2)o1)c1ccc(Oc2cccc(O)c2)cc1] |
| 4802 | 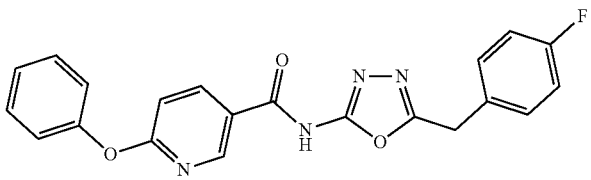 [SMILES: O=C(Nc1nnc(Cc2ccc(F)cc2)o1)c1ccc(Oc2ccccc2)nc1] |
| 4925 | 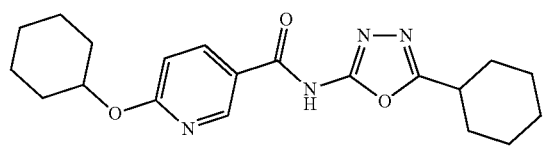 [SMILES: O=C(Nc1nnc(C2CCCCC2)o1)c1ccc(OC2CCCCC2)nc1] |
| 4926 | 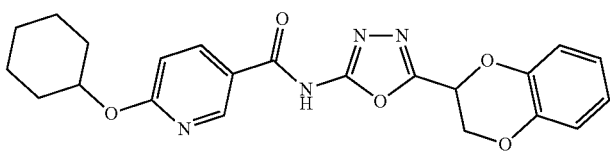 [SMILES: O=C(Nc1nnc(C2COc3ccccc3O2)o1)c1ccc(OC2CCCCC2)nc1] |

In another embodiment, the present invention is directed to a novel trans-translation inhibitor ureido oxadiazole compound having the structure of Formula Ia:

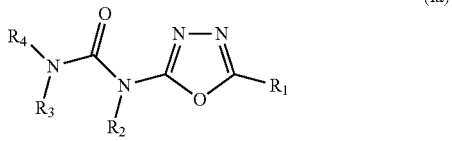

wherein:

$R_1$ is an aryl ring bearing 1-4 substituents (in addition to the oxadiazole group); a 6-membered heteroaryl ring bearing 1-4 substituents (in addition to the oxadiazole group); a 6-membered heteroaryl ring containing 2, 3, or 4 heteroatoms and bearing 0-3 substituents (in addition to the oxadiazole group); a 5-membered heteroaryl ring containing 2, 3, or 4 heteroatoms and bearing 0-3 substituents (in addition to the oxadiazole group); an unsubstituted cycloalkyl ring of 5, 6, or 7 carbon atoms; an unsubstituted linear or branched chain aliphatic group containing 5-8 carbon atoms; a substituted linear or branched chain aliphatic group containing 1-6 carbon atoms bearing 1-8 substituents (1-2 substituents per aliphatic chain carbon, or up to 3 substituents on a terminal aliphatic chain carbon) selected from alkyl, cycloalkyl, aryl, heteroaryl, haloalkyl, amino, nitro, halogen, alkoxy, alkylthio, haloalkoxy, sulfonyl, or sulfinyl; a substituted cycloalkyl ring of 3-8 carbon atoms bearing 1-8 substituents (1-2 substituents per ring carbon) selected from alkyl, cycloalkyl, aryl, heteroaryl, haloalkyl, amino, nitro, halogen, alkoxy, alkylthio, haloalkoxy, sulfonyl, or sulfinyl, which cycloalkyl ring may optionally be fused with one or more aryl, heteroaryl, cycloalkyl, or heterocycloalkyl rings; a 3-, 4-, 6-, 7-, or 8-member heterocyclic ring made up of carbon atoms and at least one ring heteroatom selected independently from oxygen, nitrogen and sulfur atoms, wherein the ring atom attached to the oxadiazole ring is carbon and said heterocyclic ring bears 0-8 substituents selected from alkyl, cycloalkyl, aryl, heteroaryl, haloalkyl, amino, nitro, halogen, alkoxy, alkylthio, haloalkoxy, sulfonyl, or sulfinyl, which heterocyclic ring may optionally be fused with one or more aryl, heteroaryl, cycloalkyl, or heterocycloalkyl rings; a 5-membered heterocyclic ring made up of carbon atoms and at least one ring heteroatom selected independently from oxygen, nitrogen and sulfur atoms, wherein the ring atom attached to the oxadiazole ring is carbon and with the proviso that the ring atoms at positions 2 and 5 (relative to the point of attachment at position 1 to the oxadiazole moiety) is not nitrogen, and wherein the ring atoms at positions 2 and 5 (relative to the point of attachment at position 1 to the oxadiazole moiety) may each optionally bear 1-2 substituents selected from alkyl, cycloalkyl, aryl, heteroaryl haloalkyl, amino, nitro, halogen, alkoxy, alkylthio, haloalkoxy, sulfonyl, or sulfinyl, and may optionally be fused with one or more aryl, heteroaryl, cycloalkyl, or heterocycloalkyl rings;

$R_2$ is hydrogen; a straight chain aliphatic group; a branched chain aliphatic group; cycloalkyl; haloalkyl; hydroxy; alkoxy; alkylamino; alkylthio; haloalkoxy; sulfonyl; sulfinyl; carboxy; alkoxycarbonyl; or an amido group;

$R_3$ is a straight chain aliphatic group; a branched chain aliphatic group; cycloalkyl; heterocycloalkyl; haloalkyl; thio; alkylthio; haloalkoxy; sulfonyl; sulfinyl; carboxy; aryl; or heteroaryl;

$R_4$ is a straight chain aliphatic group of 2-8 carbon atoms; a branched chain aliphatic group; a cycloalkyl; heterocycloalkyl; haloalkyl; thio; alkylthio; haloalkoxyalkyl; sulfonyl; sulfinyl; aryl; or heteroaryl; or, alternatively, $R_3$ and $R_4$ may be linked together to form a substituted 3-8-member cyclic or heterocyclic ring composed of carbon and oxygen and/or nitrogen atoms, the ring having 0-3 degrees of unsaturation and bearing at least 1 and up to four substituents on carbon and/or nitrogen ring members, with carbon substituents including alkyl, haloalkyl, nitro, halogen, alkoxy, alkylthio, haloalkoxy, sulfonyl, sulfinyl, carboxy, and/or alkoxycarbonyl, and with nitrogen substituents including alkyl, haloalkyl, nitro, halogen, alkoxy, alkylthio, haloalkoxy, sulfonyl, sulfinyl, carbonyl, alkoxycarbonyl, and/or aminocarbonyl groups, which substituents may optionally be fused with one or more aryl, heteroaryl, cycloalkyl, or heterocycloalkyl rings through either carbon or nitrogen attachments, or a pharmaceutically acceptable salt thereof.

Compounds according to Formula Ia of the present invention include, but are not limited to, the following:

| Compound No. MBX- | Structure |
|---|---|
| 4132 | 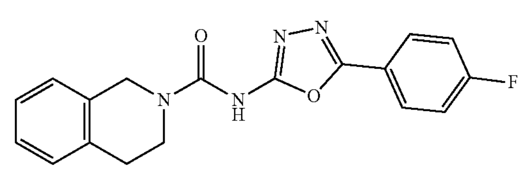 [SMILES: O=C(Nc1nnc(-c2ccc(F)cc2)o1)N1CCc2ccccc2C1] |
| 4198 | 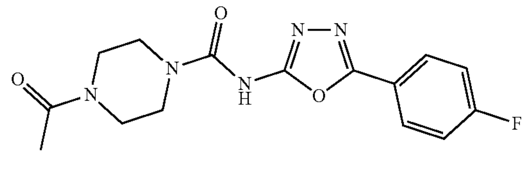 [SMILES: CC(=O)N1CCN(C(=O)Nc2nnc(-c3ccc(F)cc3)o2)CC1] |

| Compound No. MBX- | Structure |
|---|---|
| 4199 | 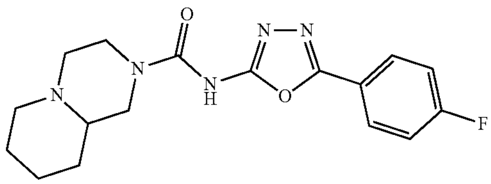 [SMILES: O=C(Nc1nnc(-c2ccc(F)cc2)o1)N1CCN2CCCCC2C1] |
| 4200 | 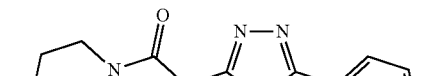 |
| 4201 | 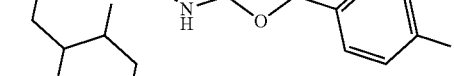 |
| 4330 | 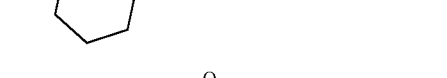 |
| 4331 | 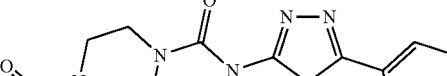 |
| 4332 | 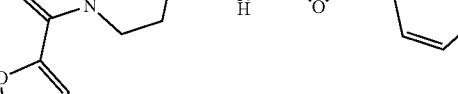 |
| 4333 | 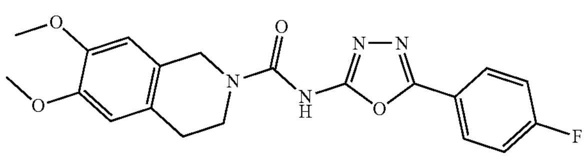 [SMILES: COc1cc2c(cc1OC)CN(C(=O)Nc1nnc(-c3ccc(F)cc3)o1)CC2] |
| 4345 | 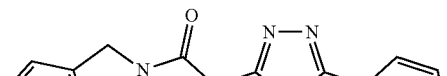 |
| 4346 | 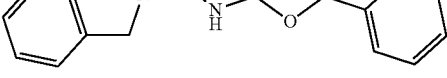 |

-continued

| Compound No. MBX- | Structure |
|---|---|
| 4347 | (structure) |
| 4348 | (structure) |
| 4349 | (structure) |
| 4350 | (structure) |
| 4351 | (structure) |
| 4366 | (structure) |
| 4380 | (structure) |
| 4381 | (structure) |
| 4406 | (structure) |

| Compound No. MBX- | Structure |
|---|---|
| 4464 | 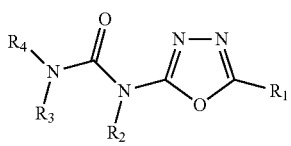 |
| 4465 | 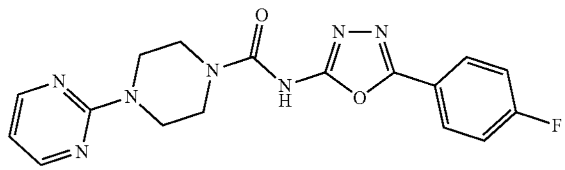 [SMILES: O=C(Nc1nnc(-c2ccc(F)cc2)o1)N1CCN(c2ncccn2)CC1] |
| 4497 | 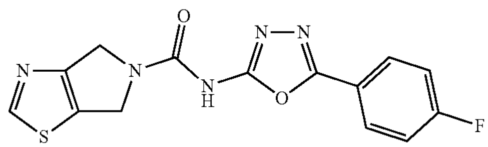 [SMILES: O=C(Nc1nnc(-c2ccc(F)cc2)o1)N1Cc2ncsc2C1] |

In another embodiment, the present invention is directed to use of the ureido oxadiazole compounds of Formula I(a) in a method for treating or preventing a bacterial infection in a mammalian subject by administration of one or more of the compounds of Formula Ia:

(Ia)

wherein:
$R_1$ is an aryl ring bearing 1-4 substituents (in addition to the oxadiazole group); a 6-membered heteroaryl ring bearing 1-4 substituents (in addition to the oxadiazole group); a 6-membered heteroaryl ring containing 2, 3, or 4 heteroatoms and bearing 0-3 substituents (in addition to the oxadiazole group); a 5-membered heteroaryl ring containing 2, 3, or 4 heteroatoms and bearing 0-3 substituents (in addition to the oxadiazole group); an unsubstituted cycloalkyl ring of 5, 6, or 7 carbon atoms; an unsubstituted linear or branched chain aliphatic group containing 5-8 carbon atoms; a substituted linear or branched chain aliphatic group containing 1-6 carbon atoms bearing 1-8 substituents (1-2 substituents per aliphatic chain carbon, or up to 3 substituents on a terminal aliphatic chain carbon) selected from alkyl, cycloalkyl, aryl, heteroaryl, haloalkyl, amino, nitro, halogen, alkoxy, alkylthio, haloalkoxy, sulfonyl, or sulfinyl; a substituted cycloalkyl ring of 3-8 carbon atoms bearing 1-8 substituents (1-2 substituents per ring carbon) selected from alkyl, cycloalkyl, aryl, heteroaryl, haloalkyl, amino, nitro, halogen, alkoxy, alkylthio, haloalkoxy, sulfonyl, or sulfinyl, which cycloalkyl ring may optionally be fused with one or more aryl, heteroaryl, cycloalkyl, or heterocycloalkyl rings; a 3-, 4-, 6-, 7-, or 8-member heterocyclic ring made up of carbon atoms and at least one ring heteroatom selected independently from oxygen, nitrogen and sulfur atoms, wherein the ring atom attached to the oxadiazole ring is carbon and said heterocyclic ring bears 0-8 substituents selected from alkyl, cycloalkyl, aryl, heteroaryl, haloalkyl, amino, nitro, halogen, alkoxy, alkylthio, haloalkoxy, sulfonyl, or sulfinyl, which heterocyclic ring may optionally be fused with one or more aryl, heteroaryl, cycloalkyl, or heterocycloalkyl rings; a 5-membered heterocyclic ring made up of carbon atoms and at least one ring heteroatom selected independently from oxygen, nitrogen and sulfur atoms, wherein the ring atom attached to the oxadiazole ring is carbon and with the proviso that the ring atoms at positions 2 and 5 (relative to the point of attachment at position 1 to the oxadiazole moiety) is not nitrogen, and whereinthe ring atoms at positions 2 and 5 (relative to the point of attachment at position 1 to the oxadiazole moiety) may each optionally bear 1-2 substituents selected from alkyl, cycloalkyl, aryl, heteroaryl haloalkyl, amino, nitro, halogen, alkoxy, alkylthio, haloalkoxy, sulfonyl, or sulfinyl, and may optionally be fused with one or more aryl, heteroaryl, cycloalkyl, or heterocycloalkyl rings;

$R_2$ is hydrogen; a straight chain aliphatic group; a branched chain aliphatic group; cycloalkyl; haloalkyl; hydroxy; alkoxy; alkylamino; alkylthio; haloalkoxy; sulfonyl; sulfinyl; carboxy; alkoxycarbonyl; or an amido group;

$R_3$ is a straight chain aliphatic group; a branched chain aliphatic group; cycloalkyl; heterocycloalkyl; haloalkyl; thio; alkylthio; haloalkoxy; sulfonyl; sulfinyl; carboxy; alkoxycarbonyl; aryl; or heteroaryl;

$R_4$ is a straight chain aliphatic group of 2-8 carbon atoms; a branched chain aliphatic group; a cycloalkyl; heterocycloalkyl; haloalkyl; thio; alkylthio; haloalkoxyalkyl; sulfonyl; sulfinyl; alkoxycarbonyl; aryl; or heteroaryl; or, alternatively, $R_3$ and $R_4$ may be linked together to form a substituted 3-8-member cyclic or heterocyclic ring composed of carbon and oxygen and/or nitrogen atoms, the ring having 0-3 degrees of unsaturation and bearing at least 1 and up to four substituents on carbon and/or nitrogen ring members, with carbon substituents including alkyl, haloalkyl, nitro, halogen, alkoxy, alkylthio, haloalkoxy, sulfonyl, sulfinyl, carboxy, and/or alkoxycarbonyl, and with nitrogen substituents including alkyl, haloalkyl, nitro, halogen, alkoxy, alkylthio, haloalkoxy, sulfonyl, sulfinyl, carbonyl, alkoxycarbonyl, and/or aminocarbonyl groups, which substituents may optionally be fused with one or more aryl, heteroaryl, cycloalkyl, or heterocycloalkyl rings through either carbon or nitrogen attachments,
or a pharmaceutically acceptable salt thereof.

Compounds for use according to the method for treating or preventing a bacterial infection by administering a compound of Formula Ia include but are not limited to, the following:

| Compound No. MBX- | Structure |
|---|---|
| 4132 | 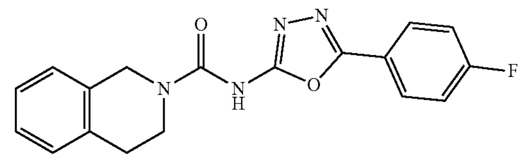 [SMILES: O=C(Nc1nnc(-c2ccc(F)cc2)o1)N1CCc2ccccc2C1] |
| 4198 | 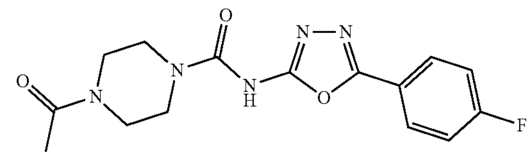 [SMILES: CC(=O)N1CCN(C(=O)Nc2nnc(-c3ccc(F)cc3)o2)CC1] |
| 4199 | 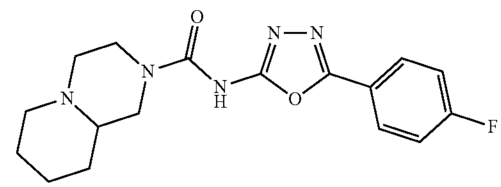 [SMILES: O=C(Nc1nnc(-c2ccc(F)cc2)o1)N1CCN2CCCCC2C1] |
| 4200 | 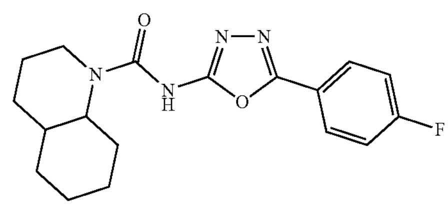 [SMILES: O=C(Nc1nnc(-c2ccc(F)cc2)o1)N1CCCC2CCCCC21] |
| 4201 | 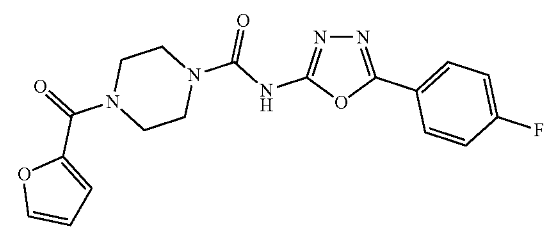 [SMILES: O=C(Nc1nnc(-c2ccc(F)cc2)o1)N1CCN(C(=O)c2ccco2)CC1] |
| 4330 | 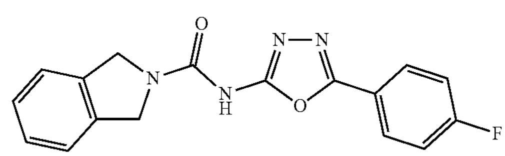 [SMILES: O=C(Nc1nnc(-c2ccc(F)cc2)o1)N1Cc2ccccc2C1] |
| 4331 | 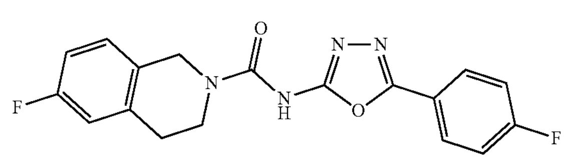 [SMILES: O=C(Nc1nnc(-c2ccc(F)cc2)o1)N1CCc2cc(F)ccc2C1] |
| 4332 | 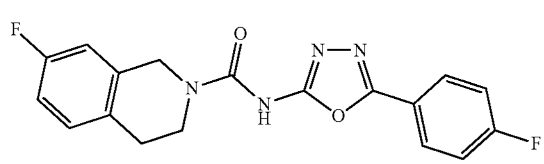 [SMILES: O=C(Nc1nnc(-c2ccc(F)cc2)o1)N1CCc2ccc(F)cc2C1] |

-continued

| Compound No. MBX- | Structure |
|---|---|
| 4333 | ![structure] 6,7-dimethoxy-3,4-dihydroisoquinoline-2(1H)-carboxamide linked to 5-(4-fluorophenyl)-1,3,4-oxadiazol-2-yl |
| 4345 | N-allyl-N-methyl urea linked to 5-(4-fluorophenyl)-1,3,4-oxadiazol-2-yl |
| 4346 | pyrrolidine-1-carboxamide linked to 5-(4-fluorophenyl)-1,3,4-oxadiazol-2-yl |
| 4347 | 4-(trifluoromethyl)-3,6-dihydropyridine-1(2H)-carboxamide linked to 5-(4-fluorophenyl)-1,3,4-oxadiazol-2-yl |
| 4348 | methyl 4-(carbamoyl)-3,6-dihydropyridine-1(2H)-carboxylate linked to 5-(4-fluorophenyl)-1,3,4-oxadiazol-2-yl |
| 4349 | 4-methyl-1,4-diazepane-1-carboxamide linked to 5-(4-fluorophenyl)-1,3,4-oxadiazol-2-yl |
| 4350 | 3-oxopiperazine-1-carboxamide linked to 5-(4-fluorophenyl)-1,3,4-oxadiazol-2-yl |
| 4351 | 4-methyl-3-oxopiperazine-1-carboxamide linked to 5-(4-fluorophenyl)-1,3,4-oxadiazol-2-yl |
| 4366 | 4-methyl-3,6-dihydropyridine-1(2H)-carboxamide linked to 5-(4-fluorophenyl)-1,3,4-oxadiazol-2-yl |
| 4380 | 3-oxa-8-azabicyclo[3.2.1] carboxamide linked to 5-(4-fluorophenyl)-1,3,4-oxadiazol-2-yl |

| Compound No. MBX- | Structure |
|---|---|
| 4381 | ![structure] |
| 4406 | ![structure] |
| 4464 | ![structure] |
| 4465 | ![structure] |
| 4497 | ![structure] |

In another embodiment, the present invention is directed to a trans-translation inhibitor aryl- or heteroaryl-amidooxadiazole compound having the structure of Formula IIa:

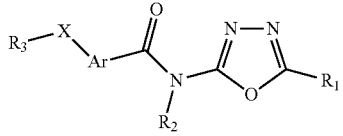

(IIa)

wherein:

$R_1$ is an aryl ring bearing 0-3 substituents (in addition to the oxadiazole group); a 6-membered heteroaryl ring bearing 0-3 substituents (in addition to the oxadiazole group); a 5-membered heteroaromatic ring containing 2, 3, or 4 heteroatoms bearing 0-3 substituents (in addition to the oxadiazole group); an unsubstituted cycloalkyl ring of 5, 6, or 7 carbon atoms; an unsubstituted linear or branched chain aliphatic group containing 5-8 carbon atoms; a substituted linear or branched chain aliphatic group containing 1-6 carbon atoms bearing 1-8 substituents (1-2 substituents per aliphatic chain carbon, or up to 3 substituents on a terminal aliphatic chain carbon) selected from alkyl, cycloalkyl, substituted aryl (bearing 1-4 substituents), heteroaryl, haloalkyl, amino, nitro, halogen, alkoxy, alkylthio, haloalkoxy, sulfonyl, or sulfinyl; a substituted cycloalkyl ring of 3-8 carbon atoms bearing 1-8 substituents (1-2 substituent per ring carbon) selected from alkyl, cycloalkyl, aryl, heteroaryl, haloalkyl, amino, nitro, halogen, alkoxy, alkylthio, haloalkoxy, sulfonyl, or sulfinyl, which cycloalkyl ring may optionally be fused with one or more aryl, heteroaryl, cycloalkyl, or heterocycloalkyl rings; a substituted heterocyclic ring of 3-8 ring atoms made up of carbon atoms and at least one ring member selected independently from oxygen, nitrogen, and sulfur atoms and bearing 1-8 substituents selected from alkyl, cycloalkyl, aryl, heteroaryl, haloalkyl, amino, nitro, halogen, alkoxy, alkylthio, haloalkoxy, sulfonyl, or sulfinyl, which heterocyclic ring may optionally be fused with one or more aryl, heteroaryl, cycloalkyl, or heterocycloalkyl rings;

$R_2$ is a hydrogen; a straight chain aliphatic group; a branched chain aliphatic group; cycloalkyl; haloalkyl; hydroxy; alkoxy; alkylamino; alkylthio; haloalkoxy; sulfonyl; sulfinyl; carboxy; alkoxycarbonyl; or an amido group;

Ar is a 5- or 6-membered aryl or heteroaryl ring bearing X—$R_3$ at C3 or C4 of a 6-membered ring relative to the carboxamide moiety or bearing X—$R_3$ at C3 of a 5-membered ring relative to the carboxamide moiety, wherein Ar may optionally bear up to 3 additional substituents selected from alkyl, cycloalkyl, aryl, heteroaryl, haloalkyl, nitro, halogen, hydroxy, alkoxy, amino, alkylamino, acylamino, thio, alkylthio, carboxy, alkoxycarbonyl, aminocarbonyl, haloalkoxy, sulfonyl, or sulfinyl;

X is oxygen, nitrogen, sulfur, or carbon, wherein if X is carbon, then X has the formula —CHR—, wherein R is hydrogen, C4-C8 alkyl, C4-C8 cycloalkyl, aryl, heteroaryl, haloalkyl, nitro, halogen, hydroxy, alkoxy, amino, alkylamino, acylamino, thio, alkylthio, carboxy, alkoxycarbonyl, aminocarbonyl, haloalkoxy, sulfonyl, or sulfinyl; wherein if X is a nitrogen, then X has the formula —NR—, wherein R is hydrogen, C4-C8 alkyl, C4-C8 cycloalkyl, aryl, heteroaryl, haloalkyl, nitro, halogen, hydroxy, alkoxy, amino, alkylamino, acylamino, thio, alkylthio, alkoxycarbonyl, aminocarbonyl, haloalkoxy, sulfonyl, or sulfinyl; and wherein if X is a sulfur, then X has the formula —S—, —SO—, —SO$_2$—, or —SNR—, wherein R is hydrogen or a linear, cyclic or branched chain aliphatic group; and R$_3$ is a branched chain aliphatic group of 5-9 carbon atoms; a cycloalkyl group of 4-8 carbon atoms; a 4- to 8-member heterocyclic ring linked to X through a ring carbon atom, aryl, heteroaryl, arylalkyl, or heteroarylalkyl, bearing 1-4 substituents (in addition to the X moiety) selected from alkyl, cycloalkyl, aryl, heteroaryl, haloalkyl, nitro, halogen, hydroxy, alkoxy, amino, alkylamino, acylamino, thio, alkylthio, carboxy, alkoxycarbonyl, aminocarbonyl, haloalkoxy, sulfonyl, or sulfinyl; or, where Ar is a heteroaryl ring, then R$_3$ may be an unsubstituted 4- to 8-member heterocyclic ring or an aryl or heteroaryl ring; or, where X is nitrogen, then R$_3$ can also be unsubstituted aryl or heteroaryl; or, where X is carbon or nitrogen, R$_3$ can also be an unsubstituted 4- to 8-member heterocyclic ring, or X and R$_3$ can together form a non-aromatic, substituted 4- to 8-member heterocyclic ring bearing 1-4 carbon substituents and/or 1-2 nitrogen substituents (in addition to the Ar moiety), where the carbon substituents are selected from alkyl, haloalkyl, nitro, oxo (O=), halogen, alkoxy, alkylthio, haloalkoxy, sulfonyl, sulfinyl, carboxy, or alkoxycarbonyl and/or additional fused cycloalkyl, heterocycloalkyl, aryl or heteroaryl rings, and the nitrogen substituents are selected from alkyl, haloalkyl, nitro, halogen, alkoxy, alkylthio, haloalkoxy, sulfonyl, sulfinyl, alkoxycarbonyl, or aminocarbonyl groups and/or additional fused cycloalkyl, heterocycloalkyl, aryl or heteroaryl rings; or a pharmaceutically acceptable salt thereof.

Compounds according to Formula IIa of the present invention include, but are not limited to, the following:

| Compound No. MBX- | Structure |
|---|---|
| 4237 | 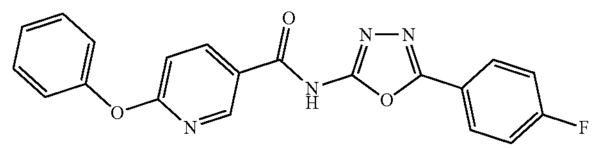 [SMILES: O=C(Nc1nnc(-c2ccc(F)cc2)o1)c1ccc(Oc2ccccc2)nc1] |
| 4258 | 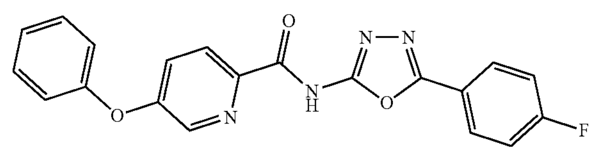 [SMILES: O=C(Nc1nnc(-c2ccc(F)cc2)o1)c1ccc(Oc2ccccc2)cn1] |
| 4284 | 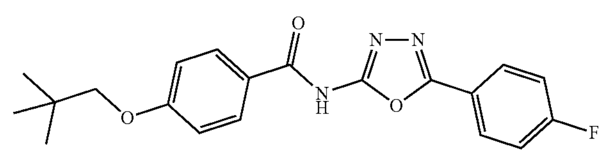 [SMILES: CC(C)(C)COc1ccc(C(=O)Nc2nnc(-c3ccc(F)cc3)o2)cc1] |
| 4285 | 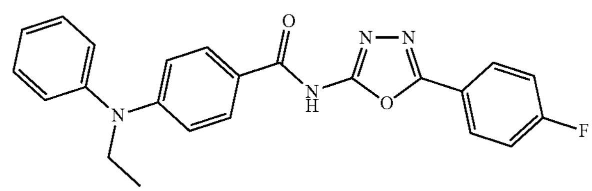 [SMILES: CCN(c1ccccc1)c1ccc(C(=O)Nc2nnc(-c3ccc(F)cc3)o2)cc1] |
| 4288 | 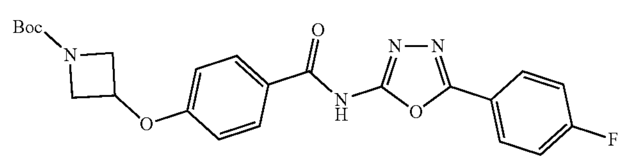 [SMILES: CC(C)(C)OC(=O)N1CC(Oc2ccc(C(=O)Nc3nnc(-c4ccc(F)cc4)o3)cc2)C1] |
| 4289 | 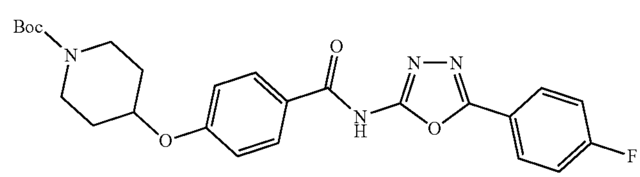 [SMILES: CC(C)(C)OC(=O)N1CCC(Oc2ccc(C(=O)Nc3nnc(-c4ccc(F)cc4)o3)cc2)CC1] |

-continued
| Compound No. MBX- | Structure |
|---|---|
| 4290 | 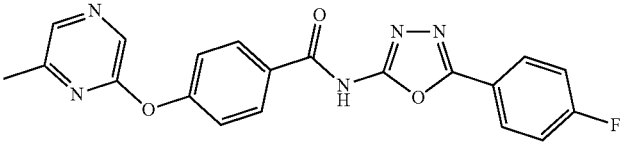 [SMILES: Cc1cncc(Oc2ccc(C(=O)Nc3nnc(-c4ccc(F)cc4)o3)cc2)n1] |
| 4292 | 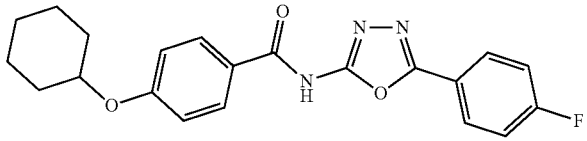 [SMILES: O=C(Nc1nnc(-c2ccc(F)cc2)o1)c1ccc(OC2CCCCC2)cc1] |
| 4293 | 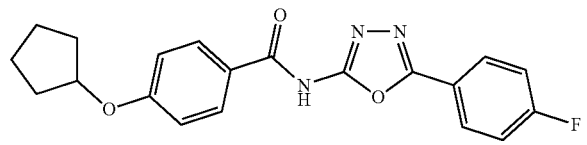 [SMILES: O=C(Nc1nnc(-c2ccc(F)cc2)o1)c1ccc(OC2CCCC2)cc1] |
| 4304 | 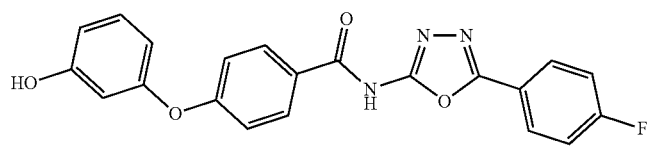 [SMILES: O=C(Nc1nnc(-c2ccc(F)cc2)o1)c1ccc(Oc2cccc(O)c2)cc1] |
| 4305 | 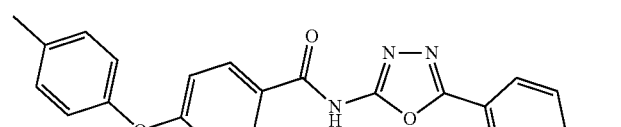 |
| 4306 | 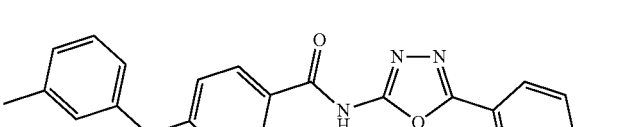 |
| 4307 | 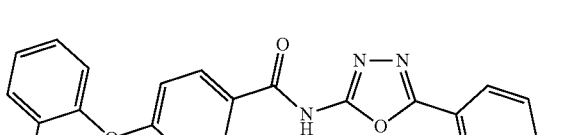 |
| 4308 | 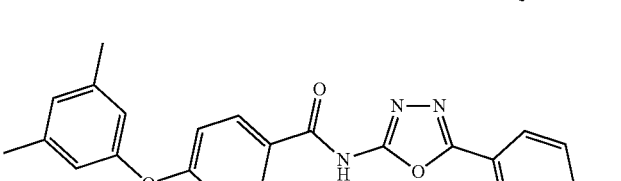 |
| 4309 | 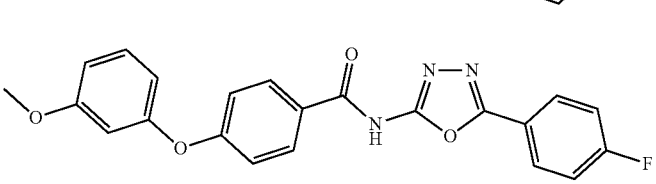 |

| Compound No. MBX- | Structure |
|---|---|
| 4310 | 4-methoxyphenoxy-phenyl-C(=O)NH-[1,3,4-oxadiazol-2-yl]-(4-fluorophenyl) |
| 4314 | 2-phenoxy-pyrimidin-5-yl-C(=O)NH-[1,3,4-oxadiazol-2-yl]-(4-fluorophenyl) |
| 4357 | 4-(1-phenylethoxy)phenyl-C(=O)NH-[1,3,4-oxadiazol-2-yl]-(4-fluorophenyl) |
| 4468 | 6-phenoxy-pyridin-3-yl-C(=O)NH-[1,3,4-oxadiazol-2-yl]-methyl |
| 4469 | 6-phenoxy-pyridin-3-yl-C(=O)NH-[1,3,4-oxadiazol-2-yl]-cyclobutyl |
| 4470 | 6-phenoxy-pyridin-3-yl-C(=O)NH-[1,3,4-oxadiazol-2-yl]-cyclopentyl |
| 4498 | 6-phenoxy-pyridin-3-yl-C(=O)NH-[1,3,4-oxadiazol-2-yl]-(2-methylphenyl) |
| 4499 | 6-phenoxy-pyridin-3-yl-C(=O)NH-[1,3,4-oxadiazol-2-yl]-(3-methylphenyl) |

In another embodiment the present invention is directed to use of one or more of the aryl- or heteroaryl-amidooxadiazole compounds of Formula IIa in a method for treating or preventing a bacterial infection by administration of at least one trans-translator inhibitor compound according to Formula IIa:

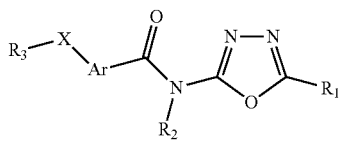

(IIa)

wherein:

R₁ is an aryl ring bearing 0-3 substituents (in addition to the oxadiazole group); a 6-membered heteroaryl ring bearing 0-3 substituents (in addition to the oxadiazole group); a 5-membered heteroaromatic ring containing 2, 3, or 4 heteroatoms bearing 0-3 substituents (in addition to the oxadiazole group); an unsubstituted cycloalkyl ring of 5, 6, or 7 carbon atoms; an unsubstituted linear or branched chain aliphatic group containing 5-8 carbon atoms; a substituted linear or branched chain aliphatic group containing 1-6 carbon atoms bearing 1-8 substituents (1-2 substituents per aliphatic chain carbon, or up to 3 substituents on a terminal aliphatic chain carbon) selected from alkyl, cycloalkyl, substituted aryl (bearing 1-4 substituents), heteroaryl, haloalkyl, amino, nitro, halogen, alkoxy, alkylthio, haloalkoxy, sulfonyl, or sulfinyl; a substituted cycloalkyl ring of 3-8 carbon atoms bearing 1-8 substituents (1-2 substituent per ring carbon) selected from alkyl, cycloalkyl, aryl, heteroaryl, haloalkyl, amino, nitro, halogen, alkoxy, alkylthio, haloalkoxy, sulfonyl, or sulfinyl, which cycloalkyl ring may optionally be fused with one or more aryl, heteroaryl, cycloalkyl, or heterocycloalkyl rings; a substituted heterocyclic ring of 3-8 ring atoms made up of carbon atoms and at least one ring member selected independently from oxygen, nitrogen, and sulfur atoms and bearing 1-8 substituents selected from alkyl, cycloalkyl, aryl, heteroaryl, haloalkyl, amino, nitro, halogen, alkoxy, alkylthio, haloalkoxy, sulfonyl, or sulfinyl, which heterocyclic ring may optionally be fused with one or more aryl, heteroaryl, cycloalkyl, or heterocycloalkyl rings;

R₂ is a hydrogen; a straight chain aliphatic group; a branched chain aliphatic group; cycloalkyl; haloalkyl; hydroxy; alkoxy; alkylamino; alkylthio; haloalkoxy; sulfonyl; sulfinyl; carboxy; alkoxycarbonyl; or an amido group;

Ar is a 5- or 6-membered aryl or heteroaryl ring bearing X—R₃ at C3 or C4 of a 6-membered ring relative to the carboxamide moiety or bearing X—R₃ at C3 of a 5-membered ring relative to the carboxamide moiety, wherein Ar may optionally bear up to 3 additional substituents selected from alkyl, cycloalkyl, aryl, heteroaryl, haloalkyl, nitro, halogen, hydroxy, alkoxy, amino, alkylamino, acylamino, thio, alkylthio, carboxy, alkoxycarbonyl, aminocarbonyl, haloalkoxy, sulfonyl, or sulfinyl;

X is oxygen, nitrogen, sulfur, or carbon, wherein if X is carbon, then X has the formula —CHR—, wherein R is hydrogen, C4-C8 alkyl, C4-C8 cycloalkyl, aryl, heteroaryl, haloalkyl, nitro, halogen, hydroxy, alkoxy, amino, alkylamino, acylamino, thio, alkylthio, carboxy, alkoxycarbonyl, aminocarbonyl, haloalkoxy, sulfonyl, or sulfinyl; wherein if X is a nitrogen, then X has the formula —NR—, wherein R is hydrogen, C4-C8 alkyl, C4-C8 cycloalkyl, aryl, heteroaryl, haloalkyl, nitro, halogen, hydroxy, alkoxy, amino, alkylamino, acylamino, thio, alkylthio, alkoxycarbonyl, aminocarbonyl, haloalkoxy, sulfonyl, or sulfinyl; and wherein if X is a sulfur, then X has the formula —S—, —SO—, —SO₂—, or —SNR—, wherein R is hydrogen or a linear, cyclic or branched chain aliphatic group; and R₃ is a branched chain aliphatic group of 5-9 carbon atoms; a cycloalkyl group of 4-8 carbon atoms; a 4- to 8-member heterocyclic ring linked to X through a ring carbon atom, aryl, heteroaryl, arylalkyl, or heteroarylalkyl, bearing 1-4 substituents (in addition to the X moiety) selected from alkyl, cycloalkyl, aryl, heteroaryl, haloalkyl, nitro, halogen, hydroxy, alkoxy, amino, alkylamino, acylamino, thio, alkylthio, carboxy, alkoxycarbonyl, aminocarbonyl, haloalkoxy, sulfonyl, or sulfinyl; or, where Ar is a heteroaryl ring, then R₃ may be an unsubstituted 4- to 8-member heterocyclic ring or an aryl or heteroaryl ring; or, where X is nitrogen, then R₃ can also be unsubstituted aryl or heteroaryl; or, where X is carbon or nitrogen, R₃ can also be an unsubstituted 4- to 8-member heterocyclic ring, or X and R₃ can together form a non-aromatic, substituted 4- to 8-member heterocyclic ring bearing 1-4 carbon substituents and/or 1-2 nitrogen substituents (in addition to the Ar moiety), where the carbon substituents are selected from alkyl, haloalkyl, nitro, oxo (O═), halogen, alkoxy, alkylthio, haloalkoxy, sulfonyl, sulfinyl, carboxy, or alkoxycarbonyl and/or additional fused cycloalkyl, heterocycloalkyl, aryl or heteroaryl rings, and the nitrogen substituents are selected from alkyl, haloalkyl, nitro, halogen, alkoxy, alkylthio, haloalkoxy, sulfonyl, sulfinyl, alkoxycarbonyl, or aminocarbonyl groups and/or additional fused cycloalkyl, heterocycloalkyl, aryl or heteroaryl rings; or a pharmaceutically acceptable salt thereof.

Compounds for use according to the method for treating or preventing a bacterial infection by administering a trans-translator inhibitor compound of Formula IIa include, but are not limited to, the following:

| Compound No. MBX- | Structure |
|---|---|
| 4237 | (structure shown) |
| 4258 | (structure shown) |

| Compound No. MBX- | Structure |
|---|---|
| 4284 | 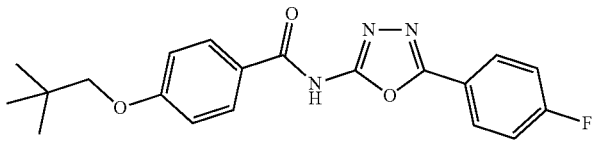 [SMILES: CC(C)(C)COc1ccc(C(=O)Nc2nnc(-c3ccc(F)cc3)o2)cc1] |
| 4285 | 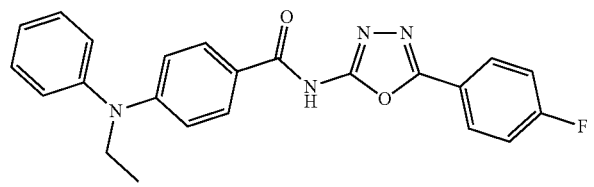 [SMILES: CCN(c1ccccc1)c1ccc(C(=O)Nc2nnc(-c3ccc(F)cc3)o2)cc1] |
| 4288 | 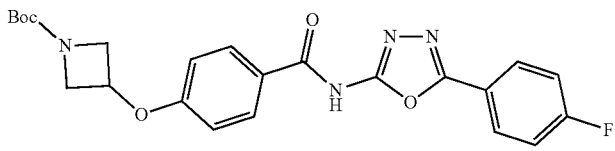 |
| 4289 | 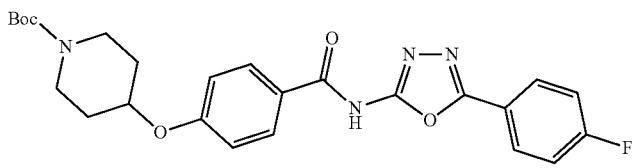 [SMILES: CC(C)(C)OC(=O)N1CCC(Oc2ccc(C(=O)Nc3nnc(-c4ccc(F)cc4)o3)cc2)CC1] |
| 4290 | 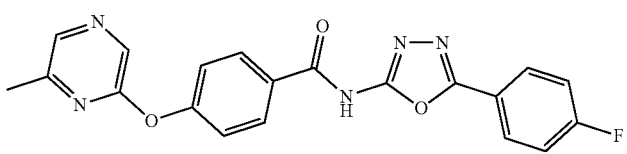 [SMILES: Cc1cncc(Oc2ccc(C(=O)Nc3nnc(-c4ccc(F)cc4)o3)cc2)n1] |
| 4292 | 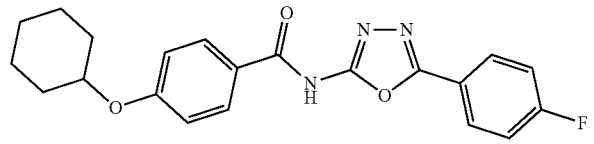 [SMILES: O=C(Nc1nnc(-c2ccc(F)cc2)o1)c1ccc(OC2CCCCC2)cc1] |
| 4293 | 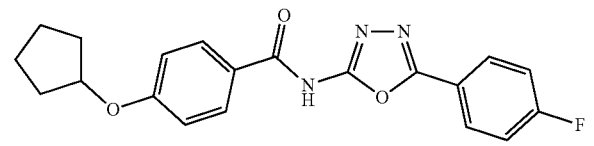 [SMILES: O=C(Nc1nnc(-c2ccc(F)cc2)o1)c1ccc(OC2CCCC2)cc1] |
| 4304 | 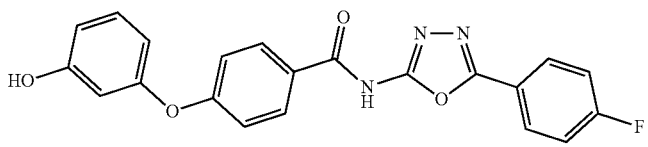 [SMILES: O=C(Nc1nnc(-c2ccc(F)cc2)o1)c1ccc(Oc2cccc(O)c2)cc1] |
| 4305 | 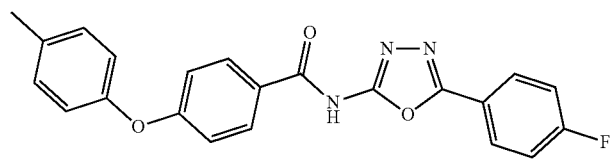 [SMILES: Cc1ccc(Oc2ccc(C(=O)Nc3nnc(-c4ccc(F)cc4)o3)cc2)cc1] |

-continued
| Compound No. MBX- | Structure |
|---|---|
| 4306 | 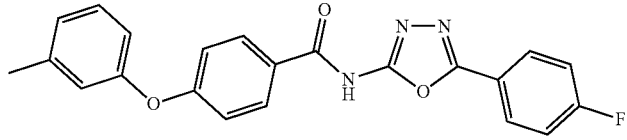 [SMILES: Cc1cccc(Oc2ccc(C(=O)Nc3nnc(-c4ccc(F)cc4)o3)cc2)c1] |
| 4307 | 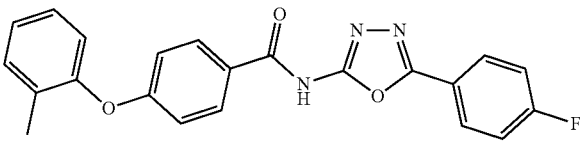 [SMILES: Cc1ccccc1Oc1ccc(C(=O)Nc2nnc(-c3ccc(F)cc3)o2)cc1] |
| 4308 | 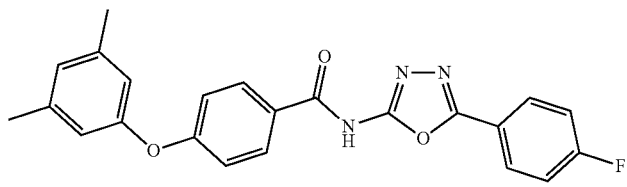 [SMILES: Cc1cc(C)cc(Oc2ccc(C(=O)Nc3nnc(-c4ccc(F)cc4)o3)cc2)c1] |
| 4309 | 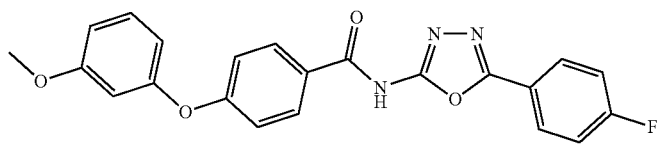 [SMILES: COc1cccc(Oc2ccc(C(=O)Nc3nnc(-c4ccc(F)cc4)o3)cc2)c1] |
| 4310 | 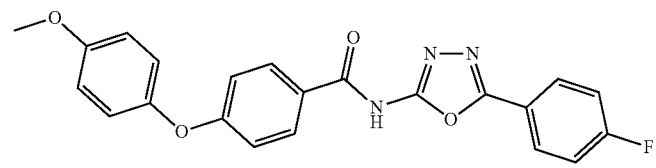 [SMILES: COc1ccc(Oc2ccc(C(=O)Nc3nnc(-c4ccc(F)cc4)o3)cc2)cc1] |
| 4314 | 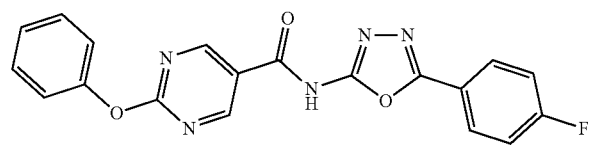 [SMILES: O=C(Nc1nnc(-c2ccc(F)cc2)o1)c1cnc(Oc2ccccc2)nc1] |
| 4357 | 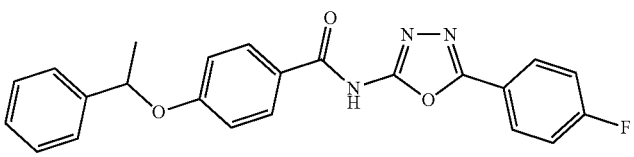 [SMILES: CC(Oc1ccc(C(=O)Nc2nnc(-c3ccc(F)cc3)o2)cc1)c1ccccc1] |
| 4468 | 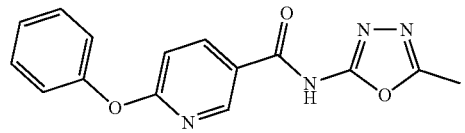 [SMILES: Cc1nnc(NC(=O)c2ccc(Oc3ccccc3)nc2)o1] |
| 4469 | 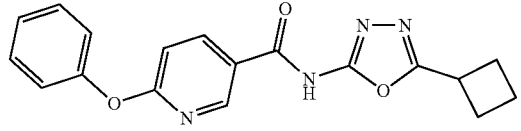 [SMILES: O=C(Nc1nnc(C2CCC2)o1)c1ccc(Oc2ccccc2)nc1] |
| 4470 | 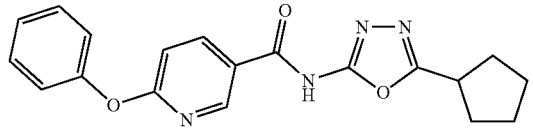 [SMILES: O=C(Nc1nnc(C2CCCC2)o1)c1ccc(Oc2ccccc2)nc1] |

| Compound No. MBX- | Structure |
|---|---|
| 4498 | 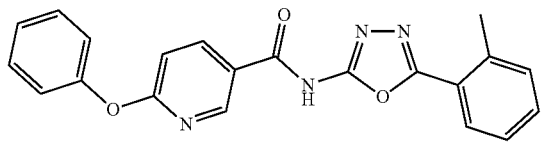 [SMILES: Cc1ccccc1-c1nnc(NC(=O)c2ccc(Oc3ccccc3)nc2)o1] |
| 4499 | 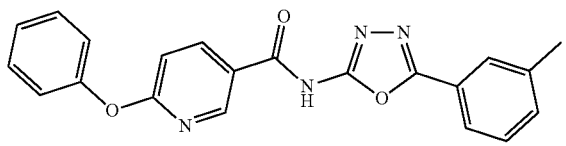 [SMILES: Cc1cccc(-c2nnc(NC(=O)c3ccc(Oc4ccccc4)nc3)o2)c1] | and pharmaceutically acceptable salts thereof.

Synthesis of Trans-Translation Inhibitor Compounds

Aminooxadizole compounds as described herein may be synthesized by the following general scheme:

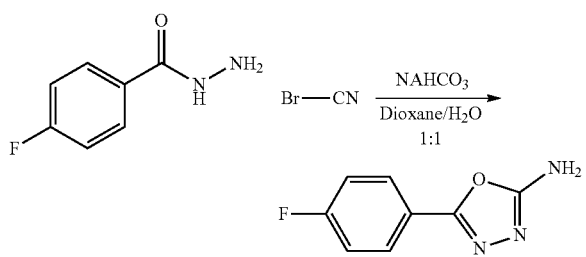

Compounds of Formula I and Formula II may be synthesized as follows:

General Procedure for Aminooxadiazole Formation:

5-(4-fluorophenyl)-1,3,4-oxadiazol-2-amine

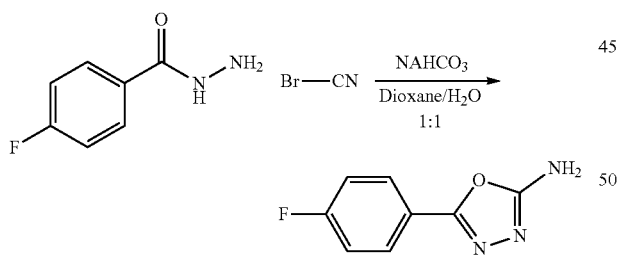

To a solution of sodium bicarbonate (5.45 g, 64.9 mmol) in 1:1 water:dioxane (100 mL total volume) was added 4-fluorobenzohydrazide (10.0 g, 64.9 mmol) and the resulting suspension stirred for 10 min at 25° C. To this was added cyanogen bromide (6.87 g, 64.9 mmol) in three portions over 15 min. After stirring at 25° C. for 18 hrs, the reaction was diluted with water (200 mL), filtered, and the resultant solid rinsed with water. The solid was dried in vacuo (12 hrs) to provide a light brown powder (11.0 g, 95%); $^1$H NMR (DMSO): 7.87-7.82 (m, 2H), 7.41-7.35 (m, 2H), 7.24 (br s, 2H); LCMS: 180.2 (M+1).

Other aminooxadiazoles were either prepared in this manner or obtained from commercial sources. Problematic aminooxadiazoles could also be generated by the condensation of an appropriately substituted aldehyde with semicarbazide hydrochloride followed by oxidation with a dihalide such as bromine or iodine as described by Rajak, H. et. al. *Biorg. Med. Chem. Lett.* 21(19):5735 (2011) and related publications.

General Procedure for Uriedooxadiazole Formation:

N-[5-(4-fluorophenyl)-1,3,4-oxadiazol-2-yl]-3,4-dihydroisoquinoline-2(1H)-carboxamide (MBX-4132)

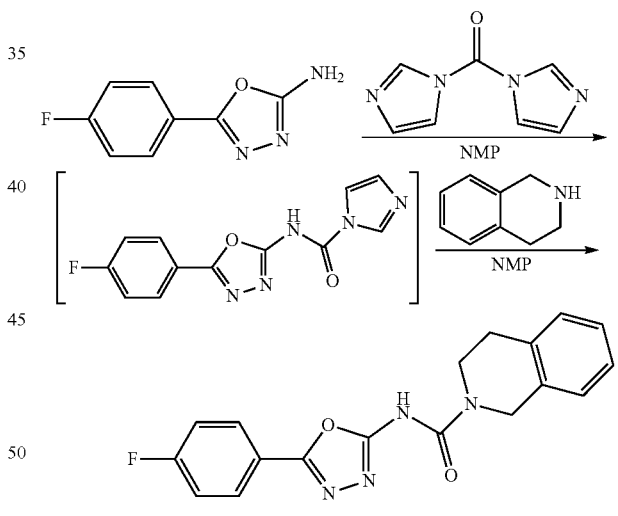

1,1'-carbonyldiimidazole (0.543 g, 3.35 mmol) was added to a suspension of 5-(4-fluorophenyl)-1,3,4-oxadiazol-2-amine (0.500 g, 2.79 mmol) in NMP (7 mL) and stirred at 65° C. for 18 hrs. To this was added a solution of tetrahydroisoquinoline (0.886 mL, 6.98 mmol) in NMP (3 mL) in a dropwise manner over ~5 minutes. The reaction mixture was removed from heat and allowed to cool to room temperature over 2 hrs. The resultant heterogenous mixture was diluted with water (~100 mL), filtered and the collected precipitate washed sequentially with water (~25 mL) and methanol (~25 mL) and then dried in vacuo to provide a white powder (0.375 g, 40%); $^1$H NMR (DMSO): 7.98-7.94 (m, 2H), 7.46-7.40 (m, 2H), 7.19 (s, 4H), 4.69 (s, 2H), 3.75 (t, 2H), 2.85 (t, 2H); LCMS: 339.1 (M+1).

Other uriedo oxadiazoles may be prepared in a similar manner, with problematic substrates reacted in a reversed order (exchanging the aminooxadiazole and the amine in the two stages of the reaction).

General Procedure for Aromatic Amidooxadiazole Formation:

2-(6-phenoxynicotinamido)-5-(4-fluorophenyl)-1,3,4-oxadiazole (MBX-4237)

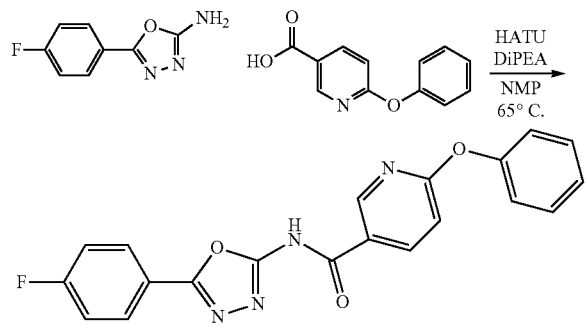

The reagents HATU (1.06 g, 2.79 mmol), 5-(4-fluorophenyl)-1,3,4-oxadiazol-2-amine (0.499 g, 2.79 mmol), and 6-phenoxynicotinic acid (0.500 g, 2.32 mmol) were combined as solids and dissolved in NMP (5 mL), to which diisopropylethylamine (0.53 mL, 3.02 mmol) was added, and the resulting solution stirred at 65° C. for 18 hrs. At this point, the reaction mixture was diluted with water (~100 mL) and filtered to provide a brown solid that was dried under vacuum. This solid was triturated with MeOH (2 mL), filtered and dried under vacuum to provide an off-white solid (0.695 g, 80%); $^1$H NMR (DMSO): 12.33 (br, 1H), 8.79 (s, 1H), 8.42 (d, 1H), 8.05-8.00 (m, 2H), 7.50-7.44 (m, 4H), 7.31-7.18 (m, 4H); LCMS: 377.2 (M+1).

Other aryl- or heteroaryl-substituted amidooxadiazoles were prepared in a similar manner from appropriate starting materials. Acids used in this step were either obtained from commercial sources or generated using standard chemical procedures from the literature.

Uses of Compounds of Formula I, Formula I(a), Formula II, and Formula II(a)

The aminooxadiazole small molecule inhibitors described herein are suitable for use in a method for treating or preventing bacterial infections in a mammal by administration of one or more inhibitors described herein to a patient or subject in need thereof. In a preferred embodiment, the trans-translation inhibitors described herein are suitable for use in a method for treating or preventing bacterial infections in humans.

Because of the essentially universal presence of the trans-translation mechanism in bacteria, and the critical role it usually plays in survival of the bacterial cell, the invention described herein provides new therapeutic compounds useful to treat or prevent bacterial infections via inhibition of trans-translation. The compounds should be especially effective to treat or prevent infection by M. tuberculosis, N. gonorrhoeae, S. flexneri, H. influenzae, S. aureus, and other species in which trans-translation is essential and which are resistant to many existing antibiotics. The compounds of the present invention can also be expected to prevent infection by S. enterica, Y. pestis, F. tularensis, S. pneumoniae, and other species that require trans-translation for virulence.

The trans-translation inhibitor compounds described herein can be administered as pharmaceutically acceptable salts. Such pharmaceutically acceptable salts include the gluconate, lactate, acetate, tartarate, citrate, phosphate, maleate, borate, nitrate, sulfate, and hydrochloride salts. The salts of the compounds described herein can be prepared, for example, by reacting the base compound with the desired acid in solution. After the reaction is complete, the salts are crystallized from solution by the addition of an appropriate amount of solvent in which the salt is insoluble. In some embodiments, the hydrochloride salt is made by passing hydrogen chloride gas into an ethanolic solution of the free base. Accordingly, in some embodiments, the pharmaceutically acceptable salt is a hydrochloride salt.

In another embodiment, the trans-translation inhibitor compounds are formulated into a pharmaceutically acceptable carrier or excipient for administration to a subject in need thereof. In another embodiment, the compounds may be formulated into a pharmaceutical formulation and further comprise an additional antibacterial compound. In another embodiment, the pharmaceutical formulation may be formulated to be administered orally, parenterally, or topically.

Compounds according to the invention show useful oral bioavailability, and thus oral dosage forms are particularly preferred as the most convenient and rapid method of administration. However, the compounds described herein may be administered by any suitable route, including intravenous, subcutaneous, intramuscular, intra-arterial, intraperitoneal, transdermal, intranasal, pulmonary, or vaginal administration in addition to oral administration.

Unless otherwise indicated, it is understood that description of the use of a trans-translation inhibitor compound in a composition or method also encompasses the embodiment wherein one or a combination of two or more trans-translation inhibitor compounds are employed as the source of bacterial inhibitory activity in a composition or method of the invention.

Pharmaceutical compositions according to the invention comprise a trans-translation inhibitor compound as described herein, or a pharmaceutically acceptable salt thereof, as the "active ingredient" and a pharmaceutically acceptable carrier (or "vehicle"), which may be a liquid, solid, or semi-solid compound.

In some embodiments, the presently disclosed subject matter is related to a method of treating or preventing a bacterial infection in a subject in need of treatment thereof wherein the method comprises administering to the subject an effective amount of a composition comprising a compound of one of Formulas I, I(a), II, and/or II(a) as disclosed herein. The compounds may be administered alone or optionally in combination with one or more additional antibacterial agents.

The compositions and methods of the presently disclosed invention are useful for treating and/or preventing bacterial infections in that they inhibit the onset, growth, or spread of the condition, cause regression of the condition, cure the condition, or otherwise improve the general well-being of a mammalian subject, preferably a human, afflicted with, or at risk of, contracting the condition. Thus, in accordance with the presently disclosed subject matter, the terms "treat", "treating", and grammatical variations thereof, as well as the phrase "method of treating" or "method of use" or "use for treating", are meant to encompass any desired therapeutic intervention, including but not limited to a method for treating an existing bacterial infection in a subject, and a method for the prophylaxis (i.e., preventing) of bacterial infection, such as in a subject that has been exposed to a bacteria as disclosed herein or that has an expectation of being exposed to the bacteria as disclosed herein.

In another aspect, the invention relates to pharmaceutical compositions comprising one or more compounds according to Formula I, Formula I(a), Formula II, or Formula II(a) herein, or a pharmaceutically acceptable salt, solvate, hydrate, or polymorph thereof, and a pharmaceutically acceptable carrier. That is, a pharmaceutical composition can be provided comprising at least one disclosed compound of the present invention, at least one product of a disclosed method, or a pharmaceutically acceptable salt, solvate, hydrate, or polymorph thereof, and a pharmaceutically acceptable carrier.

In a further aspect, the pharmaceutical composition is used to treat a mammal. In a further aspect, the mammal treated is a human. In a further aspect, the mammal has been diagnosed with a bacterial infection. In a still further aspect, the mammal has been diagnosed with a need for treatment of a bacterial infection.

In a further aspect, the pharmaceutical composition is a solid dosage form selected from a capsule, a tablet, a pill, a powder, a granule, an effervescing granule, a gel, a paste, a troche, and a pastille. In a still further aspect, the pharmaceutical composition is a liquid dosage form selected from an emulsion, a solution, a suspension, a syrup, and an elixir.

In certain aspects, the disclosed pharmaceutical compositions comprise at least one of the disclosed compounds according to Formula I, Formula I(a), Formula II, or Formula II(a) herein, (including pharmaceutically acceptable salt(s) thereof) as an active ingredient, a pharmaceutically acceptable carrier, and, optionally, other therapeutic ingredients. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (cupric and cuprous), ferric, ferrous, lithium, magnesium, manganese (manganous and manganic), potassium, sodium, zinc and the like salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets, or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

The present invention is further directed to a method for the manufacture of a medicament for treating or preventing bacterial infection in mammals (e.g., humans) comprising combining one or more disclosed trans-translation inhibitor compounds of the present invention, products, or compositions with a pharmaceutically acceptable carrier or diluent. Thus, in one aspect, the invention relates to a method for manufacturing a medicament comprising combining at least one disclosed trans-translation inhibitor compound according to the present invention or at least one disclosed product with a pharmaceutically acceptable carrier or diluent.

In another embodiment, the trans-translation inhibitor compounds of the present invention are also suitable for a method for disinfecting or sterilizing devices and solid surfaces. In a method according to the invention, inhibition or prevention of bacterial contamination on a solid surface comprises bringing at least one trans-translation inhibitor described herein into contact with bacterial cells that are on such surface. A trans-translation inhibitor described herein may be brought into contact with a surface prior to the presence of contaminating bacteria, or a trans-translation inhibitor may be brought into contact with a surface that already bears bacterial cells that are forming or capable of forming bacterial colonies thereon.

A trans-translation inhibitor compound described herein may be brought into contact with a solid surface composed of or comprising any of a variety of materials that are exposed to bacteria or that can support bacterial colonization. Such materials include, but are not limited to, plastic, glass, silicon, metal, nylon, cellulose, nylon, polymeric resin, and combinations thereof.

While in theory a trans-translation inhibitor compound described herein may be applied to a solid surface as the isolated compound alone (raw compound), it is more likely that the compound will be employed in a composition with at least one other compound. Compositions of the invention may be in any of a variety of forms particularly suited for the intended mode of applying a trans-translation inhibitor compound to a solid surface. A carrier is any compound that provides a medium for using the trans-translation inhibitor compound. A carrier may be liquid, solid, or semi-solid. A carrier for use in the compositions described herein includes, but is not limited to, water, an aqueous buffer, an organic solvent, and a solid dispersing agent. For solid compositions, conventional nontoxic solid carriers are preferred and include, but are not limited to, mannitol, lactose, starch, magnesium stearate, sodium saccharin, talc, cellulose, glucose, sucrose, magnesium carbonate, and the like. Liquid compositions may, for example, be prepared by dissolving or dispersing a trans-translation inhibitor compound as described herein in a liquid carrier to form a solution or suspension.

A composition will include, as noted above, an effective amount of the selected trans-translation inhibitor compound in combination with an acceptable carrier, and, optionally, may include one or more other agents, diluents, fillers, and excipients. An excipient is a compound that provides a desirable property to a composition other than inhibition of trans-translation. An excipient useful in a composition described herein includes, but is not limited to, a wetting agent, an emulsifying agent, pH buffering agent, a dispersing agent, co-solvent, surfactant, a gelling agent, and a drying agent.

A trans-translation inhibitor described herein may be incorporated into any of a variety of compositions to provide the benefit of bacterial trans-translation inhibition to the particular composition or to a surface to which the composition may be applied. Compositions comprising a trans-translation inhibitor described herein include, but are not limited to, solutions, suspensions, dry mixtures, gels, petroleum products, porous membranes, porous filters, liposomes, resin particles, plastics, paints, glues, pastes, cellulose products, textiles (fiber, yarn, or cloth), and nanoparticles. A trans-translation inhibitor may also be formulated by standard methods for delivery to a surface in an aerosol of fine solid particles or liquid droplets mixed with a gas. A composition described herein may optionally comprise an antibacterial growth agent (e.g., citrate, EDTA, antibiotic, or other microbial biocide) at a concentration effective to inhibit growth of or kill one or more strains of potentially contaminating bacteria that may contact the composition.

A trans-translation inhibitor described herein may be applied to, coated on, impregnated, or otherwise incorporated into a surface that is susceptible to contact with Gram-positive and/or Gram-negative bacteria that form colonies on solid surfaces. Such surfaces are found on a variety of manufactured products including, but not limited to, implantable medical devices (such as central venous catheters (CVCs), implantable pumps, artificial heart valves, and cardiac pacemakers); cardio-pulmonary bypass (CPB) pumps (heart-lung machines); dialysis equipment; artificial respirators; breathing apparatuses (oxygen and air supplies); water pipes; air ducts, air filters, water filters, and plumbing fixtures. The particular composition and properties of a particular surface will determine the preferred method by which the surface is treated to contain a trans-translation inhibitor described herein.

Implantable medical devices that have surfaces that may be treated with a trans-translation inhibitor described herein include, but are not limited to, central venous catheters (CVCs), implantable pumps, artificial heart valves, and cardiac pacemakers. The surfaces of a medical device may be coated with a trans-translation inhibitor in a manner that is dependent on the specific chemical structure of the trans-translation inhibitor compound and the type of material of which the device is constructed (reviewed by Zilberman and Elsner, *Journal of Controlled Release*, 130: 202-215 (2008)). Alternatively, a trans-translation inhibitor may be impregnated into a material, such as a hydrogel or polymer, which would then be used to coat a medical device. The use of biodegradable plastic resins, such as poly(D,L-lactic acid) and poly(D,L-lactic acid):coglycolide, combined with an anti-bacterial agent to produce antibacterial device coatings has been described (Gollwitzer et al., *J. Antimicrob Chemother.*, 51, 585-591 (2003)). Such technology may be readily adapted for preparing anti-trans-translation coatings comprising a trans-translation inhibitor compound described herein.

A trans-translation inhibitor as described herein may also be employed in a "lock solution" (solution or suspension) for use with a central venous catheter (CVC). In standard medical device lock therapies, the lumen(s) of a medical device is filled with a lock solution comprising an antibacterial agent (e.g., antiseptic, antibiotic) to prevent bacterial contamination of the device. The lock solution is introduced into the lumen(s) of the device when the device is not in use and then expelled shortly before use. A lock solution according to the invention is a solution or suspension comprising a trans-translation inhibitor described herein at a concentration sufficient to inhibit bacterial trans-translation formation by potentially contaminating bacteria. A lock solution comprising a trans-translation inhibitor as described herein may further comprise any of a variety of other compounds that enhance the prevention of bacterial contamination and infection in a medical device. Such additional compounds that may be used in preparing a lock solution of the invention include, but are not limited, one or more antibacterial growth agents (e.g., citrate, EDTA, antibiotic, microbial biocide) at a concentration effective to inhibit growth of (or kill) one or more strains of potentially contaminating bacteria and one or more excipients that provide an additional desirable property to the lock solution other than inhibition of bacterial growth and prevention of trans-translation. For example, an excipient may provide a density, osmolarity, or viscosity to the lock solution that is similar to the fluid (e.g., blood) that will fill the device lumen when the device is used or implanted. An excipient of a lock solution may also prevent occlusion of the catheter lumen caused by blood clotting and/or formation of a fibrin sheath.

Effective amounts of a trans-translation inhibitor to be applied to a surface or otherwise employed in a method or composition to inhibit or prevent trans-translation formation may be determined by the skilled practitioner who is familiar with methods for assessing effective amounts of antibiotics, antiseptics (biocides), or previously described trans-translation inhibitors on surfaces to meet or exceed standards of authoritative agencies. See, e.g., Guidelines for the prevention of intravascular device-related infections such as those issued by the United States Center for Disease Control (Atlanta, Ga.) (O'Grady et al., *Am. J. Infect. Control*, 30: 476-489 (2002); examples of biocide and antibiotic impregnated catheters (C. Potera, *Science*, 283: 1837, 1839 (1999)); assessment of effectiveness to bacterial challenge by biocide and antibiotic impregnated catheters (Sampath et al., *Infect. Control Hosp. Epidemiol.*, 22: 640-646 (2001)). Such guidelines and procedures are readily adapted to assessing and optimizing the amount and conditions for using a particular trans-translation inhibitor described herein to inhibit or prevent bacterial trans-translation formation in a particular application (e.g., surface, device, composition, or method).

In another aspect, the invention relates to a kit comprising:
(a) at least one trans-translation inhibitor compound according to Formula I or Formula II described herein, or a pharmaceutically acceptable salt, solvate, or polymorph thereof;
(b) optionally, at least one additional agent known to have antibacterial activity; and
c) instructions for administration of the compound (a) and (b) if present to a patient in need thereof for treating a bacterial infection.

Such kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound of the present invention and/or product and another component for delivery to a patient.

In a further aspect, the kit further comprises a plurality of dosage forms, the plurality comprising one or more doses, wherein each dose comprises an amount of the trans-translation inhibitor compound known to have antibacterial activity. In another aspect, the kit further comprises a plurality of dosage forms, the plurality comprising one or more doses, wherein each dose comprises an effective amount of the compound known to have antibacterial activity. In a further aspect, an effective amount is a therapeutically effective amount. In a still further aspect, an effective amount is a prophylactically effective amount.

EXAMPLES

The following Examples have been included to illustrate modes of the presently disclosed subject matter. In light of the present disclosure and the general level of skill in the art, those of skill will appreciate that the following Examples are intended to be illustrative of the invention and are not intended to limit the scope of the invention as described in this application.

Example 1. Characterization Data of Select Trans-Translation Inhibitors

Novel compounds were characterized by $^1$H NMR spectra at 300 MHz and LCMS with the m/z (typically M+1) using an electrospray ionization strategy. Table 1 (below) delineates representative data for select examples. Note: This data represents signals necessary to delineate basic structure and does not necessarily represent complete data either for all protons or coupling interactions in the proton NMR spectra or all mass signals in the mass spectroscopy experiment.

TABLE 1

| | Potency of Select trans-Translation Inhibitors | |
|---|---|---|
| Cmpd No. MBX- | ¹H NMR Spectrum (solvent) | m/z found by LCMS (M + x) |
| 4132 | (DMSO): 7.98-7.94 (m, 2H), 7.46-7.40 (m, 2H), 7.19 (s, 4H), 4.69 (s, 2H), 3.75 (t, 2H), 2.85 (t, 2H) | 339.0 (M + 1) |
| 4198 | (CDCl₃): 7.97-7.93 (m, 2H), 7.26-7.18 (m, 3H + CHCl₃), 3.92-3.52 (m, 8H), 2.17 (s, 3H) | 334.0 (M + 1) |
| 4199 | (CDCl₃ + MeOD): 8.04-7.93 (m, 2H), 7.25-7.13 (m, 2H), 4.58 (br t, 1H), 3.59-3.16 (m, 7H), 2.92-2.70 (m, 2H), 1.92-1.79 (m, 6H), 1.57 (br, 1H) | 346.1 (M + 1) |
| 4200 | (CDCl₃): 7.96-7.84 (m, 2H), 7.20-7.06 (m, 2H), 3.71-3.62 (m, 1H), 2.96-2.89 (m, 1H), 1.95-1.24 (m, 14H) | 345.2 (M + 1) |
| 4201 | (CDCl₃ + MeOD): 8.04-7.95 (m, 2H), 7.55 (s, 1H), 7.24-7.06 (m, 3H), 6.53 (d, 1H), 4.07-3.24 (m, 8H + MeOH) | 385.9 (M + 1) |
| 4237 | (DMSO): 12.33 (br, 1H), 8.79 (s, 1H), 8.42 (d, 1H), 8.05-8.00 (m, 2H), 7.50-7.44 (m, 4H), 7.31-7.18 (m, 4H) | 377.2 (M + 1) |
| 4258 | (DMSO): 11.99 (s, 1H), 8.52 (d, 1H), 8.18 (d, 1H), 8.06-8.01 (m, 2H), 7.57-7.44 (m, 5H), 7.33-7.23 (m, 3H) | 377.2 (M + 1) |
| 4285 | (CDCl₃ + MeOD): 8.08-8.03 (m, 2H), 7.84 (d, 2H), 7.46-7.41 (m, 2H), 7.29-7.27 (m, 1H + CHCl₃), 7.25-7.15 (m, 4H), 6.72 (d, 2H), 3.81 (q, 2H), 1.26 (t, 3H) | 403.0 (M + 1) |
| 4288 | (CDCl₃ + MeOD): 8.10-8.01 (m, 4H), 7.22 (t, 2H), 6.37 (d, 2H), 5.01-4.97 (m, 1H), 4.39-4.34 (m, 2H), 4.03 (dd, 2H), 1.46 (s, 9H) | 455.0 (M + 1) |
| 4289 | (CDCl₃ + MeOD): 8.10-8.01 (m, 4H), 7.22 (t, 2H), 7.01 (d, 2H), 4.64-4.60 (m, 1H), 3.74-3.66 (m, 2H), 3.43-3.35 (m, 2H), 2.02-1.94 (m, 2H), 1.85-1.76 (m, 2H), 1.48 (s, 9H) | 483.1 (M + 1) |
| 4290 | (DMSO): 12.18 (br, 1H), 8.39 (d, 2H), 8.12 (d, 2H), 8.06-8.01 (m, 2H), 7.47 (t, 2H), 7.37 (d, 2H), 2.38 (s, 3H) | 392.2 (M + 1) |
| 4292 | (DMSO): 11.92 (br, 1H), 8.05-7.99 (m, 4H), 7.47 (t, 2H), 7.08 (d, 2H), 4.50 (br, 1H), 1.94 (br, 2H), 1.73 (br, 2H), 1.52-1.39 (m, 6H) | 382.2 (M + 1) |
| 4293 | (DMSO): 11.92 (br, 1H), 8.02 (br, 4H), 7.47 (d, 2H), 7.06 (br, 2H), 4.95 (br, 1H), 1.98 (br, 2H), 1.73-1.61 (m, 6H) | 368.2 (M + 1) |
| 4304 | (CDCl₃ + MeOD): 8.10-8.00 (m, 4H), 7.23 (t, 3H), 7.08 (d, 2H), 6.70 (d, 1H), 6.57 (d, 2H) | 391.9 (M + 1) |
| 4305 | (CDCl₃ + MeOD): 8.10-8.01 (m, 4H), 7.24-7.19 (m, 4H), 7.05-6.97 (m, 4H), 2.38 (s, 3H) | 390.0 (M + 1) |
| 4306 | (CDCl₃ + MeOD): 8.06-7.99 (m, 4H), 7.30-7.18 (m, 3H), 7.05-7.03 (m, 3H), 6.89-6.86 (m, 2H), 2.36 (s, 3H) | 390.0 (M + 1) |
| 4307 | (CDCl₃): 11.58 (br, 1H), 8.18 (d, 2H), 8.07-8.03 (m, 2H), 7.32-7.18 (m, 5H + CHCl₃), 7.04-6.97 (m, 3H), 2.21 (s, 3H) | 390.1 (M + 1) |
| 4308 | (CDCl₃ + MeOD): 8.10-8.00 (m, 4H), 7.22 (t, 2H), 7.04 (d, 2H), 6.86 (s, 1H), 6.71 (s, 2H), 2.33 (s, 6H) | 404.1 (M + 1) |
| 4309 | (CDCl₃ + MeOD): 8.10-8.02 (m, 4H), 7.31 (t, 1H), 7.23 (t, 2H), 7.08 (d, 2H), 6.77 (dd, 1H), 6.69-6.65 (m, 2H), 3.80 (s, 3H) | 406.0 (M + 1) |
| 4310 | (CDCl₃ + MeOD): 8.07-7.99 (m, 4H), 7.22 (t, 2H), 7.06-6.94 (m, 6H), 3.84 (s, 3H) | 406.0 (M + 1) |
| 4314 | (DMSO): 9.18 (s, 2H), 8.05-8.00 (m, 2H), 7.51-7.43 (m, 4H), 7.34-7.26 (m, 3H) | 378.2 (M + 1) |
| 4330 | (DMSO) 8.01-7.97 (m, 2H), 7.48-7.42 (t, 2H), 7.36-7.33 (m, 4H), 4.81-4.70 (m, 4H) | 325.2 (M + 1) |
| 4331 | (CDCl₃) 7.98-7.93 (m, 2H), 7.23-7.11 (m, 3H), 6.93-6.85 (m, 2H), 4.83 (m, 2H), 3.94 (m, 2H), 2.92-2.84 (m, 2H) | 357.1 (M + 1) |
| 4332 | (CDCl₃) 7.98-7.94 (m, 2H), 7.23-7.17 (m, 2H), 7.13-7.08 (m, 1H), 6.91-6.86 (m, 2H), 4.91-4.82 (m, 2H), 3.99-3.89 (m, 2H), 2.89-2.85 (t, 2H) | 357.0 (M + 1) |
| 4333 | (DMSO) 7.97-7.92 (m, 2H), 7.45-7.39 (t, 2H), 6.76-6.75 (m, 2H), 4.59 (m, 2H), 3.72 (m, 8H), 2.77-2.73 (t, 2H) | 399.1 (M + 1) |
| 4345 | (CDCl₃) 7.98-7.93 (m, 2H), 7.20-7.15 (m, 2H), 5.90-5.79 (m, 1H), 5.23-5.20 (m, 1H), 5.17 (s, 1H), 4.14 (brs, 2H), 3.08 (s, 3H) | 277.1 (M + 1) |
| 4346 | (CDCl₃) 7.98-7.95 (m, 2H), 7.20-7.14 (m, 2H), 3.57 (m, 4H), 1.96 (m, 4H) | 277.1 (M + 1) |
| 4347 | (DMSO) 7.98-7.93 (m, 2H), 7.46-7.40 (m, 2H), 6.53 (s, 1H), 4.19 (m, 2H), 3.70 (m, 2H), 2.28 (m, 2H) | 357.2 (M + 1) |
| 4348 | (CDCl₃) 7.97-7.93 (m, 2H), 7.23-7.17 (m, 2H), 6.96 (m, 1H), 4.38 (m, 2H), 3.83 (m, 2H), 3.77 (s, 3H), 2.49-2.48 (m, 2H) | 347.1 (M + 1) |
| 4349 | (CDCl₃) 7.97-7.92 (m, 2H), 7.24-7.19 (m, 2H), 4.50-4.45 (m, 1H), 4.24 (m, 1H), 3.76-3.55 (m, 4H), 3.04 (m, 2H), 2.88 (s, 3H), 2.49 (m, 1H), 2.25-2.21 (m, 1H) | 320.0 (M + 1) |
| 4350 | (DMSO) 8.07 (bs, 1H), 7.98-7.93 (m, 2H), 7.46-7.40 (m, 2H), 4.04 (m, 2H), 3.68 (m, 2H), 3.24 (m, 2H) | 306.0 (M + 1) |
| 4351 | (CDCl₃ + MeOD) 7.97-7.93 (m, 2H), 7.23-7.18 (m, 2H), 4.32 (s, 2H), 3.95-3.92 (m, 4H), 3.02 (s, 3H) | 320.1 (M + 1) |
| 4357 | (DMSO): 11.89 (s 1H), 8.03-7.91 (m, 3H), 7.48-7.25 (m, 8H), 7.06 (d, 2H), 5.67 (q, 1H), 1.59 (d, 3H) | 404.1 (M + 1) |
| 4366 | (CDCl₃) 7.98-7.93 (m, 2H), 7.21-7.16 (t, 2H), 5.41 (m, 1H), 4.11 (m, 2H), 3.78 (m, 2H), 2.11 (m, 2H), 1.73 (s, 3H) | 303.0 (M + 1) |

TABLE 1-continued

Potency of Select trans-Translation Inhibitors

| Cmpd No. MBX- | ¹H NMR Spectrum (solvent) | m/z found by LCMS (M + x) |
|---|---|---|
| 4380 | (DMSO) 8.00-7.96 (m, 2H), 7.47-7.41 (m, 2H), 4.63-4.61 (d, 2H), 3.72-3.57 (m, 4H), 3.12-3.05 (m, 1H), 1.83-1.80 (d, 1H) | 305.1 (M + 1) |
| 4381 | (DMSO) 7.98-7.93 (m, 2H), 7.46-7.40 (m, 2H), 4.34 (m, 2H), 3.76 (m, 2H), 3.17-3.06 (m, 2H), 1.83-1.74 (m, 4H) | 319.2 (M + 1) |
| 4406 | (CDCl$_3$) 7.96-7.92 (m, 2H), 7.24-7.18 (m, 2H), 4.63 (m, 2H), 3.69-3.63 (m, 4H), 3.49 (m, 4H), 3.35 (s, 3H), 1.49-1.48 (d, 6H) | 378.1 (M + 1) |
| 4464 | (DMSO) 8.00-7.96 (m, 2H), 7.47-7.42 (m, 2H), 4.69 (m, 4H), 2.69 (s, 3H) | 346.1 (M + 1) |
| 4465 | (DMSO) 8.40-8.39 (d, 2H), 7.98-7.94 (m, 2H), 7.46-7.40 (m, 2H), 6.68-6.65 (t, 1H), 3.80-3.77 (m, 4H), 3.62-3.61 (m, 4H) | 370.0 (M + 1) |
| 4468 | (CDCl$_3$) 8.99 (m, 1H), 8.45-8.42 (m, 1H), 7.46-7.41 (t, 2H), 7.26-7.25 (m, 1H), 7.19-7.18 (d, 2H), 6.96-6.93 (d, 1H), 2.52 (s, 3H) | 297.2 (M + 1) |
| 4469 | (CDCl$_3$) 9.02 (s, 1H), 8.48-8.44 (dd, 1H), 7.46-7.41 (t, 2H), 7.26-7.25 (m, 1H), 7.19-7.16 (d, 2H), 6.95-6.92 (d, 1H), 3.71-3.63 (m, 1H), 2.52-2.41 (m, 4H), 2.20-2.03 (m, 2H) | 337.2 (M + 1) |
| 4470 | (CDCl$_3$) 9.02 (s, 1H), 8.47-8.44 (m, 1H), 7.46-7.41 (t, 2H), 7.26-7.22 (m, 1H), 7.19-7.16 (d, 2H), 6.94-6.91 (d, 1H), 3.26-3.21 (m, 1H), 2.13-2.11 (m, 2H), 2.00-1.72 (m, 6H) | 351.8 (M + 1) |
| 4497 | (DMSO) 9.05 (s, 1H), 7.94-7.89 (m, 2H), 7.41-7.35 (m, 2H), 4.69 (m, 4H) | 332.0 (M + 1) |
| 4498 | (DMSO) 8.79-8.78 (m, 1H), 8.44-8.40 (m, 1H), 7.87-7.85 (d, 1H), 7.50-7.41 (m, 5H), 7.30-7.15 (m, 4H), 2.63 (s, 3H) | 373.0 (M + 1) |
| 4499 | (CDCl$_3$ + MeOD) 8.86 (m, 1H), 8.41-8.38 (m, 1H), 7.86-7.82 (m, 2H), 7.49-7.38 (m, 4H), 7.31-7.26 (m, 1H), 7.19-7.16 (m, 2H), 7.00-6.98 (d, 1H), 2.44 (s, 3H) | 373.1 (M + 1) |
| 4770 | (CDCl$_3$) 8.96 (m, 1H), 8.43-8.39 (m, 1H), 7.47-7.42 (t, 2H), 7.28 (m, 1H), 7.18-7.16 (m, 2H), 6.99-6.92 (m, 5H), 5.49-5.47 (t, 1H), 4.57-4.55 (d, 2H) | 416.5 (M) |
| 4780 | (CDCl$_3$) 9.02-9.01 (d, 1H), 8.49-8.45 (dd, 1H), 7.47-7.41 (t, 2H), 7.27 (m, 1H), 7.20-7.16 (m, 2H), 6.96-6.93 (d, 1H), 2.87-2.82 (m, 1H), 2.12-2.08 (m, 2H), 1.85-1.84 (m, 2H), 1.76-1.70 (m, 1H), 1.65-1.57 (m, 2H), 1.44-1.26 (m, 3H) | 365.6 (M + 1) |
| 4801 | (DMSO) 8.03-8.01 (d, 2H), 7.26-7.21 (t, 1H), 7.10-7.07 (d, 2H), 6.66-6.62 (dd, 1H), 6.55-6.51 (dd, 1H), 6.48-6.46 (m, 1H), 2.94 (m, 1H), 2.02-1.98 (m, 2H), 1.78-1.73 (m, 2H), 1.63-1.28 (m, 6H) | 380.3 (M + 1) |
| 4802 | (CDCl$_3$) 8.96-8.95 (m, 1H), 8.42-8.39 (dd, 1H), 7.45-7.40 (t, 2H), 7.32-7.25 (m, 3H), 7.16-7.13 (m, 2H), 7.05-7.00 (t, 2H), 6.92-6.89 (d, 1H), 4.12 (s, 2H) | 391.3 (M + 1) |
| 4925 | (CDCl$_3$) 8.96 (s, 1H), 8.32-8.28 (dd, 1H), 6.76-6.73 (d, 1H), 5.17-5.11 (m, 1H), 2.90-2.83 (m, 1H), 2.08-2.01 (m, 4H), 1.88-1.79 (m, 5H), 1.65-1.33 (m, 11H) | 371.9 (M + 1) |
| 4926 | (CDCl$_3$ + MeOD) 8.74-8.73 (d, 1H), 8.15-8.11 (dd, 1H), 6.94-6.86 (m, 4H), 6.75-6.72 (d, 1H), 5.48-5.45 (m, 1H), 5.09-5.03 (m, 1H), 4.55-4.52 (m, 2H), 1.97 (m, 2H), 1.78-1.76 (m, 2H), 1.59-1.22 (m, 6H) | 423.6 (M + 1) |
| 4684 | (CDCl$_3$) 7.98-7.93 (m, 2H), 7.21-7.15 (m, 2H), 4.52-4.48 (m, 2H), 2.90-2.82 (m, 2H), 1.72-1.67 (m, 2H), 1.63-1.58 (m, 1H), 1.24-1.10 (m, 2H), 0.98-0.96 (d, 3H) | 305.3 (M + 1) |
| 4685 | (CDCl$_3$ + MeOD) 7.99-7.94 (m, 2H), 7.21-7.16 (m, 2H), 3.62 (m, 4H), 1.42-1.26 (m, 4H), 0.99 (s, 6H) | 319.2 (M + 1) |
| 4686 | (CDCl$_3$ + MeOD) 7.93-7.88 (m, 2H), 7.18-7.12 (m, 2H), 3.77 (m, 4H), 2.02-1.89 (m, 4H) | 327.9 (M + 1) |
| 4697 | (CDCl$_3$ + MeOD) 7.93-7.89 (m, 2H), 7.18-7.12 (m, 2H), 3.66 (m, 8H) | 293.9 (M + 1) |
| 4698 | (CDCl$_3$ + MeOD) 7.94-7.89 (m, 2H), 7.16-7.10 (m, 2H), 4.02-3.83 (m, 2H), 1.81-1.71 (m, 4H), 1.54-1.20 (m, 10H) | 345.6 (M + 1) |
| 4699 | (CDCl$_3$) 7.97-7.92 (m, 2H), 7.21-7.15 (m, 2H), 3.65 (m, 4H), 1.62 (m, 6H) | 291.5 (M + 1) |
| 4700 | (CDCl$_3$ + MeOD) 7.92-7.88 (m, 2H), 7.13-7.07 (m, 2H), 3.48 (m, 4H), 1.69 (m, 4H), 1.52-1.50 (m, 4H) | 305.7 (M + 1) |
| 4701 | (CDCl$_3$) 7.97-7.93 (m, 2H), 7.22-7.17 (m, 2H), 4.46-4.42 (m, 2H), 3.71 (s, 3H), 3.09-2.98 (m, 2H), 2.59-2.51 (m, 1H), 1.98-1.95 (m, 2H), 1.78-1.74 (m, 2H) | 349.8 (M + 1) |
| 4702 | (CDCl$_3$ + MeOD) 7.92-7.88 (m, 2H), 7.17-7.12 (m, 2H), 4.63-4.58 (m, 2H), 3.46-3.33 (m, 3H), 2.86-2.67 (m, 5H), 2.06-1.83 (m, 7H), 1.70-1.57 (m, 2H), 1.35 (m, 1H) | 374.4 (M + 1) |
| 4734 | (CDCl$_3$ + MeOD) 8.01-7.96 (m, 2H), 7.24-7.18 (m, 2H), 4.08-4.04 (m, 2H), 3.88-3.85 (m, 1H), 3.35-3.20 (m, 2H), 1.94-1.89 (m, 2H), 1.60-1.51 (m, 2H) | 307.9 (M + 1) |
| 4735 | (CDCl$_3$) 7.98-7.93 (m, 2H), 7.22-7.16 (m, 2H), 3.82-3.63 (m, 4H), 3.00-2.95 (m, 1H), 2.23-2.16 (m, 2H) | 345.9 (M + 1) |
| 4736 | (DMSO) 7.98-7.93 (m, 2H), 7.46-7.40 (m, 2H), 6.05 (m, 1H), 4.15 (m, 2H), 3.76 (m, 2H), 2.24 (m, 2H) | 323.7 (M + 1) |
| 4737 | (DMSO) 7.97-7.93 (m, 2H), 7.46-7.40 (t, 2H), 4.30 (m, 2H), 3.77 (m, 2H), 2.58 (m, 2H) | 357.7 (M + 1) |

TABLE 1-continued

Potency of Select trans-Translation Inhibitors

| Cmpd No. MBX- | ¹H NMR Spectrum (solvent) | m/z found by LCMS (M + x) |
|---|---|---|
| 4738 | (CHCl₃) 7.98-7.93 (m, 2H), 7.21-7.15 (m, 2H), 4.00 (m, 2H), 3.74 (m, 2H), 2.10 (m, 2H), 1.67 (m, 6H) | 317.9 (M + 1) |
| 4739 | (CDCl₃ + MeOD) 7.98-7.93 (m, 2H), 7.22-7.16 (m, 2H), 4.49 (s, 4H), 3.60-3.59 (m, 4H), 1.91-1.88 (m, 4H) | 333.8 (M + 1) |
| 4740 | (CDCl₃ + MeOD) 7.99-7.94 (m, 2H), 7.22-7.16 (m, 2H), 4.81-4.79 (t, 2H), 4.44-4.51 (t, 2H), 3.80 (m, 1H), 2.92-2.73 (m, 4H), 1.96-1.85 (m, 1H), 1.71-1.66 (m, 2H), 1.15-1.06 (m, 2H) | 347.2 (M + 1) |
| 4741 | (DMSO) 7.98-7.93 (m, 2H), 7.46-7.41 (m, 2H), 7.18-7.13 (m, 2H), 6.76 (m, 3H), 4.14-4.11 (m, 2H), 3.55-3.52 (m, 1H), 3.07-2.99 (m, 2H), 1.96-1.91 (m, 2H), 1.39-1.29 (m, 2H) | 382.0 (M + 1) |
| 4767 | (CDCl₃) 7.98-7.93 (m, 2H), 7.21-7.15 (m, 2H), 4.42 (m, 2H), 2.86-2.53 (m, 2H), 1.86-1.82 (m, 1H), 1.71-1.51 (m, 3H), 1.20-1.16 (m, 1H), 0.96-0.94 (d, 3H) | 305.7 (M + 1) |
| 4768 | (CDCl₃ + MeOD) 7.98-7.93 (m, 2H), 7.21-7.15 (m, 2H), 4.42-4.38 (m, 2H), 2.34-2.26 (m, 2H), 1.85-1.81 (m, 1H), 1.68-1.58 (m, 2H), 0.98-0.96 (d, 6H), 0.82-0.70 (q, 1H) | 319.2 (M + 1) |
| 4769 | (CDCl₃ + MeOD) 7.95-7.90 (m, 2H), 719-7.13 (t, 2H), 4.66-4.42 (m, 2H), 2.82-2.81 (m, 2H), 2.26-2.22 (m, 1H), 2.07-1.79 (m, 2H), 1.56-1.47 (m, 2H) | 390.4 (M + 1) |
| 4776 | (CDCl₃) 7.98-7.93 (m, 2H), 7.23-7.18 (m, 2H), 3.84-3.61 (m, 4H), 2.27-2.07 (m, 4H), 1.94-1.92 (m, 2H) | 341.6 (M + 1) |
| 4777 | (CDCl₃) 7.93 (m, 2H), 7.39 (m, 1H), 7.17-7.16 (m, 5H), 4.75-4.62 (m, 2H), 4.04-3.90 (m, 2H), 3.01-2.98 (m, 2H), 1.87-1.86 (m, 2H) | 353.9 (M + 1) |
| 4778 | (CDCl₃) 8.02-8.01 (d, 2H), 8.00-7.93 (m, 2H), 7.23-7.17 (t, 2H), 6.96-6.93 (d, 2H), 4.67-4.63 (m, 1H), 4.01 (m, 2H), 3.96 (s, 3H), 3.90-3.72 (m, 2H), 2.05-1.83 (m, 4H) | 441.2 (M + 1) |
| 4779 | (CDCl₃) 7.96-7.95 (d, 2H), 7.94-7.91 (m, 2H), 7.23-7.16 (m, 4H), 4.48 (m, 2H), 3.91 (m, 3H), 2.78 (m, 2H), 2.63-2.61 (d, 2H), 1.83-1.78 (m, 1H), 1.75-1.66 (m, 2H), 1.29-1.15 (m, 2H) | 439.5 (M + 1) |
| 4805 | (CDCl₃) 5.37 (m, 1H), 4.05 (m, 2H), 3.72-3.69 (m, 2H), 2.75-2.65 (tt, 1H), 2.07-1.99 (m, 4H), 1.82-1.78 (m, 2H), 1.70 (s, 3H), 1.56-1.52 (m, 2H), 1.38-1.30 (m, 4H) | 291.7 (M + 1) |
| 4806 | (CDCl₃) 6.32 (m, 1H), 4.27 (m, 2H), 3.80 (m, 2H), 2.73-2.65 (tt, 1H), 2.29 (m, 2H), 2.03-1.99 (m, 2H), 1.83-1.79 (m, 2H), 1.72-1.68 (m, 2H), 1.56-1.52 (m, 1H), 1.39-1.24 (m, 3H) | 345.9 (M + 1) |
| 4807 | (CDCl₃) 5.95-5.93 (m, 1H), 4.31-4.24 (m, 2H), 3.77-3.72 (m, 2H), 2.75-2.66 (tt, 1H), 2.26-2.24 (m, 2H), 2.05-2.01 (m, 2H), 1.84-1.80 (m, 2H), 1.73 (m, 1H), 1.58-1.55 (m, 2H), 1.40-1.26 (m, 3H) | 311.9 (M + 1) |
| 4808 | (CDCl₃) 4.37 (m, 1H), 3.88 (m, 1H), 3.43-3.39 (t, 1H), 2.85-2.80 (m, 1H), 2.78-2.68 (tt, 1H), 2.58-2.54 (m, 1H), 2.05-2.01 (m, 2H), 1.85-1.81 (m, 2H), 1.74-1.70 (m, 1H), 1.57-1.53 (m, 2H), 1.40-1.26 (m, 4H) | 345.2 (M + 1) |
| 4839 | (CDCl₃ + MeOD) 7.97-7.93 (m, 2H), 7.22-7.17 (m, 2H), 3.93 (m, 4H), 3.20 (m, 2H) | 413.9 (M + 1) |
| 4840 | (CDCl₃ + MeOD) 7.98-7.93 (m, 2H), 7.22-7.16 (m, 2H), 4.60-4.55 (m, 2H), 2.79 (m, 2H), 2.29-2.24 (m, 1H), 1.95-1.91 (m, 2H), 1.62-1.49 (m, 2H) | 359.9 (M + 1) |
| 4841 | (CDCl₃ + MeOD) 7.98-7.93 (m, 2H), 7.20-7.17 (t, 2H), 5.45-5.42 (t, 1H), 4.09-4.08 (m, 2H), 3.70-3.66 (t, 2H), 2.21-2.19 (m, 2H), 1.03 (s, 9H) | 345.9 (M + 1) |
| 4842 | (CDCl₃) 7.97-7.92 (m, 2H), 7.21-7.15 (t, 2H), 3.59 (m, 3H), 1.92-1.90 (m, 3H), 1.82-1.78 (m, 4H), 1.62-1.58 (t, 4H) | 331.9 (M + 1) |
| 4843 | (CDCl₃) 7.97-7.92 (m, 2H), 7.21-7.16 (t, 2H), 5.71 (m, 1H), 4.18 (m, 2H), 3.85 (s, 2H), 3.84 (m, 2H), 3.32 (s, 3H), 2.20 (m, 2H) | 333.9 (M + 1) |
| 4922 | (CDCl₃) 7.98-7.94 (m, 2H), 7.21-7.15 (t, 2H), 3.61 (m, 4H), 1.78-1.75 (m, 2H), 1.60-1.56 (m, 2H), 1.44-1.42 (m, 2H), 0.96 (s, 6H) | 333.9 (M + 1) |
| 4923 | (CDCl₃) 7.96-7.93 (m, 2H), 7.23-7.17 (t, 2H), 4.36-4.28 (m, 2H), 3.89-3.80 (m, 2H), 2.29 (s, 2H), 1.87 (s, 3H) | 381.6 (M + 1) |
| 4930 | (CDCl₃ + MeOD) 7.95-7.90 (m, 2H), 7.19-7.13 (t, 2H), 3.84-3.72 (m, 4H), 2.44-2.29 (m, 2H) | 313.1 (M + 1) |
| 4931 | (CDCl₃ + MeOD) 7.91-7.87 (m, 2H), 7.13-7.08 (m, 2H), 3.70-3.66 (m, 2H), 3.42-3.40 (m, 2H), 2.11-1.98 (m, 2H), 1.37-1.31 (m, 2H) | 339.0 (M + 1) |
| 4932 | (CDCl₃) 7.98-7.93 (m, 2H), 7.22-7.16 (m, 2H), 6.00-5.60 (td, 1H), 3.93-3.70 (m, 3H), 3.37-3.34 (m, 1H), 2.16-2.15 (m, 1H), 1.03-1.01 (m, 1H), 0.77-0.73 (m, 1H), 0.69-0.66 (m, 2H) | 353.0 (M + 1) |
| 4933 | (CDCl₃) 7.98-7.93 (m, 2H), 7.22-7.16 (t, 2H), 4.51-4.48 (m, 2H), 2.84 (m, 2H), 1.79-1.74 (m, 2H), 1.37-1.25 (m, 3H), 1.21-1.09 (m, 2H), 0.94-0.89 (t, 3H) | 319.0 (M + 1) |
| 4934 | (CDCl₃) 7.97-7.92 (m, 2H), 7.21-7.15 (t, 2H), 4.49 (m, 2H), 3.51-3.44 (m, 2H), 1.76-1.71 (m, 2H), 1.49 (m, 1H), 1.37-1.11 (m, 6H), 0.93-0.88 (t, 3H) | 333.0 (M + 1) |
| 4935 | (CDCl₃) 7.98-7.94 (m, 2H), 7.22-7.16 (t, 2H), 5.78-5.76 (t, 2H), 3.76 (m, 4H), 2.40 (m, 4H) | 303.0 (M + 1) |

TABLE 1-continued

Potency of Select trans-Translation Inhibitors

| Cmpd No. MBX- | ¹H NMR Spectrum (solvent) | m/z found by LCMS (M + x) |
|---|---|---|
| 4936 | (CDCl$_3$) 7.98-7.95 (m, 2H), 7.24-7.16 (m, 6H), 3.86 (m, 4H), 3.00-2.96 (m, 4H) | 353.0 (M + 1) |
| 4937 | (CDCl$_3$) 7.99-7.94 (m, 2H), 7.21-7.16 (m, 2H), 3.82 (m, 2H), 3.50 (m, 2H), 2.01-1.91 (m, 3H), 1.58-1.54 (m, 1H), 1.40-1.34 (m, 1H), 1.19-1.08 (m, 2H), 0.88 (s, 9H) | 361.0 (M + 1) |
| 4938 | (CDCl$_3$) 7.99-7.94 (m, 2H), 7.23-7.17 (t, 2H), 4.62-4.58 (m, 2H), 2.78 (m, 2H), 1.78-1.75 (m, 2H), 1.27-1.24 (m, 3H +H20), 0.89 (s, 9H) | 347.9 (M + 1) |
| 4939 | (DMSO) 7.94-7.92 (m, 2H), 7.44-7.34 (m, 2H), 3.48-3.44 (t, 4H), 1.59-1.54 (m, 4H), 1.43-1.37 (m, 8H) | 345.9 (M + 1) |
| 4940 | (DMSO) 7.98-7.93 (m, 2H), 7.45-7.39 (t, 2H), 7.36-7.34 (d, 1H), 6.92-6.90 (d, 1H), 4.62 (s, 2H), 3.85-3.81 (t, 2H), 2.87-2.83 (t, 2H) | 345.9 (M + 1) |
| 4993 | (CDCl$_3$) 7.98-7.93 (m, 2H), 7.23-7.17 (m, 2H), 4.14 (m, 2H), 3.60-3.50 (m, 3H), 3.42-3.37 (m, 2H), 1.95-1.90 (m, 2H), 1.67-1.56 (m, 2H), 1.26-1.22 (t, 3H) | 335.0 (M + 1) |
| 4994 | (CDCl$_3$) 7.98-7.94 (m, 2H), 7.23-7.17 (m, 2H), 4.17-4.12 (m, 2H), 3.79-3.73 (quin, 1H), 3.65-3.57 (m, 1H), 3.43-3.38 (m, 2H), 1.90-1.84 (m, 2H), 1.64-1.54 (m, 2H), 1.19-1.17 (d, 6H) | 349.0 (M + 1) |
| 4995 | (CDCl$_3$) 7.98-7.94 (m, 2H), 7.23-7.17 (m, 2H), 4.31-4.17 (m, 2H), 3.69-3.64 (m, 1H), 3.34-3.22 (m, 2H), 1.80-1.77 (m, 2H), 1.59-1.52 (m, 2H), 1.23 (s, 9H) | 363.0 (M + 1) |
| 5154 | (CDCl$_3$ + MeOD) 7.74 (s, 1H), 7.68-7.65 (d, 1H), 7.29-7.26 (m, 1H), 4.31-4.25 (m, 2H), 3.84-3.79 (m, 2H), 2.94-2.89 (t, 4H), 2.55-2.53 (m, 2H), 2.10-2.05 (m, 2H) | 379.5 (M + 1) |
| 5155 | (CDCl$_3$) 7.79 (s, 1H), 7.73-7.71 (d, 1H), 7.35-7.32 (d, 1H), 6.36 (m, 1H), 4.32 (m, 2H), 3.89 (m, 2H), 3.00-2.95 (t, 4H), 2.35 (m, 2H), 2.18-2.11 (m, 2H) | 379.2 (M + 1) |
| 5199 | (CDCl$_3$) 7.99-7.95 (m, 2H), 7.34-7.31 (m, 2H), 7.25-7.18 (m, 5H), 4.74-4.70 (m, 2H), 3.07-2.88 (m, 2H), 2.81-2.71 (m, 1H), 1.96-1.92 (m, 2H), 1.79-1.65 (m, 2H) | 367.2 (M + 1) |
| 5200 | (CDCl$_3$) 7.97-7.92 (m, 2H), 7.21-7.16 (m, 2H), 4.44-4.33 (m, 2H), 2.85-2.52 (m, 2H), 1.85-1.50 (m, 4H), 1.49-1.07 (m, 1H), 0.95 (d, 3H) | 305.1 (M + 1) |
| 5201 | (CDCl$_3$) 7.99-7.94 (m, 2H), 7.22-7.16 (m, 2H), 3.93-3.85 (m, 2H), 3.73-3.56 (m, 3H) 1.94-1.91 (m, 2H), 1.75-1.58 (m, 2H) | 307.2 (M + 1) |
| 5202 | (CDCl$_3$) 7.71 (m, 4H), 6.88-6.85 (d, 2H), 4.87 (m, 2H), 4.02-3.93 (m, 2H), 2.93-2.89 (t, 2H), 2.35 (s, 6H) | 367.1 (M + 1) |
| 5203 | (CDCl$_3$) 6.88-6.85 (d, 2H), 4.45-4.36 (m, 2H), 3.98-3.87 (m, 2H), 2.58 (m, 2H), 2.35 (s, 6H) | 385.1 (M + 1) |
| 5204 | (CDCl$_3$) 6.88-6.85 (d, 2H), 6.35 (m, 1H), 4.38 (m, 2H), 4.25 (m, 2H), 2.35 (s, 6H), 1.64 (br, 2H + H2O) | 385.2 (M + 1) |
| 5212 | (CDCl$_3$) 7.99-7.96 (m, 2H), 7.22-7.17 (m, 2H), 4.51-4.48 (m, 2H), 2.84-2.81 (m, 1H), 2.61 (m, 1H), 1.91-1.87 (m, 1H), 1.79-1.75 (m, 1H), 1.58-1.48 (m, 2H), 1.33-1.18 (m, 2H), 1.00-0.93 (m, 6H) | 333.1 (M + 1) |
| 5214 | (CDCl$_3$) 7.96-7.93 (d, 1H), 7.44-7.41 (m, 1H), 7.37-7..32 (m, 2H), 7.20-7.18 (m, 4H), 4.92 (m, 2H), 3.99 (m, 2H), 2.96-2.92 (m, 2H), 2.68 (s, 3H) | 335.2 (M + 1) |
| 5215 | (DMSO) 7.81-7.79 (d, 1H), 7.49-7.47 (m, 1H), 7.74-7.37 (m, 2H), 4.31 (m, 2H), 3.79-3.75 (m, 2H), 2.58 (m, 5H) | 353.1 (M + 1) |
| 5216 | (CDCl$_3$) 6.85 (d, 2H), 5.40 (s, 1H), 4.17-4.03 (m, 2H), 3.82-3.71 (m, 2H), 2.33 (s, 6H), 2.15-2.05 (m, 2H), 1.72 (s, 3H) | 331.1 (M + 1) |
| 5222 | (CDCl$_3$ + MeOD) 7.76-7.73 (d, 2H), 7.15 (m, 4H), 6.56-6.53 (d, 2H), 4.79 (m, 2H), 3.86 (m, 2H), 3.37-3.31 (m, 4H + MeOH), 2.90-2.88 (t, 2H), 2.04-2.00 (m, 4H) | 390.3 (M + 1) |
| 5223 | (CDCl$_3$) 7.79-7.77 (d, 2H), 6.61-6.58 (d, 2H), 6.37 (m, 1H), 4.33 (m, 2H), 3.87 (m, 2H), 3.38 (m, 4H), 2.37 (m, 2H), 2.06 (m, 4H) | 408.3 (M + 1) |

Example 2. Assays for Evaluating Trans-Translation Inhibitor Properties

A number of analogs were synthesized as set forth herein, and their trans-translation inhibitory properties were evaluated according to the following assays.

i. High Throughput Luciferase-trpAT-Based Reporter Assay

The reporter contains a gene encoding luciferase with a strong transcriptional terminator inserted before the stop codon, such that transcription results in a nonstop mRNA. *E. coli* cells containing the reporter were screened in high-throughput format to identify compounds that inhibit trans-translation. When no inhibitor is present, translation of the nonstop mRNA results in trans-translation followed by proteolysis of luciferase, and cells produce no luminescence. Conversely, active luciferase is produced when a trans-translation inhibitor is present, resulting in luminescence. (See, FIG. 2.)

ii. In Vitro Antibacterial Activity (MIC)

To evaluate the antibacterial activity of the analogs, their minimal inhibitory concentration (MIC) against a panel of various bacterial strains was determined (strains listed in Table 2). MICs were determined using the broth microdilution method as described in the CLSI guidelines (M7-A9). (CLSI. Methods for Dilution Antimicrobial Susceptibility Tests for Bacteria That Grow Aerobically; Approved Standard M07-A10. Wayne, Pa.: Clinical and Laboratory Standards Institute (2015)). MICs for the most potent analogs are carried out in the presence of 10% fetal calf serum in order to more closely mimic human serum conditions and identify compounds with strong protein binding. Compounds that exhibit MICs≤100 μM are considered active, and those exhibiting MICs≤5 μM and <16-fold increase in the presence of serum are preferred.

iii. Mammalian Cell Cytotoxicity

The selectivity of analogs with potent antibacterial activity was evaluated by measuring the cytotoxicity against mammalian cell lines. The half maximal cytotoxic concentration ($CC_{50}$) for each inhibitor compound against HeLa (ATCC accession no. CCL-2) and Vero (ATCC accession no. CCL-81) cell lines is determined as previously described in Marshall et al., *Growth Regul.*, 5(2): 69-84 (1995). Analogs that exhibit a high level of selectivity ($CC_{50}$/MIC≥10) are preferred.

iv. Non-Stop Ribosome Rescue Assay

To verify that analogs with potent antibacterial activity inhibit non-stop ribosome rescue, the inhibitors were tested against a cell-based non-stop ribosome rescue reporter assay that was constructed in an efflux-deficient strain of *E. coli*. The gain-of-signal assay may be performed essentially as previously described in Ramadoss et al., *Proc. Natl. Acad. Sci. U.S.A.*, 110(25): 10282-7 (2013), except that the dose-dependent increase of signal is used to calculate the compound concentration that produces half maximal induction of the reporter ($EC_{50}$). Compounds with $EC_{50}$ values less than or equal to the MIC are considered inhibitors of non-stop ribosome rescue.

v. Mouse/Human Liver Microsome Stability

To examine the potential for first-pass metabolism of analogs in the liver, the stability of analogs in the presence of mouse liver microsome preparations (XenoTech) was measured. The stability of compounds in the presence of NADPH was measured using the method of Kuhnz et al., *Drug Metab. Dispos.*, 26(11): 1120-7 (1998)). Analogs that are stable in the presence of mouse microsome preparations (>30% parent remaining after 0.5 hr at 37° C.) are considered suitably stable for potential use as antibiotics.

vi. Mouse Serum Binding

To determine the quantity of predicted free drug in murine plasma, serum binding was determined for mouse using equilibrium dialysis. (Banker et al., *J. Pharm. Sci.*, 92:967 (2003)). Analogs that exhibit serum binding <99% are considered preferential for use.

vii. Mouse Serum Stability

To determine the potential for metabolism during circulation, the stability of analogs in the presence of mouse serum was measured. Analogs were incubated at 5 μM and 37° C. for 4 h, the assayed by analytical LCMS and compared to an internal standard to determine the percentage of material remaining. Compounds that are stable in the presence of mouse serum (>70% of parent remaining after 4 h) are considered suitably stable for potential use as antibiotics.

viii. Solubility

The maximum aqueous solubility of analogs was determined by nephelometry using published methods, e.g., Bevan et al., *Anal. Chem.*, 72(8): 1781-1787 (2000), with particularly efficacious compounds confirmed using LC/MS. (Lee et al., *Antimicrob. Agents Chemother.*, 35(12): 2505-2508 (1991)). Analogs that are soluble in water at >50 μM are considered soluble.

ix. CYP450 Inhibition

Because inhibition of cytochrome P450 (CYP450) enzymes in vitro is predictive of potential drug interactions in vivo, CYP450 inhibition was measured using commercially available Human Cytochrome P450 kits (BD Gentest Corp., Woburn, Mass.) for the major CYP450s: CYP3A4 and CYP2D6. The assays were performed according to the manufacturer's instructions. Compounds that exhibited minimal inhibition of CYP3A4 and 2D6 (30% at 10 μM) are preferred.

x. Caco-2 Permeability

To evaluate the potential for oral bioavailability, the bidirectional ability of the inhibitory compounds to permeate a monolayer of Caco-2 intestinal epithelial cells was determined as described by Gres et al., *Pharm. Res.*, 15(5): 726-733 (1998). Compounds exhibiting a Caco-2 permeability value (Papp) $>5 \times 10^{-6}$ cm/sec are considered potentially orally bioavailable.

xi. $MIC_{90}$ Determination

To assess the antibacterial activity of prioritized analogs against a broad spectrum of bacterial clinical isolates, the $MIC_{90}$ values for a select number of the most preferred compounds was analyzed. The $MIC_{90}$ represents the MIC for 90% of the isolates tested. The $MIC_{90}$ was determined using as many as 20 recent clinically important isolates that are representative of the prevalent antibiotic-resistant and -sensitive phenotypes. These assays were performed by Micromyx, LLC (Kalamazoo, Mich.) as needed. Compounds exhibiting a $MIC_{90}$≤5 μg/ml are preferred.

xii. Single Dose PK (IV and PO)

Murine PK studies were carried out by administering each trans-translation inhibitor compound with a suitable vehicle by IV and PO at doses that fall below the MTD. Blood was collected via tail vein or retinal bleed (for plasma concentration determinations) at 6 different time intervals (5 minutes, 0.5, 1, 4, 8 and 24 hours). Three individual plasma samples for each time point were analyzed to estimate the rate and extent of uptake, time of peak plasma concentration, peak plasma concentration (Cmax), terminal plasma half-life (t½), area under the curve (AUC), volume of distribution and clearance using standard procedures. See, e.g., Gibaldi et al., *J. Pharm. Sci.*, 61(6): 952-954 (1972); Gibaldi et al., *J. Clin. Pharmacol. And New Drugs*, 12(5): 201-204 (1972); Tam et al., *Clin. Microbiol. Infect.*, 13(4): 413-418 (2007). Compound levels were determined by extraction followed by LC/MS-MS quantification.

xiii. Murine Efficacy—Thigh Model; Single Dose Studies

Initial efficacy studies examined oral efficacy against a murine thigh model. These studies utilized the challenge strain BAA1717 (TCH1516; USA300), a clinical isolate of MRSA. Each study was performed using both untreated and vancomycin treated controls (representing three experimental groups). In the described experiment, 16 CD-1 (ICR) mice (4 experimental groups; n=4 mice/group) were acclimated for 5 days, rendered neutropenic with cyclophosphamide (IP, 150 mg/kg at day −4 and 100 mg/kg at day −1), and infected at T=0 with an injection of 0.100 mL of bacterial suspension ($5.0 \times 10^5$ CFU) in the right thigh. Test agent was administered at 2 hours post infection. Additionally at this time point, one untreated control group was euthanized ($CO_2$ inhalation) and harvested. At 26 hours post-infection, all treated groups and the second untreated control group were euthanized ($CO_2$ inhalation) and harvested. Following euthanization, the right thigh of each animal was weighed, homogenized, plated and CFUs determined to provide a calculated CFU/gram.

xiv. Murine Efficacy—Vaginal Gonococcal Infection; Single Dose Studies

Two separate efficacy studies examined oral efficacy against a murine model of vaginal gonococcal infection. These studies utilized the strain H041, a highly drug-resistant Ng clinical isolate described by Ohnishi et. al. *Antimicrob. Agents Chemother.*, 55(7): 3538 (2011). Each study was performed using both untreated and gentamycin (48 mg/kg IP, QD 5 days) controls (representing 2 experimental groups). In each of two experiments, the test agent was MBX-4132 given as an oral dosage at either 3.3 mg/kg or 10 mg/kg via a single oral dosage. Two days prior to experiments, female BALB/c mice were treated with 17β-estradiol and antibiotics to increase their susceptibility to Ng as described previously (Jerse et. al., *Frontiers Microbial.*, 2: 107 (2011)).

On day 0, mice were inoculated vaginally with 20 μl of strain H041(STM$^R$) suspended in PBS; suspensions adjusted to 5×10$^5$ CFU/ml (infectious dose 80; ID$_{80}$). For H041 (STM$^R$), the ID$_{80}$ is 10$^4$ CFU/mouse. Vaginal swabs were quantitatively cultured for Ng on days 1 and 2 following vaginal inoculation to confirm infection prior to treatment. A portion of the swab sample was also inoculated onto HIA agar to monitor commensal flora. Test and control antibiotics were administered on day 2 post-bacterial inoculation after the day 2 culture was collected and for four more consecutive days. Test conditions (MBX-4132 at 10 mg/kg or 3.3 mg/kg) and the vehicle control were administered a single time orally (PO) on day 2. Gentamycin (GEN), the positive control, was administered via intraperitoneal (IP) injection once daily (QD) for 5 days initiating on day 2. Vaginal swabs were quantitatively cultured for *N. gonorrhoeae* for 8 consecutive days following treatment. Vaginal material was collected by wetting a swab in sterile PBS, gently inserting the swab into the vagina, and suspending the swab in 1 mL of GC Broth. Broth suspensions were diluted and diluted and undiluted samples were cultured on GC-VCNTS agar using the Autoplater automated plating system (Spiral Biotech). The number of viable bacteria recovered was determined using the Spiral Biotech Q-Counter Software. At the study endpoint (Day +10 post-inoculation), mice were euthanized by $CO_2$ asphyxiation and a final vaginal swab was obtained. The limit of detection for *N. gonorrhoeae* was 20 CFU/ml.

xv. Determination of Efficacy Against MRSA after Intracellular Infection of Macrophages To determine if lead compounds maintain efficacy against intracellular MRSA, compounds can be examined against intracellular macrophage infections such as described in Eissa et al., *Eur. J. Med. Chem.*, 130: 73-85 (2017). To conduct this assay, cultured murine macrophage cells (J774) are exposed to challenge strain BAA1717 (TCH1516; USA300), a clinical isolate of MRSA at approximately a multiplicity of infection of 100:1. One hour post-infection, cells are washed with gentamicin (50 μg/mL) to kill extracellular MRSA, at which point test compounds are administered at 4× the MIC. At 4 hrs, 8 hrs and 24 hrs, cells are treated with gentamicin (50 μg/mL), rinsed and lysed (triton-X 100). Viable intracellular bacteria in the lysate are then quantified by a standard serial dilution and plating method. Each assay is performed in triplicate and statistical comparisons are used to establish activity. Compounds that exhibited significantly improved outcomes compared with vancomycin (P value ≤0.05) are preferred.

Example 3. Antibacterial Activity of Select Trans-Translation Inhibitory Compounds A number of compounds of Formula I and Formula II were chosen for an analysis of their potency against a broad spectrum of both Gram-positive and Gram-negative bacterial species in an *E. coli* ΔtolC assay. The results are shown in Table 2 below.

TABLE 2

Antibacterial efficacy (MIC μg/mL) against various bacterial pathogens

| Gram (+) bacterial strains | Compound No. MBX- | | | | | | | | | | | |
|---|---|---|---|---|---|---|---|---|---|---|---|---|
| | 3535 | 4132 | 4237 | 4285 | 4288 | 4292 | 4293 | 4330 | 4331 | 4332 | 4345 | 4347 |
| S. aureus (MRSA-1234547263, Cip-res) | 0.99 | 3.17 | 2.35 | | | 0.67 | | | | | | |
| MRSA-1094 (MDR) | 0.99 | 3.17 | 2.35 | 2.52 | 5.68 | 0.75 | 0.72 | 2.03 | 3.15 | 5.00 | 19.53 | 2.23 |
| S. aureus (ATCC 35556, spec, kan-res) | 0.99 | 4.23 | 2.35 | | | 0.95 | | | | | | |
| S. aureus NRS-77 (spec-res) | 0.99 | 3.17 | 2.96 | | | 1.17 | | | | | | |
| S. aureus WTBF-19 (MSSA, osteomyelitis isolate) | 0.99 | 4.23 | 2.35 | | | 1.19 | | | | | | |
| S. aureus ATCC 25923 (MSSA, osteomyelitis isolate) | 1.49 | 6.34 | 2.35 | 6.34 | 7.16 | 1.23 | 1.15 | ≥32 | 4.45 | 7.07 | 27.6 | >35 |
| MRSA USA 300 (BAA-1717 | 0.88 | 1.06 | 2.10 | 0.63 | 2.01 | 0.30 | 0.29 | 1.01 | | | | |
| MRSA N315 NRS-70 | 1.48 | 6.34 | 4.70 | | | 1.36 | | | | | | |

TABLE 2-continued

Antibacterial efficacy (MIC μg/mL) against various bacterial pathogens

Compound No. MBX–

| | | | | | | |
|---|---|---|---|---|---|---|
| S. pneumoniae 49619 | | 33.8 | 4.70 | | 4.77 | 4.59 |
| M. pneumoniae 15531 | | >33.8 | 18.8 | | 19.1 | 18.4 |
| B. anthracis | 0.25 | 4.06 | | | | |
| M. tuberculosis | <1.64 | | | | | |

| Gram (–) bacterial strains | 3535 | 4132 | 4237 | 4285 | 4288 | 4292 | 4293 | 4330 | 4331 | 4332 | 4345 | 4347 |
|---|---|---|---|---|---|---|---|---|---|---|---|---|
| E. coli (700, TolC+) efflux pos | >33 | >35 | >39 | >40 | >45 | >39 | >36 | >32 | >35 | >35 | >27 | >27 |
| E. coli (701, TolC–) efflux neg | 0.53 | 2.14 | 0.60 | 13.3 | 1.59 | 0.43 | 0.51 | 2.02 | 1.11 | 1.11 | 6.9 | 27 |
| N. gonorrhoeae 49226 | 0.12 | 0.18 | 0.75 | | | 0.10 | 0.09 | 0.16 | 0.089 | 0.089 | | 0.089 |
| N. gonorrhoeae H041 (MDR including AZM and CTX) | 0.25 | 0.13 | | | | | | | | | | |
| Shigella flexneri | 2.0 | | | | | | | | | | | |
| Yersinia pestis | 0.98 | 8.46 | | | | | | | | | | |
| Brucella suis | 0.064 | 4.23 | | | | | | | | | | |
| Franciscella tularensis (Schu13) | <0.03 | 0.13 | 0.75 | | | | | | | | | |
| Moraxella catarrhalis 8176 | | 0.034 | 0.060 | | | <0.02 | <0.02 | | | | | |
| Legionella pneumophila 33153 | | 8.46 | 0.87 | | | 0.61 | 0.59 | | | | | |
| Haemophilus influenza 35056 | | 16.91 | 9.41 | | | >39 | 12.23 | | | | | |

MI C90

| | | | |
|---|---|---|---|
| N. gonorrhoeae | 0.25 | 0.54 | |
| Franciscella tularensis | | 0.13 | 1.51 |

The data in Table 2 demonstrate that a number of compounds represented by Formula I and Formula II above exhibit potent inhibitory activity against diverse strains of MRSA (MIC's ranged from 0.28 to 3.07) as well as a broad spectrum of other Gram-positive and Gram-negative pathogens, including N. gonorrhoeae (MICs ranged from 0.08 to 1.21).

These compounds appear to be subject to efflux in certain pathogens based on their differential activity against efflux proficient and deficient (ΔtolC) strains of E. coli, although the observed activity against Neisseria gonorrhoeae and other Gram-negative pathogens suggests that this is not necessarily a universal concern.

Example 4. Potency of Select Trans-Translation Inhibitor Compounds

Assays were performed as described above for a number of trans-translation inhibitor compounds. The results are shown in Table 3.

TABLE 3

Potency of Select trans-Translation Inhibitors

| Compound No. MBX– | TolC(–) MIC (μM)(NB) | Fold Serum Shift vs. TolC(–) | AVG Luc IC$_{50}$ ΔtolC (μM) | CC$_{50}$ |
|---|---|---|---|---|
| 4737 | 0.78 | 32 | | >100 |
| 4923 | 0.78 | 18 | | |
| 4305 | 0.781 | | 0.259 | 32 |
| 4310 | 0.781 | | 0.35 | >100 |
| 5203 | 0.781 | | | |
| 4309 | 0.98405 | | | >100 |
| 4306 | 0.9841 | | 0.37 | >100 |
| 4292 | 1.10456 | | 0.259933 | 23.7 |
| 4780 | 1.24 | | | |
| 4293 | 1.39188 | | 0.278 | 31.8 |
| 4499 | 1.56 | 20 | | >100 |
| 4925 | 1.56 | | | |
| 4926 | 1.56 | | | |
| 5215 | 1.56 | | | |
| 4237 | 1.5625 | | 0.238 | >100 |
| 4307 | 1.5625 | | | 65 |
| 4308 | 1.5625 | | | 32 |
| 4357 | 1.5625 | | 0.123 | 45 |

TABLE 3-continued

Potency of Select trans-Translation Inhibitors

| Compound No. MBX- | TolC(−) MIC (μM)(NB) | Fold Serum Shift vs. TolC(−) | AVG Luc IC$_{50}$ ΔtolC (μM) | CC$_{50}$ |
|---|---|---|---|---|
| 5154 | 1.75 | | | |
| 5155 | 1.97 | | | |
| 4498 | 2.21 | | | >100 |
| 4285 | 2.48031 | | | 59.9 |
| 4347 | 2.48031 | | 0.14 | >100 |
| 4331 | 3.125 | | 0.13 | 34 |
| 4332 | 3.125 | | 0.11 | 14.4 |
| 4801 | 3.13 | 16 | | |
| 4736 | 3.13 | 12.7 | | |
| 4769 | 3.13 | | | |
| 4839 | 3.13 | 12.5 | | |
| 4940 | 3.13 | | | |
| 4288 | 3.50769 | | | 6.6 |
| 4289 | 3.50769 | | | |
| 4304 | 3.50769 | 28.5 | 0.78 | >100 |
| 4770 | 4.42 | | | |
| 4938 | 4.96 | | | |
| 5204 | 4.96 | | | |
| 5199 | 5.57 | | | |
| 4314 | 6.25 | | | |
| 4330 | 6.25 | | 0.15 | >100 |
| 4366 | 6.25 | 4 | | 46 |
| 4465 | 6.25 | | | >100 |
| 4802 | 6.25 | | | |
| 4768 | 6.25 | | | |
| 4807 | 6.25 | | | |
| 4808 | 6.25 | | | |
| 4840 | 6.25 | 4 | | |
| 4841 | 6.25 | 8 | | |
| 4842 | 6.25 | 4 | | |
| 4933 | 6.25 | | | |
| 4934 | 6.25 | | | |
| 4936 | 6.25 | | | |
| 4939 | 6.25 | | | |
| 4738 | 7 | | | |
| 4470 | 7.02 | 7.1 | | >100 |
| 5202 | 7.02 | | | |
| 5212 | 7.02 | | | |
| 5214 | 7.02 | | | |
| 4132 | 7.87 | 12.7 | 0.593267 | 27.2 |
| 4698 | 8.84 | | | |
| 4741 | 11.1 | | | |
| 4767 | 11.1 | | | |
| 4937 | 11.1 | | | |
| 4290 | 11.1362 | | | |
| 5223 | 11.14 | | | |
| 4333 | 12.5 | | | |
| 4348 | 12.5 | | | >100 |
| 4469 | 12.5 | | | |
| 4685 | 12.5 | | | |
| 4686 | 12.5 | | | |
| 4776 | 12.5 | | | |
| 4779 | 12.5 | | | |
| 4806 | 12.5 | | | |
| 4922 | 12.5 | | | |
| 4935 | 12.5 | | | |
| 5200 | 12.5 | | | |
| 5216 | 12.5 | | | |
| 4684 | 15.75 | | | |
| 4700 | 15.75 | | | |
| 4932 | 17.67 | | | |
| 4777 | 17.68 | | | |
| 4930 | 19.8 | | | |
| 4778 | 19.84 | | | |
| 4735 | 22.27 | | | |
| 4345 | 25 | | | |
| 4699 | 25 | | | |
| 4805 | 25 | | | |
| 4843 | 25 | | | |
| 4995 | 25 | | | |
| 5222 | 25 | | | |
| 4931 | 28.06 | | | |
| 4201 | 28.0616 | | | |
| 4258 | 35.3553 | | | |
| 4993 | 44.5 | | | |
| 4994 | 44.5 | | | |
| 4200 | 50 | | | |
| 4406 | 50 | | | |
| 4701 | 50 | | | |
| 4284 | 70.7107 | | | |
| 4346 | 100 | | | |
| 4381 | 100 | | | |
| 4697 | 100 | | | |
| 4734 | 100 | | | |
| 4739 | 100 | | | |
| 4740 | 100 | | | |
| 4198 | ≥100 | | | |
| 4199 | ≥100 | | | |
| 4349 | ≥100 | | | |
| 4350 | ≥100 | | | |
| 4351 | ≥100 | | | |
| 4380 | ≥100 | | | |
| 4464 | ≥100 | | | |
| 4468 | ≥100 | | | |
| 4497 | ≥100 | | | |
| 4702 | >100 | | | |
| 5201 | >100 | | | |

Example 4. MBX-4132 Selectivity/Toxicity Analysis. (Eurofins/Panlabs Hit Profile Panel)

Assays were performed as described above for a number of trans-translation inhibitor compounds. The results are shown in Table 4.

TABLE 4

Select in vitro ADME Properties of acylaminooxadiazoles

| Compound No. MBX- | Microsomal Stability + NADPH % degraded | Serum Binding (% bound) | Serum Stability (% remain) | Solubility H$_2$O | Caco-2 P$_{app}$ (×10$^{-6}$ cm/s) |
|---|---|---|---|---|---|
| 4737 | 21 | >99 | >95 | 6.3 | |
| 4923 | | | >95 | | |
| 4305 | <30 | | | 3.13 | |
| 4310 | <30 | | | 6.25 | |
| 5203 | | | | | |
| 4309 | <30 | | | 6.25 | |
| 4306 | <30 | | | 6.25 | |
| 4292 | 20 | >99 | 82 | 6.25 | 1.0 |
| 4780 | | 99.5 | | | |
| 4293 | 59 | 99.9 | 88 | 3.125 | |
| 4499 | 19 | >99 | | 25 | |
| 4237 | 9 | 99.8 | >95 | 6.25 | 12.7 |
| 4307 | <30 | | | 12.5 | |
| 4308 | <30 | | | 3.13 | |
| 4357 | | | | 3.1 | |
| 4285 | | | | 3.125 | |
| 4347 | <30 | >99 | 93 | 3.1 | 21.8 |
| 4331 | <30 | | | 12.5 | |
| 4332 | <30 | | | 3.13 | |
| 4801 | | | >95 | 12.5 | 13.2 |
| 4736 | 30 | >99 | >95 | 3.1 | |
| 4769 | | 96.9 | | | |
| 4839 | | | >95 | 6.25 | |
| 4288 | | | | 25 | |
| 4304 | 85 | >99 | | 50 | 13.7 |
| 4330 | 43.5 | | | 3.13 | |
| 4366 | 45 | 94.9 | 95 | 25 | 67.3 |
| 4465 | | | | 12.5 | |
| 4807 | | | >95 | | 32.5 |
| 4808 | | | >95 | | 24.5 |

TABLE 4-continued

Select in vitro ADME Properties of acylaminooxadiazoles

| Compound No. MBX- | Microsomal Stability + NADPH % degraded | Serum Binding (% bound) | Serum Stability (% remain) | Solubility H$_2$O | Caco-2 P$_{app}$ (×10$^{-6}$ cm/s) |
|---|---|---|---|---|---|
| 4842 | | | | 77 | |
| 4470 | 2 | 97.8 | | 100 | |
| 4132 | 27 | | >95 | 6.25 | 65.8 |
| 4348 | | | | 25 | |
| 4284 | | | | 3.125 | |

Example 5. Selectivity/Toxicity Analysis of Select Compounds. (Eurofins/Panlabs Hit Profile Panel)

Selectivity/toxicity testing was carried out using four compounds; two uriedoaminooxadiazoles (MBX-4132 and MBX-4347) and two amidooxadiazoles (MBX-4292 and MBX-4237) as an exemplary compounds against 36 mammalian receptors in the Eurofins/Panlabs Hit Profile Panel at 10 µM (Table 5).

TABLE 5

Eurofins/Panlabs Hit Profile Panel (10 µM MBX-4132)

| Assay Name | Species | % Inhibition MBX-4132 | % Inhibition MBX-4347 | % Inhibition MBX-4292 | % Inhibition MBX-4237 |
|---|---|---|---|---|---|
| CYP450, 1A2 | human | 9 | 2 | 5 | 1 |
| CYP450, 2C19 | human | 44 | 8 | 9 | 3 |
| CYP450, 2C9 | human | 10 | 4 | 10 | 5 |
| CYP450, 2D6 | human | 10 | 9 | 2 | -4 |
| CYP450, 3A4 | human | 7 | 9 | 4 | 6 |
| Adenosine A$_1$ | human | 48 | -4 | 8 | 10 |
| Adenosine A$_{2A}$ | human | 43 | 3 | 11 | 6 |
| Adrenergic α$_{1A}$ | rat | 24 | -21 | 9 | 6 |
| Adrenergic α$_{1B}$ | rat | 21 | 7 | 3 | -2 |
| Adrenergic α$_{2A}$ | human | 54 | 9 | 3 | -8 |
| Adrenergic β$_1$ | human | -10 | 3 | 3 | -9 |
| Adrenergic β$_2$ | human | 36 | 8 | 6 | 15 |
| Calcium Channel L-type, Dihydropyridine | rat | 15 | 16 | 23 | 2 |
| Cannabinoid CB$_1$ | human | 14 | 0 | 11 | 7 |
| Dopamine D$_1$ | human | -8 | 5 | 17 | 7 |
| Dopamine D$_{2s}$ | human | 25 | -2 | 1 | -3 |
| GABA$_A$, Flunitrazepam, Central | rat | 13 | 22 | -1 | 25 |
| GABA$_A$, Muscimol, Central | rat | 1 | 4 | -4 | -6 |
| Glutamate, NMDA, Phencyclidine | rat | -3 | 5 | 0 | 9 |
| Histamine, H$_1$ | human | 17 | 22 | -8 | 6 |
| Imidazoline I$_2$, Central | rat | 33 | -5 | 10 | 14 |
| Muscarinic M$_2$ | human | 13 | 2 | 0 | 17 |
| Muscarinic M$_3$ | human | 16 | 2 | 0 | 11 |
| Nicotinic Acetylcholine | human | -8 | -4 | 1 | 8 |
| Nicotinic Acetylcholine α1, Bungarotoxin | human | 0 | 2 | -4 | -8 |
| Opiate µ(OP3, MOP) | human | 74 | -14 | 4 | 12 |
| Phorbol Ester | mouse | 4 | 7 | 2 | 2 |
| Potassium Channel (K$_{ATP}$) | hamster | 10 | 2 | 8 | 9 |
| Potassium Channel hERG | human | 64 | 0 | 8 | 8 |
| Prostanoid EP$_4$ | human | 18 | -4 | 28 | -22 |
| Rolipram | rat | 2 | -6 | -8 | 1 |
| Seritonin (5-Hydroxytryptamine) 5-HT$_{2B}$ | human | 53 | -1 | -7 | -4 |
| Sigma σ$_1$ | human | -4 | -2 | 10 | 32 |
| Sodium Channel, Site 2 | rat | 4 | -5 | -2 | -3 |
| Transporter, Norepinephrine (NET) | human | 50 | 32 | 77 | 45 |

From the testing of two of these compounds, MBX-4347 and MBX-4237, for selectivity/toxicity against 36 mammalian receptors in the Eurofins/Panlabs Hit Profile Panel at it was revealed that aminooxadiazole compounds of both series have no intrinsic liabilities (defined as <50% inhibition at 10 µM) against the potential off-target receptors described in Table 4. Additionally, two tolerability studies of MBX-4132 showed no effects distinct from vehicle controls after extended observation (10 days following multidose and 24 h following a single dose); these two studies included a multidose tolerability study of MBX-4132 examined seven days of dosing (at 25 mg/kg, SC, BID), and elevated single dose studies (at 100 mg/kg, PO) (data not shown).

Example 6. MBX-4132 Mouse PK

Figure 3:
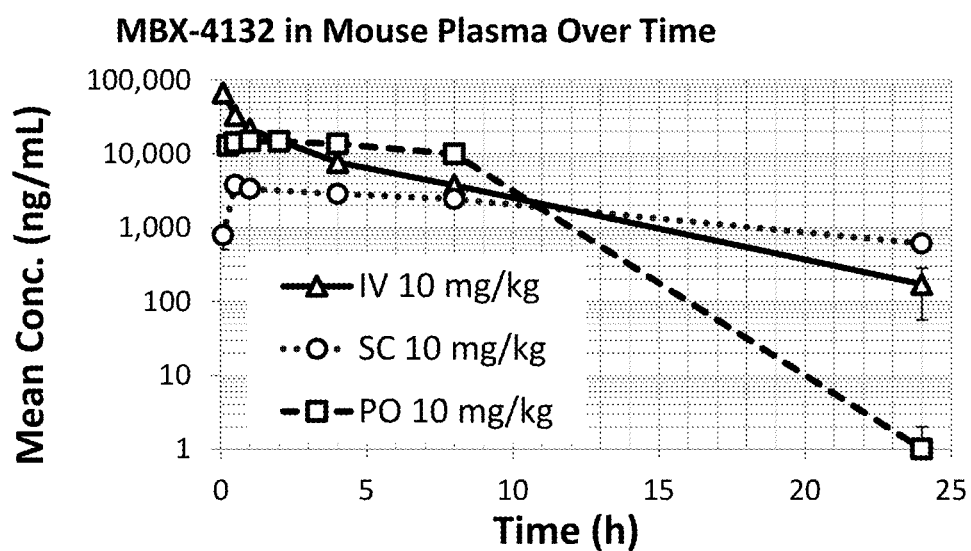
FIG. 3 is a graph showing mean concentration over time of a ureido aminooxadiazole derivative, MBX-4132, administered at 10 mg/kg to mice by various routes, i.e., intravenously (IV), subcutaneously (SC), and orally (PO, per os). Pharmacokinetic data are given below the graph, including half-life ($T_{1/2}$), highest concentration measured ($C_{0/max}$), Area Under Curve$_{last}$ ($AUC_{last}$), volume of distribution ($V_{ss}$), clearance rate (Cl), and free percentage of drug (% F) in circulation.

MBX-4132 was tested to characterize in vivo exposure and potential for toxicity. Consistent with its poor microsomal stability, preliminary PK studies of KKL-35 had indicated extremely poor bioavailability in mice (undetectable in mouse serum at 6 h). In contrast, PK studies of MBX-4132 showed excellent bioavailability (>75% available from oral dosing), area under the curve (AUC), half-life and volume of distribution. See, FIG. 3.

Example 7. MBX-4132 In Vivo Efficacy vs MRSA

Figure 4:
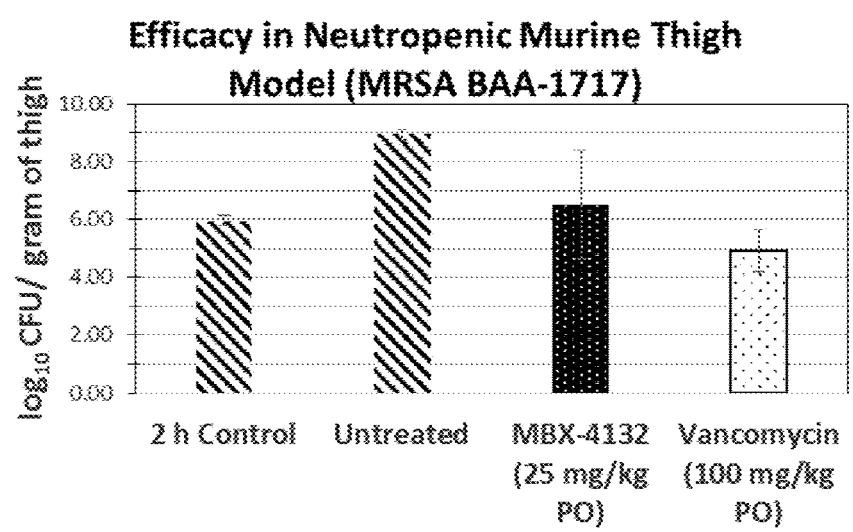
FIG. 4 is a graph showing in vivo efficacy results of oral administration of ureido aminooxazole derivative MBX-4132 to mice infected with MRSA strain BAA-1717 in a neutropenic murine thigh model. MBX-4132 was administered (25 mg/kg, PO) once 2 hours following infection. Harvesting and CFU counts were performed 24 hours after administration. Surprisingly, mice treated with MBX-4132 showed more than a 2 log drop in CFU/g following a single oral dose, compared to untreated controls (P=0.03), and the efficacy was comparable to a 100 mg/kg dose of positive control vancomycin.

Based on the PK, toxicological data, tolerability and in vitro efficacy of MBX-4132, it was selected for a pilot in vivo study (n=4) against MRSA USA300 strain BA-1717 run by Neosome®. MBX-4132 was administered once 2 h following infection PO (25 mg/kg), with harvesting and CFU counts performed 24 hrs post dosage. Mice treated with MBX-4132 showed a >2 log drop in CFU/g following a single oral dose, unambiguously demonstrating efficacy in this model (P=0.03; data shown). See, FIG. 4.

Example 8. MBX-4132 In Vivo Efficacy vs *Neisseria Gonorrhoeae*

Figure 5:
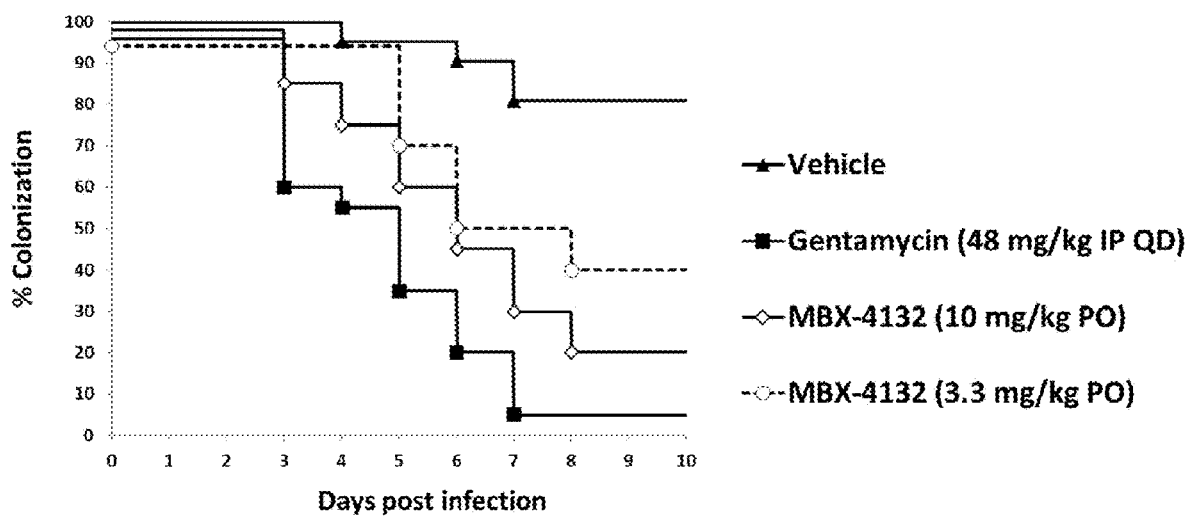
FIG. 5 is a graph showing the combined data for two independent in vivo efficacy studies of oral administration of uriedo aminooxadiazole derivative MBX-4132 to female mice infected with *Neisseria gonorrhoeae* strain H041 (STMR) in a vaginal gonococcal murine model. For a published description of the efficacy model, see, Butler, M. et. al., *Antimicrobial Agents Chemother.*, 62(5):e00321 (2018). MBX-4132 was administered (3.3 or 10 mg/kg, PO) once 2 days following infection. Vaginal swabs were taken daily and examined for viable colonies of Ng; mice in which zero colonies were detected on three consecutive days were characterized as "not colonized." When treated at 10 mg/kg with MBX-4132, 80% of mice were fully cleared of infection within 6 days of treatment, demonstrating clear efficacy relative to untreated controls (p <0.0001), and comparable to the positive control (gentamycin, dosed 5 times at 48 mg/kg IP QD; p=0.049). At a lower dose (3.3 mg/kg), MBX-4132 demonstrated a smaller effect, failing to achieve statistical significance relative to the untreated controls (p=0.058), but still showing a marked effect.

Based on the preliminary MRSA efficacy, PK, toxicological data, tolerability and in vitro efficacy of MBX-4132, it was selected for repeated and dose ranging in vivo studies (n=10/group) against *Neisseria gonorrheae* Strain H041 (STMR) run at Uniformed Services University (Bethesda, Md.). MBX-4132 was administered once 2 d following infection PO (10 mg/kg), with animals monitored for continuing infection for the following 8 days. In combined data from two independent experiments, 80% mice treated with MBX-4132 at 10 mg/kg were completely cleared of infection within 6 days of treatment, unambiguously demonstrating reproducible efficacy in this model. Moreover, mice treated with a lower dose (3.3 mg/kg) of MBX-4132 demonstrated a lower 60% clearance rate, demonstrating a dose response to this compound in this model of infection. The results are shown in FIG. 5.

Additional embodiments of the aminooxadiazole trans-translation inhibitor compounds described above may be easily produced following the description and examples provided above. The publications and documents cited above are incorporated herein by reference.

What is claimed is:

1. A compound of Formula I:

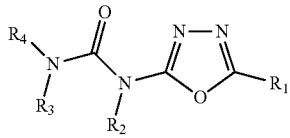

(I)

wherein:
$R_1$ is an aryl ring bearing 1-4 substituents an unsubstituted linear or branched chain aliphatic group containing 5-8 carbon atoms; a substituted linear, branched chain, or cyclic aliphatic group containing 1-6 carbon atoms bearing 1-8 substituents selected from, aryl, heteroaryl, amino, substituted amino, halogen, alkoxy, sulfonyl, aryloxy, hydroxy, acylamino, carboxy, or alkylcarboxy; a carbocyclic ring of 3-7 carbon atoms bearing 1-4 substituents selected from alkyl, cycloalkyl, aryl, heteroaryl, amino, substituted amino, halogen, alkoxy, sulfonyl, aryloxy, hydroxy, acylamino, carboxy, or alkylcarboxy, an aromatic or non-aromatic heterocyclic ring made up of carbon atoms and at least one ring heteroatom selected independently from oxygen, nitrogen and sulfur atoms, and said heterocyclic ring bears 1-4 substituents selected from alkyl, cycloalkyl, aryl, heteroaryl, amino, substituted amino, halogen, alkoxy, sulfonyl, aryloxy, hydroxy, acylamino, carboxy, or alkylcarboxy;

$R_2$ is hydrogen, methyl, $C_2$-$C_4$ alkyl or; cycloalkyl;

$R_3$ and $R_4$ are independently methyl, $C_2$-$C_6$ alkyl or cycloalkyl, an aromatic or non-aromatic heterocyclic ring bearing 1-3 substituents or; aryl bearing 1-3 substituents;

or, alternatively, $R_3$ and $R_4$ may be linked together to form a substituted 3-8-membered cyclic or heterocyclic ring selected from piperidine, piperazine, morpholine, azepine, which rings may be optionally substituted with substituents selected from -alkyl, halogen, alkoxy, sulfonyl, carboxy, alkylcarboxy, substituted phenyl groups, substituted heterocyclic groups or spirocycles; or the 3-8-membered ring may be fused with aromatic or heteroaromatic rings bearing 1-3 substituents selected from alkyl, halogen, alkoxy, sulfonyl, aryloxy, hydroxy, amino, acylamino, carboxy, alkylcarboxy aryl or heteroaryl groups;

or a pharmaceutically acceptable salt thereof.

2. A compound according to claim 1, selected from the group consisting of:

| Compound No. MBX- | Structure |
|---|---|
| 4132 | 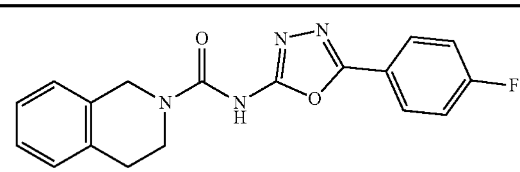 |
| 4198 | 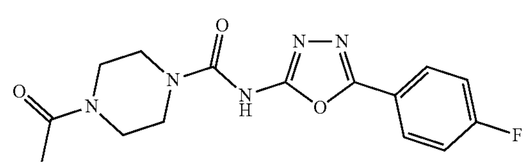 [SMILES: CC(=O)N1CCN(C(=O)Nc2nnc(-c3ccc(F)cc3)o2)CC1] |
| 4199 | 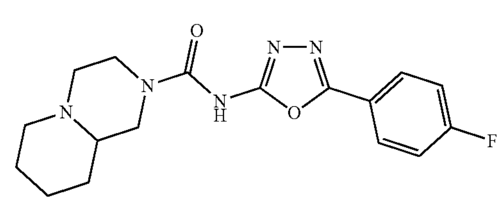 [SMILES: O=C(Nc1nnc(-c2ccc(F)cc2)o1)N1CCN2CCCCC2C1] |

| Compound No. MBX- | Structure |
|---|---|
| 4200 | 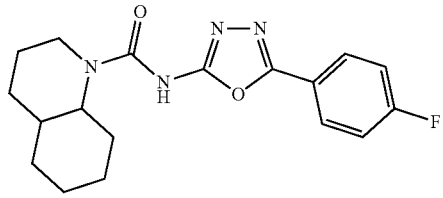 [SMILES: O=C(Nc1nnc(-c2ccc(F)cc2)o1)N1CCCC2CCCCC21] |
| 4201 | 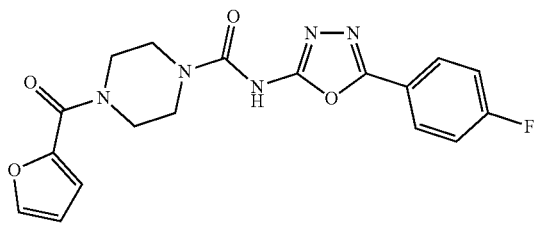 [SMILES: O=C(Nc1nnc(-c2ccc(F)cc2)o1)N1CCN(C(=O)c2ccco2)CC1] |
| 4330 | 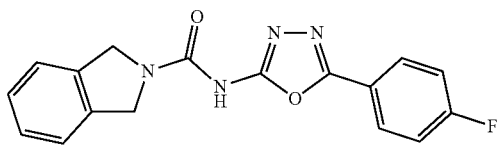 [SMILES: O=C(Nc1nnc(-c2ccc(F)cc2)o1)N1Cc2ccccc2C1] |
| 4331 | 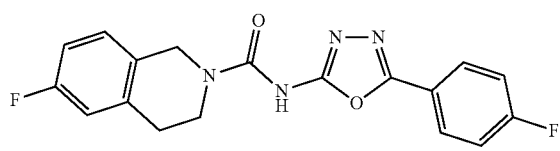 [SMILES: O=C(Nc1nnc(-c2ccc(F)cc2)o1)N1CCc2cc(F)ccc2C1] |
| 4332 | 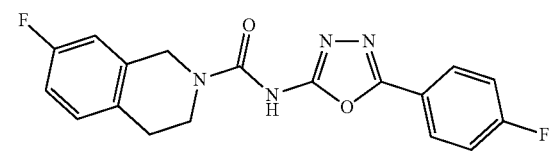 [SMILES: O=C(Nc1nnc(-c2ccc(F)cc2)o1)N1CCc2ccc(F)cc2C1] |
| 4333 | 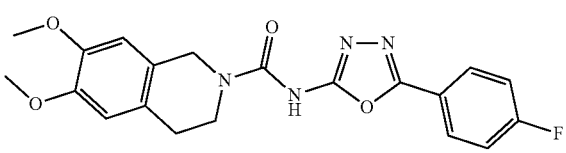 [SMILES: COc1cc2c(cc1OC)CN(C(=O)Nc1nnc(-c3ccc(F)cc3)o1)CC2] |
| 4345 | 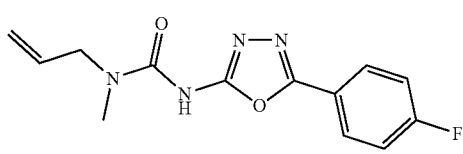 [SMILES: C=CCN(C)C(=O)Nc1nnc(-c2ccc(F)cc2)o1] |
| 4346 | 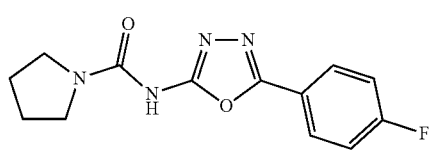 [SMILES: O=C(Nc1nnc(-c2ccc(F)cc2)o1)N1CCCC1] |
| 4347 | 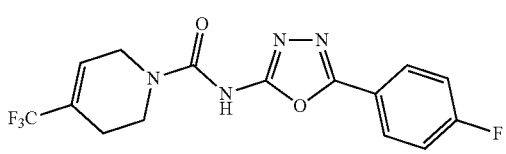 [SMILES: O=C(Nc1nnc(-c2ccc(F)cc2)o1)N1CC=C(C(F)(F)F)CC1] |

-continued

| Compound No. MBX- | Structure |
|---|---|
| 4348 | methyl 1-((5-(4-fluorophenyl)-1,3,4-oxadiazol-2-yl)carbamoyl)-1,2,3,6-tetrahydropyridine-4-carboxylate |
| 4349 | N-(5-(4-fluorophenyl)-1,3,4-oxadiazol-2-yl)-4-methyl-1,4-diazepane-1-carboxamide |
| 4350 | N-(5-(4-fluorophenyl)-1,3,4-oxadiazol-2-yl)-3-oxopiperazine-1-carboxamide |
| 4351 | N-(5-(4-fluorophenyl)-1,3,4-oxadiazol-2-yl)-4-methyl-3-oxopiperazine-1-carboxamide |
| 4366 | N-(5-(4-fluorophenyl)-1,3,4-oxadiazol-2-yl)-4-methyl-3,6-dihydropyridine-1(2H)-carboxamide |
| 4380 | N-(5-(4-fluorophenyl)-1,3,4-oxadiazol-2-yl)-2-oxa-5-azabicyclo[2.2.1]heptane-5-carboxamide |
| 4381 | N-(5-(4-fluorophenyl)-1,3,4-oxadiazol-2-yl)-2-oxa-5-azabicyclo[2.2.1]heptane-5-carboxamide |
| 4406 | (2S,6R)-N-(5-(4-fluorophenyl)-1,3,4-oxadiazol-2-yl)-4-(2-methoxyethyl)-2,6-dimethylpiperazine-1-carboxamide |
| 4464 | N-(5-(4-fluorophenyl)-1,3,4-oxadiazol-2-yl)-2-methyl-4H-pyrrolo[3,4-d]thiazole-5(6H)-carboxamide |

| Compound No. MBX- | Structure |
|---|---|
| 4465 | 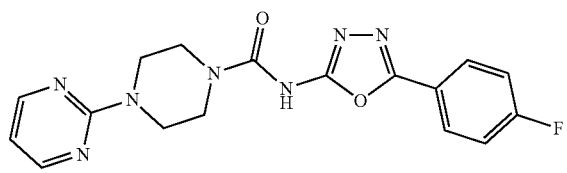 [SMILES: O=C(Nc1nnc(-c2ccc(F)cc2)o1)N1CCN(c2ncccn2)CC1] |
| 4497 | 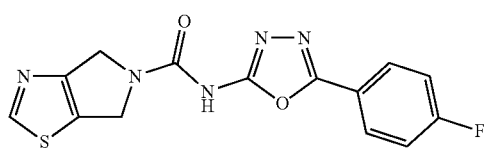 [SMILES: O=C(Nc1nnc(-c2ccc(F)cc2)o1)N1Cc2ncsc2C1] |
| 4684 | 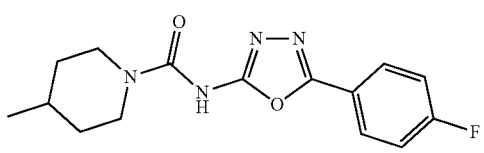 [SMILES: CC1CCN(C(=O)Nc2nnc(-c3ccc(F)cc3)o2)CC1] |
| 4685 | 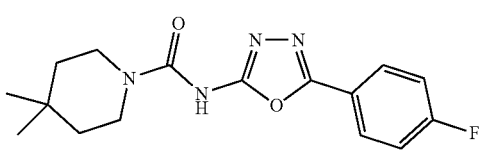 [SMILES: CC1(C)CCN(C(=O)Nc2nnc(-c3ccc(F)cc3)o2)CC1] |
| 4686 | 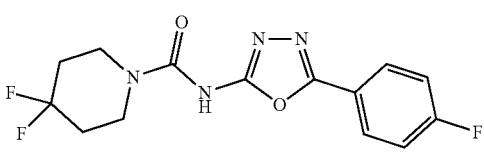 [SMILES: O=C(Nc1nnc(-c2ccc(F)cc2)o1)N1CCC(F)(F)CC1] |
| 4697 | 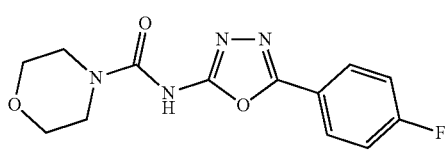 [SMILES: O=C(Nc1nnc(-c2ccc(F)cc2)o1)N1CCOCC1] |
| 4698 | 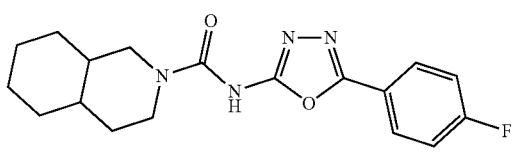 [SMILES: O=C(Nc1nnc(-c2ccc(F)cc2)o1)N1CCC2CCCCC2C1] |
| 4699 | 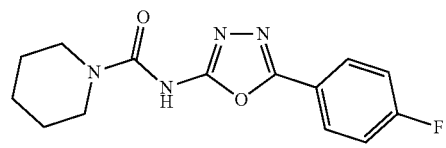 [SMILES: O=C(Nc1nnc(-c2ccc(F)cc2)o1)N1CCCCC1] |
| 4700 | 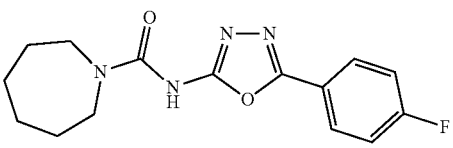 [SMILES: O=C(Nc1nnc(-c2ccc(F)cc2)o1)N1CCCCCC1] |

-continued

| Compound No. MBX- | Structure |
|---|---|
| 4701 | methyl 1-{[5-(4-fluorophenyl)-1,3,4-oxadiazol-2-yl]carbamoyl}piperidine-4-carboxylate |
| 4702 | N-[5-(4-fluorophenyl)-1,3,4-oxadiazol-2-yl]-4-(piperidin-1-yl)piperidine-1-carboxamide |
| 4734 | N-[5-(4-fluorophenyl)-1,3,4-oxadiazol-2-yl]-4-hydroxypiperidine-1-carboxamide |
| 4735 | N-[5-(4-fluorophenyl)-1,3,4-oxadiazol-2-yl]-3-(trifluoromethyl)pyrrolidine-1-carboxamide |
| 4736 | 3,4-dichloro-N-[5-(4-fluorophenyl)-1,3,4-oxadiazol-2-yl]-3,6-dihydro-2H-pyridine-1-carboxamide |
| 4737 | 3,4-dichloro-N-[5-(4-fluorophenyl)-1,3,4-oxadiazol-2-yl]-3,6-dihydro-2H-pyridine-1-carboxamide |
| 4738 | N-[5-(4-fluorophenyl)-1,3,4-oxadiazol-2-yl]-3,4-dimethyl-3,6-dihydro-2H-pyridine-1-carboxamide |
| 4739 | N-[5-(4-fluorophenyl)-1,3,4-oxadiazol-2-yl]-2-oxa-7-azaspiro[3.5]nonane-7-carboxamide |

-continued
| Compound No. MBX- | Structure |
|---|---|
| 4740 | 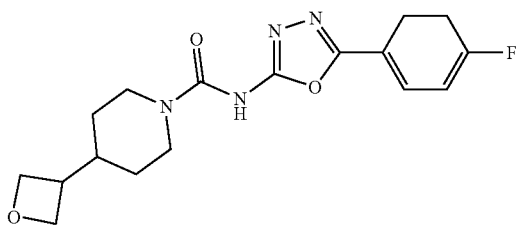 |
| 4741 | 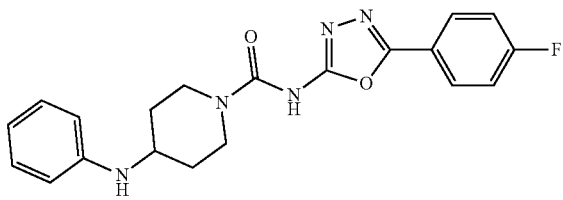 [SMILES: O=C(Nc1nnc(-c2ccc(F)cc2)o1)N1CCC(Nc2ccccc2)CC1] |
| 4767 | 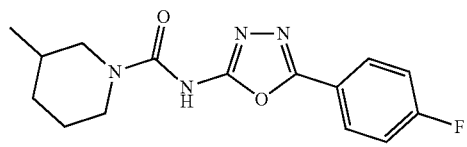 [SMILES: CC1CCCN(C(=O)Nc2nnc(-c3ccc(F)cc3)o2)C1] |
| 4768 | 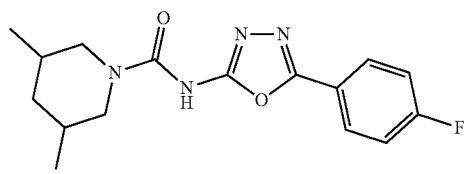 [SMILES: CC1CC(C)CN(C(=O)Nc2nnc(-c3ccc(F)cc3)o2)C1] |
| 4769 | 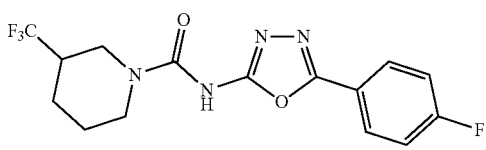 [SMILES: O=C(Nc1nnc(-c2ccc(F)cc2)o1)N1CCCC(C(F)(F)F)C1] |
| 4776 | 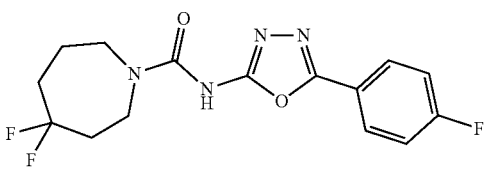 [SMILES: O=C(Nc1nnc(-c2ccc(F)cc2)o1)N1CCCC(F)(F)CC1] |
| 4777 | 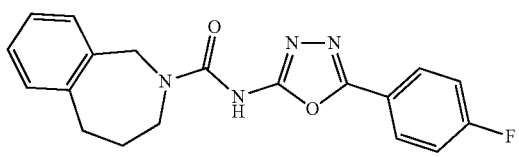 [SMILES: O=C(Nc1nnc(-c2ccc(F)cc2)o1)N1CCCc2ccccc2C1] |
| 4778 | 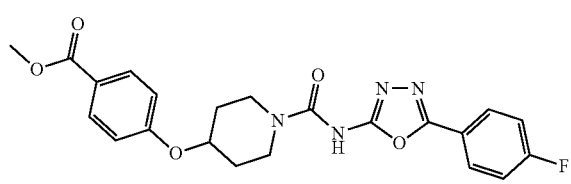 [SMILES: COC(=O)c1ccc(OC2CCN(C(=O)Nc3nnc(-c4ccc(F)cc4)o3)CC2)cc1] |

-continued
| Compound No. MBX- | Structure |
|---|---|
| 4779 | 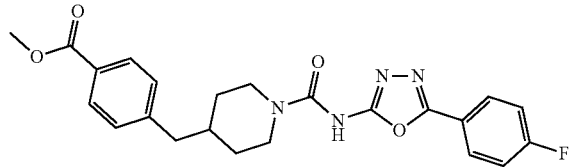 [SMILES: COC(=O)c1ccc(CC2CCN(C(=O)Nc3nnc(-c4ccc(F)cc4)o3)CC2)cc1] |
| 4805 | 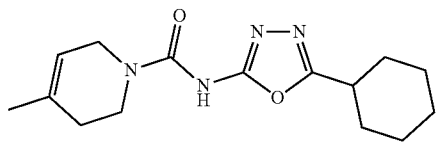 [SMILES: CC1=CCN(C(=O)Nc2nnc(C3CCCCC3)o2)CC1] |
| 4806 | 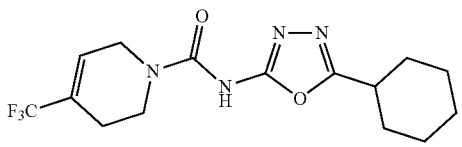 [SMILES: O=C(Nc1nnc(C2CCCCC2)o1)N1CC=C(C(F)(F)F)CC1] |
| 4807 | 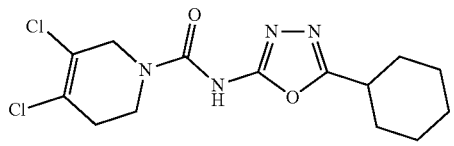 [SMILES: O=C(Nc1nnc(C2CCCCC2)o1)N1CCC(Cl)=C(Cl)C1] |
| 4808 | 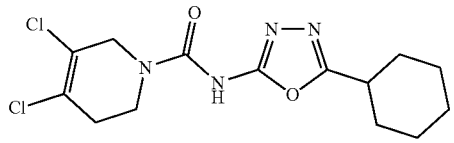 [SMILES: O=C(Nc1nnc(C2CCCCC2)o1)N1CCC(Cl)=C(Cl)C1] |
| 4839 | 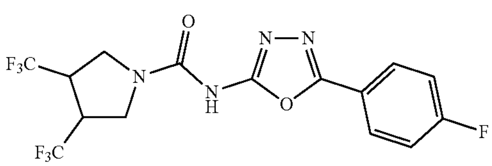 [SMILES: O=C(Nc1nnc(-c2ccc(F)cc2)o1)N1CC(C(F)(F)F)C(C(F)(F)F)C1] |
| 4840 | 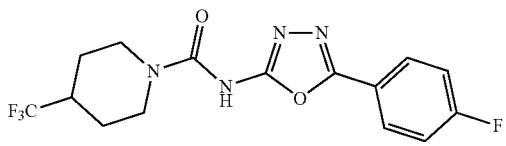 [SMILES: O=C(Nc1nnc(-c2ccc(F)cc2)o1)N1CCC(C(F)(F)F)CC1] |
| 4841 | 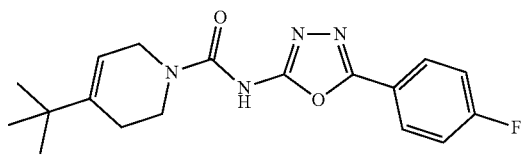 [SMILES: CC(C)(C)C1=CCN(C(=O)Nc2nnc(-c3ccc(F)cc3)o2)CC1] |
| 4842 | 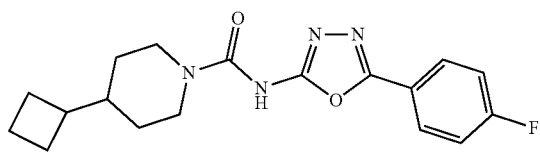 [SMILES: O=C(Nc1nnc(-c2ccc(F)cc2)o1)N1CCC(C2CCC2)CC1] |

| Compound No. MBX- | Structure |
|---|---|
| 4843 | 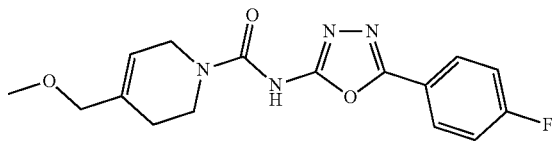 [SMILES: COCC1=CCN(C(=O)Nc2nnc(-c3ccc(F)cc3)o2)CC1] |
| 4922 | 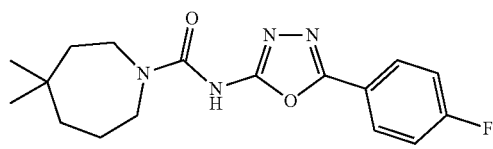 [SMILES: CC1(C)CCCN(C(=O)Nc2nnc(-c3ccc(F)cc3)o2)CC1] |
| 4923 | 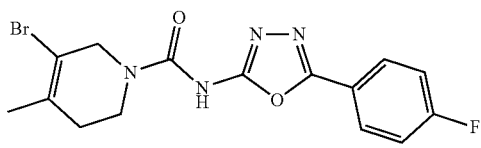 [SMILES: CC1=C(Br)CN(C(=O)Nc2nnc(-c3ccc(F)cc3)o2)CC1] |
| 4930 | 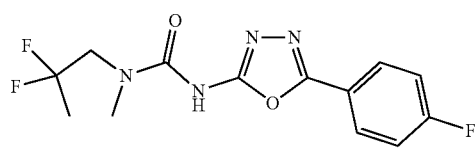 [SMILES: CN(CC(C)(F)F)C(=O)Nc1nnc(-c2ccc(F)cc2)o1] |
| 4931 | 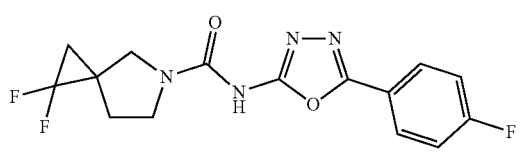 [SMILES: O=C(Nc1nnc(-c2ccc(F)cc2)o1)N1CCC2(C1)CC2(F)F] |
| 4932 | 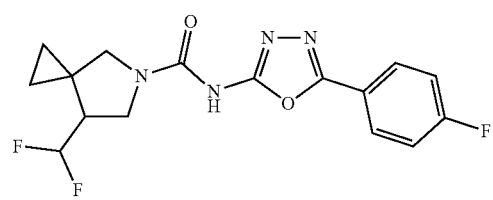 [SMILES: O=C(Nc1nnc(-c2ccc(F)cc2)o1)N1CC(C(F)F)C2(CC2)C1] |
| 4933 | 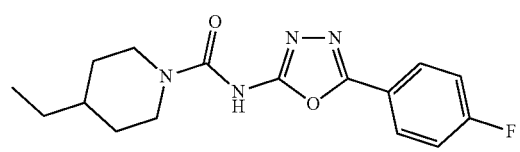 [SMILES: CCC1CCN(C(=O)Nc2nnc(-c3ccc(F)cc3)o2)CC1] |
| 4934 | 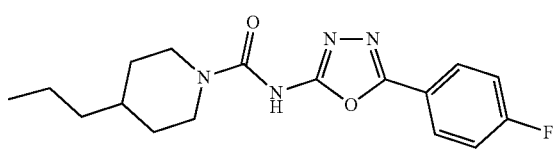 |
| 4935 | 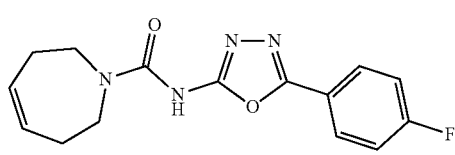 |

-continued
| Compound No. MBX- | Structure |
|---|---|
| 4936 | 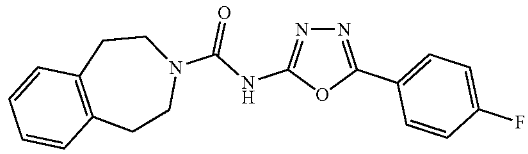 [SMILES: O=C(Nc1nnc(-c2ccc(F)cc2)o1)N1CCc2ccccc2CC1] |
| 4937 | 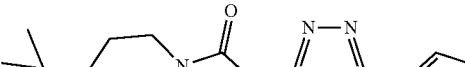 |
| 4938 | 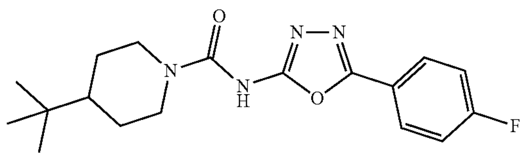 [SMILES: CC(C)(C)C1CCN(C(=O)Nc2nnc(-c3ccc(F)cc3)o2)CC1] |
| 4939 | 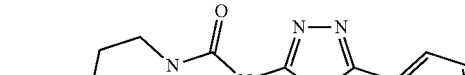 |
| 4940 | 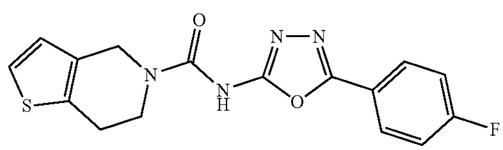 [SMILES: O=C(Nc1nnc(-c2ccc(F)cc2)o1)N1CCc2sccc2C1] |
| 4993 | 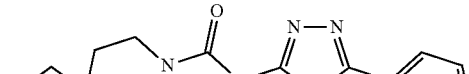 |
| 4994 | 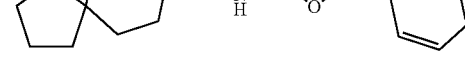 |
| 4995 | 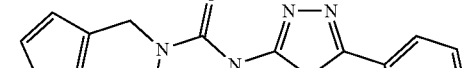 |
| 5154 | 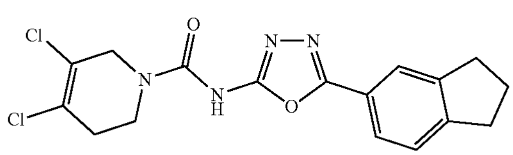 [SMILES: O=C(Nc1nnc(-c2ccc3c(c2)CCC3)o1)N1CCC(Cl)=C(Cl)C1] |
| 5155 | 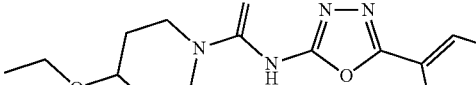 |

| Compound No. MBX- | Structure |
|---|---|
| 5199 | 4-phenylpiperidine-1-carboxamide with N-[5-(4-fluorophenyl)-1,3,4-oxadiazol-2-yl] |
| 5200 | (3R)-3-methylpiperidine-1-carboxamide with N-[5-(4-fluorophenyl)-1,3,4-oxadiazol-2-yl] |
| 5201 | 3-hydroxypiperidine-1-carboxamide with N-[5-(4-fluorophenyl)-1,3,4-oxadiazol-2-yl] |
| 5202 | 3,4-dihydroisoquinoline-2(1H)-carboxamide with N-[5-(4-fluoro-2,6-dimethylphenyl)-1,3,4-oxadiazol-2-yl] |
| 5203 | 3,4-dichloro-3,6-dihydropyridine-1(2H)-carboxamide with N-[5-(4-fluoro-2,6-dimethylphenyl)-1,3,4-oxadiazol-2-yl] |
| 5204 | 4-(trifluoromethyl)-3,6-dihydropyridine-1(2H)-carboxamide with N-[5-(4-fluoro-2,6-dimethylphenyl)-1,3,4-oxadiazol-2-yl] |
| 5212 | 3-isopropylpiperidine-1-carboxamide with N-[5-(4-fluorophenyl)-1,3,4-oxadiazol-2-yl] |
| 5214 | 3,4-dihydroisoquinoline-2(1H)-carboxamide with N-[5-(2-methylphenyl)-1,3,4-oxadiazol-2-yl] |
| 5215 | 3,4-dichloro-3,6-dihydropyridine-1(2H)-carboxamide with N-[5-(2-methylphenyl)-1,3,4-oxadiazol-2-yl] |

| Compound No. MBX- | Structure |
|---|---|
| 5216 | ![structure] |
| 5222 | ![structure] |
| 5223 | ![structure] | or a pharmaceutically acceptable salt thereof.

3. A method of treating or preventing a bacterial infection in a mammal, comprising administering to a subject in need thereof at least one compound according to claim 1.

4. The method according to claim 3, wherein the mammal is a human.

5. A method of inhibiting trans-translation-mediated bacterial growth in a mammal comprising administering an effective amount of a composition comprising at least one compound according to claim 1.

6. The method according to claim 5, wherein the mammal is a human.

7. The method according to claim 3, wherein the bacterial infection is selected from *M. tuberculosis, N. gonorrhoeae, S. flexneri, H. influenzae, S. aureus, S. enterica, Y. pestis, F. tularensis,* and *S. pneumoniae*.

8. A pharmaceutical composition comprising at least one compound according to claim 1, and a pharmaceutically acceptable carrier or excipient.

9. A method of inhibiting growth of bacterial cells on a solid surface comprising the step of contacting the surface with at least one compound according to claim 1.

10. A method of disinfecting a solid surface comprising the step of contacting the surface with at least one compound according to claim 1.

11. The method according to claim 9 or 10, wherein said solid surface is selected from the group consisting of implantable medical devices, central venous catheters (CVCs), implantable pumps, artificial heart valves, cardiac pacemakers, cardio-pulmonary bypass (CPB) pumps, heart-lung machines, dialysis equipment, artificial respirators, breathing apparatuses, water pipes, air ducts, air filters, water filters, and plumbing fixtures.

12. A method of treating or preventing a bacterial infection in a mammal, comprising administering to a subject in need thereof an effective amount of a compound of Formula I:

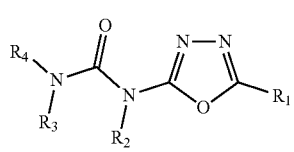

(I)

wherein:

$R_1$ is an aryl ring bearing 1-4 substituents heteroaryl an unsubstituted linear or branched chain aliphatic group containing 5-8 carbon atoms; a substituted linear, branched chain, cyclic aliphatic group containing 1-6 carbon atoms bearing 1-8 substituents aliphatic selected from aryl, heteroaryl, amino, substituted amino, halogen, alkoxy, sulfonyl, aryloxy, hydroxy, acylamino, carboxy, or alkylcarboxy; a carbocyclic ring of 3-7 carbon atoms bearing 1-4 substituents selected from alkyl, cycloalkyl, aryl, heteroaryl, amino, substituted amino, halogen, alkoxy, sulfonyl, aryloxy, hydroxy, acylamino, caroboxy, or alkylcarboxy; an aromatic or non-aromatic heterocyclic ring made up of carbon atoms and at least one ring heteroatom selected independently from oxygen, nitrogen and sulfur atoms, and said heterocyclic ring bears 1-4 substituents selected from alkyl, cycloalkyl, aryl, heteroaryl, amino, substituted amino, halogen, alkoxy, sulfonyl, aryloxy, hydroxy, acylamino, carboxy, or alkylcarboxy;

$R_2$ is hydrogen, methyl, C2-C4 alkyl or cycloalkyl;

$R_3$ and $R_4$ are independently hydrogen, methyl, C2-C6 alkyl or cycloalkyl; an aromatic or non-aromatic heterocyclic ring bearing 1-3 substituents; or aryl bearing 1-3 substituents;

or, alternatively, $R_3$ and $R_4$ may be linked together to form a substituted 3-8-member cyclic or heterocyclic ring selected from piperidine, piperazine, morpholine, or azepine, which rings may be optionally substituted with substituents selected from alkyl, halogen, alkoxy, sulfonyl, carboxy, alkylcarboxy, substituted phenyl groups, substituted heterocyclic groups or spirocycles; or the 3-8 membered ring may be fused with aromatic or heteroaromatic rings bearing 1-3 substituents selected from alkyl, halogen, alkoxy, sulfonyl, aryloxy, hydroxy, amino, acylamino, carboxy, alkylcarboxy, aryl, or heteroaryl groups;

or a pharmaceutically acceptable salt thereof.

13. The method according to claim 12, wherein the compound is selected from the group consisting of:

| Compound No. MBX- | Structure |
|---|---|
| 4132 | 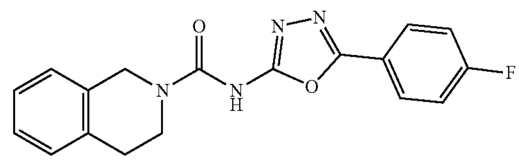 [SMILES: O=C(Nc1nnc(-c2ccc(F)cc2)o1)N1CCc2ccccc2C1] |
| 4198 | 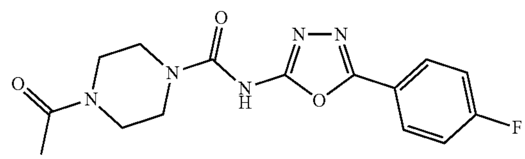 [SMILES: CC(=O)N1CCN(C(=O)Nc2nnc(-c3ccc(F)cc3)o2)CC1] |
| 4199 | 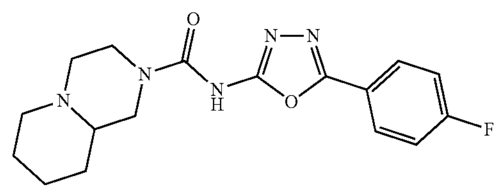 [SMILES: O=C(Nc1nnc(-c2ccc(F)cc2)o1)N1CCN2CCCCC2C1] |
| 4200 | 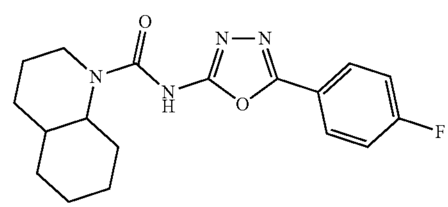 [SMILES: O=C(Nc1nnc(-c2ccc(F)cc2)o1)N1CCCC2CCCCC21] |
| 4201 | 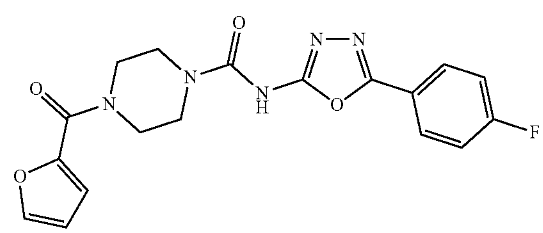 [SMILES: O=C(Nc1nnc(-c2ccc(F)cc2)o1)N1CCN(C(=O)c2ccco2)CC1] |
| 4330 | 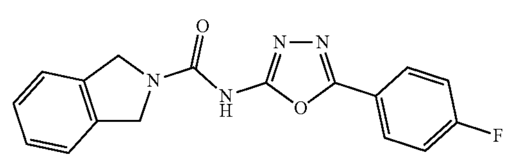 [SMILES: O=C(Nc1nnc(-c2ccc(F)cc2)o1)N1Cc2ccccc2C1] |
| 4331 | 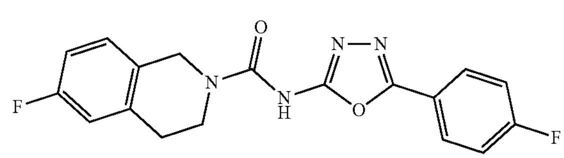 [SMILES: O=C(Nc1nnc(-c2ccc(F)cc2)o1)N1CCc2cc(F)ccc2C1] |

-continued

| Compound No. MBX- | Structure |
|---|---|
| 4332 | 7-fluoro-3,4-dihydroisoquinoline-2(1H)-carboxamide linked via NH to 5-(4-fluorophenyl)-1,3,4-oxadiazol-2-yl |
| 4333 | 6,7-dimethoxy-3,4-dihydroisoquinoline-2(1H)-carboxamide linked via NH to 5-(4-fluorophenyl)-1,3,4-oxadiazol-2-yl |
| 4345 | N-allyl-N-methyl urea linked to 5-(4-fluorophenyl)-1,3,4-oxadiazol-2-yl |
| 4346 | pyrrolidine-1-carboxamide linked to 5-(4-fluorophenyl)-1,3,4-oxadiazol-2-yl |
| 4347 | 4-(trifluoromethyl)-3,6-dihydropyridine-1(2H)-carboxamide linked to 5-(4-fluorophenyl)-1,3,4-oxadiazol-2-yl |
| 4348 | methyl 1-{[5-(4-fluorophenyl)-1,3,4-oxadiazol-2-yl]carbamoyl}-1,2,3,6-tetrahydropyridine-4-carboxylate |
| 4349 | 4-methyl-1,4-diazepane-1-carboxamide linked to 5-(4-fluorophenyl)-1,3,4-oxadiazol-2-yl |
| 4350 | 3-oxopiperazine-1-carboxamide linked to 5-(4-fluorophenyl)-1,3,4-oxadiazol-2-yl |
| 4351 | 4-methyl-3-oxopiperazine-1-carboxamide linked to 5-(4-fluorophenyl)-1,3,4-oxadiazol-2-yl |
| 4366 | 4-methyl-3,6-dihydropyridine-1(2H)-carboxamide linked to 5-(4-fluorophenyl)-1,3,4-oxadiazol-2-yl |

-continued
| Compound No. MBX- | Structure |
|---|---|
| 4380 | 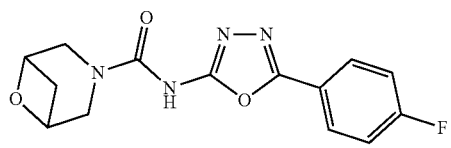 [SMILES: O=C(Nc1nnc(-c2ccc(F)cc2)o1)N1CC2CC(C1)O2] |
| 4381 | 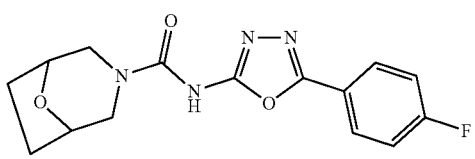 [SMILES: O=C(Nc1nnc(-c2ccc(F)cc2)o1)N1CC2CCC(C1)O2] |
| 4406 | 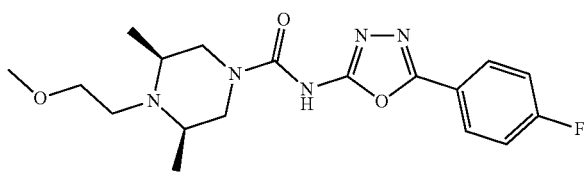 [SMILES: COCCN1[C@H](C)CN(C(=O)Nc2nnc(-c3ccc(F)cc3)o2)C[C@@H]1C] |
| 4464 | 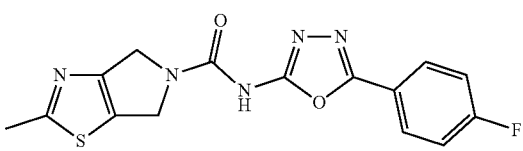 [SMILES: Cc1nc2c(s1)CN(C(=O)Nc1nnc(-c3ccc(F)cc3)o1)C2] |
| 4465 | 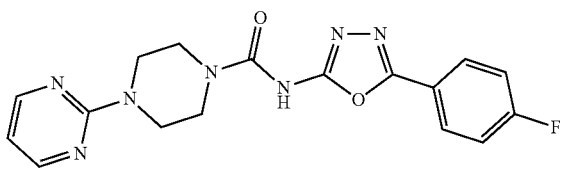 [SMILES: O=C(Nc1nnc(-c2ccc(F)cc2)o1)N1CCN(c2ncccn2)CC1] |
| 4497 | 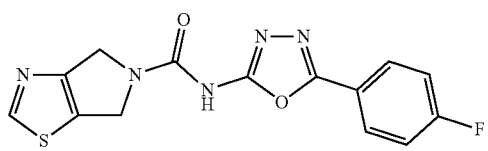 [SMILES: O=C(Nc1nnc(-c2ccc(F)cc2)o1)N1Cc2ncsc2C1] |
| 4684 | 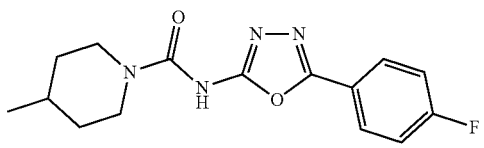 [SMILES: CC1CCN(C(=O)Nc2nnc(-c3ccc(F)cc3)o2)CC1] |
| 4685 | 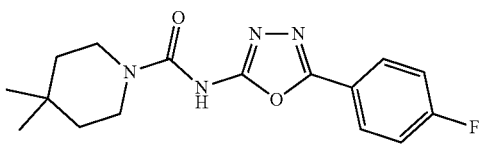 [SMILES: CC1(C)CCN(C(=O)Nc2nnc(-c3ccc(F)cc3)o2)CC1] |
| 4686 | 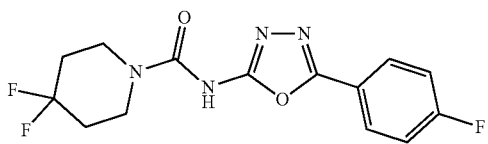 [SMILES: O=C(Nc1nnc(-c2ccc(F)cc2)o1)N1CCC(F)(F)CC1] |

-continued

| Compound No. MBX- | Structure |
|---|---|
| 4697 | (morpholine-N-C(O)-NH-[1,3,4-oxadiazol-2-yl]-5-(4-fluorophenyl)) |
| 4698 | (decahydroisoquinolin-2-yl-C(O)-NH-[1,3,4-oxadiazol-2-yl]-5-(4-fluorophenyl)) |
| 4699 | (piperidin-1-yl-C(O)-NH-[1,3,4-oxadiazol-2-yl]-5-(4-fluorophenyl)) |
| 4700 | (azepan-1-yl-C(O)-NH-[1,3,4-oxadiazol-2-yl]-5-(4-fluorophenyl)) |
| 4701 | (4-(methoxycarbonyl)piperidin-1-yl-C(O)-NH-[1,3,4-oxadiazol-2-yl]-5-(4-fluorophenyl)) |
| 4702 | (4-(piperidin-1-yl)piperidin-1-yl-C(O)-NH-[1,3,4-oxadiazol-2-yl]-5-(4-fluorophenyl)) |
| 4734 | (4-hydroxypiperidin-1-yl-C(O)-NH-[1,3,4-oxadiazol-2-yl]-5-(4-fluorophenyl)) |
| 4735 | (3-(trifluoromethyl)pyrrolidin-1-yl-C(O)-NH-[1,3,4-oxadiazol-2-yl]-5-(4-fluorophenyl)) |
| 4736 | (3,4-dichloro-3,6-dihydropyridin-1(2H)-yl-C(O)-NH-[1,3,4-oxadiazol-2-yl]-5-(4-fluorophenyl)) |

| Compound No. MBX- | Structure |
|---|---|
| 4737 | 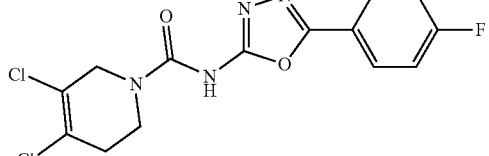 |
| 4738 | 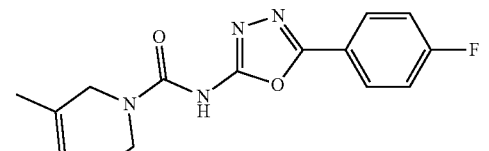 |
| 4739 | 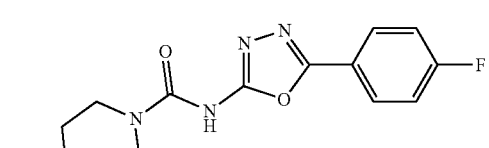 |
| 4740 | 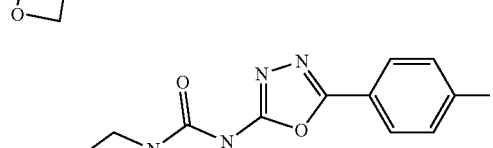 |
| 4741 | 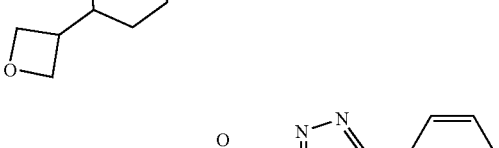 |
| 4767 | 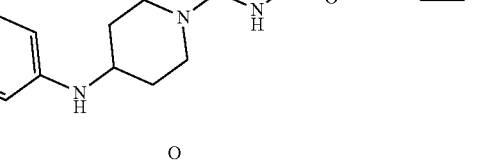 |
| 4768 | 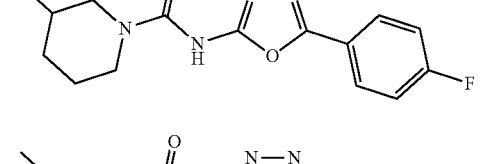 |
| 4769 | 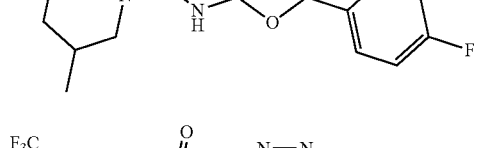 |

-continued
| Compound No. MBX- | Structure |
|---|---|
| 4776 | 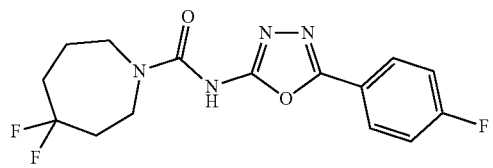 |
| 4777 | 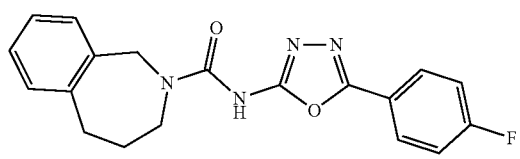 [SMILES: O=C(Nc1nnc(-c2ccc(F)cc2)o1)N1CCCc2ccccc2C1] |
| 4778 | 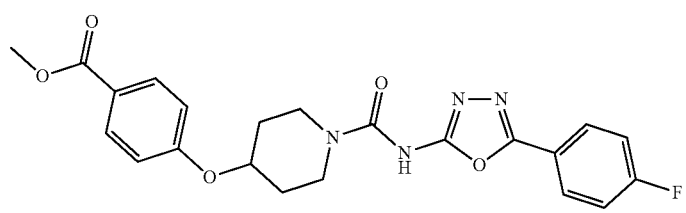 [SMILES: COC(=O)c1ccc(OC2CCN(C(=O)Nc3nnc(-c4ccc(F)cc4)o3)CC2)cc1] |
| 4779 | 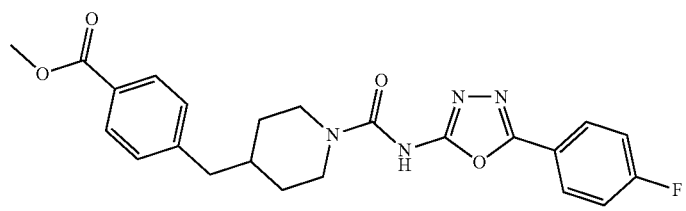 [SMILES: COC(=O)c1ccc(CC2CCN(C(=O)Nc3nnc(-c4ccc(F)cc4)o3)CC2)cc1] |
| 4805 | 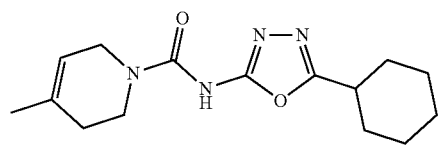 [SMILES: CC1=CCN(C(=O)Nc2nnc(C3CCCCC3)o2)CC1] |
| 4806 | 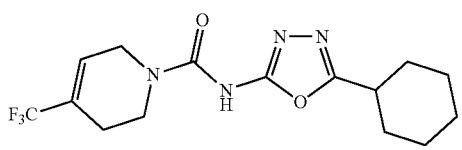 |
| 4807 | 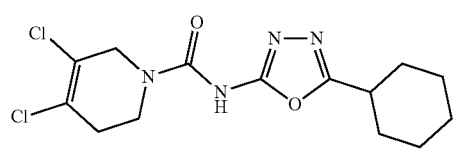 [SMILES: O=C(Nc1nnc(C2CCCCC2)o1)N1CCC(Cl)=C(Cl)C1] |
| 4808 | 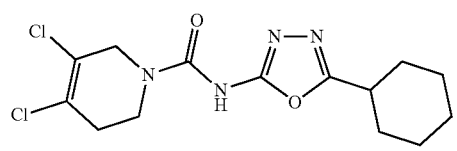 [SMILES: O=C(Nc1nnc(C2CCCCC2)o1)N1CCC(Cl)=C(Cl)C1] |
| 4839 | 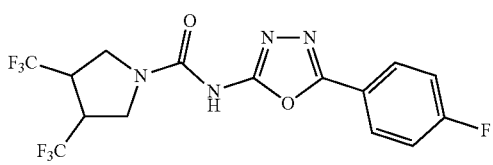 [SMILES: O=C(Nc1nnc(-c2ccc(F)cc2)o1)N1CC(C(F)(F)F)C(C(F)(F)F)C1] |

| Compound No. MBX- | Structure |
|---|---|
| 4840 | 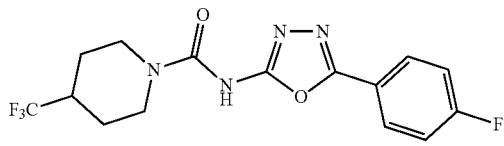 [SMILES: O=C(Nc1nnc(-c2ccc(F)cc2)o1)N1CCC(C(F)(F)F)CC1] |
| 4841 | 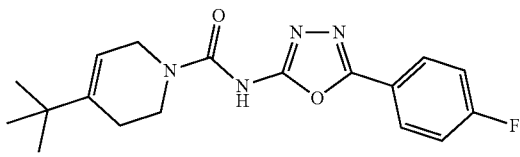 [SMILES: CC(C)(C)C1=CCN(C(=O)Nc2nnc(-c3ccc(F)cc3)o2)CC1] |
| 4842 | 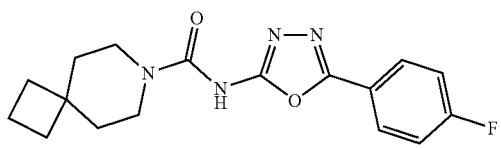 [SMILES: O=C(Nc1nnc(-c2ccc(F)cc2)o1)N1CCC2(CCC2)CC1] |
| 4843 | 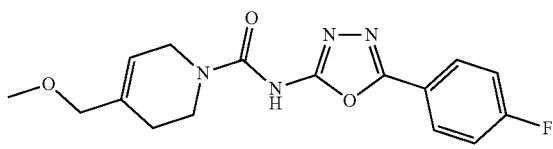 [SMILES: COCC1=CCN(C(=O)Nc2nnc(-c3ccc(F)cc3)o2)CC1] |
| 4922 | 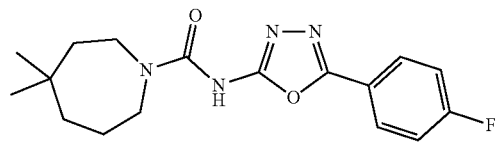 [SMILES: CC1(C)CCCN(C(=O)Nc2nnc(-c3ccc(F)cc3)o2)CC1] |
| 4923 | 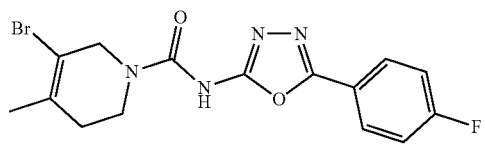 [SMILES: CC1=C(Br)CN(C(=O)Nc2nnc(-c3ccc(F)cc3)o2)CC1] |
| 4930 | 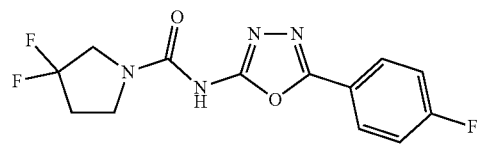 [SMILES: O=C(Nc1nnc(-c2ccc(F)cc2)o1)N1CCC(F)(F)C1] |
| 4931 | 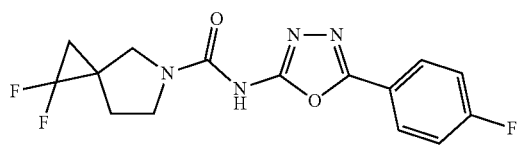 [SMILES: O=C(Nc1nnc(-c2ccc(F)cc2)o1)N1CCC2(C1)CC2(F)F] |
| 4932 | 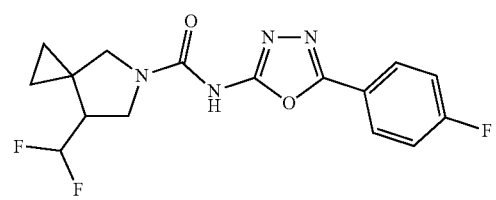 [SMILES: O=C(Nc1nnc(-c2ccc(F)cc2)o1)N1CC(C(F)F)C2(CC2)C1] |

-continued
| Compound No. MBX- | Structure |
|---|---|
| 4933 | 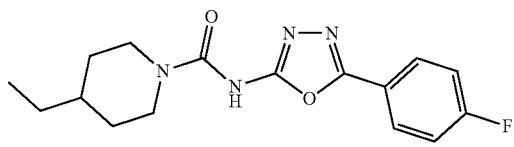 [SMILES: CCC1CCN(C(=O)Nc2nnc(-c3ccc(F)cc3)o2)CC1] |
| 4934 | 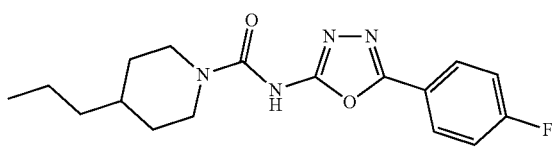 [SMILES: CCCC1CCN(C(=O)Nc2nnc(-c3ccc(F)cc3)o2)CC1] |
| 4935 | 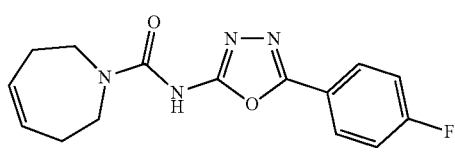 [SMILES: O=C(Nc1nnc(-c2ccc(F)cc2)o1)N1CCC=CCC1] |
| 4936 | 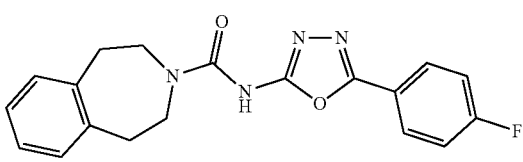 [SMILES: O=C(Nc1nnc(-c2ccc(F)cc2)o1)N1CCc2ccccc2CC1] |
| 4937 | 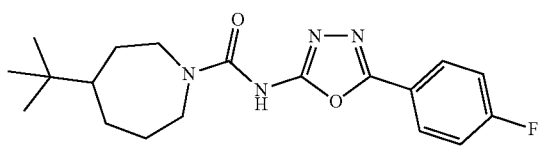 [SMILES: CC(C)(C)C1CCCN(C(=O)Nc2nnc(-c3ccc(F)cc3)o2)CC1] |
| 4938 | 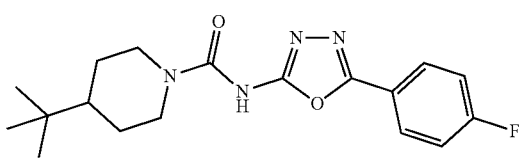 [SMILES: CC(C)(C)C1CCN(C(=O)Nc2nnc(-c3ccc(F)cc3)o2)CC1] |
| 4939 | 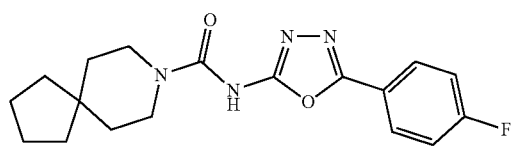 [SMILES: O=C(Nc1nnc(-c2ccc(F)cc2)o1)N1CCC2(CCCC2)CC1] |
| 4940 | 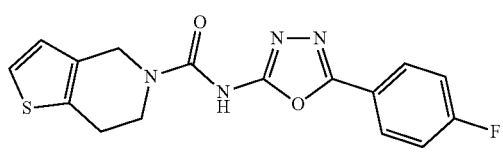 [SMILES: O=C(Nc1nnc(-c2ccc(F)cc2)o1)N1CCc2sccc2C1] |
| 4993 | 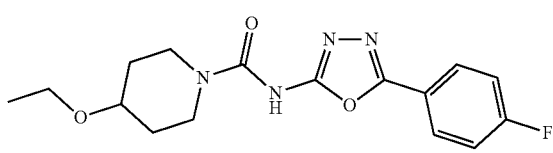 [SMILES: CCOC1CCN(C(=O)Nc2nnc(-c3ccc(F)cc3)o2)CC1] |
| 4994 | 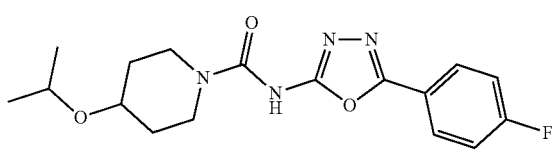 [SMILES: CC(C)OC1CCN(C(=O)Nc2nnc(-c3ccc(F)cc3)o2)CC1] |

-continued
| Compound No. MBX- | Structure |
|---|---|
| 4995 | 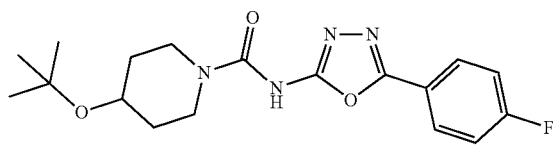 [SMILES: CC(C)(C)OC1CCN(C(=O)Nc2nnc(-c3ccc(F)cc3)o2)CC1] |
| 5154 | 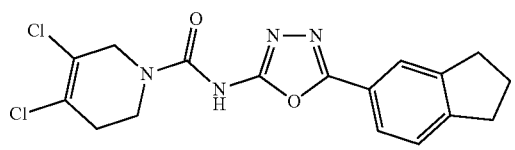 [SMILES: O=C(Nc1nnc(-c2ccc3c(c2)CCC3)o1)N1CCC(Cl)=C(Cl)C1] |
| 5155 | 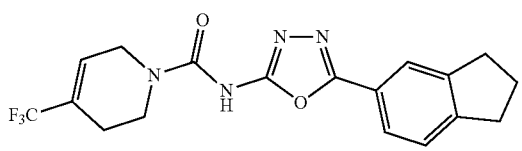 [SMILES: O=C(Nc1nnc(-c2ccc3c(c2)CCC3)o1)N1CC=C(C(F)(F)F)CC1] |
| 5199 | 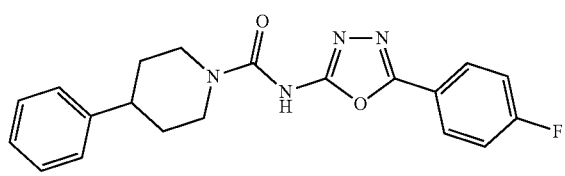 [SMILES: O=C(Nc1nnc(-c2ccc(F)cc2)o1)N1CCC(c2ccccc2)CC1] |
| 5200 | 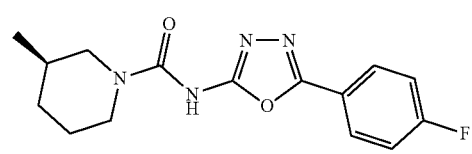 [SMILES: C[C@@H]1CCCN(C(=O)Nc2nnc(-c3ccc(F)cc3)o2)C1] |
| 5201 | 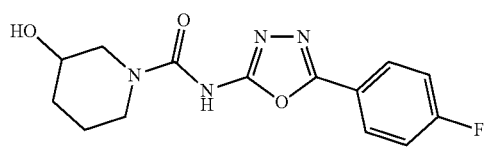 [SMILES: O=C(Nc1nnc(-c2ccc(F)cc2)o1)N1CCCC(O)C1] |
| 5202 | 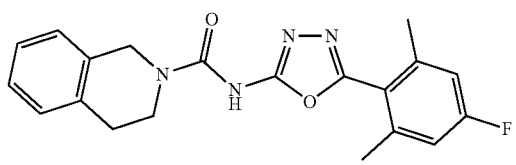 [SMILES: Cc1cc(F)cc(C)c1-c1nnc(NC(=O)N2CCc3ccccc3C2)o1] |
| 5203 | 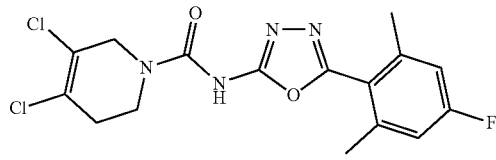 [SMILES: Cc1cc(F)cc(C)c1-c1nnc(NC(=O)N2CCC(Cl)=C(Cl)C2)o1] |
| 5204 | 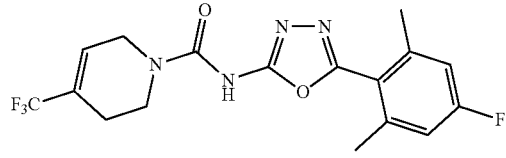 |

| Compound No. MBX- | Structure |
|---|---|
| 5212 | 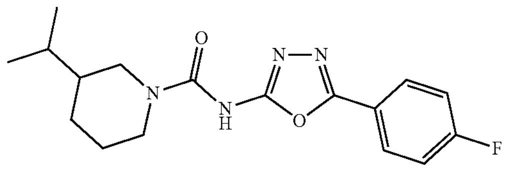 [SMILES: CC(C)C1CCCN(C(=O)Nc2nnc(-c3ccc(F)cc3)o2)C1] |
| 5214 | 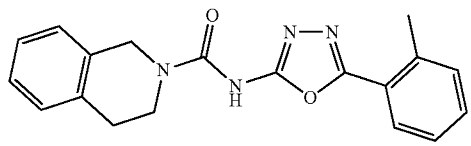 [SMILES: Cc1ccccc1-c1nnc(NC(=O)N2CCc3ccccc3C2)o1] |
| 5215 | 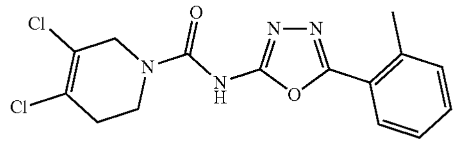 [SMILES: Cc1ccccc1-c1nnc(NC(=O)N2CCC(Cl)=C(Cl)C2)o1] |
| 5216 | 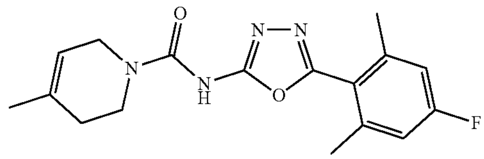 [SMILES: CC1=CCN(C(=O)Nc2nnc(-c3c(C)cc(F)cc3C)o2)CC1] |
| 5222 | 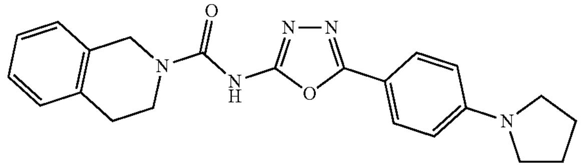 [SMILES: O=C(Nc1nnc(-c2ccc(N3CCCC3)cc2)o1)N1CCc2ccccc2C1] |
| 5223 | | or a pharmaceutically acceptable salt thereof.

14. The method according to claim 12, wherein the mammal is a human.

15. The method according to claim 12, wherein the bacterial infection is selected from *M. tuberculosis, N. gonorrhoeae, S. flexneri, H. influenzae, S. aureus, S. enterica, Y. pestis, F. tularensis*, and *S. pneumoniae*.

16. A pharmaceutical composition comprising at least one compound according to claim 12, and a pharmaceutically acceptable carrier or excipient.

17. A compound having the structure of Formula Ia:

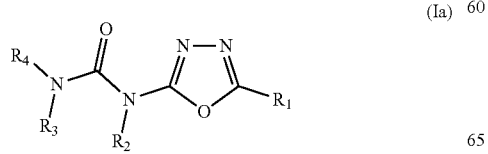

(Ia)

wherein:

$R_1$ is an aryl ring bearing 1-4 substituents an unsubstituted linear or branched chain aliphatic group containing 5-8 carbon atoms; a substituted linear, branched chain, or cyclic aliphatic group containing 1-6 carbon atoms bearing 1-8 substituents selected from aryl, heteroaryl, amino, substituted amino, halogen, alkoxy, sulfonyl, aryloxy, hydroxy, acylamino, carboxy, or alkylcarboxy; a carbocyclic ring of 3-7 carbon atoms bearing 1-4 substituents selected from alkyl, cycloalkyl, aryl, heteroaryl, amino, substituted amino, halogen, alkoxy, sulfonyl, aryloxy, hydroxy, acylamino, carboxy, or alkylcarboxy; an aromatic or non-aromatic heterocyclic ring made up of carbon atoms and at least one ring heteroatom selected independently from oxygen, nitrogen and sulfur atoms, and said heterocyclic ring bears 1-4 substituents selected from alkyl, cycloalkyl, aryl, heteroaryl, amino, substituted amino, halogen, alkoxy, sulfonyl, aryloxy, hydroxy, acylamino, carboxy, or alkylcarboxy;

$R_2$ is hydrogen, methyl, $C_2$-$C_4$ alkyl or cycloalkyl;

R₃ and R₄ are independently hydrogen, methyl, C2-C6 alkyl or cycloalkyl; an aromatic or non-aromatic heterocyclic ring bearing 1-3 substituents; or aryl bearing 1-3 substitutents;

or, alternatively,

R₃ and R₄ may be linked together to form a substituted 3-8-member cyclic or heterocyclic ring selected from piperidine, piperazine, morpholine, or azepine, which rings may be optionally substituted with substituents selected from alkyl, halogen, alkoxy, sulfonyl, carboxy, or alkylcarboxy, or the 3-8 membered ring may be fused with aromatic or heteroaromatic rings bearing 1-3 substituents selected from alkyl, halogen, alkoxy, sulfonyl, aryloxy, hydroxy, amino, acylamino, carboxy, alkylcarboxy, aryl, or heteroaryl groups;

or a pharmaceutically acceptable salt thereof.

18. A compound according to claim 17, selected from the group consisting of:

| Compound No. MBX- | Structure |
|---|---|
| 4132 | 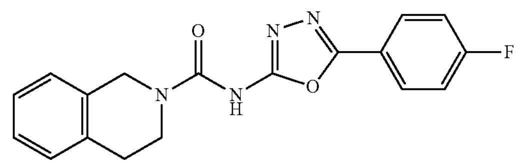 [SMILES: O=C(Nc1nnc(-c2ccc(F)cc2)o1)N1CCc2ccccc2C1] |
| 4198 | 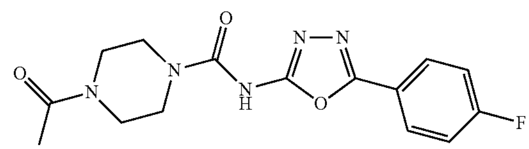 [SMILES: CC(=O)N1CCN(C(=O)Nc2nnc(-c3ccc(F)cc3)o2)CC1] |
| 4199 | 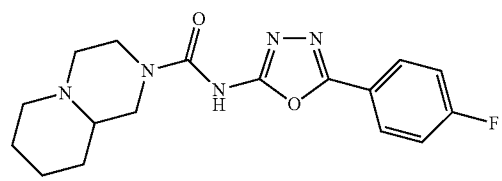 [SMILES: O=C(Nc1nnc(-c2ccc(F)cc2)o1)N1CCN2CCCCC2C1] |
| 4200 | 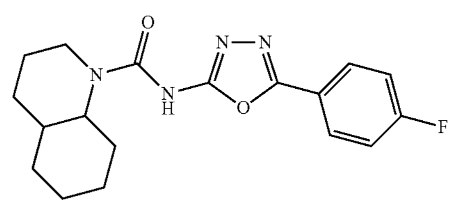 [SMILES: O=C(Nc1nnc(-c2ccc(F)cc2)o1)N1CCCC2CCCCC21] |
| 4201 | 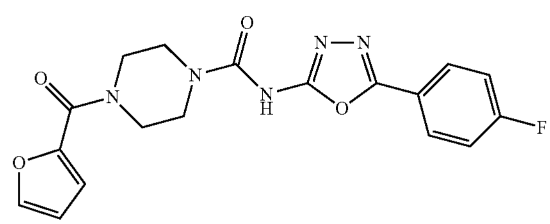 [SMILES: O=C(Nc1nnc(-c2ccc(F)cc2)o1)N1CCN(C(=O)c2ccco2)CC1] |
| 4330 | 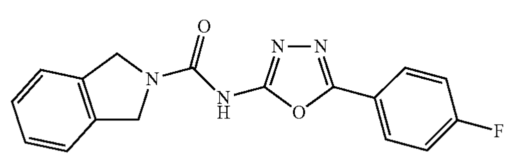 [SMILES: O=C(Nc1nnc(-c2ccc(F)cc2)o1)N1Cc2ccccc2C1] |
| 4331 | 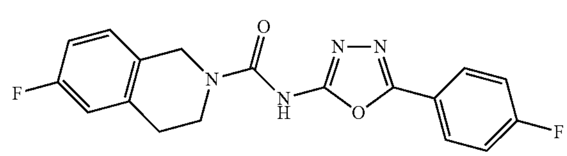 [SMILES: O=C(Nc1nnc(-c2ccc(F)cc2)o1)N1CCc2cc(F)ccc2C1] |

-continued
| Compound No. MBX- | Structure |
|---|---|
| 4332 | 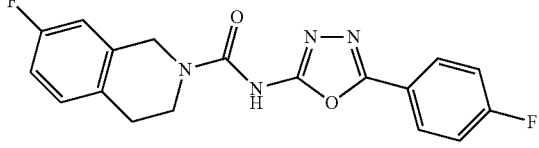 |
| 4333 | 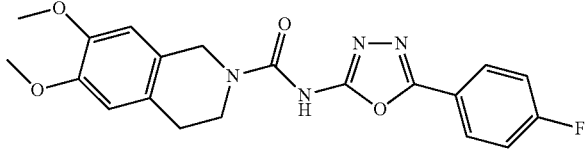 [SMILES: COc1cc2c(cc1OC)CN(C(=O)Nc1nnc(-c3ccc(F)cc3)o1)CC2] |
| 4345 | 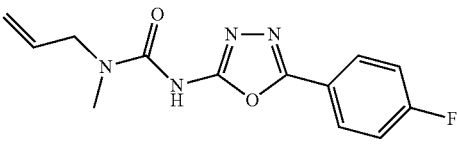 [SMILES: C=CCN(C)C(=O)Nc1nnc(-c2ccc(F)cc2)o1] |
| 4346 | 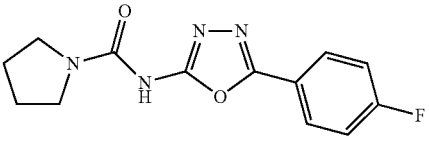 [SMILES: O=C(Nc1nnc(-c2ccc(F)cc2)o1)N1CCCC1] |
| 4347 | 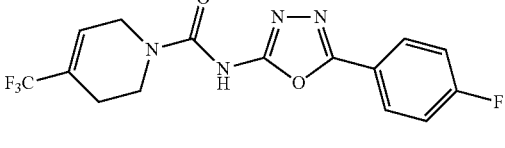 |
| 4348 | 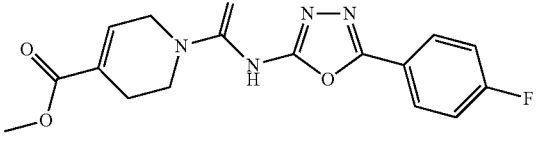 |
| 4349 | 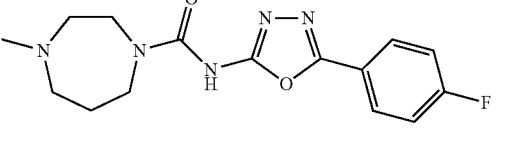 |
| 4350 | 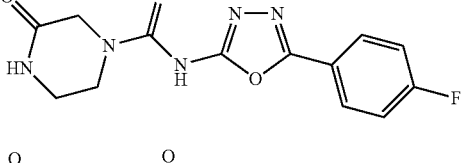 |
| 4351 | 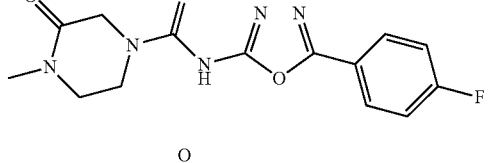 |
| 4366 | 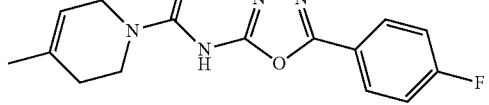 |

| Compound No. MBX- | Structure |
|---|---|
| 4380 | 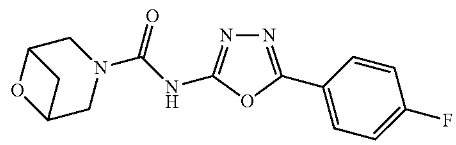 [SMILES: O=C(Nc1nnc(-c2ccc(F)cc2)o1)N1CC2CC(C1)O2] |
| 4381 | 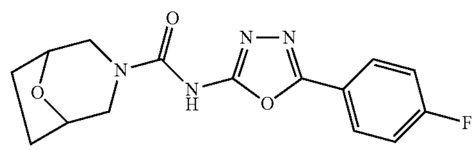 [SMILES: O=C(Nc1nnc(-c2ccc(F)cc2)o1)N1CC2CCC(C1)O2] |
| 4406 | 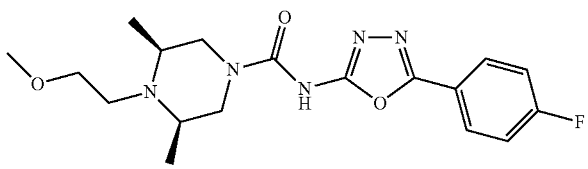 [SMILES: COCCN1[C@H](C)CN(C(=O)Nc2nnc(-c3ccc(F)cc3)o2)C[C@@H]1C] |
| 4464 | 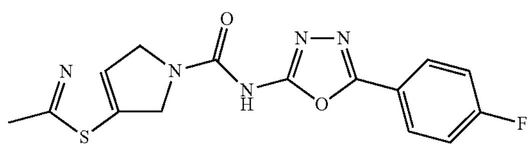 [SMILES: CC(=N)SC1=CCN(C(=O)Nc2nnc(-c3ccc(F)cc3)o2)C1] |
| 4465 | 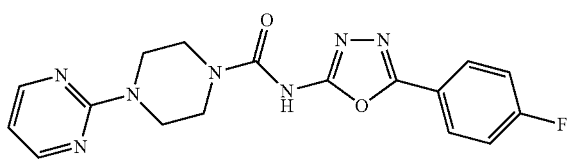 [SMILES: O=C(Nc1nnc(-c2ccc(F)cc2)o1)N1CCN(c2ncccn2)CC1] |
| 4497 | 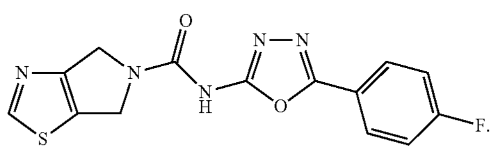 [SMILES: O=C(Nc1nnc(-c2ccc(F)cc2)o1)N1Cc2ncsc2C1] |

19. A method of treating or preventing a bacterial infection in a mammal, comprising administering to a subject in need thereof at least one compound according to claim 17.

20. The method according to claim 19, wherein the mammal is a human.

21. A method of inhibiting trans-translation-mediated bacterial growth in a mammal comprising administering an effective amount of a composition comprising at least one compound according to claim 17.

22. The method according to claim 21, wherein the mammal is a human.

23. The method according to claim 19, wherein the bacterial infection is selected from *M. tuberculosis, N. gonorrhoeae, S. flexneri, H. influenzae, S. aureus, S. enterica, Y. pestis, F. tularensis*, and *S. pneumoniae*.

24. A pharmaceutical composition comprising a compound according to claim 17, and a pharmaceutically acceptable carrier or excipient.

25. A method of inhibiting growth of bacterial cells on a solid surface comprising the step of contacting the surface with at least one compound according to claim 17.

26. A method of disinfecting a solid surface comprising the step of contacting the surface with at least one compound according to claim 17.

27. The method according to claim 25 or 26, wherein said solid surface is selected from the group consisting of implantable medical devices, central venous catheters (CVCs), implantable pumps, artificial heart valves, cardiac pacemakers, cardio-pulmonary bypass (CPB) pumps, heart-lung machines, dialysis equipment, artificial respirators, breathing apparatuses, water pipes, air ducts, air filters, water filters, and plumbing fixtures.

28. A method of treating or preventing a bacterial infection in a mammal, comprising administering to a subject in need thereof an effective amount of at least one compound of Formula Ia:

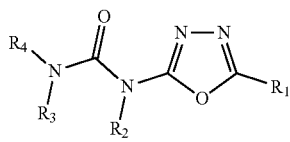

(Ia)

wherein:
R₁ is an aryl ring bearing 1-4 substituents an unsubstituted linear or branched chain aliphatic group containing 5-8 carbon atoms; a substituted linear, branched chain, or cyclic aliphatic group containing 1-6 carbon atoms bearing 1-8 substituents selected from aryl, heteroaryl, amino, substituted amino, halogen, alkoxy, sulfonyl, aryloxy, hydroxy, acylamino, carboxy, or alkylcarboxy; a carbocyclic ring of 3-7 carbon atoms bearing 1-4 substituents selected from alkyl, cycloalkyl, aryl, heteroaryl, amino, substituted amino, halogen, alkoxy, sulfonyl, aryloxy, hydroxy, acylamino, carboxy, or alkylcarboxy; an aromatic or non-aromatic heterocyclic ring made up of carbon atoms and at least one ring heteroatom selected independently from oxygen, nitrogen and sulfur atoms, and said heterocyclic ring bears 1-4 substituents selected from alkyl, cycloalkyl, aryl, heteroaryl, amino, substituted amino, halogen, alkoxy, sulfonyl, aryloxy, hydroxy, acylamino, carboxy, or alkylcarboxy;

R₂ is hydrogen, methyl, C₂-C₄ alkyl or cycloalkyl;

R₃ and R₄ are independently hydrogen, methyl, C2-C6 alkyl or cycloalkyl; an aromatic or non-aromatic heterocyclic ring bearing 1-3 substituents; or aryl bearing 1-3 substitutents;

or, alternatively,

R₃ and R₄ may be linked together to form a substituted 3-8-membered cyclic or heterocyclic ring selected from piperidine, piperazine, morpholine, or azepine, which rings may be optionally substituted with substituents selected from alkyl, halogen, alkoxy, sulfonyl, carboxy, or alkylcarboxy, or the 3-8 membered ring may be fused with aromatic or heteroaromatic rings bearing 1-3 substituents selected from alkyl, halogen, alkoxy, sulfonyl, aryloxy, hydroxy, amino, acylamino, carboxy, alkylcarboxy, aryl, or heteroaryl groups;

or a pharmaceutically acceptable salt thereof.

29. The method according to claim 28, wherein the compound is selected from the group consisting of:

| Compound No. MBX- | Structure |
|---|---|
| 4132 | 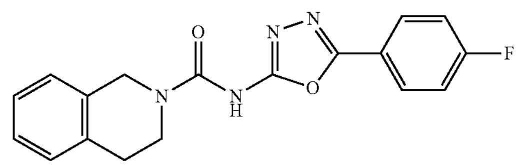 [SMILES: O=C(Nc1nnc(-c2ccc(F)cc2)o1)N1CCc2ccccc2C1] |
| 4198 | 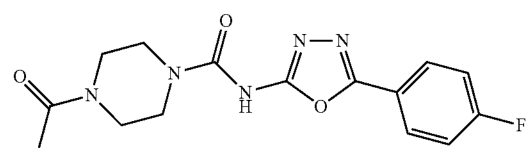 [SMILES: CC(=O)N1CCN(C(=O)Nc2nnc(-c3ccc(F)cc3)o2)CC1] |
| 4199 | 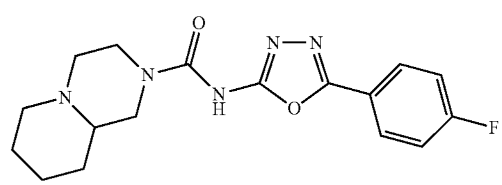 [SMILES: O=C(Nc1nnc(-c2ccc(F)cc2)o1)N1CCN2CCCCC2C1] |
| 4200 | 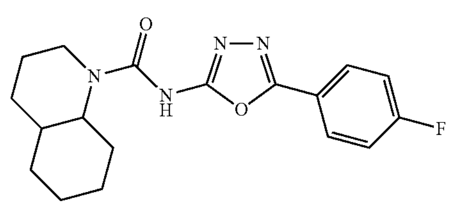 [SMILES: O=C(Nc1nnc(-c2ccc(F)cc2)o1)N1CCCC2CCCCC21] |
| 4201 | 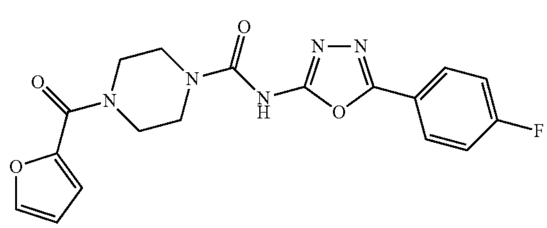 [SMILES: O=C(Nc1nnc(-c2ccc(F)cc2)o1)N1CCN(C(=O)c2ccco2)CC1] |

-continued
| Compound No. MBX- | Structure |
|---|---|
| 4330 | 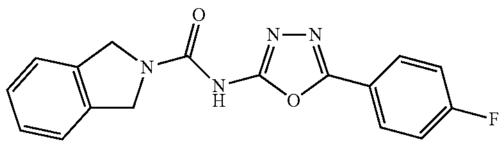 [SMILES: O=C(Nc1nnc(-c2ccc(F)cc2)o1)N1Cc2ccccc2C1] |
| 4331 | 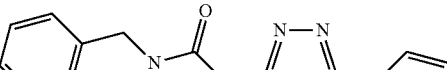 |
| 4332 | 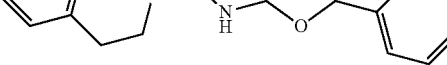 |
| 4333 | 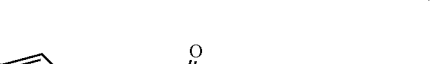 |
| 4345 | 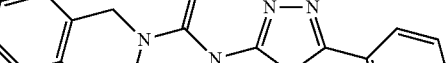 |
| 4346 | 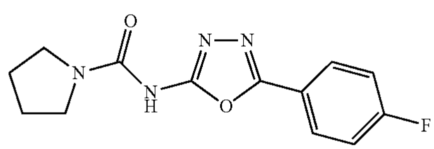 [SMILES: O=C(Nc1nnc(-c2ccc(F)cc2)o1)N1CCCC1] |
| 4347 | 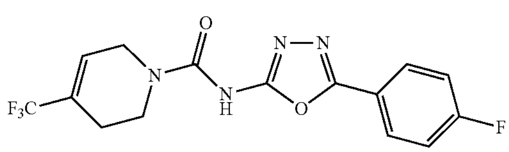 [SMILES: O=C(Nc1nnc(-c2ccc(F)cc2)o1)N1CC=C(C(F)(F)F)CC1] |
| 4348 | 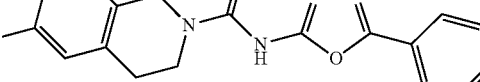 |
| 4349 | 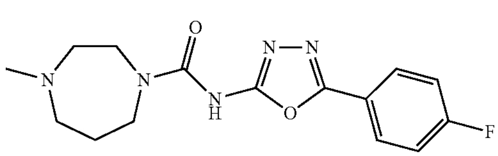 [SMILES: CN1CCCN(C(=O)Nc2nnc(-c3ccc(F)cc3)o2)CC1] |
| 4350 | 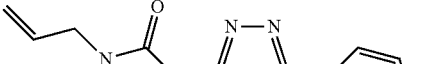 |

| Compound No. MBX- | Structure |
|---|---|
| 4351 | 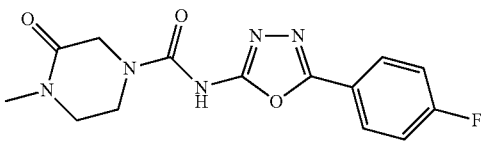 [SMILES: CN1CCN(C(=O)Nc2nnc(-c3ccc(F)cc3)o2)CC1=O] |
| 4366 | 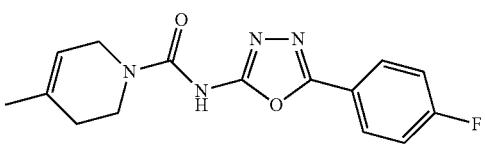 [SMILES: CC1=CCN(C(=O)Nc2nnc(-c3ccc(F)cc3)o2)CC1] |
| 4380 | 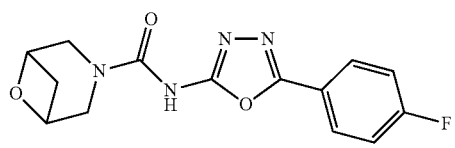 [SMILES: O=C(Nc1nnc(-c2ccc(F)cc2)o1)N1CC2CC(C1)O2] |
| 4381 | 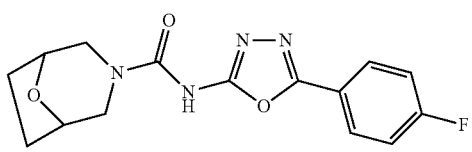 [SMILES: O=C(Nc1nnc(-c2ccc(F)cc2)o1)N1CC2CCC(C1)O2] |
| 4406 | 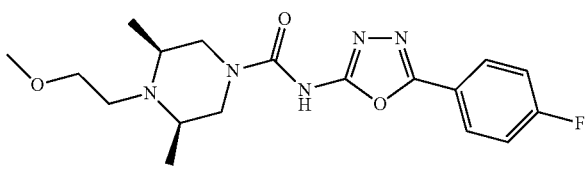 [SMILES: COCCN1[C@H](C)CN(C(=O)Nc2nnc(-c3ccc(F)cc3)o2)C[C@@H]1C] |
| 4464 | 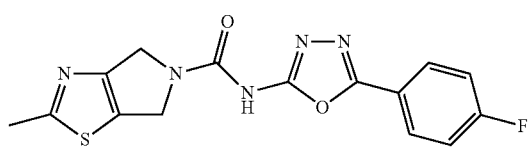 [SMILES: Cc1nc2c(s1)CN(C(=O)Nc1nnc(-c3ccc(F)cc3)o1)C2] |
| 4465 | 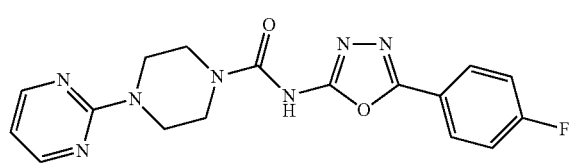 [SMILES: O=C(Nc1nnc(-c2ccc(F)cc2)o1)N1CCN(c2ncccn2)CC1] |
| 4497 | 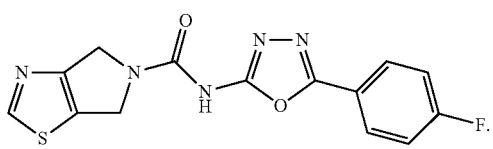 [SMILES: O=C(Nc1nnc(-c2ccc(F)cc2)o1)N1Cc2ncsc2C1] |

30. The method according to claim 28, wherein the bacterial infection is selected from *M. tuberculosis, N. gonorrhoeae, S. flexneri, H. influenzae, S. aureus, S. enterica, Y. pestis, F. tularensis*, and *S. pneumoniae*.

31. The method according to claim 28, wherein the mammal is a human.

32. A pharmaceutical composition comprising at least one compound according to claim 28, and a pharmaceutically acceptable carrier or excipient.

* * * * *